US012773447B2

(12) United States Patent
Prasad et al.

(10) Patent No.: US 12,773,447 B2
(45) Date of Patent: Oct. 27, 2026

(54) IMMUNOGENIC MULTIPLE HETERO-ANTIGEN POLYSACCHARIDE-PROTEIN CONJUGATES AND USES THEREOF

(71) Applicant: Pfizer Inc., New York, NY (US)

(72) Inventors: Avvari Krishna Prasad, Chapel Hill, NC (US); Jianxin Gu, Paramus, NJ (US); Jin-Hwan Kim, Suffern, NY (US); Suddham Singh, Monroe, NY (US)

(73) Assignee: Pfizer Inc., New York, NY (US)

( * ) Notice: Subject to any disclaimer, the term of this patent is extended or adjusted under 35 U.S.C. 154(b) by 1113 days.

(21) Appl. No.: 17/312,185

(22) PCT Filed: Dec. 9, 2019

(86) PCT No.: PCT/IB2019/060562

§ 371 (c)(1),
(2) Date: Jun. 9, 2021

(87) PCT Pub. No.: WO2020/121159

PCT Pub. Date: Jun. 18, 2020

(65) Prior Publication Data

US 2022/0016229 A1 Jan. 20, 2022

Related U.S. Application Data

(60) Provisional application No. 62/778,362, filed on Dec. 12, 2018, provisional application No. 62/778,371, (Continued)

(51) Int. Cl.
*A61K 39/09* (2006.01)
*A61K 47/64* (2017.01)
(Continued)

(52) U.S. Cl.
CPC .......... *A61K 39/092* (2013.01); *A61K 47/646* (2017.08); *A61P 31/00* (2018.01); (Continued)

(58) Field of Classification Search
None
See application file for complete search history.

(56) References Cited

U.S. PATENT DOCUMENTS 4,709,017 A 11/1987 Collier et al.
4,950,740 A 8/1990 Greenfield et al.
(Continued)

FOREIGN PATENT DOCUMENTS

CA 2004810 6/1990
CN 103495161 A 1/2014
(Continued)

OTHER PUBLICATIONS

Cipollo. "Review of manufacturing process" for Prevnar 13™ [Pneumococcal 13-valent Conjugate Vaccine (Diphtheria CRM197 Protein)] Feb. 16, 2009.*
(Continued)

*Primary Examiner* — Shanon A. Foley

(57) ABSTRACT

The present invention relates to new glycoconjugates comprising *Streptococcus pneumoniae* capsular saccharide antigens and uses thereof. Glycoconjugates of the present invention will typically comprise 2 or more saccharides antigens conjugated to the same molecule of the protein carrier. The invention also relates to vaccination of human subjects, in particular infants and elderly, against pneumoccocal infections using immunogenic compositions comprising said novel glycoconjugates.

25 Claims, 17 Drawing Sheets

33F

MW 1014.9 $C_{38}H_{62}O_{31}$

Related U.S. Application Data filed on Dec. 12, 2018, provisional application No. 62/778,382, filed on Dec. 12, 2018.

(51) Int. Cl.
*A61P 31/00* (2006.01)
*A61K 39/00* (2006.01)

(52) U.S. Cl.
CPC ................ *A61K 2039/6037* (2013.01); *A61K 2039/645* (2013.01); *A61K 2039/70* (2013.01)

(56) References Cited

U.S. PATENT DOCUMENTS

| | | | | |
|---|---|---|---|---|
| 5,843,711 | A | 12/1998 | Collier et al. | |
| 5,917,017 | A | 6/1999 | Collier et al. | |
| 6,194,388 | B1 | 2/2001 | Krieg et al. | |
| 6,207,646 | B1 | 3/2001 | Krieg et al. | |
| 6,214,806 | B1 | 4/2001 | Krieg et al. | |
| 6,218,371 | B1 | 4/2001 | Krieg et al. | |
| 6,239,116 | B1 | 5/2001 | Krieg et al. | |
| 6,339,068 | B1 | 1/2002 | Krieg et al. | |
| 6,455,673 | B1 | 9/2002 | Collier | |
| 9,517,274 | B2 | 12/2016 | Gu et al. | |
| 9,950,054 | B2 | 4/2018 | Gu et al. | |
| 10,583,187 | B2 | 3/2020 | Gu et al. | |
| 11,110,160 | B2 | 9/2021 | Gu et al. | |
| 11,723,965 | B2 | 8/2023 | Gu et al. | |
| 2006/0228380 | A1 | 10/2006 | Hausdorff et al. | |
| 2006/0228381 | A1 | 10/2006 | Bahler et al. | |
| 2007/0184071 | A1 | 8/2007 | Hausdorff et al. | |
| 2007/0184072 | A1 | 8/2007 | Hausdorff et al. | |
| 2007/0231340 | A1 | 10/2007 | Hausdorff et al. | |
| 2008/0102498 | A1 | 5/2008 | Bahler et al. | |
| 2008/0286838 | A1 | 11/2008 | Yuan et al. | |
| 2015/0202309 | A1* | 7/2015 | Emini | A61K 47/646 424/197.11 |
| 2018/0353591 | A1* | 12/2018 | Kapre | A61P 31/04 |
| 2019/0192648 | A1* | 6/2019 | Smith | A61K 39/092 |
| 2021/0077608 | A1* | 3/2021 | An | A61P 31/04 |
| 2022/0016229 | A1* | 1/2022 | Prasad | A61K 39/092 |

FOREIGN PATENT DOCUMENTS

| | | | |
|---|---|---|---|
| EP | 0 208 375 | A2 | 1/1987 |
| EP | 0 372 501 | A2 | 6/1990 |
| EP | 0 378 881 | B1 | 6/1993 |
| EP | 0 427 347 | B1 | 2/1995 |
| EP | 0 471 177 | B1 | 10/1995 |
| EP | 0 594 610 | B1 | 9/1998 |
| EP | 0 735 898 | B1 | 3/1999 |
| EP | 0 761 231 | B1 | 1/2000 |
| EP | 0 689 454 | B2 | 2/2005 |
| EP | 2 382 986 | A2 | 11/2011 |
| WO | 90/03184 | A1 | 4/1990 |
| WO | 91/01146 | A1 | 2/1991 |
| WO | 93/15760 | A1 | 8/1993 |
| WO | 93/17712 | A2 | 9/1993 |
| WO | 94/03208 | A1 | 2/1994 |
| WO | 95/08348 | A1 | 3/1995 |
| WO | 96/11711 | A1 | 4/1996 |
| WO | 96/40225 | A1 | 12/1996 |
| WO | 97/01640 | A2 | 1/1997 |
| WO | 98/36772 | A1 | 8/1998 |
| WO | 98/57659 | A1 | 12/1998 |
| WO | 98/58668 | A2 | 12/1998 |
| WO | 99/11241 | A1 | 3/1999 |
| WO | 99/42130 | A1 | 8/1999 |
| WO | 99/44636 | A2 | 9/1999 |
| WO | 99/52549 | A1 | 10/1999 |
| WO | 00/07621 | A2 | 2/2000 |
| WO | 00/23105 | A2 | 4/2000 |
| WO | 00/37105 | A2 | 6/2000 |
| WO | 00/39299 | A2 | 7/2000 |
| WO | 00/41720 | A1 | 7/2000 |
| WO | 00/48630 | A1 | 8/2000 |
| WO | 00/56357 | A2 | 9/2000 |
| WO | 00/56358 | A2 | 9/2000 |
| WO | 00/61761 | A2 | 10/2000 |
| WO | 00/62800 | A2 | 10/2000 |
| WO | 01/21152 | A1 | 3/2001 |
| WO | 01/21207 | A2 | 3/2001 |
| WO | 01/72337 | A1 | 10/2001 |
| WO | 01/98334 | A2 | 12/2001 |
| WO | 02/091998 | A2 | 11/2002 |
| WO | 03/024480 | A2 | 3/2003 |
| WO | 03/054007 | A2 | 7/2003 |
| WO | 2004/081515 | A2 | 9/2004 |
| WO | 2004/083251 | A2 | 9/2004 |
| WO | 2005/033148 | A1 | 4/2005 |
| WO | 2006/032499 | A1 | 3/2006 |
| WO | 2006/110352 | A2 | 10/2006 |
| WO | 2006/110381 | A1 | 10/2006 |
| WO | 2006/134423 | A2 | 12/2006 |
| WO | 2007/026190 | A2 | 3/2007 |
| WO | 2007/071711 | A2 | 6/2007 |
| WO | 2008/021076 | A2 | 2/2008 |
| WO | 2008/079653 | A1 | 7/2008 |
| WO | 2008/118752 | A2 | 10/2008 |
| WO | 2008/143709 | A2 | 11/2008 |
| WO | 2009/000826 | A1 | 12/2008 |
| WO | 2010/125480 | A1 | 11/2010 |
| WO | 2014/118201 | A1 | 8/2014 |
| WO | 2015/110940 | A2 | 7/2015 |
| WO | 2015/110941 | A2 | 7/2015 |
| WO | 2017/013548 | A1 | 1/2017 |
| WO | 2017/173415 | A2 | 10/2017 |
| WO | WO 2019/212846 | * | 11/2019 |

OTHER PUBLICATIONS

Astronomo and Burton, "Carbohydrate vaccines: developing sweet solutions to sticky situations?", Nature Reviews Drug Discovery 9(4):308-324 (2010).

Baraldo et al, "N19 Polyepitope as a Carrier for Enhanced Immunogenicity and Protective Efficacy of Meningococcal Conjugate Vaccines", Infection and Immunity 72(8):4884-4887 (2004).

Bethell et al, "A Novel Method of Activation of Cross-linked Agaroses with 1,1'-Carbonyldiimidazole Which Gives a Matrix for Affinity Chromatography Devoid of Additional Charged Groups", The Journal of Biological Chemistry 254(8):2572-2574 (1979).

Beynon et al, "Characterization of the capsular antigen of *Streptococcus pneumoniae* serotype 35B1", Canadian Journal of Chemistry 73:41-48 (1995).

Calix et al, "Elucidation of Structural and Antigenic Properties of Pneumococcal Serotype 11A, 11B, 11C, and 11F Polysaccharide Capsules", Journal of Bacteriology 193(19):5271-5278 (2011).

Douglas et al, "Exotoxin A of Pseudomonas aeruginosa: Substitution of Glutamic Acid 553 with Aspartic Acid Drastically Reduces Toxicity and Enzymatic Activity", Journal of Bacteriology 169(11):4967-4971 (1987).

Falugi et al, "Rationally designed strings of promiscuous CD4+ T cell epitopes provide help to Haemophilus influenzae type b oligosaccharide: a model for new conjugate vaccines", Eur. J. Immunol. 31:3816-3824 (2001).

Hearn et al, "Application of 1,1'-Carbonyldiimidazole-Activated Matrices for the Purification of Proteins: III. The Use of 1,1'-Carbonyldiimidazole-Activated Agaroses in the Biospecific Affinity Chromatographic Isolation of Serum Antibodies", Journal of Chromatography 218:509-518 (1981).

Hermand et al, "Preclinical evaluation of a chemically detoxified pneumolysin as pneumococcal vaccine antigen", Human Vaccines & Immunotherapeutics 13(1):220-228 (2017).

Hestrin et al, "The Reaction of Acetylcholine and other Carboxylic Acid Derivatives With Hydroxylamine, and Its Analytical Application", J. Biol. Chem. 180:249-261 (1949).

Jones, "Full assignment of the NMR spectrum of the capsular polysaccharide from *Streptococcus pneumoniae* serotype 10A", Carbohydrate Research 269(1):175-181 (1995).

(56) References Cited

OTHER PUBLICATIONS

Jones and Lemercinier, "Use and validation of NMR assays for the identity and O-acetyl content of capsular polysaccharides from Neisseria meningitidis used in vaccine manufacture", Journal of Pharmaceutical and Biomedical Analysis 30(4):1233-1247 (2002).
Kirkham et al, "Construction and Immunological Characterization of a Novel Nontoxic Protective Pneumolysin Mutant for Use in Future Pneumococcal Vaccines", Infection and Immunity 74(1):586-593 (2006).
Kuo et al, "Characterization of a Recombinant Pneumolysin n and Its Use as a Protein Carrier for Pneumococcal Type 18C Conjugate Vaccines", Infection and Immunity 63(7):2706-2713 (1995).
Lemercinier and Jones, "Full 1H NMR assignment and detailed O-acetylation patterns of capsular polysaccharides from Neisseria meningitidis used in vaccine production", Carbohydrate Research 296(1-4):83-96 (1996).
Lemercinier and Jones, "Full assignment of the 1H and 13C spectra and revision of the O-acetylation site of the capsular polysaccharide of *Streptococcus pneumoniae* Type 33F, a component of the current pneumococcal polysaccharide vaccine", Carbohydrate Research 341(1):68-74 (2006).
PCT International Search Report and Written Opinion for International Application No. PCT/IB2019/060562 mailed on Feb. 26, 2020.
Richards et al, "Elucidation and Comparison of the Chemical Structures of the Specific Capsular Polysaccharides of *Streptococcus pneumoniae* Groups 11 (11F, 11B, 11C, and 11A)", Advances in Experimental Medicine and Biology 228:595-596 (1988).
Richards et al, "Structural analysis of the specific capsular polysaccharide of *Streptococcus pneumoniae* type 22F1", Canadian Journal of Chemistry 67(6):1038-1050 (1989).
Sjölander et al, "ISCOMs: an adjuvant with multiple functions", J. Leukoc. Biol. 64:713-723 (1998).
Spencer et al, "Position of O-Aceytlation within the Capsular Repeat Unit Impacts the Biological Properties of Pneumococcal Serotypes 33A and 33F", Infection and Immunity 85(7):e00132-17 (2017).
Uchida et al, "Mutation in the Structural Gene for Diphtheria Toxin Carried by Temperate Phage Beta", Nature New Biology 233:8-11 (1971).
Uchida et al, "Diphtheria Toxin and Related Proteins: I. Isolation and Properties of Mutant Proteins Serologically Related to Diphtheria Toxin", The Journal of Biological Chemistry 248(11):3838-3844 (1973).

* cited by examiner

22F

MW 995.87 $C_{38}H_{60}O_{30}$

33F

MW 1014.9 $C_{38}H_{62}O_{31}$

35B

MW 945.78 $C_{33}H_{56}NO_{28}P$

10A

| Serotype | 10A+22F+33F+35B |
|---|---|
| SPRatio | 1 |
| Free Sacc (%) | < 5 |
| MW (kDa) | 4916 |

8

15A

15B

23A

23B

| Serotype | 15A+15B |
|---|---|
| SPRatio | 0.99 |
| Free Sacc (%) | 31 |
| MW (kDa) | 3189 |

11A

12F

| Serotype | 11A+23B |
|---|---|
| SPRatio | 0.83 |
| Free Sacc (%) | 7.1 |
| MW (kDa) | 3436 |

| Serotype | 8+12F |
|---|---|
| SPRatio | 1.05 |
| Free Sacc (%) | 12 |
| MW (kDa) | 2035 |

IMMUNOGENIC MULTIPLE HETERO-ANTIGEN POLYSACCHARIDE-PROTEIN CONJUGATES AND USES THEREOF

CROSS REFERENCE TO RELATED APPLICATIONS

This application is a National Stage Application of International Application No. PCT/IB2019/060562, filed Dec. 9, 2019, which claims the benefit under 35 U.S.C. § 119 (e) of U.S. Provisional Application Ser. No. 62/778,382, filed Dec. 12, 2018, U.S. Provisional Application Ser. No. 62/778,371, filed Dec. 12, 2018, and U.S. Provisional Application Ser. No. 62/778,362, filed Dec. 12, 2018, all of which are incorporated by reference in their entirety.

FIELD OF THE INVENTION

The present invention relates to new Immunogenic Multiple Hetero-Antigen Polysaccharide-Protein (iMHAPP) Conjugates (glycoconjugates) and immunogenic compositions comprising said glycoconjugates and uses thereof. The glycoconjugates of the present invention will typically comprise saccharides from serotypes of *Streptococcus pneumoniae* conjugated to a carrier protein. The invention also relates to vaccination of human subjects, in particular infants and elderly, against pneumoccocal infections using said novel glycoconjugates and immunogenic compositions.

BACKGROUND OF THE INVENTION

Infections caused by pneumococci are a major cause of morbidity and mortality all over the world. Pneumonia, febrile bacteraemia and meningitis are the most common manifestations of invasive pneumococcal disease, whereas bacterial spread within the respiratory tract may result in middle-ear infection, sinusitis or recurrent bronchitis. Compared with invasive disease, the non-invasive manifestations are usually less severe, but considerably more common.

In Europe and the United States, pneumococcal pneumonia is the most common community-acquired bacterial pneumonia, estimated to affect approximately 100 per 100,000 adults each year. The corresponding figures for febrile bacteraemia and meningitis are 15-19 per 100 000 and 1-2 per 100,000, respectively. The risk for one or more of these manifestations is much higher in infants and elderly people, as well as immune compromised persons of any age. Even in economically developed regions, invasive pneumococcal disease carries high mortality; for adults with pneumococcal pneumonia the mortality rate averages 10%-20%, whilst it may exceed 50% in the high-risk groups. Pneumonia is by far the most common cause of pneumococcal death worldwide.

The etiological agent of pneumococcal diseases, *Streptococcus pneumoniae* (pneumococcus), is a Gram-positive encapsulated coccus, surrounded by a polysaccharide capsule. Differences in the composition of this capsule permit serological differentiation between about 91 capsular types, some of which are frequently associated with pneumococcal disease, others rarely. Invasive pneumococcal infections include pneumonia, meningitis and febrile bacteremia; among the common non-invasive manifestations are otitis media, sinusitis and bronchitis.

Pneumococcal conjugate vaccines (PCVs) are pneumococcal vaccines used to protect against disease caused by *S. pneumoniae* (pneumococcus). There are currently three PCV vaccines available on the global market: PREVNAR® (called Prevenar in some countries) (heptavalent vaccine), SYNFLORIX® (a decavalent vaccine) and PREVNAR 13® (tridecavalent vaccine).

The recent development of widespread microbial resistance to essential antibiotics and the increasing number of immunocompromised persons underline the need for pneumococcal vaccines with even broader protection.

In particular, there is a need to address remaining unmet medical need for coverage of pneumococcal disease due to serotypes not found in PREVNAR 13® and potential for serotype replacement over time. The specific serotypes causing disease beyond the 13 in PREVNAR 13® vary by region, population, and may change over time due to acquisition of antibiotic resistance, pneumococcal vaccine introduction and secular trends of unknown origin. There is a need for immunogenic compositions that can be used to induce an immune response against additional *Streptococcus pneumoniae* serotypes in humans and in particular in children less than 2 years old.

SUMMARY OF THE INVENTION

Several Multiple Antigen Pneumococcal conjugates were generated from the polysaccharides from various serotypes, following the use of careful pooling strategy based on 'selective saccharide chemical reactivity'. Polysaccharides with different chemical reactivities were pooled into different groups, based on the early development studies and structural work involving the activated polysaccharides.

The present invention involves devising an approach to produce multi-valent compositions, whereby the number of manufacturing steps and individual conjugates is reduced to fewer conjugations instead of multiple individual monovalent conjugations steps required by the iterative approach currently used widely, for licensed commercial conjugate vaccines.

The present multi-serotype conjugates of the invention allow for potentially simplifying the production of multivalent pneumococcal vaccines as less drug substance will be required. The production will also require less steps. The multi-serotypes conjugates of the invention will also help to customize multi-valent pneumococcal vaccines more easily by providing for protection against several serotypes with only a limited number of conjugates.

FIGURES

Figure 6:
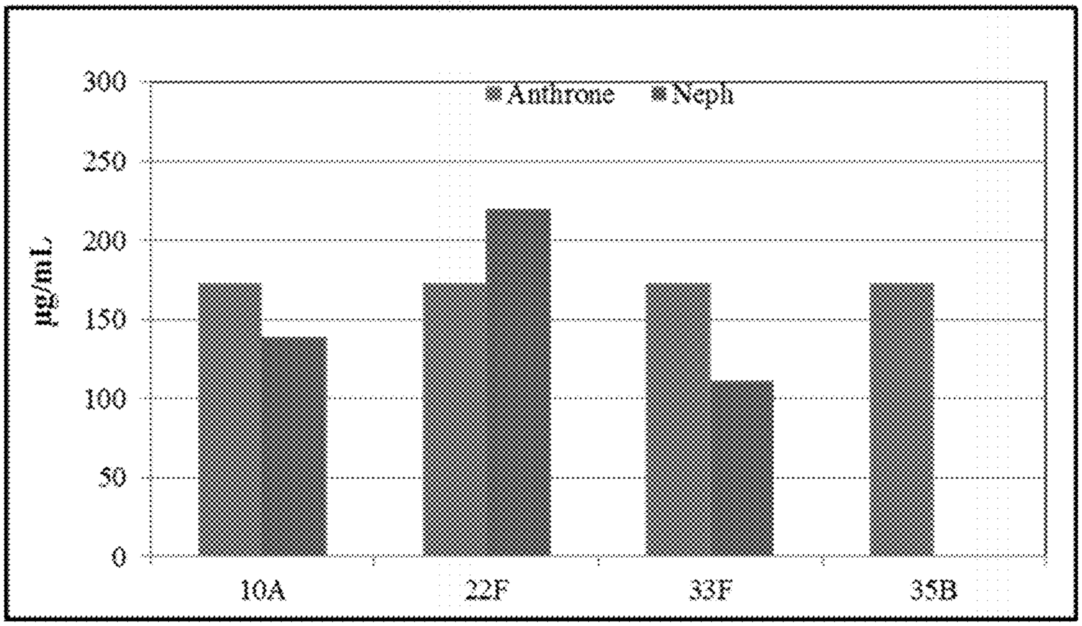

FIG. 6 Antigenicty of the conjugates tested by Nephelometry (Neph, right bar) and total saccharide content measured by Anthrone assay (left bar for each serotype and only bar for 35B).

Figure 7:
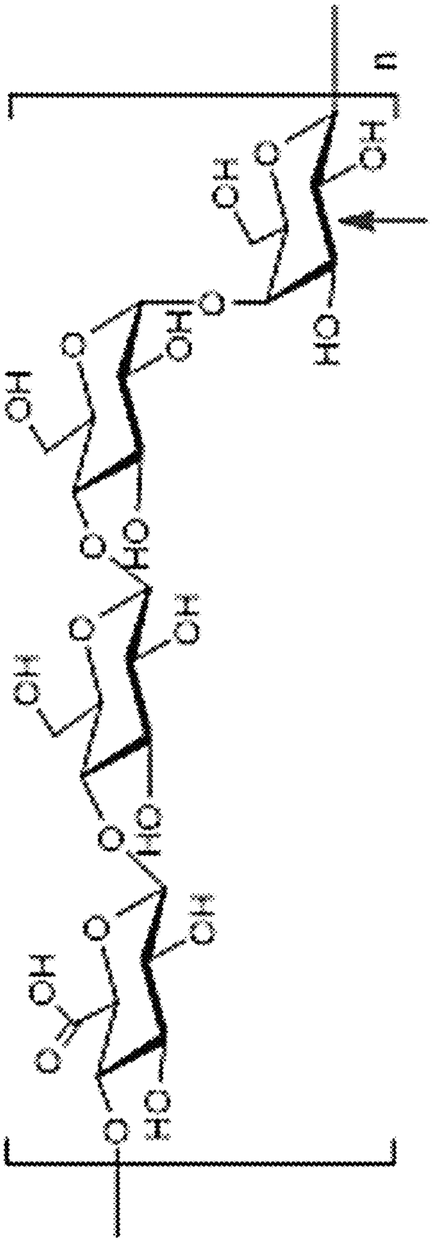

FIG. 7 shows the structure of serotype 8 pnemococcal polysaccharide having vicinal hydroxyls uniquely positioned to generate aldehydes (see arrow).

Figure 8:
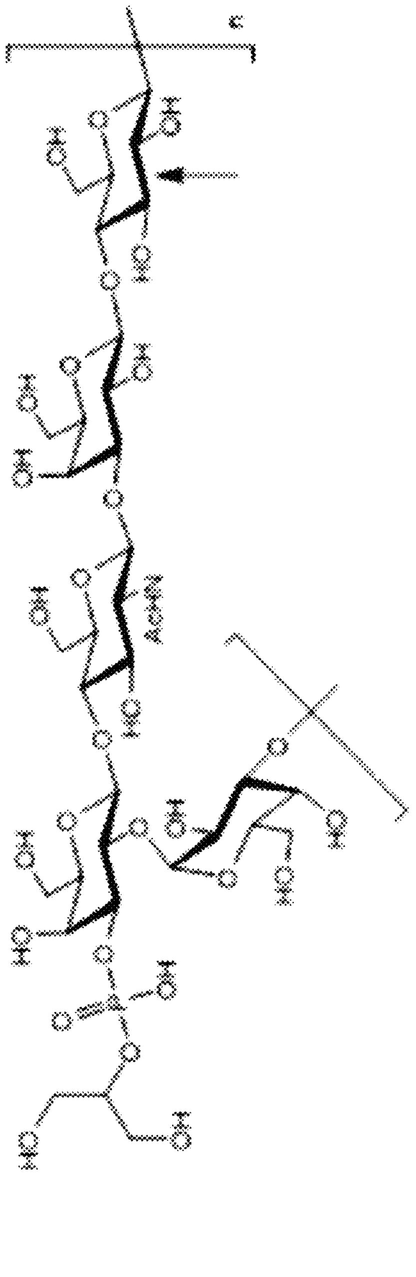

FIG. 8 shows the structure of serotype 15A pnemococcal polysaccharide having vicinal hydroxyls uniquely positioned to generate aldehydes (see arrow).

Figure 9:
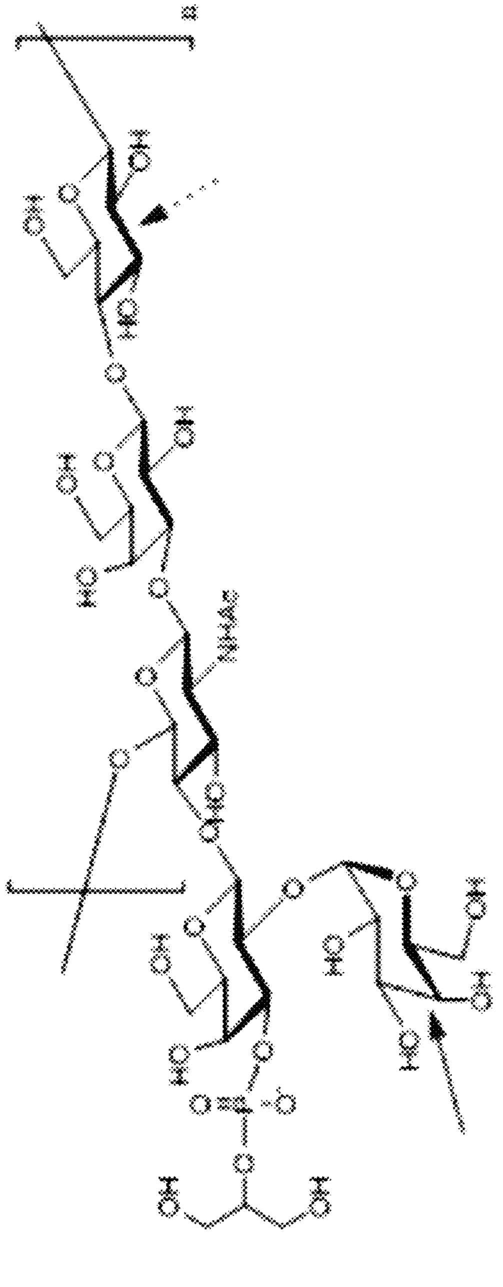

FIG. 9 shows the structure of serotype 15B pnemococcal polysaccharide having vicinal hydroxyls uniquely positioned to generate aldehydes (see arrow).

Figure 10:
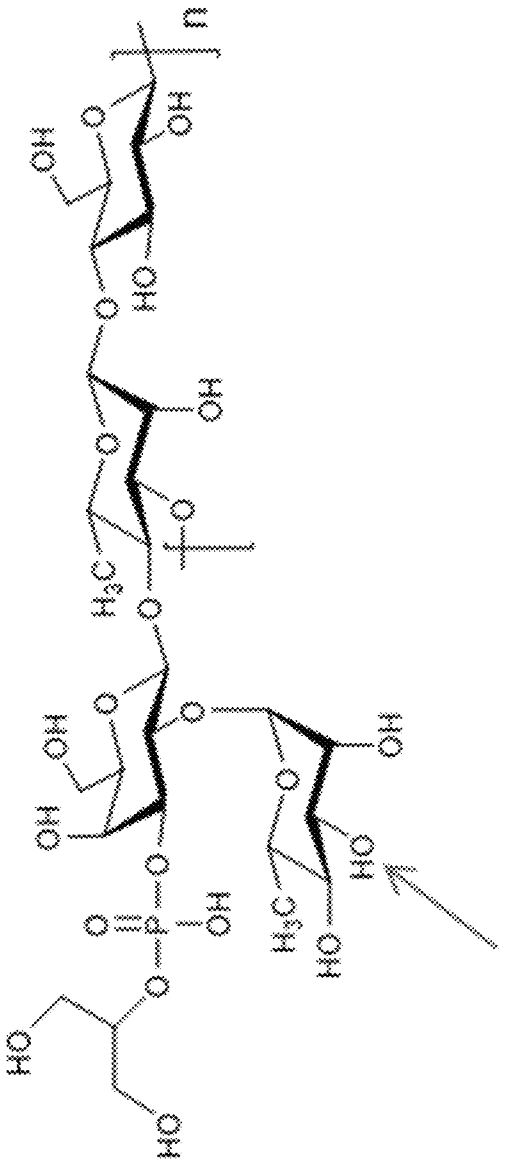

FIG. 10 shows the structure of serotype 23A pnemococcal polysaccharide having vicinal hydroxyls uniquely positioned to generate aldehydes (see arrow).

Figure 11:
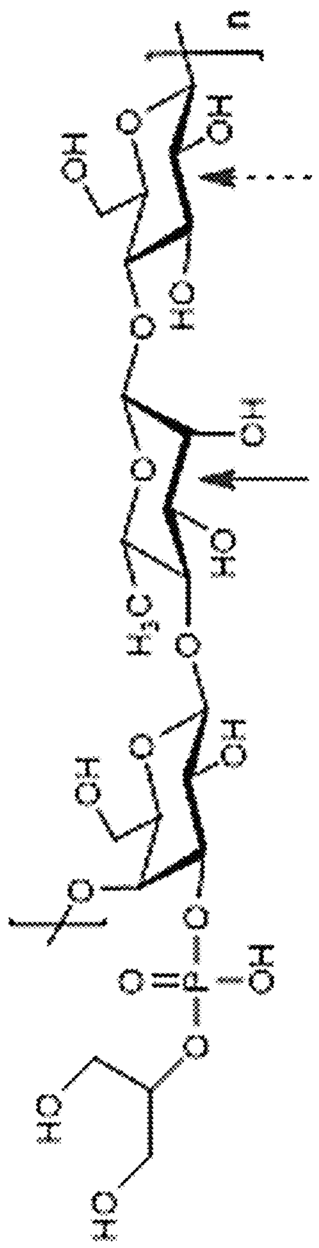

FIG. 11 shows the structure of serotype 23B pnemococcal polysaccharide having vicinal hydroxyls uniquely positioned to generate primary aldehydes (see arrow).

Figure 12:
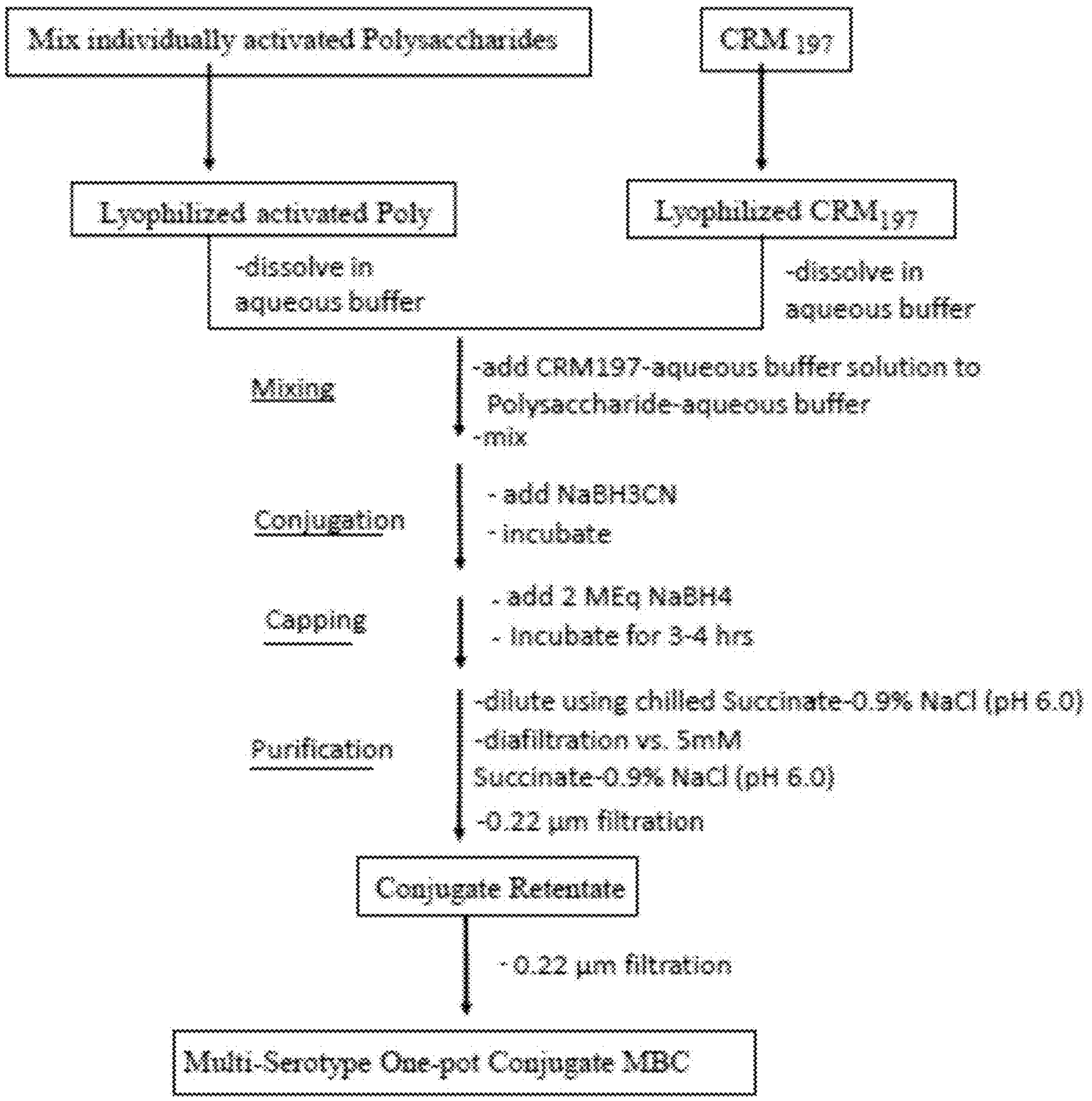

FIG. 12 shows a flow diagram of the multi-serotype one-pot conjugation process using individually activated polysaccharides as described at Example 5 and Example 7.

Figure 13:
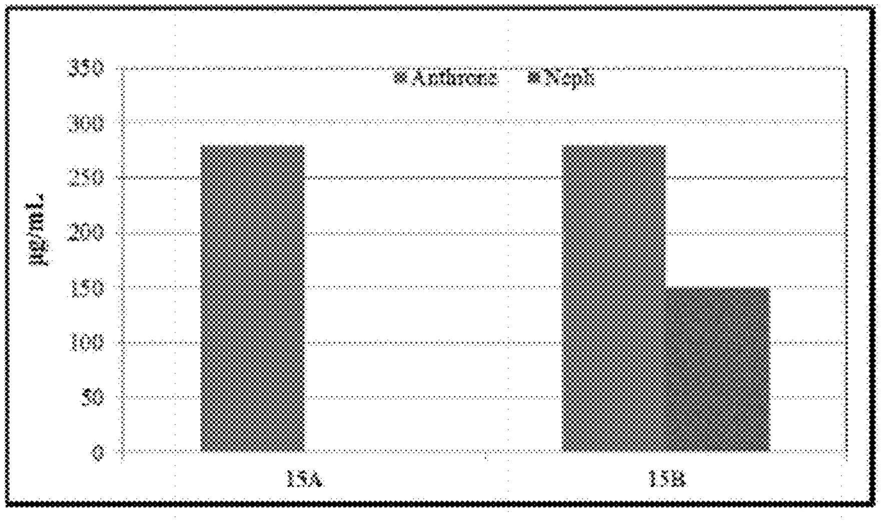

FIG. 13 Antigenicity of the conjugates tested by Nephelometry (Neph, right bar for 15B) and total saccharide content measured by Anthrone assay (left bar for 15B and only bar for 15A).

Figure 14:
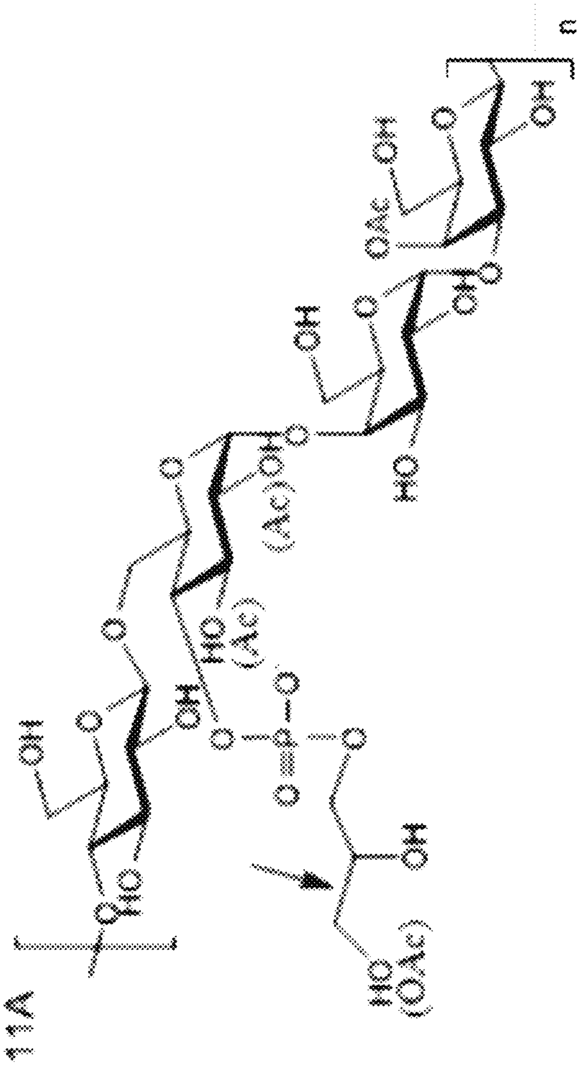

FIG. 14 shows the structure of serotype 11A pnemococcal polysaccharide having vicinal hydroxyls uniquely positioned to generate primary aldehydes (see arrow), which are significantly more reactive compared to secondary aldehydes positioned in a hindered structural position in the polysaccharide repeat unit.

Figure 15:
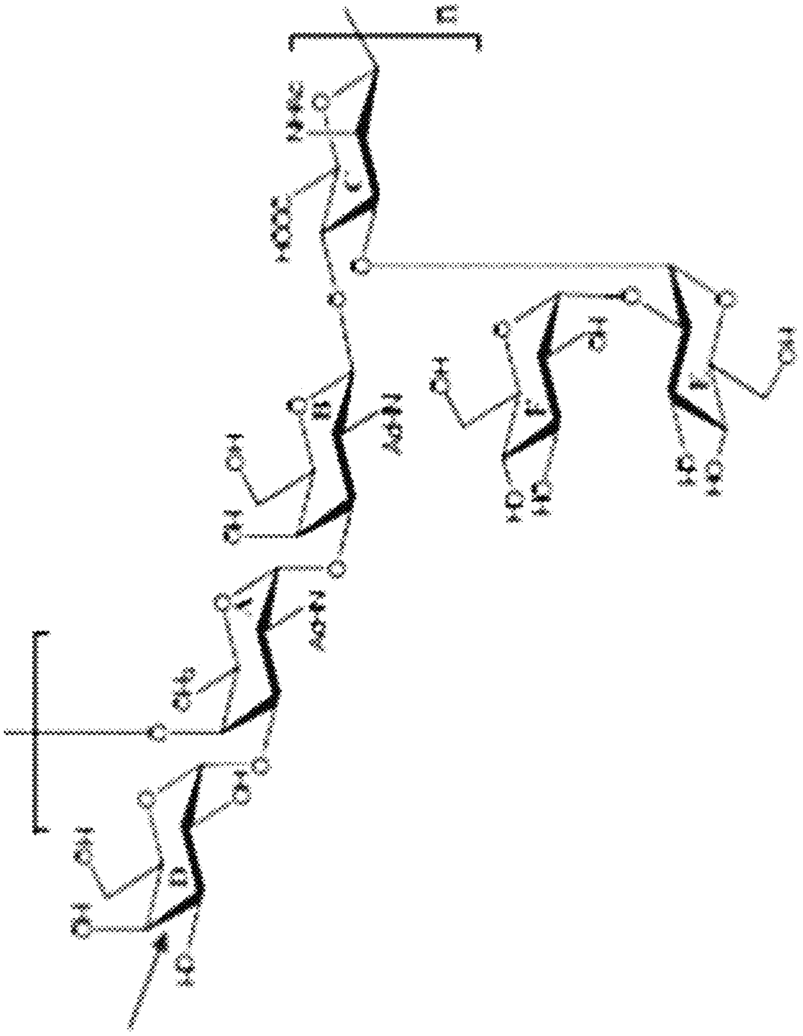

FIG. 15 shows the structure of serotype 12F pnemococcal polysaccharide having vicinal hydroxyls uniquely positioned to generate aldehydes (see arrow).

Figure 16:
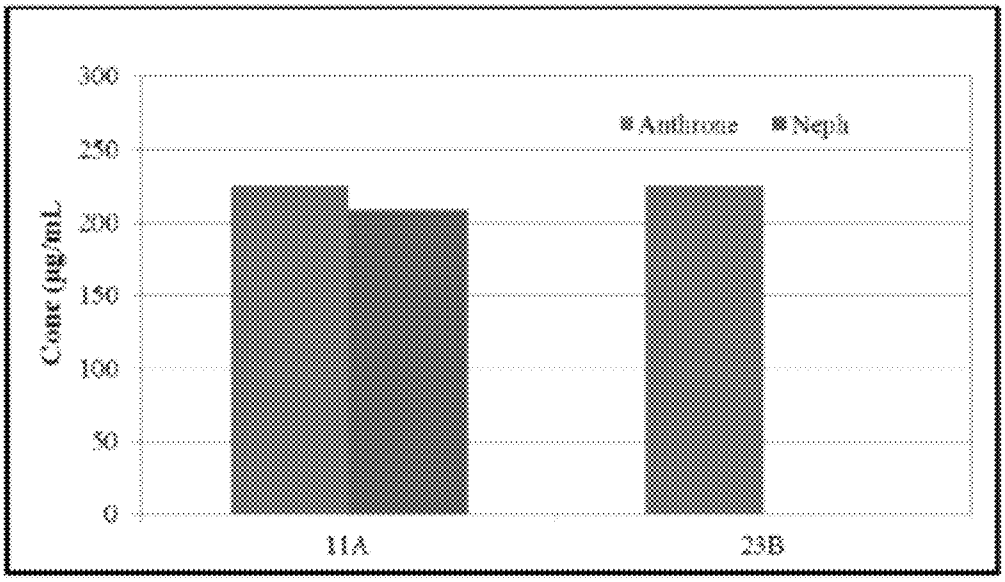

FIG. 16 Antigenicty of the multi conjugate 11A/23B tested by Nephelometry (Neph, right bar for 11A) and total saccharide content measured by Anthrone assay (left bar for 11A and only bar for 23B).

Figure 17:
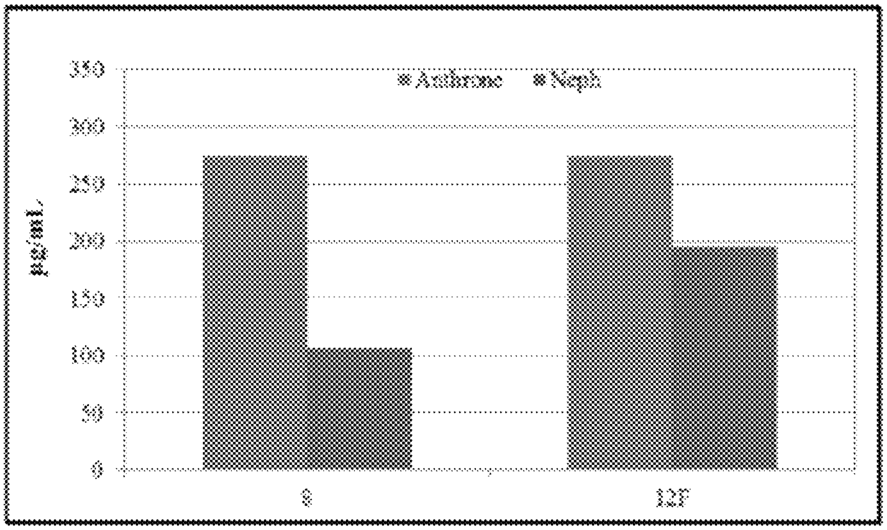

FIG. 17 Antigenicty of the multi conjugate 8/12F tested by Nephelometry (Neph, right bar) and total saccharide content measured by Anthrone assay (left bar of each serotype).

1 GLYCOCONJUGATES OF THE INVENTION

The present invention relates to new glycoconjugates (capsular saccharides conjugated to protein carriers).

For the purposes of the invention the term 'glycoconjugate' indicates capsular saccharides linked covalently to a carrier protein. In one embodiment the capsular saccharides are linked directly to the carrier protein. In a second embodiment the bacterial saccharides are linked to the carrier protein through a spacer/linker.

In particular the present invention relates to glycoconjugates wherein 2 or more saccharides antigens are conjugated to the same molecule of the protein carrier (i.e. the carrier molecules have 2 or more different capsular saccharides conjugated to them).

In an embodiment the invention relates to a glycoconjugate comprising at least two saccharides selected from the group consisting of a saccharide from *S. pneumoniae* serotype 8, a saccharide from *S. pneumoniae* serotype 15A, a saccharide from *S. pneumoniae* serotype 15B, a saccharide from *S. pneumoniae* serotype 23B and a saccharide from *S. pneumoniae* serotype 23B, conjugated to the same carrier protein.

In an embodiment the invention relates to a glycoconjugate comprising at least two saccharides selected from the group consisting of a saccharide from *S. pneumoniae* serotype 8, a saccharide from *S. pneumoniae* serotype 11A, a saccharide from *S. pneumoniae* serotype 12F, a saccharide from *S. pneumoniae* serotype 23B and a saccharide from *S. pneumoniae* serotype 23B, conjugated to the same carrier protein.

In an embodiment the invention relates to a glycoconjugate comprising at least two saccharides selected from the group consisting of a saccharide from *S. pneumoniae* serotype 10A, a saccharide from *S. pneumoniae* serotype 22F, a saccharide from *S. pneumoniae* serotype 33F and a saccharide from *S. pneumoniae* serotype 35B, conjugated to the same carrier protein.

1.1 Capsular Saccharide of the Invention

The term "saccharide" throughout this specification may indicate polysaccharide or oligosaccharide and includes both. In frequent embodiments, the saccharide is a polysaccharide, in particular a *S. pneumoniae* capsular polysaccharide.

Capsular polysaccharides are prepared by standard techniques known to those of ordinary skill in the art.

In the present invention, capsular polysaccharides may be prepared, e.g., from serotypes 8, 15A, 15B, 23A and 23B of *S. pneumoniae*, from serotypes 8, 11A, 12F, 23A and 23B of *S. pneumoniae*, or from serotypes 10A, 22F, 33F and 35B of *S. pneumoniae*. Typically capsular polysaccharides are produced by growing each *S. pneumoniae* serotype in a medium (e.g. in a soy-based medium), the polysaccharides are then prepared from the bacteria culture. Bacterial strains of *S. pneumoniae* used to make the respective polysaccharides that are used in the glycoconjugates of the invention may be obtained from established culture collections or clinical specimens.

The population of the organism (each *S. pneumoniae* serotype) is often scaled up from a seed vial to seed bottles and passaged through one or more seed fermentors of increasing volume until production scale fermentation volumes are reached. At the end of the growth cycle the cells are lysed and the lysate broth is then harvested for downstream (purification) processing (see for example WO 2006/110381, WO 2008/118752, and U.S. Patent App. Pub. Nos. 2006/0228380, 2006/0228381, 2008/0102498 and 2008/0286838).

The individual polysaccharides are typically purified through centrifugation, precipitation, ultra-filtration, and/or column chromatography (see for example WO 2006/110352 and WO 2008/118752).

Purified polysaccharides may be activated (e.g., chemically activated) to make them capable of reacting and then incorporated into glycoconjugates of the invention, as further described herein. *S. pneumoniae* capsular polysaccharides comprise repeating oligosaccharide units which may contain up to 8 sugar residues.

In an embodiment, capsular saccharide of the invention may be one oligosaccharide unit or a shorter than native length saccharide chain of repeating oligosaccharide units. In an embodiment, capsular saccharide of the invention is one repeating oligosaccharide unit of the relevant serotype.

In an embodiment, capsular saccharide of the invention may be oligosaccharides. Oligosaccharides have a low number of repeat units (typically 5-15 repeat units) and are typically derived synthetically or by hydrolysis of polysaccharides.

Preferably though, the capsular saccharides of the present invention are polysaccharides. High molecular weight capsular polysaccharides are able to induce certain antibody immune responses due to the epitopes present on the antigenic surface. The isolation and purification of high molecular weight capsular polysaccharides is preferably contemplated for use in the conjugates, compositions and methods of the present invention.

A polysaccharide can become slightly reduced in size during normal purification procedures. Additionally, as described herein, polysaccharide can be subjected to sizing techniques before conjugation. Mechanical or chemical sizing maybe employed. Chemical hydrolysis maybe conducted using acetic acid. Mechanical sizing maybe conducted using High Pressure Homogenization Shearing.

In a preferred embodiment the purified polysaccharides, are capsular polysaccharide from serotypes 8, 15A, 15B, 23A or 23B of *S. pneumoniae*. In another preferred embodiment the purified polysaccharides, are capsular polysaccharide from serotypes 8, 11A, 12F, 23A or 23B of *S. pneumoniae*. In yet another preferred embodiment the purified polysaccharides, are capsular polysaccharide from serotypes 10A, 22F, 33F or 35B of *S. pneumoniae*.

As used herein, the term "molecular weight" of polysaccharide or of carrier protein-polysaccharide conjugate refers to molecular weight calculated by size exclusion chromatography (SEC) combined with multiangle laser light scattering detector (MALLS).

In some embodiments, the pneumococcal saccharides from serotypes 15A and 15B of the invention are O-acetylated.

In some embodiments, the pneumococcal saccharides from serotypes 22F, 33F and/or 35B of the invention are O-acetylated.

In some embodiments, the pneumococcal saccharides from serotype 11A of the invention are O-acetylated.

The purified polysaccharides described herein are chemically activated to enable the saccharides capable of reacting with the carrier protein. In one embodiment, the purified polysaccharides described herein are chemically oxidized to enable the saccharides capable of reacting with the carrier protein.

Serotype 8, 10A, 11A, 12F, 15A, 15B, 22F, 23A, 23B, 33F or 35B saccharides can be obtained directly from bacteria using isolation procedures known to one of ordinary skill in the art (see for example methods disclosed in U.S. Patent App. Pub. Nos. 2006/0228380, 2006/0228381, 2007/0184071, 2007/0184072, 2007/0231340, and 2008/0102498 and WO 2008/118752). In addition, they can be produced using synthetic protocols.

Serotype 8, 10A, 11A, 12F, 15A, 15B, 22F, 23A, 23B, 33F or 35B *S. pneumoniae* strains may be obtained from established culture collections (such as for example the Streptococcal Reference Laboratory (Centers for Disease Control and Prevention, Atlanta, GA)) or clinical specimens.

1.1.1 Pneumococcal Saccharide Serotype 8

In some embodiments, the purified saccharide from *S. pneumoniae* serotype 8 before conjugation has a molecular weight of between 10 kDa and 5,000 kDa. In other such embodiments, the capsular polysaccharide has a molecular weight of between 20 kDa and 4,000 kDa. In other such embodiments, the capsular polysaccharide has a molecular weight of between 50 kDa and 3,000 kDa. In other such embodiments, the capsular polysaccharide has a molecular weight of between 100 kDa and 2500 kDa. In other such embodiments, the capsular polysaccharide has a molecular weight of between 100 kDa and 2,000 kDa. In other such embodiments, the capsular polysaccharide has a molecular weight of between 150 kDa and 2,000 kDa. In other such embodiments, the capsular polysaccharide has a molecular weight of between 150 kDa and 1,500 kDa. In other such embodiments, the capsular polysaccharide has a molecular weight of between 20 kDa and 1,500 kDa. In another embodiment, the capsular polysaccharide has a molecular weight of between 30 kDa and 1,250 kDa. In another embodiment, the capsular polysaccharide has a molecular weight of between 50 kDa and 1,000 kDa. In another embodiment, the capsular polysaccharide has a molecular weight of between 70 kDa and 900 kDa. In another embodiment, the capsular polysaccharide has a molecular weight of between 100 kDa and 800 kDa. In another embodiment, the capsular polysaccharide has a molecular weight of between 200 kDa to 600 kDa. In another embodiment, the capsular polysaccharide has a molecular weight of between 400 kDa to 700 kDa.

In further such embodiments, the saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa;

between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

A saccharide can become slightly reduced in size during normal purification procedures. Additionally, as described herein, polysaccharide can be subjected to sizing techniques before conjugation. The molecular weight ranges mentioned above refer to purified saccharides before conjugation (e.g., before activation) after an eventual sizing step.

1.1.2 Pneumococcal Saccharide Serotype 15A

The isolated serotype 15A capsular saccharide obtained by purification of serotype 15A polysaccharide from the *S. pneumoniae* lysate and optionally sizing of the purified polysaccharide can be characterized by different parameters including, for example, the molecular weight (MW), the mM of acetate per mM of said serotype 15A capsular saccharide and the mM of glycerol per mM of said serotype 15A capsular saccharide. Advantageously, the size of the purified serotype 15A polysaccharide is reduced while preserving critical features of the structure of the polysaccharide such as for example the presence of O-acetyl groups. Preferably, the size of the purified serotype 15A polysaccharide is reduced by mechanical homogenization.

In a preferred embodiment, the size of the purified serotype 15A polysaccharide is reduced by high pressure homogenization. High pressure homogenization achieves high shear rates by pumping the process stream through a flow path with sufficiently small dimensions. The shear rate is increased by using a larger applied homogenization pressure, and exposure time can be increased by recirculating the feed stream through the homogenizer.

The high-pressure homogenization process is particularly appropriate for reducing the size of the purified serotype 15A polysaccharide while preserving the structural features of the polysaccharide, such as the presence of O-acetyl groups.

In some embodiments, the purified saccharide from *S. pneumoniae* serotype 15A before conjugation has a molecular weight of between 10 kDa and 5,000 kDa. In other such embodiments, the capsular polysaccharide has a molecular weight of between 20 kDa and 4,000 kDa. In other such embodiments, the capsular polysaccharide has a molecular weight of between 50 kDa and 3,000 kDa. In other such embodiments, the capsular polysaccharide has a molecular weight of between 100 kDa and 2500 kDa. In other such embodiments, the capsular polysaccharide has a molecular weight of between 100 kDa and 2,000 kDa. In other such embodiments, the capsular polysaccharide has a molecular weight of between 150 kDa and 2,000 kDa. In other such embodiments, the capsular polysaccharide has a molecular weight of between 150 kDa and 1,500 kDa. In other such embodiments, the capsular polysaccharide has a molecular weight of between 20 kDa and 1,500 kDa. In another embodiment, the capsular polysaccharide has a molecular weight of between 30 kDa and 1,250 kDa. In another embodiment, the capsular polysaccharide has a molecular weight of between 50 kDa and 1,000 kDa. In another embodiment, the capsular polysaccharide has a molecular weight of between 70 kDa and 900 kDa. In another embodiment, the capsular polysaccharide has a molecular weight of between 100 kDa and 800 kDa. In another embodiment, the capsular polysaccharide has a molecular weight of between 200 kDa to 600 kDa. In another embodiment, the capsular polysaccharide has a molecular weight of between 400 kDa to 700 kDa.

In further such embodiments, the saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In a preferred embodiment, the isolated saccharide from *S. pneumoniae* serotype 15A has a molecular weight between 5 kDa and 500 kDa, between 50 kDa and 500 kDa, between 50 kDa and 450 kDa, between 100 kDa and 400 kDa, and between 100 kDa and 350 kDa. In a preferred embodiment, the isolated serotype 15A capsular polysaccharide has a molecular weight between 100 kDa and 350 kDa. In a preferred embodiment, the isolated serotype 15A capsular polysaccharide has a molecular weight between 100 kDa and 300 kDa. In a preferred embodiment, the isolated serotype 15A capsular polysaccharide has a molecular weight between 150 kDa and 300 kDa. In a preferred embodiment, the isolated serotype 15A capsular polysaccharide has a molecular weight between 150 kDa and 350 kDa. In further embodiments, the capsular polysaccharide has a molecular weight of between 100 kDa to 500 kDa;

between 100 kDa to 400 kDa; between 100 kDa to 300 kDa; between 100 kDa to 200 kDa; between 150 kDa to 500 kDa; between 150 kDa to 400 kDa; between 150 kDa to 300 kDa; between 150 kDa to 200 kDa; between 200 kDa to 500 kDa; between 200 kDa to 400 kDa; between 250 kDa to 500 kDa; between 250 kDa to 400 kDa; between 250 kDa to 350 kDa; between 300 kDa to 500 kDa; between 300 kDa to 400 kDa; and similar desired molecular weight ranges. Any whole number integer within any of the above ranges is contemplated as an embodiment of the disclosure. Serotype 15A polysaccharide is O-acetylated and the total amount of O-acetylation is approximately 0.8-0.9 O-acetyl groups per polysaccharide repeating unit. The degree of O-acetylation of the polysaccharide can be determined by any method known in the art, for example, by proton NMR (see for example Lemercinier et al. (1996) Carbohydrate Research 296:83-96; Jones et al. (2002) J. Pharmaceutical and Biomedical Analysis 30:1233-1247; WO 2005/033148 and WO 00/56357). Another commonly used method is described in Hestrin, S. (1949) J. Biol. Chem. 180:249-261. Preferably, the presence of O-acetyl groups is determined by ion-HPLC analysis.

The presence of O-acetyl in a purified, isolated or activated serotype 15A capsular polysaccharide or in a serotype 15A polysaccharide-carrier protein conjugate is expressed as the number of mM of acetate per mM of said polysaccharide or as the number of O-acetyl group per polysaccharide repeating unit.

In a preferred embodiment, the isolated serotype 15A saccharide comprises at least 0.1, 0.2, 0.3, 0.4, 0.5, 0.6, 0.7 or 0.8 mM acetate per mM of said serotype 15A saccharide. In a preferred embodiment, the isolated serotype 15A saccharide comprises at least 0.5, 0.6 or 0.7 mM acetate per mM of said serotype 15A saccharide. In a preferred embodiment, the isolated serotype 15A saccharide comprises at least 0.6 mM acetate per mM of said serotype 15A saccharide. In a preferred embodiment, the isolated serotype 15A saccharide comprises at least 0.7 mM acetate per mM of said serotype 15A saccharide.

The presence of glycerolphosphate side chains is determined by measurement of glycerol using high performance anion exchange chromatography with pulsed amperometric detection (HPAEC-PAD) after its release by treatment of the saccharide with hydrofluoric acid (HF). The presence of glycerol in a purified, isolated or activated serotype 15A saccharide is expressed as the number of mM of glycerol per mM of serotype 15A saccharide.

In a preferred embodiment, the isolated serotype 15A saccharide comprises at least 0.1, 0.2, 0.3, 0.4, 0.5, 0.6, 0.7 or 0.8 mM glycerol per mM of said serotype 15A saccharide. In a preferred embodiment, the isolated serotype 15A saccharide comprises at least 0.5, 0.6 or 0.7 mM glycerol per mM of said serotype 15A saccharide. In a preferred embodiment, the isolated serotype 15A saccharide comprises at least 0.6 mM glycerol per mM of said serotype 15A saccharide. In a preferred embodiment, the isolated serotype 15A saccharide comprises at least 0.7 mM glycerol per mM of said serotype 15A saccharide.

In a preferred embodiment, the isolated serotype 15A saccharide has a molecular weight between 100 kDa and 350 kDa and comprises at least 0.6 mM acetate per mM of said serotype 15A saccharide.

In a preferred embodiment, the isolated serotype 15A saccharide has a molecular weight between 100 kDa and 350 kDa and comprises at least 0.6 mM glycerol per mM of said serotype 15A saccharide.

In a preferred embodiment, the isolated serotype 15A saccharide has a molecular weight between 150 kDa and 300 kDa and comprises at least 0.6 mM acetate per mM of said serotype 15A saccharide.

In a preferred embodiment, the isolated serotype 15A saccharide has a molecular weight between 150 kDa and 300 kDa and comprises at least 0.6 mM glycerol per mM of said serotype 15A saccharide.

In a preferred embodiment, the isolated serotype 15A saccharide has a molecular weight between 150 kDa and 350 kDa and comprises at least 0.6 mM acetate per mM of said serotype 15A saccharide.

In a preferred embodiment, the isolated serotype 15A saccharide has a molecular weight between 150 kDa and 350 kDa and comprises at least 0.6 mM glycerol per mM of said serotype 15A saccharide.

In a preferred embodiment, the isolated serotype 15A saccharide comprises at least 0.6 mM acetate per mM of said serotype 15A saccharide and at least 0.6 mM glycerol per mM of said serotype 15A saccharide.

In a preferred embodiment, the isolated serotype 15A saccharide has a molecular weight between 100 kDa and 350 kDa and comprises at least 0.6 mM acetate per mM of said serotype 15A saccharide and at least 0.6 mM glycerol per mM of said serotype 15A saccharide.

In a preferred embodiment, the isolated serotype 15A saccharide has a molecular weight between 150 kDa and 300 kDa and comprises at least 0.6 mM acetate per mM of said serotype 15A saccharide and at least 0.6 mM glycerol per mM of said serotype 15A saccharide.

In a preferred embodiment, the isolated serotype 15A saccharide has a molecular weight between 150 kDa and 350 kDa and comprises at least 0.6 mM acetate per mM of said serotype 15A saccharide and at least 0.6 mM glycerol per mM of said serotype 15A saccharide.

1.1.3 Pneumococcal Saccharide Serotype 15B

The isolated serotype 15B capsular saccharide obtained by purification of serotype 15B polysaccharide from the *S. pneumoniae* lysate and optionally sizing of the purified polysaccharide can be characterized by different parameters including, for example, the molecular weight (MW), the mM of acetate per mM of said serotype 15B capsular saccharide and the mM of glycerol per mM of said serotype 15B capsular saccharide (see section 1.2.6, pages 17-21 of WO2015/110941). Advantageously, the size of the purified serotype 15B polysaccharide is reduced while preserving critical features of the structure of the polysaccharide such as for example the presence of O-acetyl groups. Preferably, the size of the purified serotype 15B polysaccharide is reduced by mechanical homogenization.

In a preferred embodiment, the size of the purified serotype 15B polysaccharide is reduced by high pressure homogenization. High pressure homogenization achieves high shear rates by pumping the process stream through a flow path with sufficiently small dimensions. The shear rate is increased by using a larger applied homogenization pressure, and exposure time can be increased by recirculating the feed stream through the homogenizer.

The high pressure homogenization process is particularly appropriate for reducing the size of the purified serotype 15B polysaccharide while preserving the structural features of the polysaccharide, such as the presence of O-acetyl groups.

In some embodiments, the purified saccharide from *S. pneumoniae* serotype 15B before conjugation has a molecular weight of between 10 kDa and 5,000 kDa. In other such embodiments, the capsular polysaccharide has a molecular weight of between 20 kDa and 4,000 kDa. In other such embodiments, the capsular polysaccharide has a molecular weight of between 50 kDa and 3,000 kDa. In other such embodiments, the capsular polysaccharide has a molecular weight of between 100 kDa and 2500 kDa. In other such embodiments, the capsular polysaccharide has a molecular weight of between 100 kDa and 2,000 kDa. In other such embodiments, the capsular polysaccharide has a molecular weight of between 150 kDa and 2,000 kDa. In other such embodiments, the capsular polysaccharide has a molecular weight of between 150 kDa and 1,500 kDa. In other such embodiments, the capsular polysaccharide has a molecular weight of between 20 kDa and 1,500 kDa. In another embodiment, the capsular polysaccharide has a molecular weight of between 30 kDa and 1,250 kDa. In another embodiment, the capsular polysaccharide has a molecular weight of between 50 kDa and 1,000 kDa. In another embodiment, the capsular polysaccharide has a molecular weight of between 70 kDa and 900 kDa. In another embodiment, the capsular polysaccharide has a molecular weight of between 100 kDa and 800 kDa. In another embodiment, the capsular polysaccharide has a molecular weight of between 200 kDa to 600 kDa. In another embodiment, the capsular polysaccharide has a molecular weight of between 400 kDa to 700 kDa.

In further such embodiments, the saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In a preferred embodiment, the isolated saccharide from *S. pneumoniae* serotype 15B has a molecular weight between 5 kDa and 500 kDa, between 50 kDa and 500 kDa, between 50 kDa and 450 kDa, between 100 kDa and 400 kDa, and between 100 kDa and 350 kDa. In a preferred embodiment, the isolated serotype 15B capsular polysaccharide has a molecular weight between 100 kDa and 350 kDa. In a preferred embodiment, the isolated serotype 15B capsular polysaccharide has a molecular weight between 100 kDa and 300 kDa. In a preferred embodiment, the isolated serotype 15B capsular polysaccharide has a molecular weight between 150 kDa and 300 kDa. In a preferred embodiment, the isolated serotype 15B capsular polysaccharide has a molecular weight between 150 kDa and 350 kDa. In further embodiments, the capsular polysaccharide has a molecular weight of 100 kDa to 500 kDa; 100 kDa to 400 kDa; 100 kDa to 300 kDa; 100 kDa to 200 kDa; 150 kDa to 500 kDa; 150 kDa to 400 kDa; 150 kDa to 300 kDa; 150 kDa to 200 kDa; 200 kDa to 500 kDa; 200 kDa to 400 kDa; 250 kDa to 500 kDa; 250 kDa to 400 kDa; 250 kDa to 350 kDa; 300 kDa to 500 kDa; 300 kDa to 400 kDa; and similar desired molecular weight ranges. Any whole number integer within any of the above ranges is contemplated as an embodiment of the disclosure.

Serotype 15B polysaccharide is O-acetylated and the total amount of O-acetylation is approximately 0.8-0.9 O-acetyl groups per polysaccharide repeating unit. The degree of O-acetylation of the polysaccharide can be determined by any method known in the art, for example, by proton NMR (see for example Lemercinier et al. (1996) Carbohydrate Research 296:83-96; Jones et al. (2002) J. Pharmaceutical and Biomedical Analysis 30:1233-1247; WO 2005/033148 and WO 00/56357). Another commonly used method is described in Hestrin, S. (1949) J. Biol. Chem. 180:249-261. Preferably, the presence of O-acetyl groups is determined by ion-HPLC analysis.

The presence of O-acetyl in a purified, isolated or activated serotype 15B capsular polysaccharide or in a serotype 15B polysaccharide-carrier protein conjugate is expressed as the number of mM of acetate per mM of said polysaccharide or as the number of O-acetyl group per polysaccharide repeating unit.

In a preferred embodiment, the isolated serotype 15B saccharide comprises at least 0.1, 0.2, 0.3, 0.4, 0.5, 0.6, 0.7 or 0.8 mM acetate per mM of said serotype 15B saccharide. In a preferred embodiment, the isolated serotype 15B saccharide comprises at least 0.5, 0.6 or 0.7 mM acetate per mM of said serotype 15B saccharide. In a preferred embodiment, the isolated serotype 15B saccharide comprises at least 0.6 mM acetate per mM of said serotype 15B saccharide. In a preferred embodiment, the isolated serotype 15B saccharide comprises at least 0.7 mM acetate per mM of said serotype 15B saccharide.

The presence of glycerolphosphate side chains is determined by measurement of glycerol using high performance anion exchange chromatography with pulsed amperometric detection (HPAEC-PAD) after its release by treatment of the saccharide with hydrofluoric acid (HF). The presence of glycerol in a purified, isolated or activated serotype 15B saccharide is expressed as the number of mM of glycerol per mM of serotype 15B saccharide.

In a preferred embodiment, the isolated serotype 15B saccharide comprises at least 0.1, 0.2, 0.3, 0.4, 0.5, 0.6, 0.7 or 0.8 mM glycerol per mM of said serotype 15B saccharide. In a preferred embodiment, the isolated serotype 15B saccharide comprises at least 0.5, 0.6 or 0.7 mM glycerol per mM of said serotype 15B saccharide. In a preferred embodiment, the isolated serotype 15B saccharide comprises at least 0.6 mM glycerol per mM of said serotype 15B saccharide. In a preferred embodiment, the isolated serotype 15B saccharide comprises at least 0.7 mM glycerol per mM of said serotype 15B saccharide.

In a preferred embodiment, the isolated serotype 15B saccharide has a molecular weight between 100 kDa and 350 kDa and comprises at least 0.6 mM acetate per mM of said serotype 15B saccharide.

In a preferred embodiment, the isolated serotype 15B saccharide has a molecular weight between 100 kDa and 350 kDa and comprises at least 0.6 mM glycerol per mM of said serotype 15B saccharide.

In a preferred embodiment, the isolated serotype 15B saccharide has a molecular weight between 150 kDa and 300 kDa and comprises at least 0.6 mM acetate per mM of said serotype 15B saccharide.

In a preferred embodiment, the isolated serotype 15B saccharide has a molecular weight between 150 kDa and 300 kDa and comprises at least 0.6 mM glycerol per mM of said serotype 15B saccharide.

In a preferred embodiment, the isolated serotype 15B saccharide has a molecular weight between 150 kDa and 350 kDa and comprises at least 0.6 mM acetate per mM of said serotype 15B saccharide.

In a preferred embodiment, the isolated serotype 15B saccharide has a molecular weight between 150 kDa and 350 kDa and comprises at least 0.6 mM glycerol per mM of said serotype 15B saccharide.

In a preferred embodiment, the isolated serotype 15B saccharide comprises at least 0.6 mM acetate per mM of said serotype 15B saccharide and at least 0.6 mM glycerol per mM of said serotype 15B saccharide.

In a preferred embodiment, the isolated serotype 15B saccharide has a molecular weight between 100 kDa and 350 kDa and comprises at least 0.6 mM acetate per mM of said serotype 15B saccharide and at least 0.6 mM glycerol per mM of said serotype 15B saccharide.

In a preferred embodiment, the isolated serotype 15B saccharide has a molecular weight between 150 kDa and 300 kDa and comprises at least 0.6 mM acetate per mM of said serotype 15B saccharide and at least 0.6 mM glycerol per mM of said serotype 15B saccharide.

In a preferred embodiment, the isolated serotype 15B saccharide has a molecular weight between 150 kDa and 350 kDa and comprises at least 0.6 mM acetate per mM of said serotype 15B saccharide and at least 0.6 mM glycerol per mM of said serotype 15B saccharide.

1.1.4 Pneumococcal Saccharide Serotype 23A

In some embodiments, the purified saccharide from *S. pneumoniae* serotype 23A before conjugation has a molecular weight of between 10 kDa and 5,000 kDa. In other such embodiments, the capsular polysaccharide has a molecular weight of between 20 kDa and 4,000 kDa. In other such embodiments, the capsular polysaccharide has a molecular weight of between 50 kDa and 3,000 kDa. In other such embodiments, the capsular polysaccharide has a molecular weight of between 100 kDa and 2500 kDa. In other such embodiments, the capsular polysaccharide has a molecular weight of between 100 kDa and 2,000 kDa. In other such embodiments, the capsular polysaccharide has a molecular weight of between 150 kDa and 2,000 kDa. In other such embodiments, the capsular polysaccharide has a molecular weight of between 150 kDa and 1,500 kDa. In other such embodiments, the capsular polysaccharide has a molecular weight of between 20 kDa and 1,500 kDa. In another embodiment, the capsular polysaccharide has a molecular weight of between 30 kDa and 1,250 kDa. In another embodiment, the capsular polysaccharide has a molecular weight of between 50 kDa and 1,000 kDa. In another embodiment, the capsular polysaccharide has a molecular weight of between 70 kDa and 900 kDa. In another embodiment, the capsular polysaccharide has a molecular weight of between 100 kDa and 800 kDa. In another embodiment, the capsular polysaccharide has a molecular weight of between 200 kDa to 600 kDa. In another embodiment, the capsular polysaccharide has a molecular weight of between 400 kDa to 700 kDa.

In further such embodiments, the saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In another embodiment, the saccharide from *S. pneumoniae* serotype 23A has a molecular weight of between 30 kDa and 1,250 kDa. In another embodiment, the saccharide from *S. pneumoniae* serotype 23A has a molecular weight of between 50 kDa and 1,000 kDa. In another embodiment, the saccharide from *S. pneumoniae* serotype 23A has a molecular weight of between 70 kDa and 900 kDa. In another embodiment, the saccharide from *S. pneumoniae* serotype 23A has a molecular weight of between 100 kDa and 800 kDa. In another embodiment, the saccharide from *S. pneumoniae* serotype 23A has a molecular weight of between 200 kDa to 600 kDa. In another embodiment, the saccharide from *S. pneumoniae* serotype 23A has a molecular weight of between 400 kDa to 700 kDa.

In further embodiments, the saccharide from *S. pneumoniae* serotype 23A has a molecular weight of between 100 kDa to 600 kDa; between 100 kDa to 500 kDa; between 100 kDa to 400 kDa; between 150 kDa to 600 kDa; between 150 kDa to 500 kDa; between 150 kDa to 400 kDa; between 200 kDa to 600 kDa; between 200 kDa to 500 kDa; between 200 kDa to 400 kDa; between 250 kDa to 600 kDa; between 250 kDa to 500 kDa; between 250 kDa to 400 kDa; between 250 kDa to 350 kDa; between 300 kDa to 600 kDa; between 300 kDa to 500 kDa; between 300 kDa to 400 kDa; between 400 kDa to 600 kDa or between 500 kDa to 600 kDa. Any whole number integer within any of the above ranges is contemplated as an embodiment of the disclosure.

A saccharide can become slightly reduced in size during normal purification procedures. Additionally, as described herein, polysaccharide can be subjected to sizing techniques before conjugation. The molecular weight ranges mentioned above refer to purified saccharides before conjugation (e.g., before activation) after an eventual sizing step.

1.1.5 Pneumococcal Saccharide Serotype 23B

In some embodiments, the purified saccharide from *S. pneumoniae* serotype 23B before conjugation has a molecular weight of between 10 kDa and 5,000 kDa. In other such embodiments, the capsular polysaccharide has a molecular weight of between 20 kDa and 4,000 kDa. In other such embodiments, the capsular polysaccharide has a molecular weight of between 50 kDa and 3,000 kDa. In other such embodiments, the capsular polysaccharide has a molecular weight of between 100 kDa and 2500 kDa. In other such embodiments, the capsular polysaccharide has a molecular weight of between 100 kDa and 2,000 kDa. In other such embodiments, the capsular polysaccharide has a molecular weight of between 150 kDa and 2,000 kDa. In other such embodiments, the capsular polysaccharide has a molecular weight of between 150 kDa and 1,500 kDa. In other such embodiments, the capsular polysaccharide has a molecular weight of between 20 kDa and 1,500 kDa. In another embodiment, the capsular polysaccharide has a molecular weight of between 30 kDa and 1,250 kDa. In another embodiment, the capsular polysaccharide has a molecular weight of between 50 kDa and 1,000 kDa. In another embodiment, the capsular polysaccharide has a molecular weight of between 70 kDa and 900 kDa. In another embodiment, the capsular polysaccharide has a molecular weight of between 100 kDa and 800 kDa. In another embodiment, the capsular polysaccharide has a molecular weight of between 200 kDa to 600 kDa. In another embodiment, the capsular polysaccharide has a molecular weight of between 400 kDa to 700 kDa.

In further such embodiments, the saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In another embodiment, the saccharide from *S. pneumoniae* serotype 23B has a molecular weight of between 30 kDa and 1,250 kDa. In another embodiment, the saccharide from *S. pneumoniae* serotype 23B has a molecular weight of between 50 kDa and 1,000 kDa. In another embodiment, the saccharide from *S. pneumoniae* serotype 23B has a molecular weight of between 70 kDa and 900 kDa. In another embodiment, the saccharide from *S. pneumoniae* serotype 23B has a molecular weight of between 100 kDa and 800 kDa. In another embodiment, the saccharide from *S. pneumoniae* serotype 23B has a molecular weight of between 200 kDa to 600 kDa. In another embodiment, the saccharide from *S. pneumoniae* serotype 23B has a molecular weight of between 400 kDa to 700 kDa.

In further embodiments, the saccharide from *S. pneumoniae* serotype 23B has a molecular weight of between 100 kDa to 600 kDa; between 100 kDa to 500 kDa; between 100 kDa to 400 kDa; between 150 kDa to 600 kDa; between 150 kDa to 500 kDa; between 150 kDa to 400 kDa; between 200 kDa to 600 kDa; between 200 kDa to 500 kDa; between 200 kDa to 400 kDa; between 250 kDa to 600 kDa; between 250 kDa to 500 kDa; between 250 kDa to 400 kDa; between 250 kDa to 350 kDa; between 300 kDa to 600 kDa; between 300 kDa to 500 kDa; between 300 kDa to 400 kDa; between 400 kDa to 600 kDa; between 500 kDa to 600 kDa; and similar desired molecular weight ranges. Any whole number integer within any of the above ranges is contemplated as an embodiment of the disclosure.

A saccharide can become slightly reduced in size during normal purification procedures. Additionally, as described herein, polysaccharide can be subjected to sizing techniques before conjugation. The molecular weight ranges mentioned above refer to purified saccharides before conjugation (e.g., before activation) after an eventual sizing step.

1.1.6 Pneumococcal Saccharide Serotype 11A

The isolated serotype 11A capsular saccharide obtained by purification of serotype 11A polysaccharide from the *S. pneumoniae* lysate and optionally sizing of the purified polysaccharide can be characterized by different parameters including, for example, the molecular weight (MW) and the mM of acetate per mM of said serotype 11A capsular saccharide (see section 1.2.4, pages 14-16 of WO2015/110941). Advantageously, the size of the purified serotype 11A polysaccharide is reduced while preserving critical features of the structure of the polysaccharide such as for example the presence of O-acetyl groups. Preferably, the size of the purified serotype 11A polysaccharide is reduced by mechanical homogenization.

In a preferred embodiment, the size of the purified serotype 11A polysaccharide is reduced by high pressure homogenization. High pressure homogenization achieves high shear rates by pumping the process stream through a flow path with sufficiently small dimensions. The shear rate is increased by using a larger applied homogenization pressure, and exposure time can be increased by recirculating the feed stream through the homogenizer.

The high-pressure homogenization process is particularly appropriate for reducing the size of the purified serotype 11A polysaccharide while preserving the structural features of the polysaccharide, such as the presence of O-acetyl groups.

In some embodiments, the purified saccharide from *S. pneumoniae* serotype 11A before conjugation has a molecular weight of between 10 kDa and 5,000 kDa. In other such embodiments, the capsular polysaccharide has a molecular weight of between 20 kDa and 4,000 kDa. In other such embodiments, the capsular polysaccharide has a molecular weight of between 50 kDa and 3,000 kDa. In other such embodiments, the capsular polysaccharide has a molecular weight of between 100 kDa and 2500 kDa. In other such embodiments, the capsular polysaccharide has a molecular weight of between 100 kDa and 2,000 kDa. In other such embodiments, the capsular polysaccharide has a molecular weight of between 150 kDa and 2,000 kDa. In other such embodiments, the capsular polysaccharide has a molecular weight of between 150 kDa and 1,500 kDa. In other such embodiments, the capsular polysaccharide has a molecular weight of between 20 kDa and 1,500 kDa. In another embodiment, the capsular polysaccharide has a molecular weight of between 30 kDa and 1,250 kDa. In another embodiment, the capsular polysaccharide has a molecular weight of between 50 kDa and 1,000 kDa. In another embodiment, the capsular polysaccharide has a molecular weight of between 70 kDa and 900 kDa. In another embodiment, the capsular polysaccharide has a molecular weight of between 100 kDa and 800 kDa. In another embodiment, the capsular polysaccharide has a molecular weight of between 200 kDa to 600 kDa. In another embodiment, the capsular polysaccharide has a molecular weight of between 400 kDa to 700 kDa.

In further such embodiments, the saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In a preferred embodiment, the isolated saccharide from *S. pneumoniae* serotype 11A has a molecular weight between 5 kDa and 500 kDa, between 50 kDa and 500 kDa, between 50 kDa and 450 kDa, between 100 kDa and 400 kDa, and between 100 kDa and 350 kDa. In a preferred embodiment, the isolated serotype 11A capsular polysaccharide has a molecular weight between 100 kDa and 350 kDa. In a preferred embodiment, the isolated serotype 11A capsular polysaccharide has a molecular weight between 100 kDa and 300 kDa. In a preferred embodiment, the isolated serotype 11A capsular polysaccharide has a molecular weight between 150 kDa and 300 kDa. In a preferred embodiment, the isolated serotype 11A capsular polysaccharide has a molecular weight between 150 kDa and 350 kDa. In further embodiments, the capsular polysaccharide has a molecular weight of between 100 kDa to 500 kDa; between 100 kDa to 400 kDa; between 100 kDa to 300 kDa; between 100 kDa to 200 kDa; between 150 kDa to 500 kDa; between 150 kDa to 400 kDa; between 150 kDa to 300 kDa; between 150 kDa to 200 kDa; between 200 kDa to 500 kDa; between 200 kDa to 400 kDa; between 250 kDa to 500 kDa; between 250 kDa to 400 kDa; between 250 kDa to 350 kDa; between 300 kDa to 500 kDa; between 300 kDa to 400 kDa;

and similar desired molecular weight ranges. Any whole number integer within any of the above ranges is contemplated as an embodiment of the disclosure.

The polysaccharide repeating unit of serotype 11A consists of a linear tetrasaccharide backbone (two galactopyranoses ($Gal_p$) and two glucopyranose ($Glc_p$)) and a pendent phosphoglycerol (Richards et al. (1988) Adv. Exp. Med. Biol. 228:595-597). The polysaccharide is O-acetylated at multiple locations and, based on the reported data in the literature (Calix et al. (2011) J Bacteriol. 193(19):5271-5278).

The degree of O-acetylation of the polysaccharide can be determined by any method known in the art, for example, by proton NMR (see for example Lemercinier et al. (1996) Carbohydrate Research 296:83-96; Jones et al. (2002) J. Pharmaceutical and Biomedical Analysis 30:1233-1247; WO 2005/033148 and WO 00/56357). Another commonly used method is described in Hestrin, S. (1949) J. Biol. Chem. 180:249-261. Preferably, the presence of O-acetyl groups is determined by ion-HPLC analysis.

The presence of O-acetyl in a purified, isolated or activated serotype 11A capsular polysaccharide or in a serotype 11A polysaccharide-carrier protein conjugate is expressed as the number of mM of acetate per mM of said polysaccharide or as the number of O-acetyl group per polysaccharide repeating unit.

In an embodiment, the isolated serotype 11A saccharide comprises at least 0.3, 0.5, 0.6, 1.0, 1.4, 1.8, 2.2, 2.6, 3.0, 3.4, 3.8, 4.2, 4.6 or 5 mM acetate per mM of said serotype 11A saccharide. In a preferred embodiment, the isolated serotype 11A saccharide comprises at least 0.6, 1, 1.4, 1.8, 2.2, 2.6, 3, 3.4, 3.8, 4.2 or 4.6 mM acetate per mM of said serotype 11A saccharide and less than about 5 mM acetate per mM of said serotype 11A saccharide. In an embodiment, the isolated serotype 11A saccharide comprises at least 0.6, 1.0, 1.4, 1.8, 2.2, 2.6, or 3.0 mM acetate per mM of said serotype 11A saccharide and less than about 3.4 mM acetate per mM of said serotype 11A saccharide. In an embodiment, the isolated serotype 11A saccharide comprises at least 0.6, 1, 1.4, 1.8, 2.2, 2.6, or about 3.0 mM acetate per mM of said serotype 11A saccharide and less than about 3.3 mM acetate per mM of said serotype 11A saccharide.

In a preferred embodiment, the isolated serotype 11A saccharide comprises at least 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5 or 2.6 mM acetate per mM of said serotype 11A saccharide. In a preferred embodiment, the isolated serotype 11A saccharide comprises at least 2.0, 2.1, 2.2, 2.3, 2.4, 2.5 or 2.6 mM acetate per mM of said serotype 11A saccharide. In a preferred embodiment, the isolated serotype 11A saccharide comprises at least 2.4, 2.5 or 2.6 mM acetate per mM of said serotype 11A saccharide. In a preferred embodiment, the isolated serotype 11A saccharide comprises at least 2.5 mM acetate per mM of said serotype 11A saccharide.

The presence of glycerolphosphate side chains is determined by measurement of glycerol using high performance anion exchange chromatography with pulsed amperometric detection (HPAEC-PAD) after its release by treatment of the saccharide with hydrofluoric acid (HF). The presence of glycerol in a purified, isolated or activated serotype 11A saccharide is expressed as the number of mM of glycerol per mM of serotype 11A saccharide.

In a preferred embodiment, the isolated serotype 11A saccharide comprises at least 0.1, 0.2, 0.3, 0.4, 0.5, 0.6, 0.7, 0.8, 0.9 or 1 mM glycerol per mM of said serotype 11A saccharide. In a preferred embodiment, the isolated serotype 11A saccharide comprises at least 0.1, 0.2, 0.3, 0.4, 0.5, 0.6, 0.7, 0.8 or 0.9 mM glycerol per mM of said serotype 11A saccharide and less than about 1.0 mM glycerol per mM of said serotype 11A saccharide. In a preferred embodiment, the isolated serotype 11A saccharide comprises at least 0.5, 0.6, 0.7, 0.8 or 0.9 mM glycerol per mM of said serotype 11A saccharide and less than about 1.0 mM glycerol per mM of said serotype 11A saccharide. In a preferred embodiment, the isolated serotype 11A saccharide comprises at least 0.5, 0.6 or 0.7 mM glycerol per mM of said serotype 11A saccharide and less than about 0.8 mM glycerol per mM of said serotype 11A saccharide. In a preferred embodiment, the isolated serotype 11A saccharide comprises at least 0.6 mM glycerol per mM of said serotype 11A saccharide. In a preferred embodiment, the isolated serotype 11A saccharide comprises at least 0.7 mM glycerol per mM of said serotype 11A saccharide.

A saccharide can become slightly reduced in size during normal purification procedures. Additionally, as described herein, polysaccharide can be subjected to sizing techniques before conjugation. The molecular weight ranges mentioned above refer to purified saccharides before conjugation (e.g., before activation) after an eventual sizing step.

1.1.7 Pneumococcal Saccharide Serotype 12F

The isolated serotype 12F capsular saccharide obtained by purification of serotype 12F polysaccharide from the *S. pneumoniae* lysate and optionally sizing of the purified polysaccharide can be characterized by different parameters including, for example, the molecular weight (MW) of said serotype 12F capsular saccharide (see section 1.2.5, pages 16-17 of WO2015/110941). Advantageously, the size of the purified serotype 12F polysaccharide is reduced while preserving critical features of the structure of the polysaccharide. Preferably, the size of the purified serotype 12F polysaccharide is reduced by mechanical homogenization.

In a preferred embodiment, the size of the purified serotype 12F polysaccharide is reduced by high pressure homogenization. High pressure homogenization achieves high shear rates by pumping the process stream through a flow path with sufficiently small dimensions. The shear rate is increased by using a larger applied homogenization pressure, and exposure time can be increased by recirculating the feed stream through the homogenizer.

The high-pressure homogenization process is particularly appropriate for reducing the size of the purified serotype 12F polysaccharide while preserving the structural features of the polysaccharide.

In some embodiments, the purified saccharide from *S. pneumoniae* serotype 12F before conjugation has a molecular weight of between 10 kDa and 5,000 kDa. In other such embodiments, the capsular polysaccharide has a molecular weight of between 20 kDa and 4,000 kDa. In other such embodiments, the capsular polysaccharide has a molecular weight of between 50 kDa and 3,000 kDa. In other such embodiments, the capsular polysaccharide has a molecular weight of between 100 kDa and 2500 kDa. In other such embodiments, the capsular polysaccharide has a molecular weight of between 100 kDa and 2,000 kDa. In other such embodiments, the capsular polysaccharide has a molecular weight of between 150 kDa and 2,000 kDa. In other such embodiments, the capsular polysaccharide has a molecular weight of between 150 kDa and 1,500 kDa. In other such embodiments, the capsular polysaccharide has a molecular weight of between 20 kDa and 1,500 kDa. In another embodiment, the capsular polysaccharide has a molecular weight of between 30 kDa and 1,250 kDa. In another embodiment, the capsular polysaccharide has a molecular weight of between 50 kDa and 1,000 kDa. In another embodiment, the capsular polysaccharide has a molecular weight of between 70 kDa and 900 kDa. In another embodiment, the capsular polysaccharide has a molecular weight of between 100 kDa and 800 kDa. In another embodiment, the capsular polysaccharide has a molecular weight of between 200 kDa to 600 kDa. In another embodiment, the capsular polysaccharide has a molecular weight of between 400 kDa to 700 kDa.

In further such embodiments, the saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In a preferred embodiment, the isolated saccharide from *S. pneumoniae* serotype 12F has a molecular weight between 5 kDa and 500 kDa, between 50 kDa and 500 kDa, between 50 kDa and 450 kDa, between 100 kDa and 400 kDa, and between 100 kDa and 350 kDa. In a preferred embodiment, the isolated serotype 12F capsular polysaccharide has a molecular weight between 100 kDa and 350 kDa. In a preferred embodiment, the isolated serotype 12F capsular polysaccharide has a molecular weight between 100 kDa and 300 kDa. In a preferred embodiment, the isolated serotype 12F capsular polysaccharide has a molecular weight between 150 kDa and 300 kDa. In a preferred embodiment, the isolated serotype 12F capsular polysaccharide has a molecular weight between 150 kDa and 350 kDa. In further embodiments, the capsular polysaccharide has a molecular weight of 100 kDa to 500 kDa; 100 kDa to 400 kDa; 100 kDa to 300 kDa; 100 kDa to 200 kDa; 150 kDa to 500 kDa; 150 kDa to 400 kDa; 150 kDa to 300 kDa; 150 kDa to 200 kDa; 200 kDa to 500 kDa; 200 kDa to 400 kDa; 250 kDa to 500 kDa; 250 kDa to 400 kDa; 250 kDa to 350 kDa; 300 kDa to 500 kDa; 300 kDa to 400 kDa; and similar desired molecular weight ranges. Any whole number integer within any of the above ranges is contemplated as an embodiment of the disclosure.

A saccharide can become slightly reduced in size during normal purification procedures. Additionally, as described herein, polysaccharide can be subjected to sizing techniques before conjugation. The molecular weight ranges mentioned above refer to purified saccharides before conjugation (e.g., before activation) after an eventual sizing step.

1.1.8 Pneumococcal Saccharide Serotype 10A

The polysaccharide repeating unit of serotype 10A consists of a branched hexasaccharide repeat unit with two galactofuranoses ($Gal_f$), three galactopyranoses ($Gal_p$), one N-acetylgalactosamine ($Gal_pNAc$) and a backbone phosphoribitol (Jones, C. (2005) Carbohydrate Research 269(1):175-181). There are two branching monosaccharides at the β-GalpNAc moiety (a β-3-Galp and a β-6-Galt).

Serotype 10A saccharides can be obtained directly from bacteria using isolation procedures known to one of ordinary skill in the art (see for example methods disclosed in U.S. Patent App. Pub. Nos. 2006/0228380, 2006/0228381, 2007/0184071, 2007/0184072, 2007/0231340, and 2008/0102498 and WO 2008/118752). In addition, they can be produced using synthetic protocols.

Serotype 10A *S. pneumoniae* strains may be obtained from established culture collections (such as for example the Streptococcal Reference Laboratory (Centers for Disease Control and Prevention, Atlanta, GA)) or clinical specimens.

In some embodiments, the purified polysaccharides from *S. pneumoniae* serotype 10A before conjugation have a molecular weight of between 10 kDa and 5,000 kDa. In other such embodiments, the capsular polysaccharide has a molecular weight of between 20 kDa and 4,000 kDa. In other such embodiments, the capsular polysaccharide has a molecular weight of between 50 kDa and 3,000 kDa. In other such embodiments, the capsular polysaccharide has a molecular weight of between 100 kDa and 2500 kDa. In other such embodiments, the capsular polysaccharide has a molecular weight of between 100 kDa and 2,000 kDa. In other such embodiments, the capsular polysaccharide has a molecular weight of between 150 kDa and 2,000 kDa. In other such embodiments, the capsular polysaccharide has a molecular weight of between 150 kDa and 1,500 kDa. In other such embodiments, the capsular polysaccharide has a molecular weight of between 20 kDa and 1,500 kDa. In another embodiment, the capsular polysaccharide has a molecular weight of between 30 kDa and 1,250 kDa. In another embodiment, the capsular polysaccharide has a molecular weight of between 50 kDa and 1,000 kDa. In another embodiment, the capsular polysaccharide has a molecular weight of between 70 kDa and 900 kDa. In another embodiment, the capsular polysaccharide has a molecular weight of between 100 kDa and 800 kDa. In another embodiment, the capsular polysaccharide has a molecular weight of between 200 kDa to 600 kDa. In another embodiment, the capsular polysaccharide has a molecular weight of between 400 kDa to 700 kDa.

In further such embodiments, the saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

A polysaccharide can become slightly reduced in size during normal purification procedures. Additionally, as described herein, polysaccharide can be subjected to sizing techniques before conjugation. The molecular weight ranges mentioned above refer to purified polysaccharides before conjugation (e.g., before activation) after an eventual sizing step.

1.1.9 Pneumococcal Polysaccharide Serotype 22F

The polysaccharide repeating unit of serotype 22F consists of a branched pentasaccharide backbone (one glucuronic acid ($Glc_pA$), one glucopyranose ($Glc_p$), one galactofuranose ($Gal_f$) and two rhamnopyranoses ($Rha_p$)) with a $\alpha Glc_p$ branch linked to the C3 hydroxyl group of $\beta Rha_p$ (Richards et al. (1989) Canadian Journal of Chemistry 67(6):1038-1050). Approximately 80% of the C2 hydroxyl groups of the $\beta Rha_p$ residue in the polysaccharide repeating unit are O-acetylated.

Serotype 22F polysaccharides can be obtained directly from bacteria using isolation procedures known to one of ordinary skill in the art (see for example methods disclosed in U.S. Patent App. Pub. Nos. 2006/0228380, 2006/0228381, 2007/0184071, 2007/0184072, 2007/0231340, and 2008/0102498 and WO 2008/118752). In addition, they can be produced using synthetic protocols.

Serotype 22F *S. pneumoniae* strains may be obtained from established culture collections (such as for example the Streptococcal Reference Laboratory (Centers for Disease Control and Prevention, Atlanta, GA)) or clinical specimens.

The isolated serotype 22F capsular polysaccharide obtained by purification of serotype 22F polysaccharide from the *S. pneumoniae* lysate and optionally sizing of the purified polysaccharide can be characterized by different parameters including, for example, the molecular weight (MW) and the mM of acetate per mM of said serotype 22F capsular polysaccharide.

Preferably, in order to generate serotype 22F conjugates with advantageous filterability characteristics and/or yields, sizing of the polysaccharide to a target molecular weight range is performed prior to the conjugation to a carrier protein. Advantageously, the size of the purified serotype 22F polysaccharide is reduced while preserving critical features of the structure of the polysaccharide such as for example the presence of O-acetyl group. Preferably, the size of the purified serotype 22F polysaccharide is reduced by mechanical homogenization.

In a preferred embodiment, the size of the purified polysaccharide is reduced by high pressure homogenization. High pressure homogenization achieves high shear rates by pumping the process stream through a flow path with sufficiently small dimensions. The shear rate is increased by using a larger applied homogenization pressure, and exposure time can be increased by recirculating the feed stream through the homogenizer.

The high-pressure homogenization process is particularly appropriate for reducing the size of the purified serotype 22F polysaccharide while preserving the structural features of the polysaccharide, such as the presence of O-acetyl groups.

In some embodiments, the purified polysaccharides from *S. pneumoniae* serotype 22F before conjugation have a molecular weight of between 10 kDa and 5,000 kDa. In other such embodiments, the capsular polysaccharide has a molecular weight of between 20 kDa and 4,000 kDa. In other such embodiments, the capsular polysaccharide has a molecular weight of between 50 kDa and 3,000 kDa. In other such embodiments, the capsular polysaccharide has a molecular weight of between 100 kDa and 2500 kDa. In other such embodiments, the capsular polysaccharide has a molecular weight of between 100 kDa and 2,000 kDa. In other such embodiments, the capsular polysaccharide has a molecular weight of between 150 kDa and 2,000 kDa. In other such embodiments, the capsular polysaccharide has a molecular weight of between 150 kDa and 1,500 kDa In some embodiments, the purified polysaccharides from *S. pneumoniae* serotype 22F before conjugation have a molecular weight of between 10 kDa and 2,000 kDa. In other such embodiments, the capsular polysaccharide has a molecular weight of between 20 kDa and 1,500 kDa. In another embodiment, the capsular polysaccharide has a molecular weight of between 30 kDa and 1,250 kDa. In another embodiment, the capsular polysaccharide has a molecular weight of between 50 kDa and 1,000 kDa. In another embodiment, the capsular polysaccharide has a molecular weight of between 70 kDa and 900 kDa. In another embodiment, the capsular polysaccharide has a molecular weight of between 100 kDa and 800 kDa. In another embodiment, the capsular polysaccharide has a molecular weight of between 200 kDa to 600 kDa. In another embodiment, the capsular polysaccharide has a molecular weight of between 400 kDa to 700 kDa.

In further such embodiments, the saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure. A polysaccharide can become slightly reduced in size during normal purification procedures. Additionally, as described hereabove, 22F polysaccharide can be subjected to sizing techniques before conjugation. The molecular weight ranges mentioned above refer to purified polysaccharides before conjugation (e.g., before activation) after an eventual sizing step.

The degree of O-acetylation of the polysaccharide can be determined by any method known in the art, for example, by proton NMR (Lemercinier et al. (1996) Carbohydrate Research 296:83-96; Jones et al. (2002) J. Pharmaceutical and Biomedical Analysis 30:1233-1247; WO 2005/033148 and WO 00/56357). Another commonly used method is described in Hestrin, S. (1949) J. Biol. Chem. 180:249-261. Preferably, the presence of O-acetyl groups is determined by ion-HPLC analysis.

The presence of O-acetyl in a purified, isolated or activated serotype 22F capsular polysaccharide is expressed as the number of mM of acetate per mM of said polysaccharide or as the number of O-acetyl group per polysaccharide repeating unit.

In a preferred embodiment, the purified polysaccharides from *S. pneumoniae* serotype 22F has at least 0.2, 0.4, 0.6, 0.8, 1, 1.2, 1.4 or 1.6, μmol acetate per μmol of said serotype 22F capsular polysaccharide.

1.1.10 Pneumococcal Polysaccharide Serotype 33F

The polysaccharide repeating unit of serotype 33F consists of a branched pentasaccharide backbone (two galactopyranoses ($Gal_p$), two galactofuranoses ($Gal_f$) and one glucopyranose ($Glc_p$) with a terminal $\alpha Gal_p$ linked to the C2 hydroxyl group of $\alpha Gal_p$ residue within the backbone (Lemercinier et al. (2006) Carbohydrate Research 341(1):68-74.). It has been reported in the literature that the C2 hydroxyl group of the backbone 3-β-$Gal_f$-residue is O-acetylated. Serotype 33F polysaccharides can be obtained directly from bacteria using isolation procedures known to one of ordinary skill in the art (see for example methods disclosed in U.S. Patent App. Pub. Nos. 2006/0228380, 2006/0228381, 2007/0184071, 2007/0184072, 2007/0231340, and 2008/0102498 and WO 2008/118752). In addition, they can be produced using synthetic protocols.

Serotype 33F *S. pneumoniae* strains may be obtained from established culture collections (such as for example the Streptococcal Reference Laboratory (Centers for Disease Control and Prevention, Atlanta, GA)) or clinical specimens.

Purified polysaccharides from serotype 33F may be activated (e.g., chemically activated) to make them capable of reacting and then incorporated into glycoconjugates of the invention, as further described herein.

The isolated serotype 33F capsular polysaccharide obtained by purification of serotype 33F polysaccharide from the *S. pneumoniae* lysate and optionally sizing of the purified polysaccharide can be characterized by different parameters including, for example, the molecular weight and the mM of acetate per mM of said serotype 33F capsular polysaccharide.

In some embodiments, the purified polysaccharides from *S. pneumoniae* serotype 33F before conjugation have a molecular weight of between between 10 kDa and 5,000 kDa. In other such embodiments, the capsular polysaccharide has a molecular weight of between 20 kDa and 4,000 kDa. In other such embodiments, the capsular polysaccharide has a molecular weight of between 50 kDa and 3,000 kDa. In other such embodiments, the capsular polysaccharide has a molecular weight of between 100 kDa and 2500 kDa. In other such embodiments, the capsular polysaccharide has a molecular weight of between 100 kDa and 2,000 kDa. In other such embodiments, the capsular polysaccharide has a molecular weight of between 150 kDa and 2,000 kDa. In other such embodiments, the capsular polysaccharide has a molecular weight of between 150 kDa and 1,500 kDa. In other such embodiments, the capsular polysaccharide has a molecular weight of between 20 kDa and 1,500 kDa. In another embodiment, the capsular polysaccharide has a molecular weight of between 30 kDa and 1,250 kDa. In another embodiment, the capsular polysaccharide has a molecular weight of between 50 kDa and 1,000 kDa. In another embodiment, the capsular polysaccharide has a molecular weight of between 70 kDa and 900 kDa. In another embodiment, the capsular polysaccharide has a molecular weight of between 100 kDa and 800 kDa. In another embodiment, the capsular polysaccharide has a molecular weight of between 200 kDa to 600 kDa. In another embodiment, the capsular polysaccharide has a molecular weight of between 400 kDa to 700 kDa.

In further such embodiments, the saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

A polysaccharide can become slightly reduced in size during normal purification procedures. Additionally, as described herein, polysaccharide can be subjected to sizing techniques before conjugation. The molecular weight ranges mentioned above refer to purified polysaccharides before conjugation (e.g., before activation) after an eventual sizing step.

The presence of O-acetyl in a purified, isolated or activated serotype 33F capsular polysaccharide or in a serotype 33F polysaccharide-carrier protein conjugate is expressed as the number of mM of acetate per mM of said polysaccharide or as the number of O-acetyl group per polysaccharide repeating unit (Spencer et al., Infect. Immun. 85 (7), 132, 2017).

In an embodiment, the purified polysaccharide from *S. pneumoniae* serotype 33F has at least 0.2, 0.4, 0.6, 0.8, 1.0, 1.2, 1.4 or 1.6, μmol acetate per μmol of said serotype 33F capsular polysaccharide. In an embodiment, the purified polysaccharide from *S. pneumoniae* serotype 33F has about 0.2, 0.4, 0.6, 0.8, 1.0, 1.2, 1.4 or 1.6, μmol acetate per μmol of said serotype 33F capsular polysaccharide. In a preferred embodiment, the purified polysaccharide from *S. pneumoniae* serotype 33F has between 0.2 and 1.6, between 0.4 and 1.6, between 0.6 and 1.6, between 0.8 and 1.6, between 1.0 and 1.6, between 1.2 and 1.6, between 1.4 and 1.6 or between 1.6 and 1.8, μmol acetate per μmol of said serotype 33F capsular polysaccharide.

1.1.11 Pneumococcal Polysaccharide Serotype 35B

The polysaccharide repeating unit of serotype 35B consists of D-galactose, D-glucose, 2-acetamido-2-deoxy-o-galactose, and ribitol (Beynon et al. (1995) Canadian Journal of Chemistry 73, 41-48). Approximately 70% of the β-D-$Gal_f$ residues glycosidically linked to the ribitol units carry an O-acetyl substituent.

Serotype 35B polysaccharides can be obtained directly from bacteria using isolation procedures known to one of ordinary skill in the art (see for example methods disclosed in U.S. Patent App. Pub. Nos. 2006/0228380, 2006/0228381, 2007/0184071, 2007/0184072, 2007/0231340, and 2008/0102498 and WO 2008/118752). In addition, they can be produced using synthetic protocols.

Serotype 35B *S. pneumoniae* strains may be obtained from established culture collections (such as for example the Streptococcal Reference Laboratory (Centers for Disease Control and Prevention, Atlanta, GA)) or clinical specimens.

The isolated serotype 35B capsular polysaccharide obtained by purification of serotype 35B polysaccharide from the *S. pneumoniae* lysate and optionally sizing of the purified polysaccharide can be characterized by different parameters including, for example, the molecular weight (MW) and the mM of acetate per mM of said serotype 35B capsular polysaccharide.

In some embodiments, the purified polysaccharides from *S. pneumoniae* serotype 35B before conjugation have a molecular weight of between 10 kDa and 5,000 kDa. In other such embodiments, the capsular polysaccharide has a molecular weight of between 20 kDa and 4,000 kDa. In other such embodiments, the capsular polysaccharide has a molecular weight of between 50 kDa and 3,000 kDa. In other such embodiments, the capsular polysaccharide has a molecular weight of between 100 kDa and 2500 kDa. In other such embodiments, the capsular polysaccharide has a molecular weight of between 100 kDa and 2,000 kDa. In other such embodiments, the capsular polysaccharide has a molecular weight of between 150 kDa and 2,000 kDa. In other such embodiments, the capsular polysaccharide has a molecular weight of between 150 kDa and 1,500 kDa In some embodiments, the purified polysaccharides from *S. pneumoniae* serotype 35B before conjugation have a molecular weight of between 10 kDa and 2,000 kDa. In other such embodiments, the capsular polysaccharide has a molecular weight of between 20 kDa and 1,500 kDa. In another embodiment, the capsular polysaccharide has a molecular weight of between 30 kDa and 1,250 kDa. In another embodiment, the capsular polysaccharide has a molecular weight of between 50 kDa and 1,000 kDa. In another embodiment, the capsular polysaccharide has a molecular weight of between 70 kDa and 900 kDa. In another embodiment, the capsular polysaccharide has a molecular weight of between 100 kDa and 800 kDa. In another embodiment, the capsular polysaccharide has a molecular weight of between 200 kDa to 600 kDa. In another embodiment, the capsular polysaccharide has a molecular weight of between 400 kDa to 700 kDa.

In further such embodiments, the saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

A polysaccharide can become slightly reduced in size during normal purification procedures. The molecular weight ranges mentioned above refer to purified polysaccharides before conjugation (e.g., before activation).

The degree of O-acetylation of the polysaccharide can be determined by any method known in the art, for example, by proton NMR (Lemercinier et al. (1996) Carbohydrate Research 296:83-96; Jones et al. (2002) J. Pharmaceutical and Biomedical Analysis 30:1233-1247; WO 2005/033148 and WO 00/56357). Another commonly used method is described in Hestrin, S. (1949) J. Biol. Chem. 180:249-261. Preferably, the presence of O-acetyl groups is determined by ion-HPLC analysis.

The presence of O-acetyl in a purified, isolated or activated serotype 35B capsular polysaccharide is expressed as the number of mM of acetate per mM of said polysaccharide or as the number of O-acetyl group per polysaccharide repeating unit.

In an embodiment, the purified polysaccharides from *S. pneumoniae* serotype 35B has at least 0.1, 0.2, 0.3, 0.4, 0.5, 0.6 or 0.7 μmol acetate per μmol of said serotype 35B capsular polysaccharide. In an embodiment, the purified polysaccharides from *S. pneumoniae* serotype 35B has about 0.1, 0.2, 0.3, 0.4, 0.5, 0.6 or 0.7 μmol acetate per μmol of said serotype 35B capsular polysaccharide. In a preferred embodiment, the purified polysaccharides from *S. pneumoniae* serotype 35B has between 0.1 and 0.7, between 0.2 and 0.7, between 0.3 and 0.7, between 0.4 and 0.7, between 0.5 and 0.7, between 0.6 and 0.7 or between 0.7 and 0.8 μmol acetate per μmol of said serotype 35B capsular polysaccharide.

1.2 Carrier Protein of the Invention

A component of the glycoconjugate of the invention is a carrier protein to which the saccharides are conjugated. The terms "protein carrier" or "carrier protein" or "carrier" may be used interchangeably herein. Carrier proteins should be amenable to standard conjugation procedures.

In a preferred embodiment, the carrier protein of the glycoconjugates is selected in the group consisting of: DT (Diphtheria toxin), TT (tetanus toxid) or fragment C of TT, $CRM_{197}$ (a nontoxic but antigenically identical variant of diphtheria toxin), other DT mutants (such as $CRM_{176}$, $CRM_{228}$, $CRM_{45}$ (Uchida et al. (1973) J. Biol. Chem. 218:3838-3844), $CRM_9$, $CRM_{102}$, $CRM_{103}$ or $CRM_{107}$; and other mutations described by Nicholls and Youle in Genetically Engineered Toxins, Ed: Frankel, Maecel Dekker Inc. (1992); deletion or mutation of Glu-148 to Asp, Gln or Ser and/or Ala 158 to Gly and other mutations disclosed in U.S. Pat. Nos. 4,709,017 and 4,950,740; mutation of at least one or more residues Lys 516, Lys 526, Phe 530 and/or Lys 534 and other mutations disclosed in U.S. Pat. Nos. 5,917,017 and 6,455,673; or fragment disclosed in U.S. Pat. No. 5,843,711, pneumococcal pneumolysin (ply) (Kuo et al. (1995) Infect Immun 63:2706-2713) including ply detoxified in some fashion, for example dPLY-GMBS (WO 2004/081515, WO 2006/032499) or dPLY-formol, PhtX, including PhtA, PhtB, PhtD, PhtE (sequences of PhtA, PhtB, PhtD or PhtE are disclosed in WO 00/37105 and WO 00/39299) and fusions of Pht proteins, for example PhtDE fusions, PhtBE fusions, Pht A-E (WO 01/98334, WO 03/054007, WO 2009/000826), OMPC (meningococcal outer membrane protein), which is usually extracted from *Neisseria meningitidis* serogroup B (EP0372501), PorB (from *N. meningitidis*), PD (*Haemophilus influenzae* protein D; see, e.g., EP0594610 B), or immunologically functional equivalents thereof, synthetic peptides (EP0378881, EP0427347), heat shock proteins (WO 93/17712, WO 94/03208), pertussis proteins (WO 98/58668, EP0471177), cytokines, lymphokines, growth factors or hormones (WO 91/01146), artificial proteins comprising multiple human CD4+ T cell epitopes from various pathogen derived antigens (Falugi et al. (2001) Eur J Immunol 31:3816-3824) such as N19 protein (Baraldoi et al. (2004) Infect Immun 72:4884-4887) pneumococcal surface protein PspA (WO 02/091998), iron uptake proteins (WO 01/72337), toxin A or B of *Clostridium difficile* (WO 00/61761), transferrin binding proteins, pneumococcal adhesion protein (PsaA), recombinant *Pseudomonas aeruginosa* exotoxin A (in particular non-toxic mutants thereof (such as exotoxin A bearing a substitution at glutamic acid 553 (Douglas et al. (1987) J. Bacteriol. 169(11): 4967-4971)). Other proteins, such as ovalbumin, keyhole limpet hemocyanin (KLH), bovine serum albumin (BSA) or purified protein derivative of tuberculin (PPD) also can be used as carrier proteins. Other suitable carrier proteins include inactivated bacterial toxins such as cholera toxoid (e.g., as described in WO 2004/083251), *Escherichia coli* LT, *E. coli* ST, and exotoxin A from *P. aeruginosa.*

In a preferred embodiment, the carrier protein of the glycoconjugates is independently selected from the group consisting of TT, DT, DT mutants (such as $CRM_{197}$), *H.*

*influenzae* protein D, PhtX, PhtD, PhtDE fusions (particularly those described in WO 01/98334 and WO 03/054007), detoxified pneumolysin, PorB, N19 protein, PspA, OMPC, toxin A or B of *C. difficile* and PsaA. In an embodiment, the carrier protein of the glycoconjugates of the invention is DT (Diphtheria toxoid). In another embodiment, the carrier protein of the glycoconjugates of the invention is TT (tetanus toxid).

In another embodiment, the carrier protein of the glycoconjugates of the invention is PD (*H. influenzae* protein D; see, e.g., EP0594610 B).

In another embodiment, the carrier protein of the glycoconjugates of the invention is detoxified pneumolysin (see e.g. Herman et al, Hum Vaccin Immunother. 2017 January; 13(1): 220-228) or a mutant nontoxic form of pneumolysin (see e.g. Kirkham L et al, Infect Immun. 2006 January; 74(1): 586-593).

In a preferred embodiment, the capsular saccharides of the invention are conjugated to $CRM_{197}$ protein. The $CRM_{197}$ protein is a nontoxic form of diphtheria toxin but is immunologically indistinguishable from the diphtheria toxin. $CRM_{197}$ is produced by *Corynebacterium diphtheriae* infected by the nontoxigenic phage $\beta197^{tox-}$ created by nitrosoguanidine mutagenesis of the toxigenic corynephage beta (Uchida et al. (1971) Nature New Biology 233:8-11). The $CRM_{197}$ protein has the same molecular weight as the diphtheria toxin but differs therefrom by a single base change (guanine to adenine) in the structural gene. This single base change causes an amino acid substitution (glutamic acid for glycine) in the mature protein and eliminates the toxic properties of diphtheria toxin. The $CRM_{197}$ protein is a safe and effective T-cell dependent carrier for saccharides. Further details about $CRM_{197}$ and production thereof can be found, e.g., in U.S. Pat. No. 5,614,382.

In an embodiment, the capsular saccharides of the invention are conjugated to $CRM_{197}$ protein or the A chain of $CRM_{197}$ (see CN103495161). In an embodiment, the capsular saccharides of the invention are conjugated the A chain of $CRM_{197}$ obtained via expression by genetically recombinant *E. coli* (see CN103495161). In an embodiment, the capsular saccharides of the invention are all conjugated to $CRM_{197}$. In an embodiment, the capsular saccharides of the invention are all conjugated to the A chain of $CRM_{197}$.

Accordingly, in frequent embodiments, the glycoconjugates of the invention comprise $CRM_{197}$ as the carrier protein, wherein the capsular polysaccharide is covalently linked to $CRM_{197}$.

1.3 Glycoconjugates of the Invention Comprising Two or More Saccharides

1.3.1 Glycoconjugates of the Invention Comprising at Least Two Saccharides Selected from the Group Consisting of a Saccharide from *S. pneumoniae* Serotype 8, a Saccharide from *S. pneumoniae* Serotype 15A, a Saccharide from *S. pneumoniae* Serotype 15B, a Saccharide from *S. pneumoniae* Serotype 23A and a Saccharide from *S. pneumoniae* Serotype 23B The present invention relates to glycoconjugates wherein 2 or more saccharides antigens are conjugated to the same molecule of the protein carrier (i.e. the carrier molecules have 2 or more different capsular saccharides conjugated to them).

In an embodiment the invention relates to a glycoconjugate comprising at least two saccharides selected from the group consisting of a saccharide from *S. pneumoniae* serotype 8, a saccharide from *S. pneumoniae* serotype 15A, a saccharide from *S. pneumoniae* serotype 15B, a saccharide from *S. pneumoniae* serotype 23A and a saccharide from *S. pneumoniae* serotype 23B, conjugated to a carrier protein.

In an embodiment the glycoconjugate of the invention comprises a saccharide from *S. pneumoniae* serotype 8, a saccharide from *S. pneumoniae* serotype 15A, a saccharide from *S. pneumoniae* serotype 15B, a saccharide from *S. pneumoniae* serotype 23A and a saccharide from *S. pneumoniae* serotype 23B, conjugated to the same carrier protein (herein after 'the serotypes 8/15A/15B/23A/23B glycoconjugate'). In said embodiment, the carrier molecules have the five different capsular saccharides conjugated to them. Preferably, the serotypes 8/15A/15B/23A/23B glycoconjugate is therefore a 5-valent glycoconjugate (i.e. it has serotypes 8, 15A, 15B, 23A and 23B conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 15A, a saccharide from *S. pneumoniae* serotype 15B and a saccharide from *S. pneumoniae* serotype 23A, conjugated to the same carrier protein (herein after 'the serotypes 8/15A/15B/23A glycoconjugate'). In said embodiment, the carrier molecules have the four different capsular saccharides conjugated to them. Preferably, the serotypes 8/15A/15B/23A glycoconjugate is therefore a 4-valent glycoconjugate (i.e. it has serotypes 8, 15A, 15B, and 23A conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 15A, a saccharide from *S. pneumoniae* serotype 15B and a saccharide from *S. pneumoniae* serotype 23B, conjugated to the same carrier protein (herein after 'the serotypes 8/15A/15B/23B glycoconjugate'). In said embodiment, the carrier molecules have the four different capsular saccharides conjugated to them. Preferably, the serotypes 8/15A/15B/23B glycoconjugate is therefore a 4-valent glycoconjugate (i.e. it has serotypes 8, 15A, 15B, and 23A conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 15A, a saccharide from *S. pneumoniae* serotype 23A and a saccharide from *S. pneumoniae* serotype 23B, conjugated to the same carrier protein (herein after 'the serotypes 8/15A/23A/23B glycoconjugate'). In said embodiment, the carrier molecules have the four different capsular saccharides conjugated to them. Preferably, the serotypes 8/15A/23A/23B glycoconjugate is therefore a 4-valent glycoconjugate (i.e. it has serotypes 8, 15A, 23A, and 23A conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 15B, a saccharide from *S. pneumoniae* serotype 23A and a saccharide from *S. pneumoniae* serotype 23B, conjugated to the same carrier protein (herein after 'the serotypes 8/15B/23A/23B glycoconjugate'). In said embodiment, the carrier molecules have the four different capsular saccharides conjugated to them. Preferably, the serotypes 8/15B/23A/23B glycoconjugate is therefore a 4-valent glycoconjugate (i.e. it has serotypes 8, 15B, 23A, and 23A conjugated to the carrier protein and no other polysaccharide antigens covalently attached to the carrier protein).

In an embodiment the glycoconjugate of the invention comprises a saccharide from *S. pneumoniae* serotype 15A, a saccharide from *S. pneumoniae* serotype 15B, a saccharide from *S. pneumoniae* serotype 23A and a saccharide from *S. pneumoniae* serotype 23B, conjugated to the same carrier protein (herein after 'the serotypes 15A/15B/23A/23B glycoconjugate'). In said embodiment, the carrier molecules have the four different capsular saccharides conjugated to them. Preferably, the serotypes 15A/15B/23A/23B glycoconjugate is therefore a 4-valent glycoconjugate (i.e. it has serotypes 15A, 15B, 23A, and 23A conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 15A and a saccharide from *S. pneumoniae* serotype 15B, conjugated to the same carrier protein (herein after 'the serotypes 8/15A/15B glycoconjugate'). In said embodiment, the carrier molecules have the three different capsular saccharides conjugated to them. Preferably, the serotypes 8/15A/15B glycoconjugate is therefore a 3-valent glycoconjugate (i.e. it has serotypes 8, 15A and 15B conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 15A and a saccharide from *S. pneumoniae* serotype 23A, conjugated to the same carrier protein (herein after 'the serotypes 8/15A/23A glycoconjugate'). In said embodiment, the carrier molecules have the three different capsular saccharides conjugated to them. Preferably, the serotypes 8/15A/23A glycoconjugate is therefore a 3-valent glycoconjugate (i.e. it has serotypes 8, 15A and 23A conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 15A and a saccharide from *S. pneumoniae* serotype 23B, conjugated to the same carrier protein (herein after 'the serotypes 8/15A/23B glycoconjugate'). In said embodiment, the carrier molecules have the three different capsular saccharides conjugated to them. Preferably, the serotypes 8/15A/23B glycoconjugate is therefore a 3-valent glycoconjugate (i.e. it has serotypes 8, 15A and 23B conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 15B and a saccharide from *S. pneumoniae* serotype 23A, conjugated to the same carrier protein (herein after 'the serotypes 8/15B/23A glycoconjugate'). In said embodiment, the carrier molecules have the three different capsular saccharides conjugated to them. Preferably, the serotypes 8/15B/23A glycoconjugate is therefore a 3-valent glycoconjugate (i.e. it has serotypes 8, 15B and 23A conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 15B and a saccharide from *S. pneumoniae* serotype 23B, conjugated to the same carrier protein (herein after 'the serotypes 8/15B/23B glycoconjugate'). In said embodiment, the carrier molecules have the three different capsular saccharides conjugated to them. Preferably, the serotypes 8/15B/23B glycoconjugate is therefore a 3-valent glycoconjugate (i.e. it has serotypes 8, 15B and 23B conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 23A and a saccharide from *S. pneumoniae* serotype 23B, conjugated to the same carrier protein (herein after 'the serotypes 8/23A/23B glycoconjugate'). In said embodiment, the carrier molecules have the three different capsular saccharides conjugated to them. Preferably, the serotypes 8/23A/23B glycoconjugate is therefore a 3-valent glycoconjugate (i.e. it has serotypes 8, 23A and 23B conjugated to the carrier protein and no other polysaccharide antigens covalently attached to the carrier protein).

In an embodiment the glycoconjugate of the invention comprises a saccharide from *S. pneumoniae* serotype 15A, a saccharide from *S. pneumoniae* serotype 15B and a saccharide from *S. pneumoniae* serotype 23A, conjugated to the same carrier protein (herein after 'the serotypes 15A/15B/23A glycoconjugate'). In said embodiment, the carrier molecules have the three different capsular saccharides conjugated to them. Preferably, the serotypes 15A/15B/23A glycoconjugate is therefore a 3-valent glycoconjugate (i.e. it has serotypes 15A, 15B and 23A conjugated to the carrier protein and no other polysaccharide antigens covalently attached to the carrier protein).

In an embodiment the glycoconjugate of the invention comprises a saccharide from *S. pneumoniae* serotype 15A, a saccharide from *S. pneumoniae* serotype 15B and a saccharide from *S. pneumoniae* serotype 23B, conjugated to the same carrier protein (herein after 'the serotypes 15A/15B/23B glycoconjugate'). In said embodiment, the carrier molecules have the three different capsular saccharides conjugated to them. Preferably, the serotypes 15A/15B/23B glycoconjugate is therefore a 3-valent glycoconjugate (i.e. it has serotypes 15A, 15B and 23B conjugated to the carrier protein and no other polysaccharide antigens covalently attached to the carrier protein).

In an embodiment the glycoconjugate of the invention comprises a saccharide from *S. pneumoniae* serotype 15A, a saccharide from *S. pneumoniae* serotype 23A and a saccharide from *S. pneumoniae* serotype 23B, conjugated to the same carrier protein (herein after 'the serotypes 15A/23A/23B glycoconjugate'). In said embodiment, the carrier molecules have the three different capsular saccharides conjugated to them. Preferably, the serotypes 15A/23A/23B glycoconjugate is therefore a 3-valent glycoconjugate (i.e. it has serotypes 15A, 23A and 23B conjugated to the carrier protein and no other polysaccharide antigens covalently attached to the carrier protein).

In an embodiment the glycoconjugate of the invention comprises a saccharide from *S. pneumoniae* serotype 15B, a saccharide from *S. pneumoniae* serotype 23A and a saccharide from *S. pneumoniae* serotype 23B, conjugated to the same carrier protein (herein after 'the serotypes 15B/23A/23B glycoconjugate'). In said embodiment, the carrier molecules have the three different capsular saccharides conjugated to them. Preferably, the serotypes 15B/23A/23B glycoconjugate is therefore a 3-valent glycoconjugate (i.e. it has serotypes 15B, 23A and 23B conjugated to the carrier protein and no other polysaccharide antigens covalently attached to the carrier protein).

In an embodiment the glycoconjugate of the invention comprises a saccharide from *S. pneumoniae* serotype 8 and a saccharide from *S. pneumoniae* serotype 15A, conjugated to the same carrier protein (herein after 'the serotypes 8/15A glycoconjugate'). In said embodiment, the carrier molecules have the two different capsular saccharides conjugated to them. Preferably, the serotypes 8/15A glycoconjugate is therefore a 2-valent glycoconjugate (i.e. it has serotypes 8 and 15A conjugated to the carrier protein and no other polysaccharide antigens covalently attached to the carrier protein).

In an embodiment the glycoconjugate of the invention comprises a saccharide from *S. pneumoniae* serotype 8 and a saccharide from *S. pneumoniae* serotype 15B, conjugated to the same carrier protein (herein after 'the serotypes 8/15B glycoconjugate'). In said embodiment, the carrier molecules have the two different capsular saccharides conjugated to them. Preferably, the serotypes 8/15B glycoconjugate is therefore a 2-valent glycoconjugate (i.e. it has serotypes 8 and 15B conjugated to the carrier protein and no other polysaccharide antigens covalently attached to the carrier protein).

In an embodiment the glycoconjugate of the invention comprises a saccharide from *S. pneumoniae* serotype 8 and a saccharide from *S. pneumoniae* serotype 23A, conjugated to the same carrier protein (herein after 'the serotypes 8/23A glycoconjugate'). In said embodiment, the carrier molecules have the two different capsular saccharides conjugated to them. Preferably, the serotypes 8/23A glycoconjugate is therefore a 2-valent glycoconjugate (i.e. it has serotypes 8 and 23A conjugated to the carrier protein and no other polysaccharide antigens covalently attached to the carrier protein).

In an embodiment the glycoconjugate of the invention comprises a saccharide from *S. pneumoniae* serotype 8 and a saccharide from *S. pneumoniae* serotype 23B, conjugated to the same carrier protein (herein after 'the serotypes 8/23B glycoconjugate'). In said embodiment, the carrier molecules have the two different capsular saccharides conjugated to them. Preferably, the serotypes 8/23B glycoconjugate is therefore a 2-valent glycoconjugate (i.e. it has serotypes 8 and 23B conjugated to the carrier protein and no other polysaccharide antigens covalently attached to the carrier protein).

In an embodiment the glycoconjugate of the invention comprises a saccharide from *S. pneumoniae* serotype 15A and a saccharide from *S. pneumoniae* serotype 15B, conjugated to the same carrier protein (herein after 'the serotypes 15A/15B glycoconjugate'). In said embodiment, the carrier molecules have the two different capsular saccharides conjugated to them. Preferably, the serotypes 15A/15B glycoconjugate is therefore a 2-valent glycoconjugate (i.e. it has serotypes 15A and 15B conjugated to the carrier protein and no other polysaccharide antigens covalently attached to the carrier protein).

In an embodiment the glycoconjugate of the invention comprises a saccharide from *S. pneumoniae* serotype 15A and a saccharide from *S. pneumoniae* serotype 23A, conjugated to the same carrier protein (herein after 'the serotypes 15A/23A glycoconjugate'). In said embodiment, the carrier molecules have the two different capsular saccharides conjugated to them. Preferably, the serotypes 15A/23A glycoconjugate is therefore a 2-valent glycoconjugate (i.e. it has serotypes 15A and 23A conjugated to the carrier protein and no other polysaccharide antigens covalently attached to the carrier protein).

In an embodiment the glycoconjugate of the invention comprises a saccharide from *S. pneumoniae* serotype 15A and a saccharide from *S. pneumoniae* serotype 23B, conjugated to the same carrier protein (herein after 'the serotypes 15A/23B glycoconjugate'). In said embodiment, the carrier molecules have the two different capsular saccharides conjugated to them. Preferably, the serotypes 15A/23B glycoconjugate is therefore a 2-valent glycoconjugate (i.e. it has serotypes 15A and 23B conjugated to the carrier protein and no other polysaccharide antigens covalently attached to the carrier protein).

In an embodiment the glycoconjugate of the invention comprises a saccharide from *S. pneumoniae* serotype 15B and a saccharide from *S. pneumoniae* serotype 23A, conjugated to the same carrier protein (herein after 'the serotypes 15B/23A glycoconjugate'). In said embodiment, the carrier molecules have the two different capsular saccharides conjugated to them. Preferably, the serotypes 15B/23A glycoconjugate is therefore a 2-valent glycoconjugate (i.e. it has serotypes 15B and 23A conjugated to the carrier protein and no other polysaccharide antigens covalently attached to the carrier protein).

In an embodiment the glycoconjugate of the invention comprises a saccharide from *S. pneumoniae* serotype 15B and a saccharide from *S. pneumoniae* serotype 23B, conjugated to the same carrier protein (herein after 'the serotypes 15B/23B glycoconjugate'). In said embodiment, the carrier molecules have the two different capsular saccharides conjugated to them. Preferably, the serotypes 15B/23B glycoconjugate is therefore a 2-valent glycoconjugate (i.e. it has serotypes 15B and 23B conjugated to the carrier protein and no other polysaccharide antigens covalently attached to the carrier protein).

In an embodiment the glycoconjugate of the invention comprises a saccharide from *S. pneumoniae* serotype 23A and a saccharide from *S. pneumoniae* serotype 23B, conjugated to the same carrier protein (herein after 'the serotypes 23A/23B glycoconjugate'). In said embodiment, the carrier molecules have the two different capsular saccharides conjugated to them. Preferably, the serotypes 23A/23B glycoconjugate is therefore a 2-valent glycoconjugate (i.e. it has serotypes 23A and 23B conjugated to the carrier protein and no other polysaccharide antigens covalently attached to the carrier protein).

In some embodiments, the serotypes 8/15A/15B/23A/23B, 8/15A/15B/23A, 8/15A/15B/23B, 8/15A/23A/23B, 8/15B/23A/23B, 8/15A/15B, 8/15A/23A, 8/15A/23B, 8/15B/23A, 8/15B/23B, 8/23A/23B, 8/15A, 8/15B, 8/23A or 8/23B glycoconjugate of the present invention comprise a serotype 8 saccharide having a molecular weight of between 10 kDa and 5,000 kDa. In other such embodiments, the serotype 8 saccharide has a molecular weight of between 20 kDa and 4,000 kDa. In other such embodiments, the serotype 8 saccharide has a molecular weight of between 50 kDa and 3,000 kDa. In other such embodiments, the serotype 8 saccharide has a molecular weight of between 100 kDa and 2500 kDa. In other such embodiments, the serotype 8 saccharide has a molecular weight of between 100 kDa and 2,000 kDa. In other such embodiments, the serotype 8 saccharide has a molecular weight of between 150 kDa and 2,000 kDa. In other such embodiments, the serotype 8 saccharide has a molecular weight of between 150 kDa and 1,500 kDa. In other such embodiments, the serotype 8 saccharide has a molecular weight of between 20 kDa and 1,500 kDa. In another embodiment, the serotype 8 saccharide has a molecular weight of between 30 kDa and 1,250 kDa. In another embodiment, the serotype 8 saccharide has a molecular weight of between 50 kDa and 1,000 kDa. In another embodiment, the serotype 8 saccharide has a molecular weight of between 70 kDa and 900 kDa. In another embodiment, the serotype 8 saccharide has a molecular weight of between 100 kDa and 800 kDa. In another embodiment, the serotype 8 saccharide has a molecular weight of between 200 kDa to 600 kDa. In another embodiment, the serotype 8 saccharide has a molecular weight of between 400 kDa to 700 kDa.

In further such embodiments, the serotype 8 saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In further embodiments, the serotype 8 saccharide has a molecular weight of between 10 kDa and 2,000 kDa. In further such embodiments, the serotype 8 saccharide has a molecular weight of between 100 kDa to 1,000 kDa; between 100 kDa to 900 kDa; between 100 kDa to 800 kDa; between 100 kDa to 700 kDa; between 100 kDa to 600 kDa; between 100 kDa to 500 kDa; between 100 kDa to 400 kDa; between 100 kDa to 300 kDa; between 150 kDa to 1,000 kDa; between 150 kDa to 900 kDa; between 150 kDa to 800 kDa; between 150 kDa to 700 kDa; between 150 kDa to 600 kDa; between 150 kDa to 500 kDa; between 150 kDa to 400 kDa; between 150 kDa to 300 kDa; between 200 kDa to 1,000 kDa; between 200 kDa to 900 kDa; between 200 kDa to 800 kDa; between 200 kDa to 700 kDa; between 200 kDa to 600 kDa; between 200 kDa to 500 kDa; between 200 kDa to 400 kDa; between 200 kDa to 300 kDa; between 250 kDa to 1,000 kDa; between 250 kDa to 900 kDa; between 250 kDa to 800 kDa; between 250 kDa to 700 kDa; between 250 kDa to 600 kDa; between 250 kDa to 500 kDa; between 250 kDa to 400 kDa; between 250 kDa to 350 kDa; between 300 kDa to 1000 kDa; between 300 kDa to 900 kDa; between 300 kDa to 800 kDa; between 300 kDa to 700 kDa; between 300 kDa to 600 kDa; between 300 kDa to 500 kDa; between 300 kDa to 400 kDa; between 400 kDa to 1,000 kDa; between 400 kDa to 900 kDa; between 400 kDa to 800 kDa; between 400 kDa to 700 kDa; between 400 kDa to 600 kDa or between 500 kDa to 600 kDa. Any whole number integer within any of the above ranges is contemplated as an embodiment of the disclosure.

In some embodiments, the serotypes 8/15A/15B/23A/23B, 8/15A/15B/23A, 8/15A/15B/23B, 8/15A/23A/23B, 15A/15B/23A/23B, 8/15A/15B, 8/15A/23A, 8/15A/23B, 15A/15B/23A, 15A/15B/23B, 15A/23A/23B, 8/15A, 15A/15B, 15A/23A or 15A/23B, glycoconjugate of the present invention comprise a serotype 15A saccharide having a molecular weight of between 10 kDa and 5,000 kDa. In other such embodiments, the serotype 15A saccharide has a molecular weight of between 20 kDa and 4,000 kDa. In other such embodiments, the serotype 15A saccharide has a molecular weight of between 50 kDa and 3,000 kDa. In other such embodiments, the serotype 15A saccharide has a molecular weight of between 100 kDa and 2500 kDa. In other such embodiments, the serotype 15A saccharide has a molecular weight of between 100 kDa and 2,000 kDa. In other such embodiments, the serotype 15A saccharide has a molecular weight of between 150 kDa and 2,000 kDa. In other such embodiments, the serotype 15A saccharide has a molecular weight of between 150 kDa and 1,500 kDa. In other such embodiments, the serotype 15A saccharide has a molecular weight of between 20 kDa and 1,500 kDa. In another embodiment, the serotype 15A saccharide has a molecular weight of between 30 kDa and 1,250 kDa. In another embodiment, the serotype 15A saccharide has a molecular weight of between 50 kDa and 1,000 kDa. In another embodiment, the serotype 15A saccharide has a molecular weight of between 70 kDa and 900 kDa. In another embodiment, the serotype 15A saccharide has a molecular weight of between 100 kDa and 800 kDa. In another embodiment, the serotype 15A saccharide has a molecular weight of between 200 kDa to 600 kDa. In another embodiment, the serotype 15A saccharide has a molecular weight of between 400 kDa to 700 kDa.

In further such embodiments, the serotype 15A saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa;

between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In further embodiments, the serotype 15A saccharide has a molecular weight of between 10 kDa and 2,000 kDa. In further such embodiments, the serotype 15A saccharide has a molecular weight of between 100 kDa to 1,000 kDa; between 100 kDa to 900 kDa; between 100 kDa to 800 kDa; between 100 kDa to 700 kDa; between 100 kDa to 600 kDa; between 100 kDa to 500 kDa; between 100 kDa to 400 kDa; between 100 kDa to 300 kDa; between 150 kDa to 1,000 kDa; between 150 kDa to 900 kDa; between 150 kDa to 800 kDa; between 150 kDa to 700 kDa; between 150 kDa to 600 kDa; between 150 kDa to 500 kDa; between 150 kDa to 400 kDa; between 150 kDa to 300 kDa; between 200 kDa to 1,000 kDa; between 200 kDa to 900 kDa; between 200 kDa to 800 kDa; between 200 kDa to 700 kDa; between 200 kDa to 600 kDa; between 200 kDa to 500 kDa; between 200 kDa to 400 kDa; between 200 kDa to 300 kDa; between 250 kDa to 1,000 kDa; between 250 kDa to 900 kDa; between 250 kDa to 800 kDa; between 250 kDa to 700 kDa; between 250 kDa to 600 kDa; between 250 kDa to 500 kDa; between 250 kDa to 400 kDa; between 250 kDa to 350 kDa; between 300 kDa to 1000 kDa; between 300 kDa to 900 kDa; between 300 kDa to 800 kDa; between 300 kDa to 700 kDa; between 300 kDa to 600 kDa; between 300 kDa to 500 kDa; between 300 kDa to 400 kDa; between 400 kDa to 1,000 kDa; between 400 kDa to 900 kDa; between 400 kDa to 800 kDa; between 400 kDa to 700 kDa; between 400 kDa to 600 kDa or between 500 kDa to 600 kDa. Any whole number integer within any of the above ranges is contemplated as an embodiment of the disclosure.

In some embodiments, the serotypes 8/15A/15B/23A/23B, 8/15A/15B/23A, 8/15A/15B/23B, 8/15B/23A/23B, 15A/15B/23A/23B, 8/15A/15B, 8/15B/23A, 8/15B/23B, 15A/15B/23A, 15A/15B/23B, 15B/23A/23B, 8/15B, 15A/15B, 15B/23A or 15B/23B, glycoconjugate of the present invention comprises a serotype 15B saccharide having a molecular weight of between 10 kDa and 5,000 kDa. In other such embodiments, the serotype 15B saccharide has a molecular weight of between 20 kDa and 4,000 kDa. In other such embodiments, the serotype 15B saccharide has a molecular weight of between 50 kDa and 3,000 kDa. In other such embodiments, the serotype 15B saccharide has a molecular weight of between 100 kDa and 2500 kDa. In other such embodiments, the serotype 15B saccharide has a molecular weight of between 100 kDa and 2,000 kDa. In other such embodiments, the serotype 15B saccharide has a molecular weight of between 150 kDa and 2,000 kDa. In other such embodiments, the serotype 15B saccharide has a molecular weight of between 150 kDa and 1,500 kDa. In other such embodiments, the serotype 15B saccharide has a molecular weight of between 20 kDa and 1,500 kDa. In another embodiment, the serotype 15B saccharide has a molecular weight of between 30 kDa and 1,250 kDa. In another embodiment, the serotype 15B saccharide has a molecular weight of between 50 kDa and 1,000 kDa. In another embodiment, the serotype 15B saccharide has a molecular weight of between 70 kDa and 900 kDa. In another embodiment, the serotype 15B saccharide has a molecular weight of between 100 kDa and 800 kDa. In another embodiment, the serotype 15B saccharide has a molecular weight of between 200 kDa to 600 kDa. In another embodiment, the serotype 15B saccharide has a molecular weight of between 400 kDa to 700 kDa.

In further such embodiments, the serotype 15B saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa;

between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In further embodiments, the serotype 15B saccharide has a molecular weight of between 10 kDa and 2,000 kDa. In further such embodiments, the serotype 15B saccharide has a molecular weight of between 100 kDa to 1,000 kDa; between 100 kDa to 900 kDa; between 100 kDa to 800 kDa; between 100 kDa to 700 kDa; between 100 kDa to 600 kDa; between 100 kDa to 500 kDa; between 100 kDa to 400 kDa; between 100 kDa to 300 kDa; between 150 kDa to 1,000 kDa; between 150 kDa to 900 kDa; between 150 kDa to 800 kDa; between 150 kDa to 700 kDa; between 150 kDa to 600 kDa; between 150 kDa to 500 kDa; between 150 kDa to 400 kDa; between 150 kDa to 300 kDa; between 200 kDa to 1,000 kDa; between 200 kDa to 900 kDa; between 200 kDa to 800 kDa; between 200 kDa to 700 kDa; between 200 kDa to 600 kDa; between 200 kDa to 500 kDa; between 200 kDa to 400 kDa; between 200 kDa to 300 kDa; between 250 kDa to 1,000 kDa; between 250 kDa to 900 kDa; between 250 kDa to 800 kDa; between 250 kDa to 700 kDa; between 250 kDa to 600 kDa; between 250 kDa to 500 kDa; between 250 kDa to 400 kDa; between 250 kDa to 350 kDa; between 300 kDa to 1000 kDa; between 300 kDa to 900 kDa; between 300 kDa to 800 kDa; between 300 kDa to 700 kDa; between 300 kDa to 600 kDa; between 300 kDa to 500 kDa; between 300 kDa to 400 kDa; between 400 kDa to 1,000 kDa; between 400 kDa to 900 kDa; between 400 kDa to 800 kDa; between 400 kDa to 700 kDa; between 400 kDa to 600 kDa or between 500 kDa to 600 kDa. Any whole number integer within any of the above ranges is contemplated as an embodiment of the disclosure.

In some embodiments, the serotypes 8/15A/15B/23A/23B, 8/15A/15B/23A, 8/15A/23A/23B, 8/15B/23A/23B, 15A/15B/23A/23B, 8/15A/23A, 8/15B/23A, 8/23A/23B, 15A/15B/23A, 15A/23A/23B, 15B/23A/23B, 8/23A, 15A/23A, 15B/23A or 23A/23B glycoconjugate of the present invention comprise a serotype 23A saccharide having a molecular weight of between 10 kDa and 5,000 kDa. In other such embodiments, the serotype 23A saccharide has a molecular weight of between 20 kDa and 4,000 kDa. In other such embodiments, the serotype 23A saccharide has a molecular weight of between 50 kDa and 3,000 kDa. In other such embodiments, the serotype 23A saccharide has a molecular weight of between 100 kDa and 2500 kDa. In other such embodiments, the serotype 23A saccharide has a molecular weight of between 100 kDa and 2,000 kDa. In other such embodiments, the serotype 23A saccharide has a molecular weight of between 150 kDa and 2,000 kDa. In other such embodiments, the serotype 23A saccharide has a molecular weight of between 150 kDa and 1,500 kDa. In other such embodiments, the serotype 23A saccharide has a molecular weight of between 20 kDa and 1,500 kDa. In another embodiment, the serotype 23A saccharide has a molecular weight of between 30 kDa and 1,250 kDa. In another embodiment, the serotype 23A saccharide has a molecular weight of between 50 kDa and 1,000 kDa. In another embodiment, the serotype 23A saccharide has a molecular weight of between 70 kDa and 900 kDa. In another embodiment, the serotype 23A saccharide has a molecular weight of between 100 kDa and 800 kDa. In another embodiment, the serotype 23A saccharide has a molecular weight of between 200 kDa to 600 kDa. In another embodiment, the serotype 23A saccharide has a molecular weight of between 400 kDa to 700 kDa.

In further such embodiments, the serotype 23A saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In further embodiments, the serotype 23A saccharide has a molecular weight of between 10 kDa and 2,000 kDa. In further such embodiments, the serotype 23A saccharide has a molecular weight of between 100 kDa to 1,000 kDa; between 100 kDa to 900 kDa; between 100 kDa to 800 kDa; between 100 kDa to 700 kDa; between 100 kDa to 600 kDa; between 100 kDa to 500 kDa; between 100 kDa to 400 kDa; between 100 kDa to 300 kDa; between 150 kDa to 1,000 kDa; between 150 kDa to 900 kDa; between 150 kDa to 800 kDa; between 150 kDa to 700 kDa; between 150 kDa to 600 kDa; between 150 kDa to 500 kDa; between 150 kDa to 400 kDa; between 150 kDa to 300 kDa; between 200 kDa to 1,000 kDa; between 200 kDa to 900 kDa; between 200 kDa to 800 kDa; between 200 kDa to 700 kDa; between 200 kDa to 600 kDa; between 200 kDa to 500 kDa; between 200 kDa to 400 kDa; between 200 kDa to 300 kDa; between 250 kDa to 1,000 kDa; between 250 kDa to 900 kDa; between 250 kDa to 800 kDa; between 250 kDa to 700 kDa; between 250 kDa to 600 kDa; between 250 kDa to 500 kDa; between 250 kDa to 400 kDa; between 250 kDa to 350 kDa; between 300 kDa to 1000 kDa; between 300 kDa to 900 kDa; between 300 kDa to 800 kDa; between 300 kDa to 700 kDa; between 300 kDa to 600 kDa; between 300 kDa to 500 kDa; between 300 kDa to 400 kDa; between 400 kDa to 1,000 kDa; between 400 kDa to 900 kDa; between 400 kDa to 800 kDa; between 400 kDa to 700 kDa; between 400 kDa to 600 kDa or between 500 kDa to 600 kDa. Any whole number integer within any of the above ranges is contemplated as an embodiment of the disclosure.

In some embodiments, the serotypes 8/15A/15B/23A/23B, 8/15A/15B/23B, 8/15A/23A/23B, 8/15B/23A/23B, 15A/15B/23A/23B, 8/15A/23B, 8/15B/23B, 8/23A/23B, 15A/15B/23B, 15A/23A/23B, 15B/23A/23B, 8/23B, 15A/23B, 15B/23B or 23A/23B glycoconjugate of the present invention comprises a serotype 23B saccharide having a molecular weight of between between 10 kDa and 5,000 kDa. In other such embodiments, the serotype 23B saccharide has a molecular weight of between 20 kDa and 4,000 kDa. In other such embodiments, the serotype 23B saccharide has a molecular weight of between 50 kDa and 3,000 kDa. In other such embodiments, the serotype 23B saccharide has a molecular weight of between 100 kDa and 2500 kDa. In other such embodiments, the serotype 23B saccharide has a molecular weight of between 100 kDa and 2,000 kDa. In other such embodiments, the serotype 23B saccharide has a molecular weight of between 150 kDa and 2,000 kDa. In other such embodiments, the serotype 23B saccharide has a molecular weight of between 150 kDa and 1,500 kDa. In other such embodiments, the serotype 23B saccharide has a molecular weight of between 20 kDa and 1,500 kDa. In another embodiment, the serotype 23B saccharide has a molecular weight of between 30 kDa and 1,250 kDa. In another embodiment, the serotype 23B saccharide has a molecular weight of between 50 kDa and 1,000 kDa. In another embodiment, the serotype 23B saccharide has a molecular weight of between 70 kDa and 900 kDa. In another embodiment, the serotype 23B saccharide has a molecular weight of between 100 kDa and 800 kDa. In another embodiment, the serotype 23B saccharide has a molecular weight of between 200 kDa to 600 kDa. In another embodiment, the serotype 23B saccharide has a molecular weight of between 400 kDa to 700 kDa.

In further such embodiments, the serotype 23B saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In further embodiments, the serotype 23B saccharide has a molecular weight of between 10 kDa and 2,000 kDa. In further such embodiments, the serotype 23B saccharide has a molecular weight of between 100 kDa to 1,000 kDa; between 100 kDa to 900 kDa; between 100 kDa to 800 kDa; between 100 kDa to 700 kDa; between 100 kDa to 600 kDa; between 100 kDa to 500 kDa; between 100 kDa to 400 kDa; between 100 kDa to 300 kDa; between 150 kDa to 1,000 kDa; between 150 kDa to 900 kDa; between 150 kDa to 800 kDa; between 150 kDa to 700 kDa; between 150 kDa to 600 kDa; between 150 kDa to 500 kDa; between 150 kDa to 400 kDa; between 150 kDa to 300 kDa; between 200 kDa to 1,000 kDa; between 200 kDa to 900 kDa; between 200 kDa to 800 kDa; between 200 kDa to 700 kDa; between 200 kDa to 600 kDa; between 200 kDa to 500 kDa; between 200 kDa to 400 kDa; between 200 kDa to 300 kDa; between 250 kDa to 1,000 kDa; between 250 kDa to 900 kDa; between 250 kDa to 800 kDa; between 250 kDa to 700 kDa; between 250 kDa to 600 kDa; between 250 kDa to 500 kDa; between 250 kDa to 400 kDa; between 250 kDa to 350 kDa; between 300 kDa to 1000 kDa; between 300 kDa to 900 kDa; between 300 kDa to 800 kDa; between 300 kDa to 700 kDa; between 300 kDa to 600 kDa; between 300 kDa to 500 kDa; between 300 kDa to 400 kDa; between 400 kDa to 1,000 kDa; between 400 kDa to 900 kDa; between 400 kDa to 800 kDa; between 400 kDa to 700 kDa; between 400 kDa to 600 kDa or between 500 kDa to 600 kDa. Any whole number integer within any of the above ranges is contemplated as an embodiment of the disclosure.

In some embodiments, the serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugate has a molecular weight of between 500 kDa and 10,000 kDa. In other embodiments, the serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugate has a molecular weight of between 1,000 kDa and 8,000 kDa. In still other embodiments, the serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugate has a molecular weight of between 2,000 kDa and 8,000 kDa or between 3,000 kDa and 7,000 kDa. In further embodiments, the serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa.

In further embodiments, the serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa.

In further embodiments, the serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate is measured by SEC-MALLS. Any whole number integer within any of the above ranges is contemplated as an embodiment of the disclosure.

Another way to characterize the serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugate of the invention is by the number of lysine residues in the carrier protein (e.g., $CRM_{197}$) that become conjugated to the saccharides which can be characterized as a range of conjugated lysines (degree of conjugation). The evidence for lysine modification of the carrier protein, due to covalent linkages to the saccharides, can be obtained by amino acid analysis using routine methods known to those of skill in the art. Conjugation results in a reduction in the number of lysine residues recovered compared to the carrier protein starting material (e.g. $CRM_{197}$) used to generate the conjugate materials. In a preferred embodiment, the degree of conjugation of the serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugate of the invention is about 2, about 3, about 4, about 5, about 6, about 7, about 8, about 9, about 10, about 11, about 12, about 13, about 14 or about 15. In a preferred embodiment, the degree of conjugation of the serotypes 8/15A/15B/23A/23B glycoconjugate of the invention is between 4 and 7. In some such embodiments, the carrier protein is $CRM_{197}$. In other such embodiments, the carrier protein is DT. In other such embodiments, the carrier protein is TT. In other such embodiments, the carrier protein is PD.

The serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugate of the invention may also be characterized by the ratio (weight/weight) of saccharide to carrier protein. In some embodiments, the ratio of saccharides to carrier protein in the glycoconjugate (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of saccharides to carrier protein in the conjugate is between 0.9 and 1.1. In some such embodiments, the carrier protein is $CRM_{197}$. In other such embodiments, the carrier protein is DT. In other such embodiments, the carrier protein is TT. In other such embodiments, the carrier protein is PD.

The serotypes 8/15A/15B/23A/23B, 8/15A/15B/23A, 8/15A/15B/23B, 8/15A/23A/23B, 8/15A/15B, 8/15A/23A, 8/15A/23B or 8/15A glycoconjugate of the invention may also be characterized by the ratio (weight/weight) of serotype 8 saccharide to serotype 15A saccharide in the glycoconjugate. In some embodiments, the ratio of serotype 8 saccharide to serotype 15A saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 8 saccharide to serotype 15A saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 8 saccharide to serotype 15A saccharide ratio (w/w) is between 0.8 and 1.2. In a preferred embodiment, the ratio of serotype 8 saccharide to serotype 15A saccharide in the conjugate is between 0.9 and 1.1, even more preferably the ratio of serotype 8 saccharide to serotype 15A saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/15A/15B/23A/23B, 8/15A/15B/23A, 8/15A/15B/23B, 8/15B/23A/23B, 8/15A/15B, 8/15B/23A, 8/15B/23B or 8/15B glycoconjugate of the invention may also be characterized by the ratio (weight/weight) of serotype 8 saccharide to serotype 15B saccharide in the glycoconjugate. In some embodiments, the ratio of serotype 8 saccharide to serotype 15B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 8 saccharide to serotype 15B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 8 saccharide to serotype 15B saccharide ratio (w/w) is between 0.8 and 1.2. In a preferred embodiment, the ratio of serotype 8 saccharide to serotype 15B saccharide in the conjugate is between 0.9 and 1.1, even more preferably the ratio of serotype 8 saccharide to serotype 15B saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/15A/15B/23A/23B, 8/15A/15B/23A, 8/15A/23A/23B, 8/15B/23A/23B, 8/15A/23A, 8/15B/23A, 8/23A/23B or 8/23A glycoconjugate of the invention may also be characterized by the ratio (weight/weight) of serotype 8 saccharide to serotype 23A saccharide in the glycoconjugate. In some embodiments, the ratio of serotype 8 saccharide to serotype 23A saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 8 saccharide to serotype 23A saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 8 saccharide to serotype 23A saccharide ratio (w/w) is between 0.8 and 1.2. In a preferred embodiment, the ratio of serotype 8 saccharide to serotype 23A saccharide in the conjugate is between 0.9 and 1.1, even more preferably the ratio of serotype 8 saccharide to serotype 23A saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/15A/15B/23A/23B, 8/15A/15B/23B, 8/15A/23A/23B, 8/15B/23A/23B, 8/15A/23B, 8/15B/23B, 8/23A/23B or 8/23B glycoconjugate of the invention may also be characterized by the ratio (weight/weight) of serotype 8 saccharide to serotype 23B saccharide in the glycoconjugate. In some embodiments, the ratio of serotype 8 saccharide to serotype 23B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 8 saccharide to serotype 23B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 8 saccharide to serotype 23B saccharide ratio (w/w) is between 0.8 and 1.2. In a preferred embodiment, the ratio of serotype 8 saccharide to serotype 23B saccharide in the conjugate is between 0.9 and 1.1, even more preferably the ratio of serotype 8 saccharide to serotype 23B saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/15A/15B/23A/23B, 8/15A/15B/23A, 8/15A/15B/23B, 15A/15B/23A/23B, 8/15A/15B, 15A/15B/23A, 15A/15B/23B or 15A/15B glycoconjugate of the invention may also be characterized by the ratio (weight/weight) of serotype 15A saccharide to serotype 15B saccharide in the glycoconjugate. In some embodiments, the ratio of serotype 15A saccharide to serotype 15B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 15A saccharide to serotype 15B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 15A saccharide to serotype 15B saccharide ratio (w/w) is between 0.8 and 1.2. In a preferred embodiment, the ratio of serotype 15A saccharide to serotype 15B saccharide in the conjugate is between 0.9 and 1.1, even more preferably the ratio of serotype 15A saccharide to serotype 15B saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/15A/15B/23A/23B, 8/15A/15B/23A, 8/15A/23A/23B, 15A/15B/23A/23B, 8/15A/23A, 15A/15B/23A, 15A/23A/23B or 15A/23A glycoconjugate of the invention may also be characterized by the ratio (weight/weight) of serotype 15A saccharide to serotype 23A saccharide in the glycoconjugate. In some embodiments, the ratio of serotype 15A saccharide to serotype 23A saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 15A saccharide to serotype 23A saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 15A saccharide to serotype 23A saccharide ratio (w/w) is between 0.8 and 1.2. In a preferred embodiment, the ratio of serotype 15A saccharide to serotype 23A saccharide in the conjugate is between 0.9 and 1.1, even more preferably the ratio of serotype 15A saccharide to serotype 23A saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/15A/15B/23A/23B, 8/15A/15B/23B, 8/15A/23A/23B, 15A/15B/23A/23B, 8/15A/23B, 15A/15B/23B, 15A/23A/23B or 15A/23B glycoconjugate of the invention may also be characterized by the ratio (weight/weight) of serotype 15A saccharide to serotype 23B saccharide in the glycoconjugate. In some embodiments, the ratio of serotype 15A saccharide to serotype 23B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 15A saccharide to serotype 23B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 15A saccharide to serotype 23B saccharide ratio (w/w) is between 0.8 and 1.2. In a preferred embodiment, the ratio of serotype 15A saccharide to serotype 23B saccharide in the conjugate is between 0.9 and 1.1, even more preferably the ratio of serotype 15A saccharide to serotype 23B saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/15A/15B/23A/23B, 8/15A/15B/23A, 8/15B/23A/23B, 15A/15B/23A/23B, 8/15B/23A, 15A/15B/23A, 15B/23A/23B or 15B/23A glycoconjugate of the invention may also be characterized by the ratio (weight/weight) of serotype 15B saccharide to serotype 23A saccharide in the glycoconjugate. In some embodiments, the ratio of serotype 15B saccharide to serotype 23A saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 15B saccharide to serotype 23A saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 15B saccharide to serotype 23A saccharide ratio (w/w) is between 0.8 and 1.2. In a preferred embodiment, the ratio of serotype 15B saccharide to serotype 23A saccharide in the conjugate is between 0.9 and 1.1, even more preferably the ratio of serotype 15B saccharide to serotype 23A saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/15A/15B/23A/23B, 8/15A/15B/23B, 8/15B/23A/23B, 15A/15B/23A/23B, 8/15B/23B, 15A/15B/23B, 15B/23A/23B or 15B/23B glycoconjugate of the invention may also be characterized by the ratio (weight/weight) of serotype 15B saccharide to serotype 23B saccharide in the glycoconjugate. In some embodiments, the ratio of serotype 15B saccharide to serotype 23B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 15B saccharide to serotype 23B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 15B saccharide to serotype 23B saccharide ratio (w/w) is between 0.8 and 1.2. In a preferred embodiment, the ratio of serotype 15B saccharide to serotype 23B saccharide in the conjugate is between 0.9 and 1.1, even more preferably the ratio of serotype 15B saccharide to serotype 23B saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/15A/15B/23A/23B, 8/15A/23A/23B, 8/15B/23A/23B, 15A/15B/23A/23B, 8/23A/23B, 15A/23A/23B, 15B/23A/23B or 23A/23B glycoconjugate of the invention may also be characterized by the ratio (weight/weight) of serotype 23A saccharide to serotype 23B saccharide in the glycoconjugate. In some embodiments, the ratio of serotype 23A saccharide to serotype 23B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 23A saccharide to serotype 23B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 23A saccharide to serotype 23B saccharide ratio (w/w) is between 0.8 and 1.2. In a preferred embodiment, the ratio of serotype 23A saccharide to serotype 23B saccharide in the conjugate is between 0.9 and 1.1, even more preferably the ratio of serotype 23A saccharide to serotype 23B saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/15A/15B/23A/23B, 8/15A/15B/23A, 8/15A/15B/23B, or 8/15A/15B glycoconjugate of the invention may also be characterized by the relative proportion (weight/weight) of serotypes 8 saccharide, serotypes 15A saccharide and serotype 15B saccharide in the glycoconjugate. In some embodiments, the relative proportion of serotype 8 saccharide, serotype 15A saccharide and serotype 15B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 15B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 8 saccharide, serotypes 15A saccharide and serotype 15B saccharide in the glycoconjugate, for example column a is to be read as: in an embodiment the relative proportion of serotype 8 saccharide, serotype 15A saccharide and serotype 15B saccharide in the serotypes 8/15A/15B/23A/23B, 8/15A/15B/23A, 8/15A/15B/23B, or 8/15A/15B glycoconjugate is respectively about 1:about 1:about 4 (about one 8 saccharide for about one 15A saccharide and for about four 15B saccharide (w/w)). Preferably, the mass of serotype 8 saccharide, serotype 15A saccharide and serotype 15B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/15A/15B/23A/23B, 8/15A/15B/23A, 8/15A/23A/23B, or 8/15A/23A glycoconjugate of the invention may also be characterized by the relative proportion (weight/weight) of serotypes 8 saccharide, serotypes 15A saccharide and serotype 23A saccharide in the glycoconjugate. In some embodiments, the relative proportion of serotype 8 saccharide, serotype 15A saccharide and serotype 23A saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 23A | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 8 saccharide, serotypes 15A saccharide and serotype 23A saccharide in the glycoconjugate, for example column a is to be read as: in an embodiment the relative proportion of serotype 8 saccharide, serotype 15A saccharide and serotype 23A saccharide in the serotypes 88/15A/15B/23A/23B, 8/15A/15B/23A, 8/15A/23A/23B, or 8/15A/23A glycoconjugate is respectively about 1:about 1:about 4 (about one 8 saccharide for about one 15A saccharide and for about four 23A saccharide (w/w)). Preferably, the mass of serotype 8 saccharide, serotype 15A saccharide and serotype 23A saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/15A/15B/23A/23B, 8/15A/15B/23B, 8/15A/23A/23B or 8/15A/23B glycoconjugate of the invention may also be characterized by the relative proportion (weight/weight) of serotypes 8 saccharide, serotypes 15A saccharide and serotype 23B saccharide in the glycoconjugate. In some embodiments, the relative proportion of serotype 8 saccharide, serotype 15A saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 8 saccharide, serotypes 15A saccharide and serotype 23B saccharide in the glycoconjugate, for example column a is to be read as: in an embodiment the relative proportion of serotype 8 saccharide, serotype 15A saccharide and serotype 23B saccharide in the serotypes 8/15A/15B/23A/23B, 8/15A/15B/23B, 8/15A/23A/23B or 8/15A/23B glycoconjugate is respectively about 1:about 1:about 4 (about one 8 saccharide for about one 15A saccharide and for about four 23B saccharide (w/w)). Preferably, the mass of serotype 8 saccharide, serotype 15A saccharide and serotype 23B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/15A/15B/23A/23B, 8/15A/15B/23A, 8/15B/23A/23B or 8/15B/23A glycoconjugate of the invention may also be characterized by the relative proportion (weight/weight) of serotypes 8 saccharide, serotypes 15B saccharide and serotype 23A saccharide in the glycoconjugate. In some embodiments, the relative proportion of serotype 8 saccharide, serotype 15B saccharide and serotype 23A saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 15B | 1 | 1 | 1 | 1 | 1 | 1 | 1 | 1 | 1 | 2 | 2 | 2 | 2 | 2 | 4 | 4 | 4 | 4 | 4 |
| 23A | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 8 saccharide, serotypes 15B saccharide and serotype 23A saccharide in the glycoconjugate, for example column a is to be read as: in an embodiment the relative proportion of serotype 8 saccharide, serotype 15B saccharide and serotype 23A saccharide in the serotypes 8/15A/15B/23A/23B, 8/15A/15B/23A, 8/15B/23A/23B or 8/15B/23A glycoconjugate is respectively about 1:about 1:about 4 (about one 8 saccharide for about one 15B saccharide and for about four 23A saccharide (w/w)). Preferably, the mass of serotype 8 saccharide, serotype 15B saccharide and serotype 23A saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/15A/15B/23A/23B, 8/15A/15B/23B, 8/15B/23A/23B or 8/15B/23B glycoconjugate of the invention may also be characterized by the relative proportion (weight/weight) of serotypes 8 saccharide, serotypes 15B saccharide and serotype 23B saccharide in the glycoconjugate. In some embodiments, the relative proportion of serotype 8 saccharide, serotype 15B saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 15B | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 8 saccharide, serotypes 15B saccharide and serotype 23B saccharide in the glycoconjugate, for example column a is to be read as: in an embodiment the relative proportion of serotype 8 saccharide, serotype 15B saccharide and serotype 23B saccharide in the serotypes 8/15A/15B/23A/23B, 8/15A/15B/23B, 8/15B/23A/23B or 8/15B/23B glycoconjugate is respectively about 1:about 1:about 4 (about one 8 saccharide for about one 15B saccharide and for about four 23B saccharide (w/w)). Preferably, the mass of serotype 8 saccharide, serotype 15B saccharide and serotype 23B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/15A/15B/23A/23B, 8/15A/23A/23B, 8/15B/23A/23B or 8/23A/23B glycoconjugate of the invention may also be characterized by the relative proportion (weight/weight) of serotypes 8 saccharide, serotypes 23A saccharide and serotype 23B saccharide in the glycoconjugate. In some embodiments, the relative proportion of serotype 8 saccharide, serotype 23A saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 23A | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 8 saccharide, serotypes 23A saccharide and serotype 23B saccharide in the glycoconjugate, for example column a is to be read as: in an embodiment the relative proportion of serotype 8 saccharide, serotype 23A saccharide and serotype 23B saccharide in the serotypes 8/15A/15B/23A/23B, 8/15A/23A/23B, 8/15B/23A/23B or 8/23A/23B glycoconjugate is respectively about 1:about 1:about 4 (about one 8 saccharide for about one 23A saccharide and for about four 23B saccharide (w/w)). Preferably, the mass of serotype 8 saccharide, serotype 23A saccharide and serotype 23B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/15A/15B/23A/23B, 8/15A/15B/23A, 15A/15B/23A/23B or 15A/15B/23A glycoconjugate of the invention may also be characterized by the relative proportion (weight/weight) of serotypes 15A saccharide, serotypes 15B saccharide and serotype 23A saccharide in the glycoconjugate. In some embodiments, the relative proportion of serotype 15A saccharide, serotype 15B saccharide and serotype 23A saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 15A | 1 | 1 | 1 | 2 | 2 | 2 | 4 | 4 | 4 | 1 | 1 | 1 | 2 | 4 | 1 | 1 | 1 | 2 | 4 |
| 15B | 1 | 1 | 1 | 1 | 1 | 1 | 1 | 1 | 1 | 2 | 2 | 2 | 2 | 2 | 4 | 4 | 4 | 4 | 4 |
| 23A | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 15A saccharide, serotypes 15B saccharide and serotype 23A saccharide in the glycoconjugate, for example column a is to be read as: in an embodiment the relative proportion of serotype 15A saccharide, serotype 15B saccharide and serotype 23A saccharide in the serotypes 8/15A/15B/23A/23B, 8/15A/15B/23A, 15A/15B/23A/23B or 15A/15B/23A glycoconjugate is respectively about 1:about 1:about 4 (about one 15A saccharide for about one 15B saccharide and for about four 23A saccharide (w/w)). Preferably, the mass of serotype 15A saccharide, serotype 15B saccharide and serotype 23A saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/15A/15B/23A/23B, 8/15A/15B/23B, 15A/15B/23A/23B or 15A/15B/23B glycoconjugate of the invention may also be characterized by the relative proportion (weight/weight) of serotypes 15A saccharide, serotypes 15B saccharide and serotype 23B saccharide in the glycoconjugate. In some embodiments, the relative proportion of serotype 15A saccharide, serotype 15B saccharide and serotype 23B saccharide in the glycoconjugate (w/w) is according to any of the one of the below table:

| | Relative proportion in the glycoconjugate | | | | | | | | | | | | | | | | | |
|---|---|---|---|---|---|---|---|---|---|---|---|---|---|---|---|---|---|---|
| | a | b | c | d | e | f | g | h | i | j | k | l | m | n | o | p | q | r | s |
| 15A | 1 | 1 | 1 | 2 | 2 | 2 | 4 | 4 | 4 | 1 | 1 | 1 | 2 | 4 | 1 | 1 | 1 | 2 | 4 |
| 15B | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 15A saccharide, serotypes 15B saccharide and serotype 23B saccharide in the glycoconjugate, for example column a is to be read as: in an embodiment the relative proportion of serotype 15A saccharide, serotype 15B saccharide and serotype 23B saccharide in the serotypes 8/15A/15B/23A/23B, 8/15A/15B/23B, 15A/15B/23A/23B or 15A/15B/23B glycoconjugate is respectively about 1:about 1:about 4 (about one 15A saccharide for about one 15B saccharide and for about four 23B saccharide (w/w)). Preferably, the mass of serotype 15A saccharide, serotype 15B saccharide and serotype 23B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/15A/15B/23A/23B, 8/15A/23A/23B, 15A/15B/23A/23B or 15A/23A/23B glycoconjugate of the invention may also be characterized by the relative proportion (weight/weight) of serotypes 15A saccharide, serotypes 23A saccharide and serotype 23B saccharide in the glycoconjugate. In some embodiments, the relative proportion of serotype 15A saccharide, serotype 23A saccharide and serotype 23B saccharide in the glycoconjugate (w/w) is according to any of the one of the below table:

| | Relative proportion in the glycoconjugate | | | | | | | | | | | | | | | | | |
|---|---|---|---|---|---|---|---|---|---|---|---|---|---|---|---|---|---|---|
| | a | b | c | d | E | f | g | h | i | j | k | l | m | n | o | p | q | r | s |
| 15A | 1 | 1 | 1 | 2 | 2 | 2 | 4 | 4 | 4 | 1 | 1 | 1 | 2 | 4 | 1 | 1 | 1 | 2 | 4 |
| 23A | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 15A saccharide, serotypes 23A saccharide and serotype 23B saccharide in the glycoconjugate, for example column a is to be read as: in an embodiment the relative proportion of serotype 15A saccharide, serotype 23A saccharide and serotype 23B saccharide in the serotypes 8/15A/15B/23A/23B, 8/15A/23A/23B, 15A/15B/23A/23B or 15A/23A/23B glycoconjugate is respectively about 1:about 1:about 4 (about one 15A saccharide for about one 23A saccharide and for about four 23B saccharide (w/w)). Preferably, the mass of serotype 15A saccharide, serotype 15B saccharide and serotype 23B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/15A/15B/23A/23B, 8/15B/23A/23B, 15A/15B/23A/23B or 15B/23A/23B glycoconjugate of the invention may also be characterized by the relative proportion (weight/weight) of serotypes 15B saccharide, serotypes 23A saccharide and serotype 23B saccharide in the glycoconjugate. In some embodiments, the relative proportion of serotype 15B saccharide, serotype 23A saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 15B | 1 | 1 | 1 | 2 | 2 | 2 | 4 | 4 | 4 | 1 | 1 | 1 | 2 | 4 | 1 | 1 | 1 | 2 | 4 |
| 23A | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 15B saccharide, serotypes 23A saccharide and serotype 23B saccharide in the glycoconjugate, for example column a is to be read as: in an embodiment the relative proportion of serotype 15B saccharide, serotype 23A saccharide and serotype 23B saccharide in the serotypes 8/15A/15B/23A/23B, 8/15B/23A/23B, 15A/15B/23A/23B or 15B/23A/23B glycoconjugate is respectively about 1:about 1:about 4 (about one 15B saccharide for about one 23A saccharide and for about four 23B saccharide (w/w)). Preferably, the mass of serotype 15B saccharide, serotype 15B saccharide and serotype 23B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/15A/15B/23A/23B or 8/15A/15B/23A glycoconjugate of the invention may also be characterized by the relative proportion (weight/weight) of serotypes 8 saccharide, serotypes 15A saccharide, serotype 15B saccharide and serotype 23A saccharide in the glycoconjugate. In some embodiments, the relative proportion of serotype 8 saccharide, serotype 15A saccharide, serotype 15B saccharide and serotype 23A saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 15A | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 15B | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23A | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 15B | 2 | 2 | 2 | 2 | 2 | 2 | 2 | 2 | 2 | 2 | 2 | 2 | 2 | 2 | 2 | 2 | 2 | 2 | 2 |
| 23A | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 15B | 4 | 4 | 4 | 4 | 4 | 4 | 4 | 4 | 4 | 4 | 4 | 4 | 4 | 4 | 4 | 4 | 4 | 4 | 4 |
| 23A | 1 | 2 | 4 | 1 | 2 | 4 | 1 | 2 | 4 | 1 | 2 | 4 | 1 | 1 | 1 | 2 | 4 | 1 | 1 |

Each column a to bm of the above tables provides the relative proportion of serotype 8 saccharide, serotype 15A saccharide, serotype 15B saccharide and serotype 23A saccharide in the glycoconjugate, for example column a is to be read as: in an embodiment the relative proportion of serotype 8 saccharide, serotype 15A saccharide, serotype 15B saccharide and serotype 23A saccharide in the serotypes 8/15A/15B/23A/23B or 8/15A/15B/23A glycoconjugate is respectively about 1:about 1:about 1:about 1 (about one 8 saccharide, for about one 15A saccharide, for about one 15B and for about one 23A saccharide (w/w)). Preferably, the mass of serotype 8 saccharide, serotype 15A saccharide, serotype 15B and serotype 23A saccharide in the serotypes 8/15A/15B/23A/23B or 8/15A/15B/23A glycoconjugate is about the same for each saccharide (ratio of about 1:1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/15A/15B/23A/23B or 8/15A/15B/23B glycoconjugate of the invention may also be characterized by the relative proportion (weight/weight) of serotypes 8 saccharide, serotypes 15A saccharide, serotype 15B saccharide and serotype 23B saccharide in the glycoconjugate. In some embodiments, the relative proportion of serotype 8 saccharide, serotype 15A saccharide, serotype 15B saccharide and serotype 23B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 15A | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 15B | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 15B | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 15B | 4 | 4 | 4 | 4 | 4 | 4 | 4 | 4 | 4 | 4 | 4 | 4 | 4 | 4 | 4 | 4 | 4 | 4 | 4 |
| 23B | 1 | 2 | 4 | 1 | 2 | 4 | 1 | 2 | 4 | 1 | 2 | 4 | 1 | 1 | 1 | 2 | 4 | 1 | 1 |

Each column a to bm of the above tables provides the relative proportion of serotype 8 saccharide, serotype 15A saccharide, serotype 15B saccharide and serotype 23B saccharide in the glycoconjugate, for example column a is to be read as: in an embodiment the relative proportion of serotype 8 saccharide, serotype 15A saccharide, serotype 15B saccharide and serotype 23B saccharide in the serotypes 8/15A/15B/23A/23B or 8/15A/15B/23B glycoconjugate is respectively about 1:about 1:about 1:about 1 (about one 8 saccharide, for about one 15A saccharide, for about one 15B and for about one 23B saccharide (w/w)). Preferably, the mass of serotype 8 saccharide, serotype 15A saccharide, serotype 15B and serotype 23B saccharide in the serotypes 8/15A/15B/23A/23B or 8/15A/15B/23B glycoconjugate is about the same for each saccharide (ratio of about 1:1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/15A/15B/23A/23B or 8/15A/23A/23B glycoconjugate of the invention may also be characterized by the relative proportion (weight/weight) of serotypes 8 saccharide, serotypes 15A saccharide, serotype 23A saccharide and serotype 23B saccharide in the glycoconjugate. In some embodiments, the relative proportion of serotype 8 saccharide, serotype 15A saccharide, serotype 23A saccharide and serotype 23B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 15A | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 23A | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 23A | 4 | 4 | 4 | 4 | 4 | 4 | 4 | 4 | 4 | 4 | 4 | 4 | 4 | 4 | 4 | 4 | 4 | 4 | 4 |
| 23B | 1 | 2 | 4 | 1 | 2 | 4 | 1 | 2 | 4 | 1 | 2 | 4 | 1 | 1 | 1 | 2 | 4 | 1 | 1 |

Each column a to bm of the above tables provides the relative proportion of serotype 8 saccharide, serotype 15A saccharide, serotype 23A saccharide and serotype 23B saccharide in the glycoconjugate, for example column a is to be read as: in an embodiment the relative proportion of serotype 8 saccharide, serotype 15A saccharide, serotype 23A saccharide and serotype 23B saccharide in the serotypes 8/15A/15B/23A/23B or 8/15A/23A/23B glycoconjugate is respectively about 1:about 1:about 1:about 1 (about one 8 saccharide, for about one 15A saccharide, for about one 23A and for about one 23B saccharide (w/w)). Preferably, the mass of serotype 8 saccharide, serotype 15A saccharide, serotype 23A and serotype 23B saccharide in the serotypes 8/15A/15B/23A/23B or 8/15A/23A/23B glycoconjugate is about the same for each saccharide (ratio of about 1:1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/15A/15B/23A/23B or 8/15B/23A/23B glycoconjugate of the invention may also be characterized by the relative proportion (weight/weight) of serotypes 8 saccharide, serotypes 15B saccharide, serotype 23A saccharide and serotype 23B saccharide in the glycoconjugate. In some embodiments, the relative proportion of serotype 8 saccharide, serotype 15B saccharide, serotype 23A saccharide and serotype 23B saccharide in the glycoconjugate (w/w) is according to any of the one of the below tables:

Each column a to bm of the above tables provides the relative proportion of serotype 8 saccharide, serotype 15B saccharide, serotype 23A saccharide and serotype 23B saccharide in the glycoconjugate, for example column a is to be read as: in an embodiment the relative proportion of serotype 8 saccharide, serotype 15B saccharide, serotype 23A saccharide and serotype 23B saccharide in the serotypes 8/15A/15B/23A/23B or 8/15B/23A/23B glycoconjugate is respectively about 1:about 1:about 1:about 1 (about one 8 saccharide, for about one 15B saccharide, for about one 23A and for about one 23B saccharide (w/w)). Preferably, the mass of serotype 8 saccharide, serotype 15B saccharide, serotype 23A and serotype 23B saccharide in the serotypes 8/15A/15B/23A/23B or 8/15B/23A/23B glycoconjugate is about the same for each saccharide (ratio of about 1:1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/15A/15B/23A/23B or 15A/15B/23A/23B glycoconjugate of the invention may also be characterized by the relative proportion (weight/weight) of serotypes 15A saccharide, serotypes 15B saccharide, serotype 23A saccharide and serotype 23B saccharide in the glycoconjugate. In some embodiments, the relative proportion of serotype 15A saccharide, serotype 15B saccharide, serotype 23A saccharide and serotype 23B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 15B | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 15B | 1 | 1 | 1 | 1 | 1 | 1 | 1 | 1 | 1 | 2 | 2 | 2 | 2 | 2 | 4 | 4 | 4 | 4 | 4 |
| 23A | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 15B | 1 | 1 | 1 | 1 | 1 | 1 | 1 | 1 | 1 | 2 | 2 | 2 | 2 | 2 | 4 | 4 | 4 | 4 | 4 |
| 23A | 4 | 4 | 4 | 4 | 4 | 4 | 4 | 4 | 4 | 4 | 4 | 4 | 4 | 4 | 4 | 4 | 4 | 4 | 4 |
| 23B | 1 | 2 | 4 | 1 | 2 | 4 | 1 | 2 | 4 | 1 | 2 | 4 | 1 | 1 | 1 | 2 | 4 | 1 | 1 |

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 15A | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 15B | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 15A | 1 | 1 | 1 | 2 | 2 | 2 | 4 | 4 | 4 | 1 | 1 | 1 | 2 | 4 | 1 | 1 | 1 | 2 | 4 |
| 15B | 1 | 1 | 1 | 1 | 1 | 1 | 1 | 1 | 1 | 2 | 2 | 2 | 2 | 2 | 4 | 4 | 4 | 4 | 4 |
| 23A | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 15A | 1 | 1 | 1 | 2 | 2 | 2 | 4 | 4 | 4 | 1 | 1 | 1 | 2 | 4 | 1 | 1 | 1 | 2 | 4 |
| 15B | 1 | 1 | 1 | 1 | 1 | 1 | 1 | 1 | 1 | 2 | 2 | 2 | 2 | 2 | 4 | 4 | 4 | 4 | 4 |
| 23A | 4 | 4 | 4 | 4 | 4 | 4 | 4 | 4 | 4 | 4 | 4 | 4 | 4 | 4 | 4 | 4 | 4 | 4 | 4 |
| 23B | 1 | 2 | 4 | 1 | 2 | 4 | 1 | 2 | 4 | 1 | 2 | 4 | 1 | 1 | 1 | 2 | 4 | 1 | 1 |

Each column a to bm of the above tables provides the relative proportion of serotype 15A saccharide, serotype 15B saccharide, serotype 23A saccharide and serotype 23B saccharide in the glycoconjugate, for example column a is to be read as: in an embodiment the relative proportion of serotype 15A saccharide, serotype 15B saccharide, serotype 23A saccharide and serotype 23B saccharide in the serotypes 8/15A/15B/23A/23B or 15A/15B/23A/23B glycoconjugate is respectively about 1:about 1:about 1:about 1 (about one 8 saccharide, for about one 15B saccharide, for about one 23A and for about one 23B saccharide (w/w)). Preferably, the mass of serotype 15A saccharide, serotype 15B saccharide, serotype 23A and serotype 23B saccharide in the serotypes 8/15A/15B/23A/23B or 15A/15B/23A/23B glycoconjugate is about the same for each saccharide (ratio of about 1:1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/15A/15B/23A/23B glycoconjugate of the invention may also be characterized by the relative proportion (weight/weight) of serotype 8 saccharide, serotype 15A saccharide, serotype 15B saccharide, serotype 23A saccharide and serotype 23B saccharide in the glycoconjugate. In some embodiments, the relative proportion of serotype 8 saccharide, serotype 15A saccharide, serotype 15B saccharide, serotype 23A saccharide and serotype 23B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 15A | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 15B | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at | au |
|---|---|---|---|---|---|---|---|---|---|---|---|---|---|---|---|---|---|---|---|---|
| 8 | 1 | 1 | 1 | 1 | 1 | 1 | 1 | 1 | 1 | 1 | 1 | 1 | 1 | 1 | 1 | 1 | 1 | 1 | 1 | 1 |
| 15A | 1 | 1 | 1 | 2 | 2 | 2 | 4 | 4 | 4 | 1 | 1 | 1 | 2 | 2 | 2 | 4 | 4 | 4 | 1 | 1 |
| 15B | 1 | 1 | 1 | 1 | 1 | 1 | 1 | 1 | 1 | 2 | 2 | 2 | 2 | 2 | 2 | 2 | 2 | 2 | 4 | 4 |
| 23A | 2 | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 2 | 4 | 1 | 2 | 4 | 1 | 2 |

| | av | aw | ax | ay | az | ba | bb | bc | bd | be | bf | bg | bh | bi | bj | bk | bl | bm | bn |
|---|---|---|---|---|---|---|---|---|---|---|---|---|---|---|---|---|---|---|---|
| 8 | 1 | 1 | 1 | 1 | 1 | 1 | 1 | 1 | 1 | 1 | 1 | 1 | 1 | 1 | 1 | 1 | 1 | 1 | 1 |
| 15A | 1 | 2 | 2 | 2 | 4 | 4 | 4 | 1 | 1 | 1 | 2 | 2 | 2 | 4 | 4 | 4 | 1 | 1 | 1 |
| 15B | 4 | 4 | 4 | 4 | 4 | 4 | 4 | 1 | 1 | 1 | 1 | 1 | 1 | 1 | 1 | 1 | 2 | 2 | 2 |
| 23A | 2 | 2 | 2 | 2 | 2 | 2 | 2 | 4 | 4 | 4 | 4 | 4 | 4 | 4 | 4 | 4 | 4 | 4 | 4 |
| 23B | 4 | 1 | 2 | 4 | 1 | 2 | 4 | 1 | 2 | 4 | 1 | 2 | 4 | 1 | 2 | 4 | 1 | 2 | 4 |

| | bo | bp | bq | br | bs | bt | bu | bv | bw | bx | by | bz | ca | cb | cd | ce | cf | cg | ch | ci |
|---|---|---|---|---|---|---|---|---|---|---|---|---|---|---|---|---|---|---|---|---|
| 8 | 1 | 1 | 1 | 1 | 1 | 1 | 1 | 1 | 1 | 1 | 1 | 1 | 1 | 1 | 1 | 2 | 2 | 2 | 2 | 2 |
| 15A | 2 | 2 | 2 | 4 | 4 | 4 | 1 | 1 | 1 | 2 | 2 | 2 | 4 | 4 | 4 | 1 | 1 | 1 | 2 | 2 |
| 15B | 2 | 2 | 2 | 2 | 2 | 2 | 4 | 4 | 4 | 4 | 4 | 4 | 4 | 4 | 4 | 1 | 1 | 1 | 1 | 1 |
| 23A | 4 | 4 | 4 | 4 | 4 | 4 | 4 | 4 | 4 | 4 | 4 | 4 | 4 | 4 | 4 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 |

| | cj | ck | cl | cm | en | co | cp | eq | cr | cs | ct | cu | cv | cw | cx | cy | cz | da |
|---|---|---|---|---|---|---|---|---|---|---|---|---|---|---|---|---|---|---|
| 8 | 2 | 2 | 2 | 2 | 2 | 2 | 2 | 2 | 2 | 2 | 2 | 2 | 2 | 2 | 2 | 2 | 2 | 2 |
| 15A | 2 | 4 | 4 | 4 | 1 | 1 | 1 | 2 | 2 | 2 | 4 | 4 | 4 | 1 | 1 | 1 | 2 | 2 |
| 15B | 1 | 1 | 1 | 1 | 2 | 2 | 2 | 2 | 2 | 2 | 2 | 2 | 2 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 |
| 23B | 4 | 1 | 2 | 4 | 1 | 2 | 4 | 1 | 2 | 4 | 1 | 2 | 4 | 1 | 2 | 4 | 1 | 2 |

| | db | dc | dd | de | df | dg | dh | di | dj | dk | dl | dm | dn | do | dp | dq | dr | ds | dt |
|---|---|---|---|---|---|---|---|---|---|---|---|---|---|---|---|---|---|---|---|
| 8 | 2 | 2 | 2 | 2 | 2 | 2 | 2 | 2 | 2 | 2 | 2 | 2 | 2 | 2 | 2 | 2 | 2 | 2 | 2 |
| 15A | 2 | 4 | 4 | 4 | 1 | 1 | 1 | 2 | 2 | 2 | 4 | 4 | 4 | 1 | 1 | 1 | 2 | 4 | 1 |
| 15B | 4 | 4 | 4 | 4 | 1 | 1 | 1 | 1 | 1 | 1 | 1 | 1 | 1 | 2 | 2 | 2 | 2 | 2 | 4 |
| 23A | 1 | 1 | 1 | 1 | 2 | 2 | 2 | 2 | 2 | 2 | 2 | 2 | 2 | 2 | 2 | 2 | 2 | 2 | 2 |
| 23B | 4 | 1 | 2 | 4 | 1 | 2 | 4 | 1 | 2 | 4 | 1 | 2 | 4 | 1 | 2 | 4 | 1 | 1 | 1 |

| | du | dv | dw | dx | dy | dz | ea | eb | ec | ed | ee | ef | eg | eh | ei | ej | ek | el | em | en | eo |
|---|---|---|---|---|---|---|---|---|---|---|---|---|---|---|---|---|---|---|---|---|---|
| 8 | 2 | 2 | 2 | 2 | 2 | 2 | 2 | 2 | 2 | 2 | 2 | 2 | 2 | 2 | 2 | 2 | 2 | 2 | 2 | 2 | 2 |
| 15A | 1 | 1 | 2 | 4 | 1 | 1 | 1 | 2 | 2 | 2 | 4 | 4 | 4 | 1 | 1 | 1 | 2 | 4 | 1 | 1 | 1 |
| 15B | 4 | 4 | 4 | 4 | 1 | 1 | 1 | 1 | 1 | 1 | 1 | 1 | 1 | 2 | 2 | 2 | 2 | 2 | 4 | 4 | 4 |
| 23A | 2 | 2 | 2 | 2 | 4 | 4 | 4 | 4 | 4 | 4 | 4 | 4 | 4 | 4 | 4 | 4 | 4 | 4 | 4 | 4 | 4 |
| 23B | 2 | 4 | 1 | 1 | 1 | 2 | 4 | 1 | 2 | 4 | 1 | 2 | 4 | 1 | 2 | 4 | 1 | 1 | 1 | 2 | 4 |

| | ep | eq | er | es | et | eu | ev | ew | xe | ey | ez | fa | fb | fc | fd | fe | ff | fg | fh | fi | fj | fk |
|---|---|---|---|---|---|---|---|---|---|---|---|---|---|---|---|---|---|---|---|---|---|---|
| 8 | 2 | 2 | 4 | 4 | 4 | 4 | 4 | 4 | 4 | 4 | 4 | 4 | 4 | 4 | 4 | 4 | 4 | 4 | 4 | 4 | 4 | 4 |
| 15A | 2 | 4 | 1 | 1 | 2 | 2 | 2 | 4 | 4 | 4 | 1 | 1 | 1 | 2 | 2 | 2 | 4 | 4 | 4 | 1 | 1 | 1 |
| 15B | 4 | 4 | 1 | 1 | 1 | 1 | 1 | 1 | 1 | 1 | 2 | 2 | 2 | 2 | 2 | 2 | 2 | 2 | 2 | 4 | 4 | 4 |
| 23A | 4 | 4 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 1 | 2 | 4 | 1 | 2 | 4 | 1 | 2 | 4 | 1 | 2 | 4 | 1 | 2 | 4 | 1 | 2 | 4 | 1 | 2 | 4 |

| | fl | fm | fn | fo | fp | fq | fr | fs | ft | fu | fv | fw | fx | fy | fz | ga | gb | gc | gd |
|---|---|---|---|---|---|---|---|---|---|---|---|---|---|---|---|---|---|---|---|
| 8 | 4 | 4 | 4 | 4 | 4 | 4 | 4 | 4 | 4 | 4 | 4 | 4 | 4 | 4 | 4 | 4 | 4 | 4 | 4 |
| 15A | 2 | 2 | 2 | 4 | 4 | 4 | 1 | 1 | 1 | 2 | 2 | 2 | 4 | 4 | 4 | 1 | 1 | 1 | 2 |
| 15B | 4 | 4 | 4 | 4 | 4 | 4 | 1 | 1 | 1 | 1 | 1 | 1 | 1 | 1 | 1 | 2 | 2 | 2 | 2 |
| 23A | 1 | 1 | 1 | 1 | 1 | 1 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 2 | 4 | 1 | 2 | 4 | 1 |

| | ge | gf | gg | gh | gi | gj | gk | gl | gl | gn | go | gp | gq | gr | gs | gt | gu | gv | gw | gx | gy | gz |
|---|---|---|---|---|---|---|---|---|---|---|---|---|---|---|---|---|---|---|---|---|---|---|
| 8 | 4 | 4 | 4 | 4 | 4 | 4 | 4 | 4 | 4 | 4 | 4 | 4 | 4 | 4 | 4 | 4 | 4 | 4 | 4 | 4 | 4 | 4 |
| 15A | 4 | 1 | 1 | 1 | 2 | 4 | 1 | 1 | 1 | 2 | 2 | 2 | 4 | 4 | 4 | 1 | 1 | 1 | 2 | 4 | 1 | 1 |
| 15B | 2 | 4 | 4 | 4 | 4 | 4 | 1 | 1 | 1 | 1 | 1 | 1 | 1 | 1 | 1 | 2 | 2 | 2 | 2 | 2 | 4 | 4 |
| 23A | 2 | 2 | 2 | 2 | 2 | 2 | 4 | 4 | 4 | 4 | 4 | 4 | 4 | 4 | 4 | 4 | 4 | 4 | 4 | 4 | 4 | 4 |
| 23B | 1 | 1 | 2 | 4 | 1 | 1 | 1 | 2 | 4 | 1 | 2 | 4 | 1 | 2 | 4 | 1 | 2 | 4 | 1 | 1 | 1 | 2 |

| | ha | hb | hc |
|---|---|---|---|
| 8 | 4 | 4 | 4 |
| 15A | 1 | 2 | 4 |
| 15B | 4 | 4 | 4 |
| 23A | 4 | 4 | 4 |
| 23B | 4 | 1 | 1 |

Each column a to hc of the above tables provides the relative proportion of serotype 8 saccharide, serotype 15A saccharide, serotype 15B saccharide, serotype 23A saccharide and serotype 23B saccharide in the glycoconjugate, for example column a is to be read as: in an embodiment the relative proportion of serotype 8 saccharide, serotype 15A saccharide, serotype 15B saccharide, serotype 23A saccharide and serotype 23B saccharide in the serotypes 8/15A/15B/23A/23B glycoconjugate is respectively about 1:about 1:about 1:about 1:about 1 (about one 8 saccharide, for about one 15A saccharide, for about one 15B saccharide, for about one 23A and for about one 23B saccharide (w/w)). Preferably, the mass of serotype 8 saccharide, serotype 15A saccharide, serotype 15B saccharide, serotype 23A and serotype 23B saccharide in the serotypes 8/15A/15B/23A/23B glycoconjugate is about the same for each saccharide (ratio of about 1:1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

In an embodiment, the serotypes 8/15A/15B/23A/23B, 8/15A/15B/23A, 8/15A/15B/23B, 8/15A/23A/23B, 15A/15B/23A/23B, 8/15A/15B, 8/15A/23A, 8/15A/23B, 15A/15B/23A, 15A/15B/23B, 15A/23A/23B, 8/15A, 15A/15B, 15A/23A or 15A/23B glycoconjugate of the invention comprises at least 0.1, 0.2, 0.3, 0.4, 0.5, 0.6 or 0.7 or about 0.8 mM acetate per mM serotype 15A saccharide. In a preferred embodiment, the glycoconjugate comprises 0.1 to 1.0 mM acetate per mM serotype 15A saccharide. In a preferred embodiment, the glycoconjugate comprises at least 0.5, 0.6 or 0.7 mM acetate per mM serotype 15A saccharide. In a preferred embodiment, the glycoconjugate comprises at least 0.6 mM acetate per mM serotype 15A saccharide. In a preferred embodiment, the glycoconjugate comprises at least 0.7 mM acetate per mM serotype 15A saccharide. In a preferred embodiment, the presence of O-acetyl groups is determined by ion-HPLC analysis.

In an embodiment, the serotypes 8/15A/15B/23A/23B, 8/15A/15B/23A, 8/15A/15B/23B, 8/15B/23A/23B, 15A/15B/23A/23B, 8/15A/15B, 8/15B/23A, 8/15B/23B, 15A/15B/23A, 15A/15B/23B, 15B/23A/23B, 8/15B, 15A/15B, 15B/23A or 15B/23B glycoconjugate of the invention comprises at least 0.1, 0.2, 0.3, 0.4, 0.5, 0.6 or 0.7 or about 0.8 mM acetate per mM serotype 15B saccharide. In a preferred embodiment, the glycoconjugate comprises 0.1 to 1.0 mM acetate per mM serotype 15B saccharide. In a preferred embodiment, the glycoconjugate comprises at least 0.5, 0.6 or 0.7 mM acetate per mM serotype 15B saccharide. In a preferred embodiment, the glycoconjugate comprises at least 0.6 mM acetate per mM serotype 15B saccharide. In a preferred embodiment, the glycoconjugate comprises at least 0.7 mM acetate per mM serotype 15B saccharide. In a preferred embodiment, the presence of O-acetyl groups is determined by ion-HPLC analysis.

In an embodiment, the serotypes 8/15A/15B/23A/23B, 8/15A/15B/23A, 8/15A/15B/23B, 8/15A/23A/23B, 15A/15B/23A/23B, 8/15A/15B, 8/15A/23A, 8/15A/23B, 15A/15B/23A, 15A/15B/23B, 15A/23A/23B, 8/15A, 15A/15B, 15A/23A or 15A/23B glycoconjugate of the invention comprises at least 0.1, 0.2, 0.3, 0.4, 0.5, 0.6, 0.7 or 0.8 mM glycerol per mM of serotype 15A saccharide. In a preferred embodiment, the glycoconjugate comprises 0.1 to 1.0 mM glycerol per mM serotype 15A saccharide. In a preferred embodiment, the glycoconjugate comprises at least 0.5, 0.6 or 0.7 mM glycerol per mM of serotype 15A saccharide. In a preferred embodiment, the glycoconjugate comprises at least 0.6 mM glycerol per mM of serotype 15A saccharide. In a preferred embodiment, the glycoconjugate comprises at least 0.7 mM glycerol per mM of serotype 15A saccharide.

In an embodiment, the serotypes 8/15A/15B/23A/23B, 8/15A/15B/23A, 8/15A/15B/23B, 8/15B/23A/23B, 15A/15B/23A/23B, 8/15A/15B, 8/15B/23A, 8/15B/23B, 15A/15B/23A, 15A/15B/23B, 15B/23A/23B, 8/15B, 15A/15B, 15B/23A or 15B/23B glycoconjugate of the invention comprises at least 0.1, 0.2, 0.3, 0.4, 0.5, 0.6, 0.7 or 0.8 mM glycerol per mM of serotype 15B saccharide. In a preferred embodiment, the glycoconjugate comprises 0.1 to 1.0 mM glycerol per mM serotype 15B saccharide. In a preferred embodiment, the glycoconjugate comprises at least 0.5, 0.6 or 0.7 mM glycerol per mM of serotype 15B saccharide. In a preferred embodiment, the glycoconjugate comprises at least 0.6 mM glycerol per mM of serotype 15B saccharide. In a preferred embodiment, the glycoconjugate comprises at least 0.7 mM glycerol per mM of serotype 15B saccharide.

In an embodiment, the serotypes 8/15A/15B/23A/23B, 8/15A/15B/23A, 8/15A/23A/23B, 8/15B/23A/23B, 15A/15B/23A/23B, 8/15A/23A, 8/15B/23A, 8/23A/23B, 15A/15B/23A, 15A/23A/23B, 15B/23A/23B, 8/23A, 15A/23A, 15B/23A, or 23A/23B glycoconjugate of the invention comprises at least 0.1, 0.2, 0.3, 0.4, 0.5, 0.6, 0.7 or 0.8 mM glycerol per mM of serotype 23A saccharide. In a preferred embodiment, the glycoconjugate comprises 0.1 to 1.0 mM glycerol per mM serotype 23A saccharide. In a preferred embodiment, the glycoconjugate comprises at least 0.5, 0.6 or 0.7 mM glycerol per mM of serotype 23A saccharide. In a preferred embodiment, the glycoconjugate comprises at least 0.6 mM glycerol per mM of serotype 23A saccharide. In a preferred embodiment, the glycoconjugate comprises at least 0.7 mM glycerol per mM of serotype 23A saccharide.

In some embodiments, the serotypes 8/15A/15B/23A/23B, 8/15A/15B/23B, 8/15A/23A/23B, 8/15B/23A/23B, 15A/15B/23A/23B, 8/15A/23B, 8/15B/23B, 8/23A/23B, 15A/15B/23B, 15A/23A/23B, 15B/23A/23B, 8/23B, 15A/23B, 15B/23B or 23A/23B glycoconjugate of the invention comprises at least 0.1, 0.2, 0.3, 0.4, 0.5, 0.6, 0.7 or 0.8 mM glycerol per mM of serotype 23B saccharide. In a preferred embodiment, the glycoconjugate comprises 0.1 to 1.0 mM glycerol per mM serotype 23B saccharide. In a preferred embodiment, the glycoconjugate comprises at least 0.5, 0.6 or 0.7 mM glycerol per mM of serotype 23B saccharide. In a preferred embodiment, the glycoconjugate comprises at least 0.6 mM glycerol per mM of serotype 23B saccharide. In a preferred embodiment, the glycoconjugate comprises at least 0.7 mM glycerol per mM of serotype 23B saccharide.

The serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d$=0), and the fraction representing the maximum retention ($V_i$), ($K_d$=1). The fraction at which a specified sample attribute is reached ($V_e$), is related to $K_d$ by the expression, $K_d=(V_e-V_0)/(V_i-V_0)$.

In a preferred embodiment, at least 30% of the glycoconjugate has a $K_d$ below or equal to 0.3 in a CL-4B column. In a preferred embodiment, at least 40% of the glycoconjugate has a $K_d$ below or equal to 0.3 in a CL-4B column. In a preferred embodiment, at least 45%, 50%, 55%, 60%, 65%, 70%, 75%, 80%, or 85% of the glycoconjugate has a $K_d$ below or equal to 0.3 in a CL-4B column. In a preferred embodiment, at least 60% of the glycoconjugate has a $K_d$ below or equal to 0.3 in a CL-4B column. In a preferred embodiment, between 50% and 80% of the glycoconjugate has a $K_d$ below or equal to 0.3 in a CL-4B column. In a preferred embodiment, between 65% and 80% of the glycoconjugate has a $K_d$ below or equal to 0.3 in a CL-4B column.

The serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugate of the invention may contain free saccharide that is not covalently conjugated to the carrier protein, but is nevertheless present in the glycoconjugate composition. The free saccharide may be noncovalently associated with (i.e., noncovalently bound to, adsorbed to, or entrapped in or with) the glycoconjugate. By free saccharide is meant the amount of free saccharide of the serotypes composing the glycoconjugate (e.g. for a serotypes 8/15A/15B/23A/23B glycoconjugate it is meant to be the free serotypes 8, 15A, 15B, 23A and 23B saccharide, for a serotypes 8/15A glycoconjugate it is meant to be the free serotypes 8, and 15A saccharide). It is compared to the total amount of saccharide of the serotypes composing the glycoconjugate (e.g. for a serotypes 8/15A/15B/23A/23B glycoconjugate it is meant to be the total amount of serotypes 8, 15A, 15B, 23A and 23B saccharide, for a serotypes 8/15A glycoconjugate it is meant to be the total amount of serotypes 8 and 15A saccharide).

In a preferred embodiment, the serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugate comprises less than about 50%, 45%, 40%, 35%, 30%, 25%, 20% or 15% of free saccharide compared to the total amount of saccharide. In a preferred embodiment the glycoconjugate comprises less than about 40% of free saccharide compared to the total amount of saccharide. In a preferred embodiment the glycoconjugate comprises less than about 25% of free saccharide compared to the total amount of saccharide. In a preferred embodiment the glycoconjugate comprises less than about 20% of free saccharide compared to the total amount saccharide. In a preferred embodiment the glycoconjugate comprises less than about 15% of free saccharide compared to the total amount of saccharide.

In preferred embodiments, the serotype 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugates of the invention are prepared using reductive amination.

Reductive amination involves two steps, (1) oxidation (activation) of the saccharide, (2) reduction of the activated saccharide and a carrier protein (e.g., $CRM_{197}$, DT, TT or PD) to form a conjugate. Before oxidation, sizing of the serotype 8, 15A, 15B, 23A and/or 23B saccharide to a target molecular weight (MW) range can be performed. Mechanical or chemical hydrolysis may be employed. Chemical hydrolysis may be conducted using acetic acid. Advantageously, the size of the purified serotypes 8, 15A, 15B, 23A and/or 23B saccharide is reduced while preserving critical features of the structure of the saccharide such as for example the presence of O-acetyl groups. Therefore preferably, the size of the purified serotypes 8, 15A, 15B, 23A and/or 23B saccharide is reduced by mechanical homogenization.

In an embodiment, serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides are activated (oxidized) by a process comprising the step of:

(a) reacting a mixture of isolated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides with an oxidizing agent.

Said process can further comprise a quenching step.

Therefore in an embodiment, serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides are activated (oxidized) by a process comprising the step of:

(a) reacting a mixture of isolated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides with an oxidizing agent;

(b) quenching the oxidation reaction by addition of a quenching agent resulting in activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides.

In these embodiments, the saccharides are therefore activated altogether as a mixture.

In another embodiment, serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides are activated (oxidized) separately and the activated saccharides are then mixed.

In said embodiment, serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides are activated (oxidized) by a process comprising the step of:

(a) individually reacting an isolated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides with an oxidizing agent;

(b) mixing the activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides.

Said process can further comprise a quenching step.

Therefore in an embodiment, serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides are activated (oxidized) by a process comprising the step of:

(a) individually reacting an isolated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides with an oxidizing agent;

(b) quenching the oxidation reactions by addition of a quenching agent resulting in activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides;

(b) mixing the activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides.

The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate).

In a preferred embodiment, the oxidizing agent is sodium periodate. In a preferred embodiment, the periodate used for the oxidation is metaperiodate. In a preferred embodiment the periodate used for the oxidation is sodium metaperiodate.

In one embodiment, the quenching agent is selected from vicinal diols, 1,2-aminoalcohols, amino acids, glutathione, sulfite, bisulfate, dithionite, metabisulfite, thiosulfate, phosphites, hypophosphites or phosphorous acid.

In one embodiment, the quenching agent is a 1,2-aminoalcohols of formula (I):

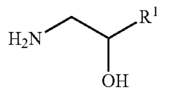

(I)

wherein $R^1$ is selected from H, methyl, ethyl, propyl or isopropyl.

In one embodiment, the quenching agent is selected from sodium and potassium salts of sulfite, bisulfate, dithionite, metabisulfite, thiosulfate, phosphites, hypophosphites or phosphorous acid. In one embodiment, the quenching agent is an amino acid. In such embodiments, said amino acid may be selected from serine, threonine, cysteine, cystine, methionine, proline, hydroxyproline, tryptophan, tyrosine, and histidine.

In one embodiment, the quenching agent is a sulfite such as bisulfate, dithionite, metabisulfite, thiosulfate.

In one embodiment, the quenching agent is a compound comprising two vicinal hydroxyl groups (vicinal diols), i.e., two hydroxyl groups covalently linked to two adjacent carbon atoms.

Preferably, the quenching agent is a compound of formula (II):

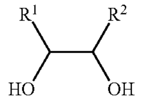

(II)

wherein $R^1$ and $R^2$ are each independently selected from H, methyl, ethyl, propyl or isopropyl. In a preferred embodiment, the quenching agent is glycerol, ethylene glycol, propan-1,2-diol, butan-1,2-diol or butan-2,3-diol, or ascorbic acid. In a preferred embodiment, the quenching agent is butan-2,3-diol.

In a preferred embodiment, the isolated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides are activated by a process comprising the step of:

(a) reacting a mixture of isolated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides with periodate;

(b) quenching the oxidation reaction by addition of butan-2,3-diol resulting in a mixture of activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides.

Following the oxidation step of the saccharides, the saccharides are said to be activated and is referred to as "activated saccharides" here below.

In a preferred embodiment, the mixture of activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides are purified. The mixture of activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides are purified according to methods known to the man skilled in the art such as gel permeation chromatography (GPC), dialysis or ultrafiltration/diafiltration. For example, the mixture of activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides are purified by concentration and diafiltration using an ultrafiltration device.

In a preferred embodiment the degree of oxidation of the activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides is between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25. In a preferred embodiment the degree of oxidation of the activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides is between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20.

In a preferred embodiment, the mixture of activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides have a molecular weight between 25 kDa and 1,000 kDa, between 100 kDa and 1,000 kDa, between 300 kDa and 800 kDa, between 300 kDa and 700 kDa, between 300 kDa and 600 kDa, between 400 kDa and 1,000 kDa, between 400 kDa and 800 kDa, between 400 kDa and 700 kDa or between 400 kDa and 600 kDa. In an embodiment, the mixture of activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides have a molecular weight between 300 kDa and 800 kDa. In an embodiment, the mixture of activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides have a molecular weight between 400 kDa and 600 kDa. In a preferred embodiment, the mixture of activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides have a molecular weight between 400 kda and 600 kDa and a degree of oxidation between 10 and 25, between 10 and 20, between 12 and 20 or between 14 and 18. In a preferred embodiment, the mixture of activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides have a molecular weight between 400 kDa and 600 kDa and a degree of oxidation between 10 and 20.

The activated saccharides and/or the carrier protein may be lyophilised (freeze-dried), either independently (discrete lyophilization) or together (co-lyophilized).

In an embodiment, the mixture of activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides are lyophilized, optionally in the presence of a saccharide such as sucrose, trehalose, raffinose, stachyose, melezitose, dextran, mannitol, lactitol or palatinit. In a preferred embodiment, said saccharide is sucrose. In one embodiment, the lyophilized mixture of activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides are then compounded with a solution comprising the carrier protein.

In another embodiment the mixture of activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides and the carrier protein are co-lyophilised. In such embodiments, the mixture of activated 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides are compounded with the carrier protein and lyophilized, optionally in the presence of a saccharide such as sucrose, trehalose, raffinose, stachyose, melezitose, dextran, mannitol, lactitol and palatinit. In a preferred embodiment, said saccharide is sucrose. The co-lyophilized mixture of activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides and carrier protein can then be resuspended in solution and reacted with a reducing agent.

The second step of the conjugation process is the reduction of the activated saccharides and a carrier protein to form a conjugate (reductive amination), using a reducing agent.

The mixture of activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides can be conjugated to a carrier protein by a process comprising the step of:

(c) compounding the mixture of activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides with a carrier protein; and (d) reacting the compounded mixture of activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides and carrier protein with a reducing agent to form a serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugate.

In an embodiment, the reduction reaction is carried out in aqueous solvent, preferably a buffered aqueous solvent. In an embodiment, the reduction reaction is carried in a buffer which does not contain an amine group. In an embodiment, the buffer is selected from the group consisting of a salt of acetic acid (acetate), sodium hydrogen carbonate (bicarbonate), boric acid, dimethylarsinic acid (cacodylate), sodium carbonate (carbonate), a salt of citric acid (citrate), a salt of formic acid (formate), a salt of malic acid (malate), a salt of maleic acid (maleate), a salt of phosphoric acid (phosphate) and a salt of succinic acid (succinate). In an embodiment, the buffer is selected from the group consisting of a salt of acetic acid (acetate), a salt of citric acid (citrate), a salt of phosphoric acid (phosphate) and a salt of succinic acid (succinate). In an embodiment, the buffer is a salt of phosphoric acid (phosphate). In an embodiment, the buffer is sodium phosphate Preferably said buffer has a concentration between 1-100 mM, 1-50 mM, 1-25 mM, 1-10 mM, 5-50 mM, 5-15 mM, 5-10 mM, 8-12 mM or 9-11 mM. in an embodiment, said buffer has a concentration of about 1, 2, 3, 4, 5, 6, 7, 8, 9,10, 11, 12, 12, 13, 14, 15 20, 25, 30, 35, 40, 45 or 50 mM. The aqueous solvent may be used to reconstitute the mixture of activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides and carrier protein which has been lyophilised.

In an embodiment, the reducing agent is sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^{i}$PrN—$BH_3$, benzylamine-$BH_3$ or 5-ethyl-2-methylpyridine borane (PEMB). In a preferred embodiment, the reducing agent is sodium cyanoborohydride.

At the end of the reduction reaction, there may be unreacted aldehyde groups remaining in the conjugates, these may be capped using a suitable capping agent. In one embodiment this capping agent is sodium borohydride ($NaBH_4$).

Following conjugation of serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides to the carrier protein, the glycoconjugate can be purified (enriched with respect to the amount of saccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration.

1.3.2 Glycoconjugates of the Invention Comprising at Least Two Saccharides Selected from the Group Consisting of a Saccharide from *S. pneumoniae* Serotype 8, a Saccharide from *S. pneumoniae* Serotype 11A, a Saccharide from *S. pneumoniae* Serotype 12F, a Saccharide from *S. pneumoniae* Serotype 23A and a Saccharide from *S. pneumoniae* Serotype 23B The present invention relates to glycoconjugates wherein 2 or more saccharides antigens are conjugated to the same molecule of the protein carrier (i.e. the carrier molecules have 2 or more different capsular saccharides conjugated to them).

In an embodiment the invention relates to a glycoconjugate comprising at least two saccharides selected from the group consisting of a saccharide from *S. pneumoniae* serotype 8, a saccharide from *S. pneumoniae* serotype 11A, a saccharide from *S. pneumoniae* serotype 12F, a saccharide from *S. pneumoniae* serotype 23A and a saccharide from *S. pneumoniae* serotype 23B, conjugated to a carrier protein.

In an embodiment the glycoconjugate of the invention comprises a saccharide from *S. pneumoniae* serotype 8, a saccharide from *S. pneumoniae* serotype 11A, a saccharide from *S. pneumoniae* serotype 12F, a saccharide from *S. pneumoniae* serotype 23A and a saccharide from *S. pneumoniae* serotype 23B, conjugated to the same carrier protein (herein after 'the serotypes 8/11A/12F/23A/23B glycoconjugate'). In said embodiment, the carrier molecules have the five different capsular saccharides conjugated to them. Preferably, the serotypes 8/11A/12F/23A/23B glycoconjugate is therefore a 5-valent glycoconjugate (i.e. it has serotypes 8, 11A, 12F, 23A and 23B conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 11A, a saccharide from *S. pneumoniae* serotype 12F and a saccharide from *S. pneumoniae* serotype 23A, conjugated to the same carrier protein (herein after 'the serotypes 8/11A/12F/23A glycoconjugate'). In said embodiment, the carrier molecules have the four different capsular saccharides conjugated to them. Preferably, the serotypes 8/11A/12F/23A glycoconjugate is therefore a 4-valent glycoconjugate (i.e. it has serotypes 8, 11A, 12F, and 23A conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 11A, a saccharide from *S. pneumoniae* serotype 12F and a saccharide from *S. pneumoniae* serotype 23B, conjugated to the same carrier protein (herein after 'the serotypes 8/11A/12F/23B glycoconjugate'). In said embodiment, the carrier molecules have the four different capsular saccharides conjugated to them. Preferably, the serotypes 8/11A/12F/23B glycoconjugate is therefore a 4-valent glycoconjugate (i.e. it has serotypes 8, 11A, 12F, and 23B conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 11A, a saccharide from *S. pneumoniae* serotype 23A and a saccharide from *S. pneumoniae* serotype 23B, conjugated to the same carrier protein (herein after 'the serotypes 8/11A/23A/23B glycoconjugate'). In said embodiment, the carrier molecules have the four different capsular saccharides conjugated to them. Preferably, the serotypes 8/11A/23A/23B glycoconjugate is therefore a 4-valent glycoconjugate (i.e. it has serotypes 8, 11A, 23A, and 23B conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 12F, a saccharide from *S. pneumoniae* serotype 23A and a saccharide from *S. pneumoniae* serotype 23B, conjugated to the same carrier protein (herein after 'the serotypes 8/12F/23A/23B glycoconjugate'). In said embodiment, the carrier molecules have the four different capsular saccharides conjugated to them. Preferably, the serotypes 8/12F/23A/23B glycoconjugate is therefore a 4-valent glycoconjugate (i.e. it has serotypes 8, 12F, 23A, and 23B conjugated to the carrier protein and no other polysaccharide antigens covalently attached to the carrier protein).

In an embodiment the glycoconjugate of the invention comprises a saccharide from *S. pneumoniae* serotype 11A, a saccharide from *S. pneumoniae* serotype 12F, a saccharide from *S. pneumoniae* serotype 23A and a saccharide from *S. pneumoniae* serotype 23B, conjugated to the same carrier protein (herein after 'the serotypes 11A/12F/23A/23B glycoconjugate'). In said embodiment, the carrier molecules have the four different capsular saccharides conjugated to them. Preferably, the serotypes 11A/12F/23A/23B glycoconjugate is therefore a 4-valent glycoconjugate (i.e. it has serotypes 11A, 12F, 23A, and 23B conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 11A and a saccharide from *S. pneumoniae* serotype 12F, conjugated to the same carrier protein (herein after 'the serotypes 8/11A/12F glycoconjugate'). In said embodiment, the carrier molecules have the three different capsular saccharides conjugated to them. Preferably, the serotypes 8/11A/12F glycoconjugate is therefore a 3-valent glycoconjugate (i.e. it has serotypes 8, 11A and 12F conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 11A and a saccharide from *S. pneumoniae* serotype 23A, conjugated to the same carrier protein (herein after 'the serotypes 8/11A/23A glycoconjugate'). In said embodiment, the carrier molecules have the three different capsular saccharides conjugated to them. Preferably, the serotypes 8/11A/23A glycoconjugate is therefore a 3-valent glycoconjugate (i.e. it has serotypes 8, 11A and 23A conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 11A and a saccharide from *S. pneumoniae* serotype 23B, conjugated to the same carrier protein (herein after 'the serotypes 8/11A/23B glycoconjugate'). In said embodiment, the carrier molecules have the three different capsular saccharides conjugated to them. Preferably, the serotypes 8/11A/23B glycoconjugate is therefore a 3-valent glycoconjugate (i.e. it has serotypes 8, 11A and 23B conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 12F and a saccharide from *S. pneumoniae* serotype 23A, conjugated to the same carrier protein (herein after 'the serotypes 8/12F/23A glycoconjugate'). In said embodiment, the carrier molecules have the three different capsular saccharides conjugated to them. Preferably, the serotypes 8/12F/23A glycoconjugate is therefore a 3-valent glycoconjugate (i.e. it has serotypes 8, 12F and 23A conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 12F and a saccharide from *S. pneumoniae* serotype 23B, conjugated to the same carrier protein (herein after 'the serotypes 8/12F/23B glycoconjugate'). In said embodiment, the carrier molecules have the three different capsular saccharides conjugated to them. Preferably, the serotypes 8/12F/23B glycoconjugate is therefore a 3-valent glycoconjugate (i.e. it has serotypes 8, 12F and 23B conjugated to the carrier protein and no other polysaccharide antigens covalently attached to the carrier protein).

In an embodiment the glycoconjugate of the invention comprises a saccharide from *S. pneumoniae* serotype 8, a saccharide from *S. pneumoniae* serotype 23A and a saccharide from *S. pneumoniae* serotype 23B, conjugated to the same carrier protein (herein after 'the serotypes 8/23A/23B glycoconjugate'). In said embodiment, the carrier molecules have the three different capsular saccharides conjugated to them. Preferably, the serotypes 8/23A/23B glycoconjugate is therefore a 3-valent glycoconjugate (i.e. it has serotypes 8, 23A and 23B conjugated to the carrier protein and no other polysaccharide antigens covalently attached to the carrier protein).

In an embodiment the glycoconjugate of the invention comprises a saccharide from *S. pneumoniae* serotype 11A, a saccharide from *S. pneumoniae* serotype 12F and a saccharide from *S. pneumoniae* serotype 23A, conjugated to the same carrier protein (herein after 'the serotypes 11A/12F/23A glycoconjugate'). In said embodiment, the carrier molecules have the three different capsular saccharides conjugated to them. Preferably, the serotypes 11A/12F/23A glycoconjugate is therefore a 3-valent glycoconjugate (i.e. it has serotypes 11A, 12F and 23A conjugated to the carrier protein and no other polysaccharide antigens covalently attached to the carrier protein).

In an embodiment the glycoconjugate of the invention comprises a saccharide from *S. pneumoniae* serotype 11A, a saccharide from *S. pneumoniae* serotype 12F and a saccharide from *S. pneumoniae* serotype 23B, conjugated to the same carrier protein (herein after 'the serotypes 11A/12F/23B glycoconjugate'). In said embodiment, the carrier molecules have the three different capsular saccharides conjugated to them. Preferably, the serotypes 11A/12F/23B glycoconjugate is therefore a 3-valent glycoconjugate (i.e. it has serotypes 11A, 12F and 23B conjugated to the carrier protein and no other polysaccharide antigens covalently attached to the carrier protein).

In an embodiment the glycoconjugate of the invention comprises a saccharide from *S. pneumoniae* serotype 11A, a saccharide from *S. pneumoniae* serotype 23A and a saccharide from *S. pneumoniae* serotype 23B, conjugated to the same carrier protein (herein after 'the serotypes 11A/23A/23B glycoconjugate'). In said embodiment, the carrier molecules have the three different capsular saccharides conjugated to them. Preferably, the serotypes 11A/23A/23B glycoconjugate is therefore a 3-valent glycoconjugate (i.e. it has serotypes 11A, 23A and 23B conjugated to the carrier protein and no other polysaccharide antigens covalently attached to the carrier protein).

In an embodiment the glycoconjugate of the invention comprises a saccharide from *S. pneumoniae* serotype 12F, a saccharide from *S. pneumoniae* serotype 23A and a saccharide from *S. pneumoniae* serotype 23B, conjugated to the same carrier protein (herein after 'the serotypes 12F/23A/23B glycoconjugate'). In said embodiment, the carrier molecules have the three different capsular saccharides conjugated to them. Preferably, the serotypes 12F/23A/23B glycoconjugate is therefore a 3-valent glycoconjugate (i.e. it has serotypes 12F, 23A and 23B conjugated to the carrier protein and no other polysaccharide antigens covalently attached to the carrier protein).

In an embodiment the glycoconjugate of the invention comprises a saccharide from *S. pneumoniae* serotype 8 and a saccharide from *S. pneumoniae* serotype 11A, conjugated to the same carrier protein (herein after 'the serotypes 8/11A glycoconjugate'). In said embodiment, the carrier molecules have the two different capsular saccharides conjugated to them. Preferably, the serotypes 8/11A glycoconjugate is therefore a 2-valent glycoconjugate (i.e. it has serotypes 8 and 11A conjugated to the carrier protein and no other polysaccharide antigens covalently attached to the carrier protein).

In an embodiment the glycoconjugate of the invention comprises a saccharide from *S. pneumoniae* serotype 8 and a saccharide from *S. pneumoniae* serotype 12F, conjugated to the same carrier protein (herein after 'the serotypes 8/12F glycoconjugate'). In said embodiment, the carrier molecules have the two different capsular saccharides conjugated to them. Preferably, the serotypes 8/12F glycoconjugate is therefore a 2-valent glycoconjugate (i.e. it has serotypes 8 and 12F conjugated to the carrier protein and no other polysaccharide antigens covalently attached to the carrier protein).

In an embodiment the glycoconjugate of the invention comprises a saccharide from *S. pneumoniae* serotype 8 and a saccharide from *S. pneumoniae* serotype 23A, conjugated to the same carrier protein (herein after 'the serotypes 8/23A glycoconjugate'). In said embodiment, the carrier molecules have the two different capsular saccharides conjugated to them. Preferably, the serotypes 8/23A glycoconjugate is therefore a 2-valent glycoconjugate (i.e. it has serotypes 8 and 23A conjugated to the carrier protein and no other polysaccharide antigens covalently attached to the carrier protein).

In an embodiment the glycoconjugate of the invention comprises a saccharide from *S. pneumoniae* serotype 8 and a saccharide from *S. pneumoniae* serotype 23B, conjugated to the same carrier protein (herein after 'the serotypes 8/23B glycoconjugate'). In said embodiment, the carrier molecules have the two different capsular saccharides conjugated to them. Preferably, the serotypes 8/23B glycoconjugate is therefore a 2-valent glycoconjugate (i.e. it has serotypes 8 and 23B conjugated to the carrier protein and no other polysaccharide antigens covalently attached to the carrier protein).

In an embodiment the glycoconjugate of the invention comprises a saccharide from *S. pneumoniae* serotype 11A and a saccharide from *S. pneumoniae* serotype 12F, conjugated to the same carrier protein (herein after 'the serotypes 11A/12F glycoconjugate'). In said embodiment, the carrier molecules have the two different capsular saccharides conjugated to them. Preferably, the serotypes 11A/12F glycoconjugate is therefore a 2-valent glycoconjugate (i.e. it has serotypes 11A and 12F conjugated to the carrier protein and no other polysaccharide antigens covalently attached to the carrier protein).

In an embodiment the glycoconjugate of the invention comprises a saccharide from *S. pneumoniae* serotype 11A and a saccharide from *S. pneumoniae* serotype 23A, conjugated to the same carrier protein (herein after 'the serotypes 11A/23A glycoconjugate'). In said embodiment, the carrier molecules have the two different capsular saccharides conjugated to them. Preferably, the serotypes 11A/23A glycoconjugate is therefore a 2-valent glycoconjugate (i.e. it has serotypes 11A and 23A conjugated to the carrier protein and no other polysaccharide antigens covalently attached to the carrier protein).

In an embodiment the glycoconjugate of the invention comprises a saccharide from *S. pneumoniae* serotype 11A and a saccharide from *S. pneumoniae* serotype 23B, conjugated to the same carrier protein (herein after 'the serotypes 11A/23B glycoconjugate'). In said embodiment, the carrier molecules have the two different capsular saccharides conjugated to them. Preferably, the serotypes 11A/23B glycoconjugate is therefore a 2-valent glycoconjugate (i.e. it has serotypes 11A and 23B conjugated to the carrier protein and no other polysaccharide antigens covalently attached to the carrier protein).

In an embodiment the glycoconjugate of the invention comprises a saccharide from *S. pneumoniae* serotype 12F and a saccharide from *S. pneumoniae* serotype 23A, conjugated to the same carrier protein (herein after 'the serotypes 12F/23A glycoconjugate'). In said embodiment, the carrier molecules have the two different capsular saccharides conjugated to them. Preferably, the serotypes 12F/23A glycoconjugate is therefore a 2-valent glycoconjugate (i.e. it has serotypes 12F and 23A conjugated to the carrier protein and no other polysaccharide antigens covalently attached to the carrier protein).

In an embodiment the glycoconjugate of the invention comprises a saccharide from *S. pneumoniae* serotype 12F and a saccharide from *S. pneumoniae* serotype 23B, conjugated to the same carrier protein (herein after 'the serotypes 12F/23B glycoconjugate'). In said embodiment, the carrier molecules have the two different capsular saccharides conjugated to them. Preferably, the serotypes 12F/23B glycoconjugate is therefore a 2-valent glycoconjugate (i.e. it has serotypes 12F and 23B conjugated to the carrier protein and no other polysaccharide antigens covalently attached to the carrier protein).

In an embodiment the glycoconjugate of the invention comprises a saccharide from *S. pneumoniae* serotype 23A and a saccharide from *S. pneumoniae* serotype 23B, conjugated to the same carrier protein (herein after 'the serotypes 23A/23B glycoconjugate'). In said embodiment, the carrier molecules have the two different capsular saccharides conjugated to them. Preferably, the serotypes 23A/23B glycoconjugate is therefore a 2-valent glycoconjugate (i.e. it has serotypes 23A and 23B conjugated to the carrier protein and no other polysaccharide antigens covalently attached to the carrier protein).

In some embodiments, the serotypes 8/11A/12F/23A/23B, 8/11A/12F/23A, 8/11A/12F/23B, 8/11A/23A/23B, 8/12F/23A/23B, 8/11A/12F, 8/11A/23A, 8/11A/23B, 8/12F/23A, 8/12F/23B, 8/23A/23B, 8/11A, 8/12F, 8/23A or 8/23B glycoconjugate of the present invention comprise a serotype 8 saccharide having a molecular weight of between 10 kDa and 5,000 kDa. In other such embodiments, the serotype 8 saccharide has a molecular weight of between 20 kDa and 4,000 kDa. In other such embodiments, the serotype 8 saccharide has a molecular weight of between 50 kDa and 3,000 kDa. In other such embodiments, the serotype 8 saccharide has a molecular weight of between 100 kDa and 2500 kDa. In other such embodiments, the serotype 8 saccharide has a molecular weight of between 100 kDa and 2,000 kDa. In other such embodiments, the serotype 8 saccharide has a molecular weight of between 150 kDa and 2,000 kDa. In other such embodiments, the serotype 8 saccharide has a molecular weight of between 150 kDa and 1,500 kDa. In other such embodiments, the serotype 8 saccharide has a molecular weight of between 20 kDa and 1,500 kDa. In another embodiment, the serotype 8 saccharide has a molecular weight of between 30 kDa and 1,250 kDa. In another embodiment, the serotype 8 saccharide has a molecular weight of between 50 kDa and 1,000 kDa. In another embodiment, the serotype 8 saccharide has a molecular weight of between 70 kDa and 900 kDa. In another embodiment, the serotype 8 saccharide has a molecular weight of between 100 kDa and 800 kDa. In another embodiment, the serotype 8 saccharide has a molecular weight of between 200 kDa to 600 kDa. In another embodiment, the serotype 8 saccharide has a molecular weight of between 400 kDa to 700 kDa.

In further such embodiments, the serotype 8 saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In further embodiments, the serotype 8 saccharide has a molecular weight of between 10 kDa and 2,000 kDa. In further such embodiments, the serotype 8 saccharide has a molecular weight of between 100 kDa to 1,000 kDa; between 100 kDa to 900 kDa; between 100 kDa to 800 kDa; between 100 kDa to 700 kDa; between 100 kDa to 600 kDa; between 100 kDa to 500 kDa; between 100 kDa to 400 kDa; between 100 kDa to 300 kDa; between 150 kDa to 1,000 kDa; between 150 kDa to 900 kDa; between 150 kDa to 800 kDa; between 150 kDa to 700 kDa; between 150 kDa to 600 kDa; between 150 kDa to 500 kDa; between 150 kDa to 400 kDa; between 150 kDa to 300 kDa; between 200 kDa to 1,000 kDa; between 200 kDa to 900 kDa; between 200 kDa to 800 kDa; between 200 kDa to 700 kDa; between 200 kDa to 600 kDa; between 200 kDa to 500 kDa; between 200 kDa to 400 kDa; between 200 kDa to 300 kDa; between 250 kDa to 1,000 kDa; between 250 kDa to 900 kDa; between 250 kDa to 800 kDa; between 250 kDa to 700 kDa; between 250 kDa to 600 kDa; between 250 kDa to 500 kDa; between 250 kDa to 400 kDa; between 250 kDa to 350 kDa; between 300 kDa to 1000 kDa; between 300 kDa to 900 kDa; between 300 kDa to 800 kDa; between 300 kDa to 700 kDa; between 300 kDa to 600 kDa; between 300 kDa to 500 kDa; between 300 kDa to 400 kDa; between 400 kDa to 1,000 kDa; between 400 kDa to 900 kDa; between 400 kDa to 800 kDa; between 400 kDa to 700 kDa; between 400 kDa to 600 kDa or between 500 kDa to 600 kDa. Any whole number integer within any of the above ranges is contemplated as an embodiment of the disclosure.

In some embodiments, the serotypes 8/11A/12F/23A/23B, 8/11A/12F/23A, 8/11A/12F/23B, 8/11A/23A/23B, 11A/12F/23A/23B, 8/11A/12F, 8/11A/23A, 8/11A/23B, 11A/12F/23A, 11A/12F/23B, 11A/23A/23B, 8/11A, 11A/12F, 11A/23A or 11A/23B, glycoconjugate of the present invention comprise a serotype 11A saccharide having a molecular weight of between 10 kDa and 5,000 kDa. In other such embodiments, the serotype 11A saccharide has a molecular weight of between 20 kDa and 4,000 kDa. In other such embodiments, the serotype 11A saccharide has a molecular weight of between 50 kDa and 3,000 kDa. In other such embodiments, the serotype 11A saccharide has a molecular weight of between 100 kDa and 2500 kDa. In other such embodiments, the serotype 11A saccharide has a molecular weight of between 100 kDa and 2,000 kDa. In other such embodiments, the serotype 11A saccharide has a molecular weight of between 150 kDa and 2,000 kDa. In other such embodiments, the serotype 11A saccharide has a molecular weight of between 150 kDa and 1,500 kDa. In other such embodiments, the serotype 11A saccharide has a molecular weight of between 20 kDa and 1,500 kDa. In another embodiment, the serotype 11A saccharide has a molecular weight of between 30 kDa and 1,250 kDa. In another embodiment, the serotype 11A saccharide has a molecular weight of between 50 kDa and 1,000 kDa. In another embodiment, the serotype 11A saccharide has a molecular weight of between 70 kDa and 900 kDa. In another embodiment, the serotype 11A saccharide has a molecular weight of between 100 kDa and 800 kDa. In another embodiment, the serotype 11A saccharide has a molecular weight of between 200 kDa to 600 kDa. In another embodiment, the serotype 11A saccharide has a molecular weight of between 400 kDa to 700 kDa.

In further such embodiments, the serotype 11A saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In further embodiments, the serotype 11A saccharide has a molecular weight of between 10 kDa and 2,000 kDa. In further such embodiments, the serotype 11A saccharide has a molecular weight of between 100 kDa to 1,000 kDa; between 100 kDa to 900 kDa; between 100 kDa to 800 kDa; between 100 kDa to 700 kDa; between 100 kDa to 600 kDa; between 100 kDa to 500 kDa; between 100 kDa to 400 kDa; between 100 kDa to 300 kDa; between 150 kDa to 1,000 kDa; between 150 kDa to 900 kDa; between 150 kDa to 800 kDa; between 150 kDa to 700 kDa; between 150 kDa to 600 kDa; between 150 kDa to 500 kDa; between 150 kDa to 400 kDa; between 150 kDa to 300 kDa; between 200 kDa to 1,000 kDa; between 200 kDa to 900 kDa; between 200 kDa to 800 kDa; between 200 kDa to 700 kDa; between 200 kDa to 600 kDa; between 200 kDa to 500 kDa; between 200 kDa to 400 kDa; between 200 kDa to 300 kDa; between 250 kDa to 1,000 kDa; between 250 kDa to 900 kDa; between 250 kDa to 800 kDa; between 250 kDa to 700 kDa; between 250 kDa to 600 kDa; between 250 kDa to 500 kDa; between 250 kDa to 400 kDa; between 250 kDa to 350 kDa; between 300 kDa to 1000 kDa; between 300 kDa to 900 kDa; between 300 kDa to 800 kDa; between 300 kDa to 700 kDa; between 300 kDa to 600 kDa; between 300 kDa to 500 kDa; between 300 kDa to 400 kDa; between 400 kDa to 1,000 kDa; between 400 kDa to 900 kDa; between 400 kDa to 800 kDa; between 400 kDa to 700 kDa; between 400 kDa to 600 kDa or between 500 kDa to 600 kDa. Any whole number integer within any of the above ranges is contemplated as an embodiment of the disclosure.

In some embodiments, the serotypes 8/11A/12F/23A/23B, 8/11A/12F/23A, 8/11A/12F/23B, 8/12F/23A/23B, 11A/12F/23A/23B, 8/11A/12F, 8/12F/23A, 8/12F/23B, 11A/12F/23A, 11A/12F/23B, 12F/23A/23B, 8/12F, 11A/12F, 12F/23A or 12F/23B, glycoconjugate of the present invention comprises a serotype 12F saccharide having a molecular weight of between 10 kDa and 5,000 kDa. In other such embodiments, the serotype 12F saccharide has a molecular weight of between 20 kDa and 4,000 kDa. In other such embodiments, the serotype 12F saccharide has a molecular weight of between 50 kDa and 3,000 kDa. In other such embodiments, the serotype 12F saccharide has a molecular weight of between 100 kDa and 2500 kDa. In other such embodiments, the serotype 12F saccharide has a molecular weight of between 100 kDa and 2,000 kDa. In other such embodiments, the serotype 12F saccharide has a molecular weight of between 150 kDa and 2,000 kDa. In other such embodiments, the serotype 12F saccharide has a molecular weight of between 150 kDa and 1,500 kDa. In other such embodiments, the serotype 12F saccharide has a molecular weight of between 20 kDa and 1,500 kDa. In another embodiment, the serotype 12F saccharide has a molecular weight of between 30 kDa and 1,250 kDa. In another embodiment, the serotype 12F saccharide has a molecular weight of between 50 kDa and 1,000 kDa. In another embodiment, the serotype 12F saccharide has a molecular weight of between 70 kDa and 900 kDa. In another embodiment, the serotype 12F saccharide has a molecular weight of between 100 kDa and 800 kDa. In another embodiment, the serotype 12F saccharide has a molecular weight of between 200 kDa to 600 kDa. In another embodiment, the serotype 12F saccharide has a molecular weight of between 400 kDa to 700 kDa.

In further such embodiments, the serotype 12F saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In further embodiments, the serotype 12F saccharide has a molecular weight of between 10 kDa and 2,000 kDa. In further such embodiments, the serotype 12F saccharide has a molecular weight of between 100 kDa to 1,000 kDa; between 100 kDa to 900 kDa; between 100 kDa to 800 kDa; between 100 kDa to 700 kDa; between 100 kDa to 600 kDa; between 100 kDa to 500 kDa; between 100 kDa to 400 kDa; between 100 kDa to 300 kDa; between 150 kDa to 1,000 kDa; between 150 kDa to 900 kDa; between 150 kDa to 800 kDa; between 150 kDa to 700 kDa; between 150 kDa to 600 kDa; between 150 kDa to 500 kDa; between 150 kDa to 400 kDa; between 150 kDa to 300 kDa; between 200 kDa to 1,000 kDa; between 200 kDa to 900 kDa; between 200 kDa to 800 kDa; between 200 kDa to 700 kDa; between 200 kDa to 600 kDa; between 200 kDa to 500 kDa; between 200 kDa to 400 kDa; between 200 kDa to 300 kDa; between 250 kDa to 1,000 kDa; between 250 kDa to 900 kDa; between 250 kDa to 800 kDa; between 250 kDa to 700 kDa; between 250 kDa to 600 kDa; between 250 kDa to 500 kDa; between 250 kDa to 400 kDa; between 250 kDa to 350 kDa; between 300 kDa to 1000 kDa; between 300 kDa to 900 kDa; between 300 kDa to 800 kDa; between 300 kDa to 700 kDa; between 300 kDa to 600 kDa; between 300 kDa to 500 kDa; between 300 kDa to 400 kDa; between 400 kDa to 1,000 kDa; between 400 kDa to 900 kDa; between 400 kDa to 800 kDa; between 400 kDa to 700 kDa; between 400 kDa to 600 kDa or between 500 kDa to 600 kDa. Any whole number integer within any of the above ranges is contemplated as an embodiment of the disclosure.

In some embodiments, the serotypes 8/11A/12F/23A/23B, 8/11A/12F/23A, 8/11A/23A/23B, 8/12F/23A/23B, 11A/12F/23A/23B, 8/11A/23A, 8/12F/23A, 8/23A/23B, 11A/12F/23A, 11A/23A/23B, 12F/23A/23B, 8/23A, 11A/23A, 12F/23A or 23A/23B glycoconjugate of the present invention comprise a serotype 23A saccharide having a molecular weight of between 10 kDa and 5,000 kDa. In other such embodiments, the serotype 23A saccharide has a molecular weight of between 20 kDa and 4,000 kDa. In other such embodiments, the serotype 23A saccharide has a molecular weight of between 50 kDa and 3,000 kDa. In other such embodiments, the serotype 23A saccharide has a molecular weight of between 100 kDa and 2500 kDa. In other such embodiments, the serotype 23A saccharide has a molecular weight of between 100 kDa and 2,000 kDa. In other such embodiments, the serotype 23A saccharide has a molecular weight of between 150 kDa and 2,000 kDa. In other such embodiments, the serotype 23A saccharide has a molecular weight of between 150 kDa and 1,500 kDa. In other such embodiments, the serotype 23A saccharide has a molecular weight of between 20 kDa and 1,500 kDa. In another embodiment, the serotype 23A saccharide has a molecular weight of between 30 kDa and 1,250 kDa. In another embodiment, the serotype 23A saccharide has a molecular weight of between 50 kDa and 1,000 kDa. In another embodiment, the serotype 23A saccharide has a molecular weight of between 70 kDa and 900 kDa. In another embodiment, the serotype 23A saccharide has a molecular weight of between 100 kDa and 800 kDa. In another embodiment, the serotype 23A saccharide has a molecular weight of between 200 kDa to 600 kDa. In another embodiment, the serotype 23A saccharide has a molecular weight of between 400 kDa to 700 kDa.

In further such embodiments, the serotype 23A saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In further embodiments, the serotype 23A saccharide has a molecular weight of between 10 kDa and 2,000 kDa. In further such embodiments, the serotype 23A saccharide has a molecular weight of between 100 kDa to 1,000 kDa; between 100 kDa to 900 kDa; between 100 kDa to 800 kDa; between 100 kDa to 700 kDa; between 100 kDa to 600 kDa; between 100 kDa to 500 kDa; between 100 kDa to 400 kDa; between 100 kDa to 300 kDa; between 150 kDa to 1,000 kDa; between 150 kDa to 900 kDa; between 150 kDa to 800 kDa; between 150 kDa to 700 kDa; between 150 kDa to 600 kDa; between 150 kDa to 500 kDa; between 150 kDa to 400 kDa; between 150 kDa to 300 kDa; between 200 kDa to 1,000 kDa; between 200 kDa to 900 kDa; between 200 kDa to 800 kDa; between 200 kDa to 700 kDa; between 200 kDa to 600 kDa; between 200 kDa to 500 kDa; between 200 kDa to 400 kDa; between 200 kDa to 300 kDa; between 250 kDa to 1,000 kDa; between 250 kDa to 900 kDa; between 250 kDa to 800 kDa; between 250 kDa to 700 kDa; between 250 kDa to 600 kDa; between 250 kDa to 500 kDa; between 250 kDa to 400 kDa; between 250 kDa to 350 kDa; between 300 kDa to 1000 kDa; between 300 kDa to 900 kDa; between 300 kDa to 800 kDa; between 300 kDa to 700 kDa; between 300 kDa to 600 kDa; between 300 kDa to 500 kDa; between 300 kDa to 400 kDa; between 400 kDa to 1,000 kDa; between 400 kDa to 900 kDa; between 400 kDa to 800 kDa; between 400 kDa to 700 kDa; between 400 kDa to 600 kDa or between 500 kDa to 600 kDa. Any whole number integer within any of the above ranges is contemplated as an embodiment of the disclosure.

In some embodiments, the serotypes 8/11A/12F/23A/23B, 8/11A/12F/23B, 8/11A/23A/23B, 8/12F/23A/23B, 11A/12F/23A/23B, 8/11A/23B, 8/12F/23B, 8/23A/23B, 11A/12F/23B, 11A/23A/23B, 12F/23A/23B, 8/23B, 11A/23B, 12F/23B or 23A/23B glycoconjugate of the present invention comprises a serotype 23B saccharide having a molecular weight of between between 10 kDa and 5,000 kDa. In other such embodiments, the serotype 23B saccharide has a molecular weight of between 20 kDa and 4,000 kDa. In other such embodiments, the serotype 23B saccharide has a molecular weight of between 50 kDa and 3,000 kDa. In other such embodiments, the serotype 23B saccharide has a molecular weight of between 100 kDa and 2500 kDa. In other such embodiments, the serotype 23B saccharide has a molecular weight of between 100 kDa and 2,000 kDa. In other such embodiments, the serotype 23B saccharide has a molecular weight of between 150 kDa and 2,000 kDa. In other such embodiments, the serotype 23B saccharide has a molecular weight of between 150 kDa and 1,500 kDa. In other such embodiments, the serotype 23B saccharide has a molecular weight of between 20 kDa and 1,500 kDa. In another embodiment, the serotype 23B saccharide has a molecular weight of between 30 kDa and 1,250 kDa. In another embodiment, the serotype 23B saccharide has a molecular weight of between 50 kDa and 1,000 kDa. In another embodiment, the serotype 23B saccharide has a molecular weight of between 70 kDa and 900 kDa. In another embodiment, the serotype 23B saccharide has a molecular weight of between 100 kDa and 800 kDa. In another embodiment, the serotype 23B saccharide has a molecular weight of between 200 kDa to 600 kDa. In another embodiment, the serotype 23B saccharide has a molecular weight of between 400 kDa to 700 kDa.

In further such embodiments, the serotype 23B saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 50 kDa and 400 kDa; between 50 kDa and 300 kDa; between 50 kDa and 200 kDa; between 50 kDa and 100 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In further embodiments, the serotype 23B saccharide has a molecular weight of between 10 kDa and 2,000 kDa. In further such embodiments, the serotype 23B saccharide has a molecular weight of between 100 kDa to 1,000 kDa; between 100 kDa to 900 kDa; between 100 kDa to 800 kDa; between 100 kDa to 700 kDa; between 100 kDa to 600 kDa; between 100 kDa to 500 kDa; between 100 kDa to 400 kDa; between 100 kDa to 300 kDa; between 150 kDa to 1,000 kDa; between 150 kDa to 900 kDa; between 150 kDa to 800 kDa; between 150 kDa to 700 kDa; between 150 kDa to 600 kDa; between 150 kDa to 500 kDa; between 150 kDa to 400 kDa; between 150 kDa to 300 kDa; between 200 kDa to 1,000 kDa; between 200 kDa to 900 kDa; between 200 kDa to 800 kDa; between 200 kDa to 700 kDa; between 200 kDa to 600 kDa; between 200 kDa to 500 kDa; between 200 kDa to 400 kDa; between 200 kDa to 300 kDa; between 250 kDa to 1,000 kDa; between 250 kDa to 900 kDa; between 250 kDa to 800 kDa; between 250 kDa to 700 kDa; between 250 kDa to 600 kDa; between 250 kDa to 500 kDa; between 250 kDa to 400 kDa; between 250 kDa to 350 kDa; between 300 kDa to 1000 kDa; between 300 kDa to 900 kDa; between 300 kDa to 800 kDa; between 300 kDa to 700 kDa; between 300 kDa to 600 kDa; between 300 kDa to 500 kDa; between 300 kDa to 400 kDa; between 400 kDa to 1,000 kDa; between 400 kDa to 900 kDa; between 400 kDa to 800 kDa; between 400 kDa to 700 kDa; between 400 kDa to 600 kDa or between 500 kDa to 600 kDa. Any whole number integer within any of the above ranges is contemplated as an embodiment of the disclosure.

In some embodiments, the serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugate has a molecular weight of between 500 kDa and 10,000 kDa. In other embodiments, the serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugate has a molecular weight of between 1,000 kDa and 8,000 kDa. In still other embodiments, the serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugate has a molecular weight of between 2,000 kDa and 8,000 kDa or between 3,000 kDa and 7,000 kDa. In further embodiments, the serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa.

In further embodiments, the serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa.

In further embodiments, the serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate is measured by SEC-MALLS. Any whole number integer within any of the above ranges is contemplated as an embodiment of the disclosure.

Another way to characterize the serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugate of the invention is by the number of lysine residues in the carrier protein (e.g., $CRM_{197}$) that become conjugated to the saccharides which can be characterized as a range of conjugated lysines (degree of conjugation). The evidence for lysine modification of the carrier protein, due to covalent linkages to the saccharides, can be obtained by amino acid analysis using routine methods known to those of skill in the art. Conjugation results in a reduction in the number of lysine residues recovered compared to the carrier protein starting material (e.g. $CRM_{197}$) used to generate the conjugate materials. In a preferred embodiment, the degree of conjugation of the serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugate of the invention is about 2, about 3, about 4, about 5, about 6, about 7, about 8, about 9, about 10, about 11, about 12, about 13, about 14 or about 15. In a preferred embodiment, the degree of conjugation of the serotypes 8/11A/12F/23A/23B glycoconjugate of the invention is between 4 and 7. In some such embodiments, the carrier protein is $CRM_{197}$. In other such embodiments, the carrier protein is DT. In other such embodiments, the carrier protein is TT. In other such embodiments, the carrier protein is PD.

The serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugate of the invention may also be characterized by the ratio (weight/weight) of saccharide to carrier protein. In some embodiments, the ratio of saccharides to carrier protein in the glycoconjugate (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of saccharides to carrier protein in the conjugate is between 0.9 and 1.1. In some such embodiments, the carrier protein is $CRM_{197}$. In other such embodiments, the carrier protein is DT. In other such embodiments, the carrier protein is TT. In other such embodiments, the carrier protein is PD.

The serotypes 8/11A/12F/23A/23B, 8/11A/12F/23A, 8/11A/12F/23B, 8/11A/23A/23B, 8/11A/12F, 8/11A/23A, 8/11A/23B or 8/11A glycoconjugate of the invention may also be characterized by the ratio (weight/weight) of serotype 8 saccharide to serotype 11A saccharide in the glycoconjugate. In some embodiments, the ratio of serotype 8 saccharide to serotype 11A saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 8 saccharide to serotype 11A saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 8 saccharide to serotype 11A saccharide ratio (w/w) is between 0.8 and 1.2. In a preferred embodiment, the ratio of serotype 8 saccharide to serotype 11A saccharide in the conjugate is between 0.9 and 1.1, even more preferably the ratio of serotype 8 saccharide to serotype 11A saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/11A/12F/23A/23B, 8/11A/12F/23A, 8/11A/12F/23B, 8/12F/23A/23B, 8/11A/12F, 8/12F/23A, 8/12F/23B or 8/12F glycoconjugate of the invention may also be characterized by the ratio (weight/weight) of serotype 8 saccharide to serotype 12F saccharide in the glycoconjugate. In some embodiments, the ratio of serotype 8 saccharide to serotype 12F saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 8 saccharide to serotype 12F saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 8 saccharide to serotype 12F saccharide ratio (w/w) is between 0.8 and 1.2. In a preferred embodiment, the ratio of serotype 8 saccharide to serotype 12F saccharide in the conjugate is between 0.9 and 1.1, even more preferably the ratio of serotype 8 saccharide to serotype 12F saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/11A/12F/23A/23B, 8/11A/12F/23A, 8/11A/23A/23B, 8/12F/23A/23B, 8/11A/23A, 8/12F/23A, 8/23A/23B or 8/23A glycoconjugate of the invention may also be characterized by the ratio (weight/weight) of serotype 8 saccharide to serotype 23A saccharide in the glycoconjugate. In some embodiments, the ratio of serotype 8 saccharide to serotype 23A saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 8 saccharide to serotype 23A saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 8 saccharide to serotype 23A saccharide ratio (w/w) is between 0.8 and 1.2. In a preferred embodiment, the ratio of serotype 8 saccharide to serotype 23A saccharide in the conjugate is between 0.9 and 1.1, even more preferably the ratio of serotype 8 saccharide to serotype 23A saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/11A/12F/23A/23B, 8/11A/12F/23B, 8/11A/23A/23B, 8/12F/23A/23B, 8/11A/23B, 8/12F/23B, 8/23A/23B or 8/23B glycoconjugate of the invention may also be characterized by the ratio (weight/weight) of serotype 8 saccharide to serotype 23B saccharide in the glycoconjugate. In some embodiments, the ratio of serotype 8 saccharide to serotype 23B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 8 saccharide to serotype 23B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 8 saccharide to serotype 23B saccharide ratio (w/w) is between 0.8 and 1.2. In a preferred embodiment, the ratio of serotype 8 saccharide to serotype 23B saccharide in the conjugate is between 0.9 and 1.1, even more preferably the ratio of serotype 8 saccharide to serotype 23B saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/11A/12F/23A/23B, 8/11A/12F/23A, 8/11A/12F/23B, 11A/12F/23A/23B, 8/11A/12F, 11A/12F/23A, 11A/12F/23B or 11A/12F glycoconjugate of the invention may also be characterized by the ratio (weight/weight) of serotype 11A saccharide to serotype 12F saccharide in the glycoconjugate. In some embodiments, the ratio of serotype 11A saccharide to serotype 12F saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 11A saccharide to serotype 12F saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 11A saccharide to serotype 12F saccharide ratio (w/w) is between 0.8 and 1.2. In a preferred embodiment, the ratio of serotype 11A saccharide to serotype 12F saccharide in the conjugate is between 0.9 and 1.1, even more preferably the ratio of serotype 11A saccharide to serotype 12F saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/11A/12F/23A/23B, 8/11A/12F/23A, 8/11A/23A/23B, 11A/12F/23A/23B, 8/11A/23A, 11A/12F/23A, 11A/23A/23B or 11A/23A glycoconjugate of the invention may also be characterized by the ratio (weight/weight) of serotype 11A saccharide to serotype 23A saccharide in the glycoconjugate. In some embodiments, the ratio of serotype 11A saccharide to serotype 23A saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 11A saccharide to serotype 23A saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 11A saccharide to serotype 23A saccharide ratio (w/w) is between 0.8 and 1.2. In a preferred embodiment, the ratio of serotype 11A saccharide to serotype 23A saccharide in the conjugate is between 0.9 and 1.1, even more preferably the ratio of serotype 11A saccharide to serotype 23A saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/11A/12F/23A/23B, 8/11A/12F/23B, 8/11A/23A/23B, 11A/12F/23A/23B, 8/11A/23B, 11A/12F/23B, 11A/23A/23B or 11A/23B glycoconjugate of the invention may also be characterized by the ratio (weight/weight) of serotype 11A saccharide to serotype 23B saccharide in the glycoconjugate. In some embodiments, the ratio of serotype 11A saccharide to serotype 23B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 11A saccharide to serotype 23B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 11A saccharide to serotype 23B saccharide ratio (w/w) is between 0.8 and 1.2. In a preferred embodiment, the ratio of serotype 11A saccharide to serotype 23B saccharide in the conjugate is between 0.9 and 1.1, even more preferably the ratio of serotype 11A saccharide to serotype 23B saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/11A/12F/23A/23B, 8/11A/12F/23A, 8/12F/23A/23B, 11A/12F/23A/23B, 8/12F/23A, 11A/12F/23A, 12F/23A/23B or 12F/23A glycoconjugate of the invention may also be characterized by the ratio (weight/weight) of serotype 12F saccharide to serotype 23A saccharide in the glycoconjugate. In some embodiments, the ratio of serotype 12F saccharide to serotype 23A saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 12F saccharide to serotype 23A saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 12F saccharide to serotype 23A saccharide ratio (w/w) is between 0.8 and 1.2. In a preferred embodiment, the ratio of serotype 12F saccharide to serotype 23A saccharide in the conjugate is between 0.9 and 1.1, even more preferably the ratio of serotype 12F saccharide to serotype 23A saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/11A/12F/23A/23B, 8/11A/12F/23B, 8/12F/23A/23B, 11A/12F/23A/23B, 8/12F/23B, 11A/12F/23B, 12F/23A/23B or 12F/23B glycoconjugate of the invention may also be characterized by the ratio (weight/weight) of serotype 12F saccharide to serotype 23B saccharide in the glycoconjugate. In some embodiments, the ratio of serotype 12F saccharide to serotype 23B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 12F saccharide to serotype 23B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 12F saccharide to serotype 23B saccharide ratio (w/w) is between 0.8 and 1.2. In a preferred embodiment, the ratio of serotype 12F saccharide to serotype 23B saccharide in the conjugate is between 0.9 and 1.1, even more preferably the ratio of serotype 12F saccharide to serotype 23B saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/11A/12F/23A/23B, 8/11A/23A/23B, 8/12F/23A/23B, 11A/12F/23A/23B, 8/23A/23B, 11A/23A/23B, 12F/23A/23B or 23A/23B glycoconjugate of the invention may also be characterized by the ratio (weight/weight) of serotype 23A saccharide to serotype 23B saccharide in the glycoconjugate. In some embodiments, the ratio of serotype 23A saccharide to serotype 23B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 23A saccharide to serotype 23B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 23A saccharide to serotype 23B saccharide ratio (w/w) is between 0.8 and 1.2. In a preferred embodiment, the ratio of serotype 23A saccharide to serotype 23B saccharide in the conjugate is between 0.9 and 1.1, even more preferably the ratio of serotype 23A saccharide to serotype 23B saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 8/11A/12F/23A/23B, 8/11A/12F/23A, 8/11A/12F/23B, or 8/11A/12F glycoconjugate of the invention may also be characterized by the relative proportion (weight/weight) of serotypes 8 saccharide, serotypes 11A saccharide and serotype 12F saccharide in the glycoconjugate. In some embodiments, the relative proportion of serotype 8 saccharide, serotype 11A saccharide and serotype 12F saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | J | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 12F | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 8 saccharide, serotypes 11A saccharide and serotype 12F saccharide in the glycoconjugate, for example column a is to be read as: in an embodiment the relative proportion of serotype 8 saccharide, serotype 11A saccharide and serotype 12F saccharide in the serotypes 8/11A/12F/23A/23B, 8/11A/12F/23A, 8/11A/12F/23B, or 8/11A/12F glycoconjugate is respectively about 1:about 1:about 4 (about one 8 saccharide for about one 11A saccharide and for about four 12F saccharide (w/w)). Preferably, the mass of serotype 8 saccharide, serotype 11A saccharide and serotype 12F saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/11A/12F/23A/23B, 8/11A/12F/23A, 8/11A/23A/23B, or 8/11A/23A glycoconjugate of the invention may also be characterized by the relative proportion (weight/weight) of serotypes 8 saccharide, serotypes 11A saccharide and serotype 23A saccharide in the glycoconjugate. In some embodiments, the relative proportion of serotype 8 saccharide, serotype 11A saccharide and serotype 23A saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | J | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 23A | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 8 saccharide, serotypes 11A saccharide and serotype 23A saccharide in the glycoconjugate, for example column a is to be read as: in an embodiment the relative proportion of serotype 8 saccharide, serotype 11A saccharide and serotype 23A saccharide in the serotypes 8/11A/12F/23A/23B, 8/11A/12F/23A, 8/11A/23A/23B, or 8/11A/23A glycoconjugate is respectively about 1:about 1: about 4 (about one 8 saccharide for about one 11A saccharide and for about four 23A saccharide (w/w)). Preferably, the mass of serotype 8 saccharide, serotype 11A saccharide and serotype 23A saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/11A/12F/23A/23B, 8/11A/12F/23B, 8/11A/23A/23B or 8/11A/23B glycoconjugate of the invention may also be characterized by the relative proportion (weight/weight) of serotypes 8 saccharide, serotypes 11A saccharide and serotype 23B saccharide in the glycoconjugate. In some embodiments, the relative proportion of serotype 8 saccharide, serotype 11A saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | J | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 8 saccharide, serotypes 11A saccharide and serotype 23B saccharide in the glycoconjugate, for example column a is to be read as: in an embodiment the relative proportion of serotype 8 saccharide, serotype 11A saccharide and serotype 23B saccharide in the serotypes 8/11A/12F/23A/23B, 8/11A/12F/23B, 8/11A/23A/23B or 8/11A/23B glycoconjugate is respectively about 1:about 1:about 4 (about one 8 saccharide for about one 11A saccharide and for about four 23B saccharide (w/w)). Preferably, the mass of serotype 8 saccharide, serotype 11A saccharide and serotype 23B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/11A/12F/23A/23B, 8/11A/12F/23A, 8/12F/23A/23B or 8/12F/23A glycoconjugate of the invention may also be characterized by the relative proportion (weight/weight) of serotypes 8 saccharide, serotypes 12F saccharide and serotype 23A saccharide in the glycoconjugate. In some embodiments, the relative proportion of serotype 8 saccharide, serotype 12F saccharide and serotype 23A saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | J | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 12F | 1 | 1 | 1 | 1 | 1 | 1 | 1 | 1 | 1 | 2 | 2 | 2 | 2 | 2 | 4 | 4 | 4 | 4 | 4 |
| 23A | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 8 saccharide, serotypes 12F saccharide and serotype 23A saccharide in the glycoconjugate, for example column a is to be read as: in an embodiment the relative proportion of serotype 8 saccharide, serotype 12F saccharide and serotype 23A saccharide in the serotypes 8/11A/12F/23A/23B, 8/11A/12F/23A, 8/12F/23A/23B or 8/12F/23A glycoconjugate is respectively about 1:about 1:about 4 (about one 8 saccharide for about one 12F saccharide and for about four 23A saccharide (w/w)). Preferably, the mass of serotype 8 saccharide, serotype 12F saccharide and serotype 23A saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/11A/12F/23A/23B, 8/11A/12F/23B, 8/12F/23A/23B or 8/12F/23B glycoconjugate of the invention may also be characterized by the relative proportion (weight/weight) of serotypes 8 saccharide, serotypes 12F saccharide and serotype 23B saccharide in the glycoconjugate. In some embodiments, the relative proportion of serotype 8 saccharide, serotype 12F saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | J | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 12F | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 8 saccharide, serotypes 12F saccharide and serotype 23B saccharide in the glycoconjugate, for example column a is to be read as: in an embodiment the relative proportion of serotype 8 saccharide, serotype 12F saccharide and serotype 23B saccharide in the serotypes 8/11A/12F/23A/23B, 8/11A/12F/23B, 8/12F/23A/23B or 8/12F/23B glycoconjugate is respectively about 1:about 1:about 4 (about one 8 saccharide for about one 12F saccharide and for about four 23B saccharide (w/w)). Preferably, the mass of serotype 8 saccharide, serotype 12F saccharide and serotype 23B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/11A/12F/23A/23B, 8/11A/23A/23B, 8/12F/23A/23B or 8/23A/23B glycoconjugate of the invention may also be characterized by the relative proportion (weight/weight) of serotypes 8 saccharide, serotypes 23A saccharide and serotype 23B saccharide in the glycoconjugate. In some embodiments, the relative proportion of serotype 8 saccharide, serotype 23A saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | J | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 23A | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 8 saccharide, serotypes 23A saccharide and serotype 23B saccharide in the glycoconjugate, for example column a is to be read as: in an embodiment the relative proportion of serotype 8 saccharide, serotype 23A saccharide and serotype 23B saccharide in the serotypes 8/11A/12F/23A/23B, 8/11A/23A/23B, 8/12F/23A/23B or 8/23A/23B glycoconjugate is respectively about 1:about 1:about 4 (about one 8 saccharide for about one 23A saccharide and for about four 23B saccharide (w/w)). Preferably, the mass of serotype 8 saccharide, serotype 23A saccharide and serotype 23B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/11A/12F/23A/23B, 8/11A/12F/23A, 11A/12F/23A/23B or 11A/12F/23A glycoconjugate of the invention may also be characterized by the relative proportion (weight/weight) of serotypes 11A saccharide, serotypes 12F saccharide and serotype 23A saccharide in the glycoconjugate. In some embodiments, the relative proportion of serotype 11A saccharide, serotype 12F saccharide and serotype 23A saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | J | k | l | m | n | o | p | q | r | s |
| 11A | 1 | 1 | 1 | 2 | 2 | 2 | 4 | 4 | 4 | 1 | 1 | 1 | 2 | 4 | 1 | 1 | 1 | 2 | 4 |
| 12F | 1 | 1 | 1 | 1 | 1 | 1 | 1 | 1 | 1 | 2 | 2 | 2 | 2 | 2 | 4 | 4 | 4 | 4 | 4 |
| 23A | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 11A saccharide, serotypes 12F saccharide and serotype 23A saccharide in the glycoconjugate, for example column a is to be read as: in an embodiment the relative proportion of serotype 11A saccharide, serotype 12F saccharide and serotype 23A saccharide in the serotypes 8/11A/12F/23A/23B, 8/11A/12F/23A, 11A/12F/23A/23B or 11A/12F/23A glycoconjugate is respectively about 1:about 1:about 4 (about one 11A saccharide for about one 12F saccharide and for about four 23A saccharide (w/w)). Preferably, the mass of serotype 11A saccharide, serotype 12F saccharide and serotype 23A saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/11A/12F/23A/23B, 8/11A/12F/23B, 11A/12F/23A/23B or 11A/12F/23B glycoconjugate of the invention may also be characterized by the relative proportion (weight/weight) of serotypes 11A saccharide, serotypes 12F saccharide and serotype 23B saccharide in the glycoconjugate. In some embodiments, the relative proportion of serotype 11A saccharide, serotype 12F saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 11A | 1 | 1 | 1 | 2 | 2 | 2 | 4 | 4 | 4 | 1 | 1 | 1 | 2 | 4 | 1 | 1 | 1 | 2 | 4 |
| 12F | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 11A saccharide, serotypes 12F saccharide and serotype 23B saccharide in the glycoconjugate, for example column a is to be read as: in an embodiment the relative proportion of serotype 11A saccharide, serotype 12F saccharide and serotype 23B saccharide in the serotypes 8/11A/12F/23A/23B, 8/11A/12F/23B, 11A/12F/23A/23B or 11A/12F/23B glycoconjugate is respectively about 1:about 1:about 4 (about one 11A saccharide for about one 12F saccharide and for about four 23B saccharide (w/w)). Preferably, the mass of serotype 11A saccharide, serotype 12F saccharide and serotype 23B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/11A/12F/23A/23B, 8/11A/23A/23B, 11A/12F/23A/23B or 11A/23A/23B glycoconjugate of the invention may also be characterized by the relative proportion (weight/weight) of serotypes 11A saccharide, serotypes 23A saccharide and serotype 23B saccharide in the glycoconjugate. In some embodiments, the relative proportion of serotype 11A saccharide, serotype 23A saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | J | k | l | m | n | o | p | q | r | s |
| 11A | 1 | 1 | 1 | 2 | 2 | 2 | 4 | 4 | 4 | 1 | 1 | 1 | 2 | 4 | 1 | 1 | 1 | 2 | 4 |
| 23A | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 11A saccharide, serotypes 23A saccharide and serotype 23B saccharide in the glycoconjugate, for example column a is to be read as: in an embodiment the relative proportion of serotype 11A saccharide, serotype 23A saccharide and serotype 23B saccharide in the serotypes 8/11A/12F/23A/23B, 8/11A/23A/23B, 11A/12F/23A/23B or 11A/23A/23B glycoconjugate is respectively about 1:about 1:about 4 (about one 11A saccharide for about one 23A saccharide and for about four 23B saccharide (w/w)). Preferably, the mass of serotype 11A saccharide, serotype 12F saccharide and serotype 23B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/11A/12F/23A/23B, 8/12F/23A/23B, 11A/12F/23A/23B or 12F/23A/23B glycoconjugate of the invention may also be characterized by the relative proportion (weight/weight) of serotypes 12F saccharide, serotypes 23A saccharide and serotype 23B saccharide in the glycoconjugate. In some embodiments, the relative proportion of serotype 12F saccharide, serotype 23A saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | J | k | l | m | n | o | p | q | r | s |
| 12F | 1 | 1 | 1 | 2 | 2 | 2 | 4 | 4 | 4 | 1 | 1 | 1 | 2 | 4 | 1 | 1 | 1 | 2 | 4 |
| 23A | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 12F saccharide, serotypes 23A saccharide and serotype 23B saccharide in the glycoconjugate, for example column a is to be read as: in an embodiment the relative proportion of serotype 12F saccharide, serotype 23A saccharide and serotype 23B saccharide in the serotypes 8/11A/12F/23A/23B, 8/12F/23A/23B, 11A/12F/23A/23B or 12F/23A/23B glycoconjugate is respectively about 1:about 1:about 4 (about one 12F saccharide for about one 23A saccharide and for about four 23B saccharide (w/w)). Preferably, the mass of serotype 12F saccharide, serotype 12F saccharide and serotype 23B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/11A/12F/23A/23B or 8/11A/12F/23A glycoconjugate of the invention may also be characterized by the relative proportion (weight/weight) of serotypes 8 saccharide, serotypes 11A saccharide, serotype 12F saccharide and serotype 23A saccharide in the glycoconjugate. In some embodiments, the relative proportion of serotype 8 saccharide, serotype 11A saccharide, serotype 12F saccharide and serotype 23A saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 11A | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 12F | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23A | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 12F | 2 | 2 | 2 | 2 | 2 | 2 | 2 | 2 | 2 | 2 | 2 | 2 | 2 | 2 | 2 | 2 | 2 | 2 | 2 |
| 23A | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 12F | 4 | 4 | 4 | 4 | 4 | 4 | 4 | 4 | 4 | 4 | 4 | 4 | 4 | 4 | 4 | 4 | 4 | 4 | 4 |
| 23A | 1 | 2 | 4 | 1 | 2 | 4 | 1 | 2 | 4 | 1 | 2 | 4 | 1 | 1 | 1 | 2 | 4 | 1 | 1 |

Each column a to bm of the above tables provides the relative proportion of serotype 8 saccharide, serotype 11A saccharide, serotype 12F saccharide and serotype 23A saccharide in the glycoconjugate, for example column a is to be read as: in an embodiment the relative proportion of serotype 8 saccharide, serotype 11A saccharide, serotype 12F saccharide and serotype 23A saccharide in the serotypes 8/11A/12F/23A/23B or 8/11A/12F/23A glycoconjugate is respectively about 1:about 1:about 1:about 1 (about one 8 saccharide, for about one 11A saccharide, for about one 12F and for about one 23A saccharide (w/w)). Preferably, the mass of serotype 8 saccharide, serotype 11A saccharide, serotype 12F and serotype 23A saccharide in the serotypes 8/11A/12F/23A/23B or 8/11A/12F/23A glycoconjugate is about the same for each saccharide (ratio of about 1:1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/11A/12F/23A/23B or 8/11A/12F/23B glycoconjugate of the invention may also be characterized by the relative proportion (weight/weight) of serotypes 8 saccharide, serotypes 11A saccharide, serotype 12F saccharide and serotype 23B saccharide in the glycoconjugate. In some embodiments, the relative proportion of serotype 8 saccharide, serotype 11A saccharide, serotype 12F saccharide and serotype 23B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 11A | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 12F | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | Aj | ak | al | am | an | ao | ap | aq | ar | as | at |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 12F | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | Bf | bg | bh | bi | bj | bk | bl | bm |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 12F | 4 | 4 | 4 | 4 | 4 | 4 | 4 | 4 | 4 | 4 | 4 | 4 | 4 | 4 | 4 | 4 | 4 | 4 | 4 |
| 23B | 1 | 2 | 4 | 1 | 2 | 4 | 1 | 2 | 4 | 1 | 2 | 4 | 1 | 1 | 1 | 2 | 4 | 1 | 1 |

Each column a to bm of the above tables provides the relative proportion of serotype 8 saccharide, serotype 11A saccharide, serotype 12F saccharide and serotype 23B saccharide in the glycoconjugate, for example column a is to be read as: in an embodiment the relative proportion of serotype 8 saccharide, serotype 11A saccharide, serotype 12F saccharide and serotype 23B saccharide in the serotypes 8/11A/12F/23A/23B or 8/11A/12F/23B glycoconjugate is respectively about 1:about 1:about 1:about 1 (about one 8 saccharide, for about one 11A saccharide, for about one 12F and for about one 23B saccharide (w/w)). Preferably, the mass of serotype 8 saccharide, serotype 11A saccharide, serotype 12F and serotype 23B saccharide in the serotypes 8/11A/12F/23A/23B or 8/11A/12F/23B glycoconjugate is about the same for each saccharide (ratio of about 1:1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/11A/12F/23A/23B or 8/11A/23A/23B glycoconjugate of the invention may also be characterized by the relative proportion (weight/weight) of serotypes 8 saccharide, serotypes 11A saccharide, serotype 23A saccharide and serotype 23B saccharide in the glycoconjugate. In some embodiments, the relative proportion of serotype 8 saccharide, serotype 11A saccharide, serotype 23A saccharide and serotype 23B saccharide in the glycoconjugate (w/w) is according to any of the one of the below tables:

| | a | b | c | d | e | f | g | h | i | j | k | l | m | n | k | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 11A | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 23A | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | Bf | bg | bh | bi | bj | bk | bl | bm |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 23A | 4 | 4 | 4 | 4 | 4 | 4 | 4 | 4 | 4 | 4 | 4 | 4 | 4 | 4 | 4 | 4 | 4 | 4 | 4 |
| 23B | 1 | 2 | 4 | 1 | 2 | 4 | 1 | 2 | 4 | 1 | 2 | 4 | 1 | 1 | 1 | 2 | 4 | 1 | 1 |

Each column a to bm of the above tables provides the relative proportion of serotype 8 saccharide, serotype 11A saccharide, serotype 23A saccharide and serotype 23B saccharide in the glycoconjugate, for example column a is to be read as: in an embodiment the relative proportion of serotype 8 saccharide, serotype 11A saccharide, serotype 23A saccharide and serotype 23B saccharide in the serotypes 8/11A/12F/23A/23B or 8/11A/23A/23B glycoconjugate is respectively about 1:about 1:about 1:about 1 (about one 8 saccharide, for about one 11A saccharide, for about one 23A and for about one 23B saccharide (w/w)). Preferably, the mass of serotype 8 saccharide, serotype 11A saccharide, serotype 23A and serotype 23B saccharide in the serotypes 8/11A/12F/23A/23B or 8/11A/23A/23B glycoconjugate is about the same for each saccharide (ratio of about 1:1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/11A/12F/23A/23B or 8/12F/23A/23B glycoconjugate of the invention may also be characterized by the relative proportion (weight/weight) of serotypes 8 saccharide, serotypes 12F saccharide, serotype 23A saccharide and serotype 23B saccharide in the glycoconjugate. In some embodiments, the relative proportion of serotype 8 saccharide, serotype 12F saccharide, serotype 23A saccharide and serotype 23B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 12F | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 12F | 1 | 1 | 1 | 1 | 1 | 1 | 1 | 1 | 1 | 2 | 2 | 2 | 2 | 2 | 4 | 4 | 4 | 4 | 4 |

-continued

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 23A | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 12F | 1 | 1 | 1 | 1 | 1 | 1 | 1 | 1 | 1 | 2 | 2 | 2 | 2 | 2 | 4 | 4 | 4 | 4 | 4 |
| 23A | 4 | 4 | 4 | 4 | 4 | 4 | 4 | 4 | 4 | 4 | 4 | 4 | 4 | 4 | 4 | 4 | 4 | 4 | 4 |
| 23B | 1 | 2 | 4 | 1 | 2 | 4 | 1 | 2 | 4 | 1 | 2 | 4 | 1 | 1 | 1 | 2 | 4 | 1 | 1 |

Each column a to bm of the above tables provides the relative proportion of serotype 8 saccharide, serotype 12F saccharide, serotype 23A saccharide and serotype 23B saccharide in the glycoconjugate, for example column a is to be read as: in an embodiment the relative proportion of serotype 8 saccharide, serotype 12F saccharide, serotype 23A saccharide and serotype 23B saccharide in the serotypes 8/11A/12F/23A/23B or 8/12F/23A/23B glycoconjugate is respectively about 1:about 1:about 1:about 1 (about one 8 saccharide, for about one 12F saccharide, for about one 23A and for about one 23B saccharide (w/w)). Preferably, the mass of serotype 8 saccharide, serotype 12F saccharide, serotype 23A and serotype 23B saccharide in the serotypes 8/11A/12F/23A/23B or 8/12F/23A/23B glycoconjugate is about the same for each saccharide (ratio of about 1:1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/11A/12F/23A/23B or 11A/12F/23A/23B glycoconjugate of the invention may also be characterized by the relative proportion (weight/weight) of serotypes 11A saccharide, serotypes 12F saccharide, serotype 23A saccharide and serotype 23B saccharide in the glycoconjugate. In some embodiments, the relative proportion of serotype 11A saccharide, serotype 12F saccharide, serotype 23A saccharide and serotype 23B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 11A | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 12F | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 11A | 1 | 1 | 1 | 2 | 2 | 2 | 4 | 4 | 4 | 1 | 1 | 1 | 2 | 4 | 1 | 1 | 1 | 2 | 4 |
| 12F | 1 | 1 | 1 | 1 | 1 | 1 | 1 | 1 | 1 | 2 | 2 | 2 | 2 | 2 | 4 | 4 | 4 | 4 | 4 |
| 23A | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 11A | 1 | 1 | 1 | 2 | 2 | 2 | 4 | 4 | 4 | 1 | 1 | 1 | 2 | 4 | 1 | 1 | 1 | 2 | 4 |
| 12F | 1 | 1 | 1 | 1 | 1 | 1 | 1 | 1 | 1 | 2 | 2 | 2 | 2 | 2 | 4 | 4 | 4 | 4 | 4 |
| 23A | 4 | 4 | 4 | 4 | 4 | 4 | 4 | 4 | 4 | 4 | 4 | 4 | 4 | 4 | 4 | 4 | 4 | 4 | 4 |
| 23B | 1 | 2 | 4 | 1 | 2 | 4 | 1 | 2 | 4 | 1 | 2 | 4 | 1 | 1 | 1 | 2 | 4 | 1 | 1 |

Each column a to bm of the above tables provides the relative proportion of serotype 11A saccharide, serotype 12F saccharide, serotype 23A saccharide and serotype 23B saccharide in the glycoconjugate, for example column a is to be read as: in an embodiment the relative proportion of serotype 11A saccharide, serotype 12F saccharide, serotype 23A saccharide and serotype 23B saccharide in the serotypes 8/11A/12F/23A/23B or 11A/12F/23A/23B glycoconjugate is respectively about 1:about 1:about 1:about 1 (about one 8 saccharide, for about one 12F saccharide, for about one 23A and for about one 23B saccharide (w/w)).

Preferably, the mass of serotype 11A saccharide, serotype 12F saccharide, serotype 23A and serotype 23B saccharide in the serotypes 8/11A/12F/23A/23B or 11A/12F/23A/23B glycoconjugate is about the same for each saccharide (ratio of about 1:1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 8/11A/12F/23A/23B glycoconjugate of the invention may also be characterized by the relative proportion (weight/weight) of serotype 8 saccharide, serotype 11A saccharide, serotype 12F saccharide, serotype 23A saccharide and serotype 23B saccharide in the glycoconjugate. In some embodiments, the relative proportion of serotype 8 saccharide, serotype 11A saccharide, serotype 12F saccharide, serotype 23A saccharide and serotype 23B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 11A | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 12F | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at | au |
|---|---|---|---|---|---|---|---|---|---|---|---|---|---|---|---|---|---|---|---|---|
| 8 | 1 | 1 | 1 | 1 | 1 | 1 | 1 | 1 | 1 | 1 | 1 | 1 | 1 | 1 | 1 | 1 | 1 | 1 | 1 | 1 |
| 11A | 1 | 1 | 1 | 2 | 2 | 2 | 4 | 4 | 4 | 1 | 1 | 1 | 2 | 2 | 2 | 4 | 4 | 4 | 1 | 1 |
| 12F | 1 | 1 | 1 | 1 | 1 | 1 | 1 | 1 | 1 | 2 | 2 | 2 | 2 | 2 | 2 | 2 | 2 | 2 | 4 | 4 |
| 23A | 2 | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 2 | 4 | 1 | 2 | 4 | 1 | 2 |

| | av | aw | ax | ay | az | ba | bb | bc | bd | Be | bf | bg | bh | bi | bj | bk | bl | bm | bn |
|---|---|---|---|---|---|---|---|---|---|---|---|---|---|---|---|---|---|---|---|
| 8 | 1 | 1 | 1 | 1 | 1 | 1 | 1 | 1 | 1 | 1 | 1 | 1 | 1 | 1 | 1 | 1 | 1 | 1 | 1 |
| 11A | 1 | 2 | 2 | 2 | 4 | 4 | 4 | 1 | 1 | 1 | 2 | 2 | 2 | 4 | 4 | 4 | 1 | 1 | 1 |
| 12F | 4 | 4 | 4 | 4 | 4 | 4 | 4 | 1 | 1 | 1 | 1 | 1 | 1 | 1 | 1 | 1 | 2 | 2 | 2 |
| 23A | 2 | 2 | 2 | 2 | 2 | 2 | 2 | 4 | 4 | 4 | 4 | 4 | 4 | 4 | 4 | 4 | 4 | 4 | 4 |
| 23B | 4 | 1 | 2 | 4 | 1 | 2 | 4 | 1 | 2 | 4 | 1 | 2 | 4 | 1 | 2 | 4 | 1 | 2 | 4 |

| | bo | bp | bq | br | bs | bt | bu | bv | bw | bx | by | bz | ca | cb | cd | ce | cf | cg | ch | ci |
|---|---|---|---|---|---|---|---|---|---|---|---|---|---|---|---|---|---|---|---|---|
| 8 | 1 | 1 | 1 | 1 | 1 | 1 | 1 | 1 | 1 | 1 | 1 | 1 | 1 | 1 | 1 | 2 | 2 | 2 | 2 | 2 |
| 11A | 2 | 2 | 2 | 4 | 4 | 4 | 1 | 1 | 1 | 2 | 2 | 2 | 4 | 4 | 4 | 1 | 1 | 1 | 2 | 2 |
| 12F | 2 | 2 | 2 | 2 | 2 | 2 | 4 | 4 | 4 | 4 | 4 | 4 | 4 | 4 | 4 | 1 | 1 | 1 | 1 | 1 |
| 23A | 4 | 4 | 4 | 4 | 4 | 4 | 4 | 4 | 4 | 4 | 4 | 4 | 4 | 4 | 4 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 |

| | cj | ck | cl | cm | cn | co | cp | cq | cr | cs | ct | cu | cv | cw | cx | cy | cz | da |
|---|---|---|---|---|---|---|---|---|---|---|---|---|---|---|---|---|---|---|
| 8 | 2 | 2 | 2 | 2 | 2 | 2 | 2 | 2 | 2 | 2 | 2 | 2 | 2 | 2 | 2 | 2 | 2 | 2 |
| 11A | 2 | 4 | 4 | 4 | 1 | 1 | 1 | 2 | 2 | 2 | 4 | 4 | 4 | 1 | 1 | 1 | 2 | 2 |
| 12F | 1 | 1 | 1 | 1 | 2 | 2 | 2 | 2 | 2 | 2 | 2 | 2 | 2 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 |
| 23B | 4 | 1 | 2 | 4 | 1 | 2 | 4 | 1 | 2 | 4 | 1 | 2 | 4 | 1 | 2 | 4 | 1 | 2 |

| | db | dc | dd | de | df | dg | dh | di | dj | dk | dl | dm | dn | do | dp | dq | dr | ds | dt |
|---|---|---|---|---|---|---|---|---|---|---|---|---|---|---|---|---|---|---|---|
| 8 | 2 | 2 | 2 | 2 | 2 | 2 | 2 | 2 | 2 | 2 | 2 | 2 | 2 | 2 | 2 | 2 | 2 | 2 | 2 |
| 11A | 2 | 4 | 4 | 4 | 1 | 1 | 1 | 2 | 2 | 2 | 4 | 4 | 4 | 1 | 1 | 1 | 2 | 4 | 1 |
| 12F | 4 | 4 | 4 | 4 | 1 | 1 | 1 | 1 | 1 | 1 | 1 | 1 | 1 | 2 | 2 | 2 | 2 | 2 | 4 |

-continued

| | db | dc | dd | de | df | dg | dh | di | dj | dk | dl | dm | dn | do | dp | dq | dr | ds | dt |
|---|---|---|---|---|---|---|---|---|---|---|---|---|---|---|---|---|---|---|---|
| 23A | 1 | 1 | 1 | 1 | 2 | 2 | 2 | 2 | 2 | 2 | 2 | 2 | 2 | 2 | 2 | 2 | 2 | 2 | 2 |
| 23B | 4 | 1 | 2 | 4 | 1 | 2 | 4 | 1 | 2 | 4 | 1 | 2 | 4 | 1 | 2 | 4 | 1 | 1 | 1 |

| | du | dv | dw | dx | dy | dz | ea | eb | ec | ed | ee | ef | eg | eh | ei | ej | ek | el | em | en | eo |
|---|---|---|---|---|---|---|---|---|---|---|---|---|---|---|---|---|---|---|---|---|---|
| 8 | 2 | 2 | 2 | 2 | 2 | 2 | 2 | 2 | 2 | 2 | 2 | 2 | 2 | 2 | 2 | 2 | 2 | 2 | 2 | 2 | 2 |
| 11A | 1 | 1 | 2 | 4 | 1 | 1 | 1 | 2 | 2 | 2 | 4 | 4 | 4 | 1 | 1 | 1 | 2 | 4 | 1 | 1 | 1 |
| 12F | 4 | 4 | 4 | 4 | 1 | 1 | 1 | 1 | 1 | 1 | 1 | 1 | 1 | 2 | 2 | 2 | 2 | 2 | 4 | 4 | 4 |
| 23A | 2 | 2 | 2 | 2 | 4 | 4 | 4 | 4 | 4 | 4 | 4 | 4 | 4 | 4 | 4 | 4 | 4 | 4 | 4 | 4 | 4 |
| 23B | 2 | 4 | 1 | 1 | 1 | 2 | 4 | 1 | 2 | 4 | 1 | 2 | 4 | 1 | 2 | 4 | 1 | 1 | 1 | 2 | 4 |

| | ep | eq | er | es | et | eu | ev | ew | ex | ey | ez | fa | fb | fc | fd | fe | ff | fg | fh | fi | fj | fk |
|---|---|---|---|---|---|---|---|---|---|---|---|---|---|---|---|---|---|---|---|---|---|---|
| 8 | 2 | 2 | 4 | 4 | 4 | 4 | 4 | 4 | 4 | 4 | 4 | 4 | 4 | 4 | 4 | 4 | 4 | 4 | 4 | 4 | 4 | 4 |
| 11A | 2 | 4 | 1 | 1 | 2 | 2 | 2 | 4 | 4 | 4 | 1 | 1 | 1 | 2 | 2 | 2 | 4 | 4 | 4 | 1 | 1 | 1 |
| 12F | 4 | 4 | 1 | 1 | 1 | 1 | 1 | 1 | 1 | 1 | 2 | 2 | 2 | 2 | 2 | 2 | 2 | 2 | 2 | 4 | 4 | 4 |
| 23A | 4 | 4 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 1 | 2 | 4 | 1 | 2 | 4 | 1 | 2 | 4 | 1 | 2 | 4 | 1 | 2 | 4 | 1 | 2 | 4 | 1 | 2 | 4 |

| | fl | fm | fn | fo | fp | fq | fr | fs | ft | fu | fv | fw | fx | fy | fz | ga | gb | gc | gd |
|---|---|---|---|---|---|---|---|---|---|---|---|---|---|---|---|---|---|---|---|
| 8 | 4 | 4 | 4 | 4 | 4 | 4 | 4 | 4 | 4 | 4 | 4 | 4 | 4 | 4 | 4 | 4 | 4 | 4 | 4 |
| 11A | 2 | 2 | 2 | 4 | 4 | 4 | 1 | 1 | 1 | 2 | 2 | 2 | 4 | 4 | 4 | 1 | 1 | 1 | 2 |
| 12F | 4 | 4 | 4 | 4 | 4 | 4 | 1 | 1 | 1 | 1 | 1 | 1 | 1 | 1 | 1 | 2 | 2 | 2 | 2 |
| 23A | 1 | 1 | 1 | 1 | 1 | 1 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 2 | 4 | 1 | 2 | 4 | 1 |

| | ge | gf | gg | gh | gi | gj | gk | gl | gl | gn | go | gp | gq | gr | gs | gt | gu | gv | gw | gx | gy | gz |
|---|---|---|---|---|---|---|---|---|---|---|---|---|---|---|---|---|---|---|---|---|---|---|
| 8 | 4 | 4 | 4 | 4 | 4 | 4 | 4 | 4 | 4 | 4 | 4 | 4 | 4 | 4 | 4 | 4 | 4 | 4 | 4 | 4 | 4 | 4 |
| 11A | 4 | 1 | 1 | 1 | 2 | 4 | 1 | 1 | 1 | 2 | 2 | 2 | 4 | 4 | 4 | 1 | 1 | 1 | 2 | 4 | 1 | 1 |
| 12F | 2 | 4 | 4 | 4 | 4 | 4 | 1 | 1 | 1 | 1 | 1 | 1 | 1 | 1 | 1 | 2 | 2 | 2 | 2 | 2 | 4 | 4 |
| 23A | 2 | 2 | 2 | 2 | 2 | 2 | 4 | 4 | 4 | 4 | 4 | 4 | 4 | 4 | 4 | 4 | 4 | 4 | 4 | 4 | 4 | 4 |
| 23B | 1 | 1 | 2 | 4 | 1 | 1 | 1 | 2 | 4 | 1 | 2 | 4 | 1 | 2 | 4 | 1 | 2 | 4 | 1 | 1 | 1 | 2 |

| | ha | hb | hc |
|---|---|---|---|
| 8 | 4 | 4 | 4 |
| 11A | 1 | 2 | 4 |
| 12F | 4 | 4 | 4 |
| 23A | 4 | 4 | 4 |
| 23B | 4 | 1 | 1 |

Each column a to hc of the above tables provides the relative proportion of serotype 8 saccharide, serotype 11A saccharide, serotype 12F saccharide, serotype 23A saccharide and serotype 23B saccharide in the glycoconjugate, for example column a is to be read as: in an embodiment the relative proportion of serotype 8 saccharide, serotype 11A saccharide, serotype 12F saccharide, serotype 23A saccharide and serotype 23B saccharide in the serotypes 8/11A/12F/23A/23B glycoconjugate is respectively about 1:about 1:about 1:about 1:about 1 (about one 8 saccharide, for about one 11A saccharide, for about one 12F saccharide, for about one 23A and for about one 23B saccharide (w/w)). Preferably, the mass of serotype 8 saccharide, serotype 11A saccharide, serotype 12F saccharide, serotype 23A and serotype 23B saccharide in the serotypes 8/11A/12F/23A/23B glycoconjugate is about the same for each saccharide (ratio of about 1:1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

In an embodiment, the serotypes 8/11A/12F/23A/23B, 8/11A/12F/23A, 8/11A/12F/23B, 8/11A/23A/23B, 11A/12F/23A/23B, 8/11A/12F, 8/11A/23A, 8/11A/23B, 11A/12F/23A, 11A/12F/23B, 11A/23A/23B, 8/11A, 11A/12F, 11A/23A or 11A/23B glycoconjugate of the invention comprises at least 0.3, 0.5, 0.6, 1.0, 1.4, 1.8, 2.2, 2.6, 3.0, 3.4, 3.8, 4.2, 4.6 or 5 mM acetate per mM serotype 11A saccharide. In a preferred embodiment, the glycoconjugate comprises 0.3 to 5 mM acetate per mM serotype 11A saccharide. In a preferred embodiment, the glycoconjugate comprises at least 0.6, 1, 1.4, 1.8, 2.2, 2.6, 3, 3.4, 3.8, 4.2 or 4.6 mM acetate per mM serotype 11A saccharide and less than about 5 mM acetate per mM serotype 11A saccharide. In a preferred embodiment, the glycoconjugate comprises at least 0.6, 1.0, 1.4, 1.8, 2.2, 2.6, or 3.0 mM acetate per mM serotype 11A saccharide and less than about 3.4 mM acetate per mM serotype 11A saccharide. In a preferred embodiment, the glycoconjugate comprises at least 0.8 mM acetate per mM serotype 11A saccharide. In a preferred embodiment, the presence of O-acetyl groups is determined by ion-HPLC analysis.

In an embodiment, the serotypes 8/11A/12F/23A/23B, 8/11A/12F/23A, 8/11A/12F/23B, 8/11A/23A/23B, 11A/12F/23A/23B, 8/11A/12F, 8/11A/23A, 8/11A/23B, 11A/12F/23A, 11A/12F/23B, 11A/23A/23B, 8/11A, 11A/12F, 11A/23A or 11A/23B glycoconjugate of the invention comprises at least 0.1, 0.2, 0.3, 0.4, 0.5, 0.6, 0.7 or 0.8 mM glycerol per mM of serotype 11A saccharide. In a preferred embodiment, the glycoconjugate comprises 0.1 to 1.0 mM glycerol per mM serotype 11A saccharide. In a preferred embodiment, the glycoconjugate comprises at least 0.1, 0.2, 0.3, 0.4, 0.5, 0.6, 0.7, 0.8 or 0.9 mM glycerol per mM serotype 11A saccharide and less than about 1.0 mM glycerol per mM serotype 11A saccharide. In a preferred embodiment, the glycoconjugate comprises at least 0.3, 0.4, 0.5, 0.6, or 0.7 mM glycerol per mM of serotype 11A saccharide. In a preferred embodiment, the glycoconjugate comprises at least 0.6 mM glycerol per mM of serotype 11A saccharide. In a preferred embodiment, the glycoconjugate comprises at least 0.7 mM glycerol per mM of serotype 11A saccharide.

In an embodiment, the serotypes 8/11A/12F/23A/23B, 8/11A/12F/23A, 8/11A/23A/23B, 8/12F/23A/23B, 11A/12F/23A/23B, 8/11A/23A, 8/12F/23A, 8/23A/23B, 11A/12F/23A, 11A/23A/23B, 12F/23A/23B, 8/23A, 11A/23A, 12F/23A, or 23A/23B glycoconjugate of the invention comprises at least 0.1, 0.2, 0.3, 0.4, 0.5, 0.6, 0.7 or 0.8 mM glycerol per mM of serotype 23A saccharide. In a preferred embodiment, the glycoconjugate comprises 0.1 to 1.0 mM glycerol per mM serotype 23A saccharide. In a preferred embodiment, the glycoconjugate comprises at least 0.5, 0.6 or 0.7 mM glycerol per mM of serotype 23A saccharide. In a preferred embodiment, the glycoconjugate comprises at least 0.6 mM glycerol per mM of serotype 23A saccharide. In a preferred embodiment, the glycoconjugate comprises at least 0.7 mM glycerol per mM of serotype 23A saccharide.

In some embodiments, the serotypes 8/11A/12F/23A/23B, 8/11A/12F/23B, 8/11A/23A/23B, 8/12F/23A/23B, 11A/12F/23A/23B, 8/11A/23B, 8/12F/23B, 8/23A/23B, 11A/12F/23B, 11A/23A/23B, 12F/23A/23B, 8/23B, 11A/23B, 12F/23B or 23A/23B glycoconjugate of the invention comprises at least 0.1, 0.2, 0.3, 0.4, 0.5, 0.6, 0.7 or 0.8 mM glycerol per mM of serotype 23B saccharide. In a preferred embodiment, the glycoconjugate comprises 0.1 to 1.0 mM glycerol per mM serotype 23B saccharide. In a preferred embodiment, the glycoconjugate comprises at least 0.5, 0.6 or 0.7 mM glycerol per mM of serotype 23B saccharide. In a preferred embodiment, the glycoconjugate comprises at least 0.6 mM glycerol per mM of serotype 23B saccharide. In a preferred embodiment, the glycoconjugate comprises at least 0.7 mM glycerol per mM of serotype 23B saccharide.

The serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d$=0), and the fraction representing the maximum retention ($V_i$), ($K_d$=1). The fraction at which a specified sample attribute is reached ($V_e$), is related to $K_d$ by the expression, $K_d=(V_e-V_0)/(V_i-V_0)$.

In a preferred embodiment, at least 30% of the glycoconjugate has a $K_d$ below or equal to 0.3 in a CL-4B column. In a preferred embodiment, at least 40% of the glycoconjugate has a $K_d$ below or equal to 0.3 in a CL-4B column. In a preferred embodiment, at least 45%, 50%, 55%, 60%, 65%, 70%, 75%, 80%, or 85% of the glycoconjugate has a $K_d$ below or equal to 0.3 in a CL-4B column. In a preferred embodiment, at least 60% of the glycoconjugate has a $K_d$ below or equal to 0.3 in a CL-4B column. In a preferred embodiment, between 50% and 80% of the glycoconjugate has a $K_d$ below or equal to 0.3 in a CL-4B column. In a preferred embodiment, between 65% and 80% of the glycoconjugate has a $K_d$ below or equal to 0.3 in a CL-4B column.

The serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugate of the invention may contain free saccharide that is not covalently conjugated to the carrier protein, but is nevertheless present in the glycoconjugate composition. The free saccharide may be noncovalently associated with (i.e., noncovalently bound to, adsorbed to, or entrapped in or with) the glycoconjugate. By free saccharide is meant the amount of free saccharide of the serotypes composing the glycoconjugate (e.g. for a serotypes 8/11A/12F/23A/23B glycoconjugate it is meant to be the free serotypes 8, 11A, 12F, 23A and 23B saccharide, for a serotypes 8/11A glycoconjugate it is meant to be the free serotypes 8, and 11A saccharide). It is compared to the total amount of saccharide of the serotypes composing the glycoconjugate (e.g. for a serotypes 8/11A/12F/23A/23B glycoconjugate it is meant to be the total amount of serotypes 8, 11A, 12F, 23A and 23B saccharide, for a serotypes 8/11A glycoconjugate it is meant to be the total amount of serotypes 8 and 11A saccharide).

In a preferred embodiment, the serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugate comprises less than about 50%, 45%, 40%, 35%, 30%, 25%, 20% or 15% of free saccharide compared to the total amount of saccharide. In a preferred embodiment the glycoconjugate comprises less than about 40% of free saccharide compared to the total amount of saccharide. In a preferred embodiment the glycoconjugate comprises less than about 25% of free saccharide compared to the total amount of saccharide. In a preferred embodiment the glycoconjugate comprises less than about 20% of free saccharide compared to the total amount saccharide. In a preferred embodiment the glycoconjugate comprises less than about 15% of free saccharide compared to the total amount of saccharide.

In preferred embodiments, the serotype 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugates of the invention are prepared using reductive amination.

Reductive amination involves two steps, (1) oxidation (activation) of the saccharide, (2) reduction of the activated saccharide and a carrier protein (e.g., $CRM_{197}$, DT, TT or PD) to form a conjugate. Before oxidation, sizing of the serotype 8, 11A, 12F, 23A and/or 23B saccharide to a target molecular weight (MW) range can be performed. Mechanical or chemical hydrolysis may be employed. Chemical hydrolysis may be conducted using acetic acid. Advantageously, the size of the purified serotypes 8, 11A, 12F, 23A and/or 23B saccharide is reduced while preserving critical features of the structure of the saccharide such as for example the presence of O-acetyl groups. Therefore preferably, the size of the purified serotypes 8, 11A, 12F, 23A and/or 23B saccharide is reduced by mechanical homogenization.

In an embodiment, serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides are activated (oxidized) by a process comprising the step of:

(a) reacting a mixture of isolated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides with an oxidizing agent.

Said process can further comprise a quenching step.

Therefore in an embodiment, serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides are activated (oxidized) by a process comprising the step of:

(a) reacting a mixture of isolated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides with an oxidizing agent;

(b) quenching the oxidation reaction by addition of a quenching agent resulting in activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides.

In these embodiments, the saccharides are therefore activated altogether as a mixture.

In another embodiment, serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides are activated (oxidized) separately and the activated saccharides are then mixed.

In said embodiment, serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides are activated (oxidized) by a process comprising the step of:

(a) individually reacting an isolated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides with an oxidizing agent;

(b) mixing the activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides.

Said process can further comprise a quenching step.

Therefore in an embodiment, serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides are activated (oxidized) by a process comprising the step of:

(a) individually reacting an isolated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides with an oxidizing agent;

(b) quenching the oxidation reactions by addition of a quenching agent resulting in activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides;

(b) mixing the activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides.

The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate).

In a preferred embodiment, the oxidizing agent is sodium periodate. In a preferred embodiment, the periodate used for the oxidation is metaperiodate. In a preferred embodiment the periodate used for the oxidation is sodium metaperiodate.

In one embodiment, the quenching agent is selected from vicinal diols, 1,2-aminoalcohols, amino acids, glutathione, sulfite, bisulfate, dithionite, metabisulfite, thiosulfate, phosphites, hypophosphites or phosphorous acid.

In one embodiment, the quenching agent is a 1,2-aminoalcohols of formula (I):

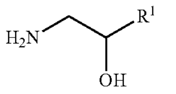

(I)

wherein $R^1$ is selected from H, methyl, ethyl, propyl or isopropyl.

In one embodiment, the quenching agent is selected from sodium and potassium salts of sulfite, bisulfate, dithionite, metabisulfite, thiosulfate, phosphites, hypophosphites or phosphorous acid. In one embodiment, the quenching agent is an amino acid. In such embodiments, said amino acid may be selected from serine, threonine, cysteine, cystine, methionine, proline, hydroxyproline, tryptophan, tyrosine, and histidine.

In one embodiment, the quenching agent is a sulfite such as bisulfate, dithionite, metabisulfite, thiosulfate.

In one embodiment, the quenching agent is a compound comprising two vicinal hydroxyl groups (vicinal diols), i.e., two hydroxyl groups covalently linked to two adjacent carbon atoms.

Preferably, the quenching agent is a compound of formula (II):

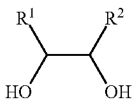

(II)

wherein $R^1$ and $R^2$ are each independently selected from H, methyl, ethyl, propyl or isopropyl. In a preferred embodiment, the quenching agent is glycerol, ethylene glycol, propan-1,2-diol, butan-1,2-diol or butan-2,3-diol, or ascorbic acid. In a preferred embodiment, the quenching agent is butan-2,3-diol.

In a preferred embodiment, the isolated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides are activated by a process comprising the step of:

(a) reacting a mixture of isolated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides with periodate;

(b) quenching the oxidation reaction by addition of butan-2,3-diol resulting in a mixture of activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides.

Following the oxidation step of the saccharides, the saccharides are said to be activated and is referred to as "activated saccharides" here below.

In a preferred embodiment, the mixture of activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides are purified. The mixture of activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides are purified according to methods known to the man skilled in the art such as gel permeation chromatography (GPC), dialysis or ultrafiltration/diafiltration. For example, the mixture of activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides are purified by concentration and diafiltration using an ultrafiltration device.

In a preferred embodiment the degree of oxidation of the activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides is between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25. In a preferred embodiment the degree of oxidation of the activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides is between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20. In a preferred embodiment, the mixture of activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides have a molecular weight between 25 kDa and 1,000 kDa, between 100 kDa and 1,000 kDa, between 300 kDa and 800 kDa, between 300 kDa and 700 kDa, between 300 kDa and 600 kDa, between 400 kDa and 1,000 kDa, between 400 kDa and 800 kDa, between 400 kDa and 700 kDa or between 400 kDa and 600 kDa. In an embodiment, the mixture of activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides have a molecular weight between 300 kDa and 800 kDa. In an embodiment, the mixture of activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides have a molecular weight between 400 kDa and 600 kDa. In a preferred embodiment, the mixture of activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides have a molecular weight between 400 kda and 600 kDa and a degree of oxidation between 10 and 25, between 10 and 20, between 12 and 20 or between 14 and 18. In a preferred embodiment, the mixture of activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides have a molecular weight between 400 kDa and 600 kDa and a degree of oxidation between 10 and 20.

The activated saccharides and/or the carrier protein may be lyophilised (freeze-dried), either independently (discrete lyophilization) or together (co-lyophilized).

In an embodiment, the mixture of activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides are lyophilized, optionally in the presence of a saccharide such as sucrose, trehalose, raffinose, stachyose, melezitose, dextran, mannitol, lactitol or palatinit. In a preferred embodiment, said saccharide is sucrose. In one embodiment, the lyophilized mixture of activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides are then compounded with a solution comprising the carrier protein.

In another embodiment the mixture of activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides and the carrier protein are co-lyophilised. In such embodiments, the mixture of activated 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides are compounded with the carrier protein and lyophilized, optionally in the presence of a saccharide such as sucrose, trehalose, raffinose, stachyose, melezitose, dextran, mannitol, lactitol and palatinit. In a preferred embodiment, said saccharide is sucrose. The co-lyophilized mixture of activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides and carrier protein can then be resuspended in solution and reacted with a reducing agent.

The second step of the conjugation process is the reduction of the activated saccharides and a carrier protein to form a conjugate (reductive amination), using a reducing agent.

The mixture of activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides can be conjugated to a carrier protein by a process comprising the step of:

(c) compounding the mixture of activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides with a carrier protein; and (d) reacting the compounded mixture of activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides and carrier protein with a reducing agent to form a serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugate.

In an embodiment, the reductive amination reaction is carried out in aqueous solvent, preferably a buffered aqueous solvent. In an embodiment, the reduction reaction is carried in a buffer which does not contain an amine group. In an embodiment, the buffer is selected from the group consisting of a salt of acetic acid (acetate), sodium hydrogen carbonate (bicarbonate), boric acid, dimethylarsinic acid (cacodylate), sodium carbonate (carbonate), a salt of citric acid (citrate), a salt of formic acid (formate), a salt of malic acid (malate), a salt of maleic acid (maleate), a salt of phosphoric acid (phosphate) and a salt of succinic acid (succinate). In an embodiment, the buffer is selected from the group consisting of a salt of acetic acid (acetate), a salt of citric acid (citrate), a salt of phosphoric acid (phosphate) and a salt of succinic acid (succinate). In an embodiment, the buffer is a salt of phosphoric acid (phosphate). In an embodiment, the buffer is sodium phosphate Preferably said buffer has a concentration between 1-100 mM, 1-50 mM, 1-25 mM, 1-10 mM, 5-50 mM, 5-15 mM, 5-10 mM, 8-12 mM or 9-11 mM. in an embodiment, said buffer has a concentration of about 1, 2, 3, 4, 5, 6, 7, 8, 9,10, 11, 12, 12, 13, 14, 15 20, 25, 30, 35, 40, 45 or 50 mM.

The aqueous solvent may be used to reconstitute the mixture of activated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides and carrier protein which has been lyophilised.

In an embodiment, the reducing agent is sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^i$PrN—$BH_3$, benzylamine-$BH_3$ or 5-ethyl-2-methylpyridine borane (PEMB). In a preferred embodiment, the reducing agent is sodium cyanoborohydride.

At the end of the reduction reaction, there may be unreacted aldehyde groups remaining in the conjugates, these may be capped using a suitable capping agent. In one embodiment this capping agent is sodium borohydride ($NaBH_4$).

Following conjugation of serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides to the carrier protein, the glycoconjugate can be purified (enriched with respect to the amount of saccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration.

1.3.3 Glycoconjugates of the Invention Comprising at Least Two Saccharides Selected from the Group Consisting of a Saccharide from *S. pneumoniae* Serotype 10A, a Saccharide from *S. pneumoniae* Serotype 22F, a Saccharide from *S. pneumoniae* Serotype 33F and a Saccharide from *S. pneumoniae* Serotype 35B, Conjugated to a Carrier Protein The present invention relates to glycoconjugates wherein 2 or more saccharides antigens are conjugated to the same molecule of the protein carrier (i.e. the carrier molecules have 2 or more different capsular saccharides conjugated to them).

In an embodiment the invention relates to a glycoconjugate comprising at least two saccharides selected from the group consisting of a saccharide from *S. pneumoniae* serotype 10A, a saccharide from *S. pneumoniae* serotype 22F, a saccharide from *S. pneumoniae* serotype 33F and a saccharide from *S. pneumoniae* serotype 35B, conjugated to a carrier protein.

1.3.3.1 Glycoconjugates Comprising a Saccharide from *S. pneumoniae* Serotype 10A, a Saccharide from *S. pneumoniae* Serotype 22F, a Saccharide from *S. pneumoniae* Serotype 33F and a Saccharide from *S. pneumoniae* Serotype 35B, Conjugated to a Carrier Protein In an embodiment the glycoconjugates of the invention comprises a saccharide from *S. pneumoniae* serotype 10A, a saccharide from *S. pneumoniae* serotype 22F, a saccharide from *S. pneumoniae* serotype 33F and a saccharide from *S. pneumoniae* serotype 35B, conjugated to the same carrier protein (herein after 'the serotypes 10A/22F/33F/35B glycoconjugate'). In said embodiment, the carrier molecules have the four different capsular saccharides conjugated to them. Preferably, the glycoconjugates of this section (1.3.3.1) are therefore 4-valent glycoconjugates (i.e. they have serotypes 10A, 22F, 33F and 35B conjugated to the carrier protein and no other polysaccharide antigens covalently attached to the carrier protein).

In some embodiments, the serotypes 10A/22F/33F/35B glycoconjugate of the present invention comprise a serotype 10A saccharide having a molecular weight of between 10 kDa and 5,000 kDa. In other such embodiments, the serotype 10A saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 10A saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/22F/33F/35B glycoconjugate of the present invention comprise a serotype 22F saccharide having a molecular weight of between 10 kDa and 5,000 kDa. In other such embodiments, the serotype 22F saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa.

In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 22F saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/22F/33F/35B glycoconjugate of the present invention comprise a serotype 33F saccharide having a molecular weight of between 10 kDa and 5,000 kDa. In other such embodiments, the serotype 33F saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharide has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 33F saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/22F/33F/35B glycoconjugate of the present invention comprise a serotype 35B saccharide having a molecular weight of between 10 kDa and 5,000 kDa. In other such embodiments, the serotype 35B saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 35B saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/22F/33F/35B glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the serotypes 10A/22F/33F/35B glycoconjugate has a molecular weight of between 500 kDa and 10,000 kDa. In other embodiments, the serotypes 10A/22F/33F/35B glycoconjugate has a molecular weight of between 1,000 kDa and 8,000 kDa.

In still other embodiments, the serotypes 10A/22F/33F/35B glycoconjugate has a molecular weight of between 2,000 kDa and 8,000 kDa or between 3,000 kDa and 7,000 kDa. In further embodiments, the serotypes 10A/22F/33F/

35B glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa.

In further embodiments, the serotypes 10A/22F/33F/35B glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa.

In further embodiments, the serotypes 10A/22F/33F/35B glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate is measured by SEC-MALLS. Any whole number integer within any of the above ranges is contemplated as an embodiment of the disclosure.

Another way to characterize the serotypes 10A/22F/33F/35B glycoconjugate of the invention is by the number of lysine residues in the carrier protein (e.g., $CRM_{197}$) that become conjugated to the saccharides which can be characterized as a range of conjugated lysines (degree of conjugation). The evidence for lysine modification of the carrier protein, due to covalent linkages to the saccharides, can be obtained by amino acid analysis using routine methods known to those of skill in the art. Conjugation results in a reduction in the number of lysine residues recovered compared to the carrier protein starting material (e.g. $CRM_{197}$) used to generate the conjugate materials. In a preferred embodiment, the degree of conjugation of the serotypes 10A/22F/33F/35B glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotypes 10A/22F/33F/35B glycoconjugate of the invention is about 2, about 3, about 4, about 5, about 6, about 7, about 8, about 9, about 10, about 11, about 12, about 13, about 14 or about 15. In a preferred embodiment, the degree of conjugation of the serotypes 10A/22F/33F/35B glycoconjugate of the invention is between 4 and 7. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/22F/33F/35B glycoconjugate of the invention may also be characterized by the ratio (weight/weight) of saccharide to carrier protein. In some embodiments, the ratio of serotypes 10A, 22F, 33F and 35B saccharides to carrier protein in the glycoconjugate (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of serotypes 10A, 22F, 33F and 35B saccharides to carrier protein in the conjugate is between 0.9 and 1.1. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/22F/33F/35B glycoconjugate of the invention may also be characterized by the ratio (weight/weight) of serotype 10A saccharide to serotype 22F saccharide in the glycoconjugate. In some embodiments, the ratio of serotype 10A saccharide to serotype 22F saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 10A saccharide to serotype 22F saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 10A saccharide to serotype 22F saccharide ratio (w/w) is between 0.8 and 1.2. In a preferred embodiment, the ratio of serotype 10A saccharide to serotype 22F saccharide in the conjugate is between 0.9 and 1.1, even more preferably the ratio of serotype 10A saccharide to serotype 22F saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/22F/33F/35B glycoconjugate of the invention may also be characterized by the ratio (weight/weight) of serotype 10A saccharide to serotype 33F saccharide in the glycoconjugate. In some embodiments, the ratio of serotype 10A saccharide to serotype 33F saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 10A saccharide to serotype 33F saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 10A saccharide to serotype 33F saccharide ratio (w/w) is between 0.8 and 1.2. In a preferred embodiment, the ratio of serotype 10A saccharide to serotype 33F saccharide in the conjugate is between 0.9 and 1.1, even more preferably the ratio of serotype 10A saccharide to serotype 33F saccharide in the conjugate is about 1.0. In some such embodiments, the carrier protein is $CRM_{197}$. In other such embodiments, the carrier protein is DT. In other such embodiments, the carrier protein is TT. In other such embodiments the carrier protein is PD.

The serotypes 10A/22F/33F/35B glycoconjugate of the invention may also be characterized by the ratio (weight/weight) of serotype 10A saccharide to serotype 35B saccharide in the glycoconjugate. In some embodiments, the ratio of serotype 10A saccharide to serotype 35B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 10A saccharide to serotype 35B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 10A saccharide to serotype 35B saccharide ratio (w/w) is between 0.8 and 1.2. In a preferred embodiment, the ratio of serotype 10A saccharide to serotype 35B saccharide in the conjugate is between 0.9 and 1.1, even more preferably the ratio of serotype 10A saccharide to serotype 35B saccharide in the conjugate is about 1.0. In some such embodiments, the carrier protein is $CRM_{197}$. In other such embodiments, the carrier protein is DT. In other such embodiments the carrier protein is TT. In other such embodiments the carrier protein is PD.

The serotypes 10A/22F/33F/35B glycoconjugate of the invention may also be characterized by the ratio (weight/weight) of serotype 22F saccharide to serotype 33F saccharide in the glycoconjugate. In some embodiments, the ratio of serotype 22F saccharide to serotype 33F saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 22F saccharide to serotype 33F saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 22F saccharide to serotype 33F saccharide ratio (w/w) is between 0.8 and 1.2. In a preferred embodiment, the ratio of serotype 22F saccharide to serotype 33F saccharide in the conjugate is between 0.9 and 1.1, even more preferably the ratio of serotype 22F saccharide to serotype 33F saccharide in the conjugate is about 1.0. In some such embodiments, the carrier protein is $CRM_{197}$. In other such embodiments, the carrier protein is DT. In other such embodiments, the carrier protein is TT. In other such embodiments the carrier protein is PD.

The serotypes 10A/22F/33F/35B glycoconjugate of the invention may also be characterized by the ratio (weight/weight) of serotype 22F saccharide to serotype 35B saccharide in the glycoconjugate. In some embodiments, the ratio of serotype 22F saccharide to serotype 35B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 22F saccharide to serotype 35B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 22F saccharide to serotype 35B saccharide ratio (w/w) is between 0.8 and 1.2. In a preferred embodiment, the ratio of serotype 22F saccharide to serotype 35B saccharide in the conjugate is between 0.9 and 1.1, even more preferably the ratio of serotype 22F saccharide to serotype 35B saccharide in the conjugate is about 1.0. In some such embodiments, the carrier protein is $CRM_{197}$. In other such embodiments, the carrier protein is DT. In other such embodiments, the carrier protein is TT. In other such embodiments the carrier protein is PD.

The serotypes 10A/22F/33F/35B glycoconjugate of the invention may also be characterized by the ratio (weight/weight) of serotype 33F saccharide to serotype 35B saccharide in the glycoconjugate. In some embodiments, the ratio of serotype 33F saccharide to serotype 35B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 33F saccharide to serotype 35B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 33F saccharide to serotype 35B saccharide ratio (w/w) is between 0.8 and 1.2. In a preferred embodiment, the ratio of serotype 33F saccharide to serotype 35B saccharide in the conjugate is between 0.9 and 1.1, even more preferably the ratio of serotype 33F saccharide to serotype 35B saccharide in the conjugate is about 1.0. In some such embodiments, the carrier protein is $CRM_{197}$. In other such embodiments, the carrier protein is DT. In other such embodiments, the carrier protein is TT. In other such embodiments the carrier protein is PD.

The serotypes 10A/22F/33F/35B glycoconjugate of the invention may also be characterized by the relative proportion (weight/weight) of serotypes 10A saccharide, serotypes 22F saccharide and serotype 33F saccharide in the glycoconjugate. In some embodiments, the relative proportion of serotype 10A saccharide, serotype 22F saccharide and serotype 33F saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | K | l | m | n | o | p | q | r | S |
| 10A | 1 | 1 | 1 | 2 | 2 | 2 | 4 | 4 | 4 | 1 | 1 | 1 | 2 | 4 | 1 | 1 | 1 | 2 | 4 |
| 22F | 1 | 1 | 1 | 1 | 1 | 1 | 1 | 1 | 1 | 2 | 2 | 2 | 2 | 2 | 4 | 4 | 4 | 4 | 4 |
| 33F | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 10A saccharide, serotypes 22F saccharide and serotype 33F saccharide in the glycoconjugate, for example column a is to be read as: in an embodiment the relative proportion of serotype 10A saccharide, serotype 22F saccharide and serotype 33F saccharide in the serotypes 10A/22F/33F/35B glycoconjugate is respectively about 1:about 1:about 4 (about one 10A saccharide for about one 22F saccharide and for about four 33F saccharide (w/w)). Preferably, the mass of serotype 10A saccharide, serotype 22F saccharide and serotype 33F saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 10A/22F/33F/35B glycoconjugate of the invention may also be characterized by the relative proportion (weight/weight) of serotypes 10A saccharide, serotypes 22F saccharide and serotype 35B saccharide in the glycoconjugate. In some embodiments, the relative proportion of serotype 10A saccharide, serotype 22F saccharide and serotype 35B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | K | l | m | n | o | p | q | r | s |
| 10A | 1 | 1 | 1 | 2 | 2 | 2 | 4 | 4 | 4 | 1 | 1 | 1 | 2 | 4 | 1 | 1 | 1 | 2 | 4 |
| 22F | 1 | 1 | 1 | 1 | 1 | 1 | 1 | 1 | 1 | 2 | 2 | 2 | 2 | 2 | 4 | 4 | 4 | 4 | 4 |
| 35B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 10A saccharide, serotypes 22F saccharide and serotype 35B saccharide in the glycoconjugate, for example column a is to be read as: in an embodiment the relative proportion of serotype 10A saccharide, serotype 22F saccharide and serotype 35B saccharide in the serotypes 10A/22F/33F/35B glycoconjugate is respectively about 1:about 1:about 4 (about one 10A saccharide for about one 22F saccharide and for about four 35B saccharide (w/w)). Preferably, the mass of serotype 10A saccharide, serotype 22F saccharide and serotype 35B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 10A/22F/33F/35B glycoconjugate of the invention may also be characterized by the relative proportion (weight/weight) of serotypes 10A saccharide, serotypes 33F saccharide and serotype 35B saccharide in the glycoconjugate. In some embodiments, the relative proportion of serotype 10A saccharide, serotype 33F saccharide and serotype 35B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | K | l | m | n | o | p | q | r | s |
| 10A | 1 | 1 | 1 | 2 | 2 | 2 | 4 | 4 | 4 | 1 | 1 | 1 | 2 | 4 | 1 | 1 | 1 | 2 | 4 |
| 33F | 1 | 1 | 1 | 1 | 1 | 1 | 1 | 1 | 1 | 2 | 2 | 2 | 2 | 2 | 4 | 4 | 4 | 4 | 4 |
| 35B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 10A saccharide, serotypes 33F saccharide and serotype 35B saccharide in the glycoconjugate, for example column a is to be read as: in an embodiment the relative proportion of serotype 10A saccharide, serotype 33F saccharide and serotype 35B saccharide in the serotypes 10A/22F/33F/35B glycoconjugate is respectively about 1:about 1:about 4 (about one 10A saccharide for about one 33F saccharide and for about four 35B saccharide (w/w)). Preferably, the mass of serotype 10A saccharide, serotype 33F saccharide and serotype 35B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 10A/22F/33F/35B glycoconjugate of the invention may also be characterized by the relative proportion (weight/weight) of serotypes 22F saccharide, serotypes 33F saccharide and serotype 35B saccharide in the glycoconjugate. In some embodiments, the relative proportion of serotype 22F saccharide, serotype 33F saccharide and serotype 35B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | K | l | m | n | o | p | q | r | S |
| 22F | 1 | 1 | 1 | 2 | 2 | 2 | 4 | 4 | 4 | 1 | 1 | 1 | 2 | 4 | 1 | 1 | 1 | 2 | 4 |
| 33F | 1 | 1 | 1 | 1 | 1 | 1 | 1 | 1 | 1 | 2 | 2 | 2 | 2 | 2 | 4 | 4 | 4 | 4 | 4 |
| 35B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 22F saccharide, serotypes 33F saccharide and serotype 35B saccharide in the glycoconjugate, for example column a is to be read as: in an embodiment the relative proportion of serotype 22F saccharide, serotype 33F saccharide and serotype 35B saccharide in the serotypes 10A/22F/33F/35B glycoconjugate is respectively about 1:about 1:about 4 (about one 22F saccharide for about one 33F saccharide and for about four 35B saccharide (w/w)). Preferably, the mass of serotype 22F saccharide, serotype 33F saccharide and serotype 35B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

The serotypes 10A/22F/33F/35B glycoconjugate of the invention may also be characterized by the relative proportion (weight/weight) of serotypes 10A saccharide, serotypes 22F saccharide, serotype 33F saccharide and serotype 35B saccharide in the glycoconjugate. In some embodiments, the relative proportion of serotype 10A saccharide, serotype 22F saccharide, serotype 33F saccharide and serotype 35B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 10A | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 22F | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 33F | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 35B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 10A | 1 | 1 | 1 | 2 | 2 | 2 | 4 | 4 | 4 | 1 | 1 | 1 | 2 | 4 | 1 | 1 | 1 | 2 | 4 |
| 22F | 1 | 1 | 1 | 1 | 1 | 1 | 1 | 1 | 1 | 2 | 2 | 2 | 2 | 2 | 4 | 4 | 4 | 4 | 4 |
| 33F | 2 | 2 | 2 | 2 | 2 | 2 | 2 | 2 | 2 | 2 | 2 | 2 | 2 | 2 | 2 | 2 | 2 | 2 | 2 |
| 35B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 10A | 1 | 1 | 1 | 2 | 2 | 2 | 4 | 4 | 4 | 1 | 1 | 1 | 2 | 4 | 1 | 1 | 1 | 2 | 4 |
| 22F | 1 | 1 | 1 | 1 | 1 | 1 | 1 | 1 | 1 | 2 | 2 | 2 | 2 | 2 | 4 | 4 | 4 | 4 | 4 |
| 33F | 4 | 4 | 4 | 4 | 4 | 4 | 4 | 4 | 4 | 4 | 4 | 4 | 4 | 4 | 4 | 4 | 4 | 4 | 4 |
| 35B | 1 | 2 | 4 | 1 | 2 | 4 | 1 | 2 | 4 | 1 | 2 | 4 | 1 | 1 | 1 | 2 | 4 | 1 | 1 |

Each column a to bm of the above tables provides the relative proportion of serotype 10A saccharide, serotype 22F saccharide, serotype 33F saccharide and serotype 35B saccharide in the glycoconjugate, for example column a is to be read as: in an embodiment the relative proportion of serotype 10A saccharide, serotype 22F saccharide, serotype 33F saccharide and serotype 35B saccharide in the serotypes 10A/22F/33F/35B glycoconjugate is respectively about 1:about 1:about 1:about 1 (about one 10A saccharide, for about one 22F saccharide, for about one 33F and for about one 35B saccharide (w/w)). Preferably, the mass of serotype 10A saccharide, serotype 22F saccharide, serotype 33F and serotype 35B saccharide in the serotypes 10A/22F/33F/35B glycoconjugate is about the same for each saccharide (ratio of about 1:1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

In an embodiment, the serotypes 10A/22F/33F/35B glycoconjugate of the invention comprises at least 0.1, 0.2, 0.3, 0.4, 0.5, 0.6 or 0.7 or about 0.8 mM acetate per mM serotype 22F polysaccharide. In a preferred embodiment, the serotypes 10A/22F/33F/35B glycoconjugate comprises at least 0.5, 0.6 or 0.7 mM acetate per mM serotype 22F polysaccharide. In a preferred embodiment, the serotypes 10A/22F/33F/35B glycoconjugate comprises at least 0.6 mM acetate per mM serotype 22F polysaccharide. In a preferred embodiment, the serotypes 10A/22F/33F/35B glycoconjugate comprises at least 0.7 mM acetate per mM serotype 22F polysaccharide.

In an embodiment, the serotypes 10A/22F/33F/35B glycoconjugate of the invention comprises at least 0.1, 0.2, 0.3, 0.4, 0.5, 0.6, 0.7 or 0.8 mM acetate per mM serotype 33F capsular polysaccharide. In a preferred embodiment, the glycoconjugate comprises at least 0.5, 0.6 or 0.7 mM acetate per mM serotype 33F capsular polysaccharide. In a preferred embodiment, the glycoconjugate comprises at least 0.6 mM acetate per mM serotype 33F capsular polysaccharide. In a preferred embodiment, the glycoconjugate comprises at least 0.7 mM acetate per mM serotype 33F capsular polysaccharide. In a preferred embodiment, the presence of O-acetyl groups is determined by NMR analysis.

In an embodiment, the serotypes 10A/22F/33F/35B glycoconjugate of the invention comprises at least 0.1, 0.2, 0.3, 0.4, 0.5, 0.6, 0.7 or 0.8 mM acetate per mM serotype 35B capsular polysaccharide. In a preferred embodiment, the glycoconjugate comprises at least 0.5, 0.6 or 0.7 mM acetate per mM serotype 35B capsular polysaccharide. In a preferred embodiment, the glycoconjugate comprises at least 0.6 mM acetate per mM serotype 35B capsular polysaccharide. In a preferred embodiment, the glycoconjugate comprises at least 0.7 mM acetate per mM serotype 33F capsular polysaccharide. In a preferred embodiment, the presence of O-acetyl groups is determined by NMR analysis.

The serotypes 10A/22F/33F/35B glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d$=0), and the fraction representing the maximum retention ($V_i$), ($K_d$=1). The fraction at which a specified sample attribute is reached ($V_e$), is related to $K_d$ by the expression, $K_d=(V_e-V_0)/(V_i-V_0)$.

In a preferred embodiment, at least 30% of the serotypes 10A/22F/33F/35B glycoconjugate has a $K_d$ below or equal to 0.3 in a CL-4B column. In a preferred embodiment, at least 40% of the serotypes 10A/22F/33F/35B glycoconjugate has a $K_d$ below or equal to 0.3 in a CL-4B column. In a preferred embodiment, at least 45%, 50%, 55%, 60%, 65%, 70%, 75%, 80%, or 85% of the serotypes 10A/22F/33F/35B glycoconjugate has a $K_d$ below or equal to 0.3 in a CL-4B column. In a preferred embodiment, at least 60% of the serotypes 10A/22F/33F/35B glycoconjugate has a $K_d$ below or equal to 0.3 in a CL-4B column. In a preferred embodiment, between 50% and 80% of the serotypes 10A/22F/33F/35B glycoconjugate has a $K_d$ below or equal to 0.3 in a CL-4B column. In a preferred embodiment, between 65% and 80% of the serotypes 10A/22F/33F/35B glycoconjugate has a $K_d$ below or equal to 0.3 in a CL-4B column.

The serotypes 10A/22F/33F/35B glycoconjugate of the invention may contain free saccharide that is not covalently conjugated to the carrier protein, but is nevertheless present in the serotypes 10A/22F/33F/35B glycoconjugate composition. The free saccharide may be noncovalently associated with (i.e., noncovalently bound to, adsorbed to, or entrapped in or with) the serotypes 10A/22F/33F/35B glycoconjugate.

In a preferred embodiment, the serotypes 10A/22F/33F/35B glycoconjugate comprises less than about 50%, 45%, 40%, 35%, 30%, 25%, 20% or 15% of free serotypes 10A, 22F, 33F and 35B saccharide compared to the total amount of serotypes 10A, 22F, 33F and 35B saccharide. In a preferred embodiment the serotypes 10A/22F/33F/35B glycoconjugate comprises less than about 40% of free serotypes 10A, 22F, 33F and 35B saccharide compared to the total amount of serotypes 10A, 22F, 33F and 35B saccharide. In a preferred embodiment the serotypes 10A/22F/33F/35B glycoconjugate comprises less than about 25% of free serotypes 10A, 22F, 33F and 35B saccharide compared to the total amount of serotypes 10A, 22F, 33F and 35B saccharide. In a preferred embodiment the serotypes 10A/22F/33F/35B glycoconjugate comprises less than about 20% of free serotypes 10A, 22F, 33F and 35B saccharide compared to the total amount of serotypes 10A, 22F, 33F and 35B saccharide. In a preferred embodiment the serotypes 10A/22F/33F/35B glycoconjugate comprises less than about 15% of free serotypes 10A, 22F, 33F and 35B saccharide compared to the total amount of serotypes 10A, 22F, 33F and 35B saccharide.

In preferred embodiments, the serotype 10A/22F/33F/35B glycoconjugates of the invention are prepared using reductive amination.

Reductive amination involves two steps, (1) oxidation (activation) of the saccharide, (2) reduction of the activated saccharide and a carrier protein (e.g., $CRM_{197}$, DT, TT or PD) to form a conjugate.

Before oxidation, sizing of the serotype 10A, 22F, 33F and/or 35B saccharide to a target molecular weight (MW) range can be performed. Mechanical or chemical hydrolysis may be employed. Chemical hydrolysis may be conducted using acetic acid. Advantageously, the size of the purified serotype 10A, 22F, 33F and/or 35B saccharide is reduced while preserving critical features of the structure of the saccharide such as for example the presence of O-acetyl groups. Therefore preferably, the size of the purified serotype 10A, 22F, 33F and/or 35B saccharide is reduced by mechanical homogenization.

In an embodiment, serotypes 10A, 22F, 33F and 35B saccharides are activated (oxidized) by a process comprising the step of:

(a) reacting a mixture of isolated serotypes 10A, 22F, 33F and 35B saccharides with an oxidizing agent.

Said process can further comprise a quenching step.

Therefore in an embodiment, serotypes 10A, 22F, 33F and 35B saccharides are activated (oxidized) by a process comprising the step of:

(a) reacting a mixture of isolated serotypes 10A, 22F, 33F and 35B saccharides with an oxidizing agent;
(b) quenching the oxidation reaction by addition of a quenching agent resulting in activated serotypes 10A, 22F, 33F and 35B saccharides.

In these embodiments, the saccharides are therefore activated altogether as a mixture.

In another embodiment, serotypes 10A, 22F, 33F and 35B saccharides are activated (oxidized) separately and the activated saccharides are then mixed.

In said embodiment, serotypes 10A, 22F, 33F and 35B saccharides are activated (oxidized) by a process comprising the step of:

(a) individually reacting an isolated serotypes 10A, 22F, 33F and 35B saccharides with an oxidizing agent;
(b) mixing the activated serotypes 10A, 22F, 33F and 35B saccharides.

Said process can further comprise a quenching step.

Therefore in an embodiment, serotypes 10A, 22F, 33F and 35B saccharides are activated (oxidized) by a process comprising the step of:

(a) individually reacting an isolated serotypes 10A, 22F, 33F and 35B saccharides with an oxidizing agent;
(b) quenching the oxidation reactions by addition of a quenching agent resulting in activated serotypes 10A, 22F, 33F and 35B saccharides;
(b) mixing the activated serotypes 10A, 22F, 33F and 35B saccharides.

The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate).

In a preferred embodiment, the oxidizing agent is sodium periodate. In a preferred embodiment, the periodate used for the oxidation of serotypes 10A, 22F, 33F and 35B saccharides is metaperiodate. In a preferred embodiment the periodate used for the oxidation of serotypes 10A, 22F, 33F and 35B saccharides is sodium metaperiodate.

In one embodiment, the quenching agent is selected from vicinal diols, 1,2-aminoalcohols, amino acids, glutathione, sulfite, bisulfate, dithionite, metabisulfite, thiosulfate, phosphites, hypophosphites or phosphorous acid.

In one embodiment, the quenching agent is a 1,2-aminoalcohols of formula (I):

(I)

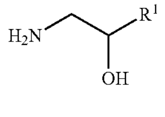

wherein $R^1$ is selected from H, methyl, ethyl, propyl or isopropyl.

In one embodiment, the quenching agent is selected from sodium and potassium salts of sulfite, bisulfate, dithionite, metabisulfite, thiosulfate, phosphites, hypophosphites or phosphorous acid. In one embodiment, the quenching agent is a sulfite such as bisulfate, dithionite, metabisulfite, thiosulfate.

In one embodiment, the quenching agent is a compound comprising two vicinal hydroxyl groups (vicinal diols), i.e., two hydroxyl groups covalently linked to two adjacent carbon atoms.

Preferably, the quenching agent is a compound of formula (II):

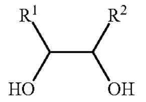
(II)

wherein $R^1$ and $R^2$ are each independently selected from H, methyl, ethyl, propyl or isopropyl.

In a preferred embodiment, the quenching agent is glycerol, ethylene glycol, propan-1,2-diol, butan-1,2-diol or butan-2,3-diol, or ascorbic acid. In a preferred embodiment, the quenching agent is butan-2,3-diol.

In a preferred embodiment, the isolated serotypes 10A, 22F, 33F and 35B saccharides are activated by a process comprising the step of:

(a) reacting a mixture of isolated serotypes 10A, 22F, 33F and 35B saccharides with periodate;

(b) quenching the oxidation reaction by addition of butan-2,3-diol resulting in a mixture of activated serotypes 10A, 22F, 33F and 35B saccharides.

Following the oxidation step of the saccharides, the saccharides are said to be activated and is referred to as "activated saccharides" here below.

In a preferred embodiment, the activated serotypes 10A, 22F, 33F and 35B saccharides are purified. The activated serotypes 10A, 22F, 33F and 35B saccharides are purified according to methods known to the man skilled in the art such as gel permeation chromatography (GPC), dialysis or ultrafiltration/diafiltration. For example, the activated serotypes 10A, 22F, 33F and 35B saccharides are purified by concentration and diafiltration using an ultrafiltration device.

In a preferred embodiment the degree of oxidation of the activated serotypes 10A, 22F, 33F and 35B saccharides are between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25. In a preferred embodiment the degree of oxidation of the activated serotypes 10A, 22F, 33F and 35B saccharides are between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20.

In a preferred embodiment, the activated serotypes 10A, 22F, 33F and 35B saccharides have a molecular weight of between 10 kDa and 5,000 kDa; between 20 kDa and 4,000 kDa; between 50 kDa and 3,000 kDa; between 100 kDa and 2500 kDa; 100 kDa and 2,000 kDa; between 150 kDa and 2,000 kDa; between 150 kDa and 1,500 kDa; between 10 kDa and 2,000 kDa; between 20 kDa and 1,500 kDa; between 30 kDa and 1,250 kDa; between 50 kDa and 1,000 kDa; between 70 kDa and 900 kDa; between 100 kDa and 800 kDa; between 200 kDa to 600 kDa or between 400 kDa to 700 kDa.

In an embodiment, the activated serotypes 10A, 22F, 33F and 35B saccharides have a molecular weight between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In an embodiment, the activated serotypes 10A, 22F, 33F and 35B saccharides have a molecular weight between 25 kDa and 3,000 kDa, between 50 kDa and 2,000 kDa, between 100 kDa and 1,500 kDa, between 100 kDa and 1,000 kDa, between 300 kDa and 800 kDa, between 300 kDa and 700 kDa, between 300 kDa and 600 kDa, between 400 kDa and 1,000 kDa, between 400 kDa and 800 kDa, between 400 kDa and 700 kDa or between 400 kDa and 600 kDa. In an embodiment, the activated serotypes 10A, 22F, 33F and 35B saccharides have a molecular weight between 100 kDa and 3,000 kDa, between 200 kDa and 2,000 kDa, between 250 kDa and 1,500 kDa, between 250 kDa and 1,000 kDa, between 250 kDa and 800 kDa, between 250 kDa and 700 kDa, between 250 kDa and 600 kDa, between 300 kDa and 1,000 kDa, between 300 kDa and 800 kDa, between 300 kDa and 700 kDa or between 300 kDa and 600 kDa.

In an embodiment, the activated serotypes 10A, 22F, 33F and 35B saccharides have a molecular weight between 300 kDa and 800 kDa. In an embodiment, the activated serotypes 10A, 22F, 33F and 35B saccharides have a molecular weight between 400 kDa and 600 kDa. In a preferred embodiment, the activated serotypes 10A, 22F, 33F and 35B saccharides have a molecular weight between 400 kda and 600 kDa and a degree of oxidation between 10 and 25, between 10 and 20, between 12 and 20 or between 14 and 18. In a preferred embodiment, the activated serotypes 10A, 22F, 33F and 35B saccharides have a molecular weight between 400 kDa and 600 kDa and a degree of oxidation between 10 and 20.

The activated polysaccharides and/or the carrier protein may be lyophilised (freeze-dried), either independently (discrete lyophilization) or together (co-lyophilized).

In an embodiment, the activated serotypes 10A, 22F, 33F and 35B saccharides are lyophilized, optionally in the presence of saccharide such as sucrose, trehalose, raffinose, stachyose, melezitose, dextran, mannitol, lactitol or palatinit. In a preferred embodiment, the saccharide is sucrose. In one embodiment, the lyophilized activated serotypes 10A, 22F, 33F and 35B saccharides are then compounded with a solution comprising the carrier protein.

In another embodiment the activated serotypes 10A, 22F, 33F and 35B saccharides and the carrier protein are co-lyophilised. In such embodiments, the activated serotypes 10A, 22F, 33F and 35B saccharides are compounded with the carrier protein and lyophilized, optionally in the presence of a saccharide such as sucrose, trehalose, raffinose, stachyose, melezitose, dextran, mannitol, lactitol and palatinit. In a preferred embodiment, the saccharide is sucrose. The co-lyophilized activated serotypes 10A, 22F, 33F and 35B saccharides and carrier protein can then be resuspended in solution and reacted with a reducing agent.

The second step of the conjugation process is the reduction of the activated saccharides and a carrier protein to form a conjugate (reductive amination), using a reducing agent.

The activated serotypes 10A, 22F, 33F and 35B saccharides can be conjugated to a carrier protein by a process comprising the step of:

(c) compounding the activated serotypes 10A, 22F, 33F and 35B saccharides with a carrier protein; and
(d) reacting the compounded activated serotypes 10A, 22F, 33F and 35B saccharides and carrier protein with a reducing agent to form a serotypes 10A/22F/33F/35B glycoconjugate.

In an embodiment, the reduction reaction is carried out in aqueous solvent. Preferably though, the reaction is carried out in aprotic solvent. In a preferred embodiment, the reduction reaction is carried out in DMSO (dimethylsulfoxide) or in DMF (dimethylformamide)) solvent. The DMSO or DMF solvent may be used to reconstitute the activated serotypes 10A, 22F, 33F and 35B saccharides and carrier protein which have been lyophilised.

The conjugation of activated serotypes 10A, 22F, 33F and 35B saccharides with a protein carrier by reductive amination in dimethylsulfoxide (DMSO) is suitable to preserve the O-acetyl content of the saccharides as compared, for example, to reductive amination in aqueous phase where the level of O-acetylation of the saccharides may be significantly reduced. Therefore in a preferred embodiment, step (c) and step (d) are carried out in DMSO.

In an embodiment, the reducing agent is sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^i$PrN—$BH_3$, benzylamine-$BH_3$ or 5-ethyl-2-methylpyridine borane (PEMB). In a preferred embodiment, the reducing agent is sodium cyanoborohydride.

At the end of the reduction reaction, there may be unreacted aldehyde groups remaining in the conjugates, these may be capped using a suitable capping agent. In one embodiment this capping agent is sodium borohydride ($NaBH_4$).

Following conjugation of serotypes 10A, 22F, 33F and 35B saccharides to the carrier protein, the glycoconjugate can be purified (enriched with respect to the amount of saccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration.

1.3.3.2 Glycoconjugates Comprising a Saccharide from *S. pneumoniae* Serotype 10A, a Saccharide from *S. pneumoniae* Serotype 22F and a Saccharide from *S. pneumoniae* Serotype 33F and Conjugated to a Carrier Protein In an embodiment the glycoconjugates of the invention comprises a saccharide from *S. pneumoniae* serotype 10A, a saccharide from *S. pneumoniae* serotype 22F and a saccharide from *S. pneumoniae* serotype 33F conjugated to the same carrier protein (herein after 'the serotypes 10A/22F/33F glycoconjugate'). In said embodiment, the carrier molecules have the three different capsular saccharides conjugated to them. Preferably, the glycoconjugates of this section (1.3.3.2) are therefore 3-valent glycoconjugates (i.e. they have serotypes 10A, 22F and 33F conjugated to the carrier protein and have no other polysaccharide antigens covalently attached to the carrier protein).

In some embodiments, the serotypes 10A/22F/33F glycoconjugate of the present invention comprise a serotype 10A saccharide having a molecular weight of between 10 kDa and 5,000 kDa. In other such embodiments, the serotype 10A saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 10A saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa;

between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/22F/33F glycoconjugate of the present invention comprise a serotype 22F saccharide having a molecular weight of between 10 kDa and 5,000 kDa. In other such embodiments, the serotype 22F saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 22F saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/22F/33F glycoconjugate of the present invention comprise a serotype 33F saccharide having a molecular weight of between 10 kDa and 5,000 kDa. In other such embodiments, the serotype 33F saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharide has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 33F saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/22F/33F glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the serotypes 10A/22F/33F glycoconjugate has a molecular weight of between 500 kDa and 10,000 kDa. In other embodiments, the serotypes 10A/22F/33F glycoconjugate has a molecular weight of between 1,000 kDa and 8,000 kDa. In still other embodiments, the serotypes 10A/22F/33F glycoconjugate has a molecular weight of between 2,000 kDa and 8,000 kDa or between 3,000 kDa and 7,000 kDa. In further embodiments, the serotypes 10A/22F/33F glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa. In further embodiments, the serotypes 10A/22F/33F glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa.

In further embodiments, the serotypes 10A/22F/33F glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate is measured by SEC-MALLS. Any whole number integer within any of the above ranges is contemplated as an embodiment of the disclosure.

Another way to characterize the serotypes 10A/22F/33F glycoconjugate of the invention is by the number of lysine residues in the carrier protein (e.g., $CRM_{197}$) that become conjugated to the saccharides which can be characterized as a range of conjugated lysines (degree of conjugation). The evidence for lysine modification of the carrier protein, due to covalent linkages to the saccharides, can be obtained by amino acid analysis using routine methods known to those of skill in the art. Conjugation results in a reduction in the number of lysine residues recovered compared to the carrier protein starting material (e.g. $CRM_{197}$) used to generate the conjugate materials. In a preferred embodiment, the degree of conjugation of the serotypes 10A/22F/33F glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotypes 10A/22F/33F glycoconjugate of the invention is about 2, about 3, about 4, about 5, about 6, about 7, about 8, about 9, about 10, about 11, about 12, about 13, about 14 or about 15. In a preferred embodiment, the degree of conjugation of the serotypes 10A/22F/33F glycoconjugate of the invention is between 4 and 7. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/22F/33F glycoconjugate of the invention may also be characterized by the ratio (weight/weight) of saccharide to carrier protein. In some embodiments, the ratio of serotypes 10A, 22F and 33F saccharides to carrier protein in the glycoconjugate (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of serotypes 10A, 22F and 33F saccharides to carrier protein in the conjugate is between 0.9 and 1.1. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/22F/33F glycoconjugate of the invention may also be characterized by the ratio (weight/weight) of serotype 10A saccharide to serotype 22F saccharide in the glycoconjugate. In some embodiments, the ratio of serotype 10A saccharide to serotype 22F saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 10A saccharide to serotype 22F saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 10A saccharide to serotype 22F saccharide ratio (w/w) is between 0.8 and 1.2. In a preferred embodiment, the ratio of serotype 10A saccharide to serotype 22F saccharide in the conjugate is between 0.9 and 1.1, even more preferably the ratio of serotype 10A saccharide to serotype 22F saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/22F/33F glycoconjugate of the invention may also be characterized by the ratio (weight/weight) of serotype 10A saccharide to serotype 33F saccharide in the glycoconjugate. In some embodiments, the ratio of serotype 10A saccharide to serotype 33F saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 10A saccharide to serotype 33F saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 10A saccharide to serotype 33F saccharide ratio (w/w) is between 0.8 and 1.2. In a preferred embodiment, the ratio of serotype 10A saccharide to serotype 33F saccharide in the conjugate is between 0.9 and 1.1, even more preferably the ratio of serotype 10A saccharide to serotype 33F saccharide in the conjugate is about 1.0. In some such embodiments, the carrier protein is $CRM_{197}$. In other such embodiments, the carrier protein is DT. In other such embodiments, the carrier protein is TT. In other such embodiments the carrier protein is PD.

The serotypes 10A/22F/33F glycoconjugate of the invention may also be characterized by the ratio (weight/weight) of serotype 22F saccharide to serotype 33F saccharide in the glycoconjugate. In some embodiments, the ratio of serotype 22F saccharide to serotype 33F saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 22F saccharide to serotype 33F saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 22F saccharide to serotype 33F saccharide ratio (w/w) is between 0.8 and 1.2. In a preferred embodiment, the ratio of serotype 22F saccharide to serotype 33F saccharide in the conjugate is between 0.9 and 1.1, even more preferably the ratio of serotype 22F saccharide to serotype 33F saccharide in the conjugate is about 1.0. In some such embodiments, the carrier protein is $CRM_{197}$. In other such embodiments, the carrier protein is DT. In other such embodiments, the carrier protein is TT. In other such embodiments the carrier protein is PD.

The serotypes 10A/22F/33F glycoconjugate of the invention may also be characterized by the relative proportion (weight/weight) of serotypes 10A saccharide, serotypes 22F saccharide and serotype 33F saccharide in the glycoconjugate. In some embodiments, the relative proportion of serotype 10A saccharide, serotype 22F saccharide and serotype 33F saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | K | l | M | n | o | p | q | r | s |
| 10A | 1 | 1 | 1 | 2 | 2 | 2 | 4 | 4 | 4 | 1 | 1 | 1 | 2 | 4 | 1 | 1 | 1 | 2 | 4 |
| 22F | 1 | 1 | 1 | 1 | 1 | 1 | 1 | 1 | 1 | 2 | 2 | 2 | 2 | 2 | 4 | 4 | 4 | 4 | 4 |
| 33F | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 10A saccharide, serotypes 22F saccharide and serotype 33F saccharide in the glycoconjugate, for example column a is to be read as: in an embodiment the relative proportion of serotype 10A saccharide, serotype 22F saccharide and serotype 33F saccharide in the serotypes 10A/22F/33F glycoconjugate is respectively about 1:about 1:about 4 (about one 10A saccharide for about one 22F saccharide and for about four 33F saccharide (w/w)). Preferably, the mass of serotype 10A saccharide, serotype 22F saccharide and serotype 33F saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

In an embodiment, the serotypes 10A/22F/33F glycoconjugate of the invention comprises at least 0.1, 0.2, 0.3, 0.4, 0.5, 0.6 or 0.7 or about 0.8 mM acetate per mM serotype 22F polysaccharide. In a preferred embodiment, the serotypes 10A/22F/33F glycoconjugate comprises at least 0.5, 0.6 or 0.7 mM acetate per mM serotype 22F polysaccharide. In a preferred embodiment, the serotypes 10A/22F/33F glycoconjugate comprises at least 0.6 mM acetate per mM serotype 22F polysaccharide. In a preferred embodiment, the serotypes 10A/22F/33F glycoconjugate comprises at least 0.7 mM acetate per mM serotype 22F polysaccharide.

In an embodiment, the serotypes 10A/22F/33F glycoconjugate of the invention comprises at least 0.1, 0.2, 0.3, 0.4, 0.5, 0.6, 0.7 or 0.8 mM acetate per mM serotype 33F capsular polysaccharide. In a preferred embodiment, the glycoconjugate comprises at least 0.5, 0.6 or 0.7 mM acetate per mM serotype 33F capsular polysaccharide. In a preferred embodiment, the glycoconjugate comprises at least 0.6 mM acetate per mM serotype 33F capsular polysaccharide. In a preferred embodiment, the glycoconjugate comprises at least 0.7 mM acetate per mM serotype 33F capsular polysaccharide. In a preferred embodiment, the presence of O-acetyl groups is determined by NMR analysis.

The serotypes 10A/22F/33F glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d$=0), and the fraction representing the maximum retention ($V_i$), ($K_d$=1). The fraction at which a specified sample attribute is reached ($V_e$), is related to $K_d$ by the expression, $K_d=(V_e-V_0)/(V_i-V_0)$.

In a preferred embodiment, at least 30% of the serotypes 10A/22F/33F glycoconjugate has a $K_d$ below or equal to 0.3 in a CL-4B column. In a preferred embodiment, at least 40% of the serotypes 10A/22F/33F glycoconjugate has a $K_d$ below or equal to 0.3 in a CL-4B column. In a preferred embodiment, at least 45%, 50%, 55%, 60%, 65%, 70%, 75%, 80%, or 85% of the serotypes 10A/22F/33F glycoconjugate has a $K_d$ below or equal to 0.3 in a CL-4B column. In a preferred embodiment, at least 60% of the serotypes 10A/22F/33F glycoconjugate has a $K_d$ below or equal to 0.3 in a CL-4B column. In a preferred embodiment, between 50% and 80% of the serotypes 10A/22F/33F glycoconjugate has a $K_d$ below or equal to 0.3 in a CL-4B column. In a preferred embodiment, between 65% and 80% of the serotypes 10A/22F/33F glycoconjugate has a $K_d$ below or equal to 0.3 in a CL-4B column.

The serotypes 10A/22F/33F glycoconjugate of the invention may contain free saccharide that is not covalently conjugated to the carrier protein, but is nevertheless present in the serotypes 10A/22F/33F glycoconjugate composition. The free saccharide may be noncovalently associated with (i.e., noncovalently bound to, adsorbed to, or entrapped in or with) the serotypes 10A/22F/33F glycoconjugate.

In a preferred embodiment, the serotypes 10A/22F/33F glycoconjugate comprises less than about 50%, 45%, 40%, 35%, 30%, 25%, 20% or 15% of free serotypes 10A, 22F and 33F saccharide compared to the total amount of serotypes 10A, 22F and 33F saccharide. In a preferred embodiment the serotypes 10A/22F/33F glycoconjugate comprises less than about 40% of free serotypes 10A, 22F and 33F saccharide compared to the total amount of serotypes 10A, 22F and 33F saccharide. In a preferred embodiment the serotypes 10A/22F/33F glycoconjugate comprises less than about 25% of free serotypes 10A, 22F and 33F saccharide compared to the total amount of serotypes 10A, 22F and 33F saccharide. In a preferred embodiment the serotypes 10A/22F/33F glycoconjugate comprises less than about 20% of free serotypes 10A, 22F and 33F saccharide compared to the total amount of serotypes 10A, 22F and 33F saccharide. In a preferred embodiment the serotypes 10A/22F/33F glycoconjugate comprises less than about 15% of free serotypes 10A, 22F and 33F saccharide compared to the total amount of serotypes 10A, 22F and 33F saccharide.

In preferred embodiments, the serotype 10A/22F/33F glycoconjugates of the invention are prepared using reductive amination.

Reductive amination involves two steps, (1) oxidation (activation) of the saccharide, (2) reduction of the activated saccharide and a carrier protein (e.g., $CRM_{197}$, DT, TT or PD) to form a conjugate. Before oxidation, sizing of the serotype 10A, 22F and/or 33F saccharide to a target molecular weight (MW) range can be performed. Mechanical or chemical hydrolysis may be employed. Chemical hydrolysis may be conducted using acetic acid. Advantageously, the size of the purified serotype 10A, 22F and/or 33F saccharide is reduced while preserving critical features of the structure of the saccharide such as for example the presence of O-acetyl groups. Therefore preferably, the size of the purified serotype 10A, 22F and/or 33F saccharide is reduced by mechanical homogenization.

In an embodiment, serotypes 10A, 22F and 33F saccharides are activated (oxidized) by a process comprising the step of:

(a) reacting a mixture of isolated serotypes 10A, 22F and 33F saccharides with an oxidizing agent. Said process can further comprise a quenching step.

Therefore in an embodiment, serotypes 10A, 22F and 33F saccharides are activated (oxidized) by a process comprising the step of:

(a) reacting a mixture of isolated serotypes 10A, 22F and 33F saccharides with an oxidizing agent;
(b) quenching the oxidation reaction by addition of a quenching agent resulting in activated serotypes 10A, 22F and 33F saccharides.

In these embodiments, the saccharides are therefore activated altogether as a mixture.

In another embodiment, serotypes 10A, 22F and 33F saccharides are activated (oxidized) separately and the activated saccharides are then mixed.

In said embodiment, serotypes 10A, 22F and 33F saccharides are activated (oxidized) by a process comprising the step of:

(a) individually reacting an isolated serotypes 10A, 22F and 33F saccharides with an oxidizing agent;

(b) mixing the activated serotypes 10A, 22F and 33F saccharides.

Said process can further comprise a quenching step.

Therefore in an embodiment, serotypes 10A, 22F and 33F saccharides are activated (oxidized) by a process comprising the step of:

(a) individually reacting an isolated serotypes 10A, 22F and 33F saccharides with an oxidizing agent;

(b) quenching the oxidation reactions by addition of a quenching agent resulting in activated serotypes 10A, 22F and 33F saccharides;

(b) mixing the activated serotypes 10A, 22F and 33F saccharides.

The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate).

In a preferred embodiment, the oxidizing agent is sodium periodate. In a preferred embodiment, the periodate used for the oxidation of serotypes 10A, 22F and 33F saccharides is metaperiodate. In a preferred embodiment the periodate used for the oxidation of serotypes 10A, 22F and 33F saccharides is sodium metaperiodate.

In one embodiment, the quenching agent is selected from vicinal diols, 1,2-aminoalcohols, amino acids, glutathione, sulfite, bisulfate, dithionite, metabisulfite, thiosulfate, phosphites, hypophosphites or phosphorous acid.

In one embodiment, the quenching agent is a 1,2-aminoalcohols of formula (I):

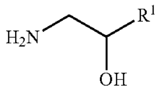

(I)

wherein $R^1$ is selected from H, methyl, ethyl, propyl or isopropyl.

In one embodiment, the quenching agent is selected from sodium and potassium salts of sulfite, bisulfate, dithionite, metabisulfite, thiosulfate, phosphites, hypophosphites or phosphorous acid. In one embodiment, the quenching agent is a sulfite such as bisulfate, dithionite, metabisulfite, thiosulfate.

In one embodiment, the quenching agent is a compound comprising two vicinal hydroxyl groups (vicinal diols), i.e., two hydroxyl groups covalently linked to two adjacent carbon atoms.

Preferably, the quenching agent is a compound of formula (II):

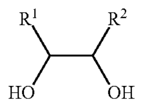

(II)

wherein $R^1$ and $R^2$ are each independently selected from H, methyl, ethyl, propyl or isopropyl.

In a preferred embodiment, the quenching agent is glycerol, ethylene glycol, propan-1,2-diol, butan-1,2-diol or butan-2,3-diol, or ascorbic acid. In a preferred embodiment, the quenching agent is butan-2,3-diol.

In a preferred embodiment, the isolated serotypes 10A, 22F and 33F saccharides are activated by a process comprising the step of:

(a) reacting a mixture of isolated serotypes 10A, 22F and 33F saccharides with periodate;

(b) quenching the oxidation reaction by addition of butan-2,3-diol resulting in a mixture of activated serotypes 10A, 22F and 33F saccharides.

Following the oxidation step of the saccharides, the saccharides are said to be activated and is referred to as "activated saccharides" here below.

In a preferred embodiment, the activated serotypes 10A, 22F and 33F saccharides are purified.

The activated serotypes 10A, 22F and 33F saccharides are purified according to methods known to the man skilled in the art such as gel permeation chromatography (GPC), dialysis or ultrafiltration/diafiltration. For example, the activated serotypes 10A, 22F and 33F saccharides are purified by concentration and diafiltration using an ultrafiltration device.

In a preferred embodiment the degree of oxidation of the activated serotypes 10A, 22F and 33F saccharides are between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25. In a preferred embodiment the degree of oxidation of the activated serotypes 10A, 22F and 33F saccharides are between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20.

In a preferred embodiment, the activated serotypes 10A, 22F and 33F saccharides have a molecular weight between 10 kDa and 5,000 kDa; between 20 kDa and 4,000 kDa; between 50 kDa and 3,000 kDa; between 100 kDa and 2500 kDa; 100 kDa and 2,000 kDa; between 150 kDa and 2,000 kDa; between 150 kDa and 1,500 kDa; between 10 kDa and 2,000 kDa; between 20 kDa and 1,500 kDa; between 30 kDa and 1,250 kDa; between 50 kDa and 1,000 kDa; between 70 kDa and 900 kDa; between 100 kDa and 800 kDa; between 200 kDa to 600 kDa or between 400 kDa to 700 kDa.

In an embodiment, the activated serotypes 10A, 22F and 33F saccharides have a molecular weight between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In an embodiment, the activated serotypes 10A, 22F and 33F saccharides have a molecular weight between 25 kDa and 3,000 kDa, between 50 kDa and 2,000 kDa, between 100 kDa and 1,500 kDa, between 100 kDa and 1,000 kDa, between 300 kDa and 800 kDa, between 300 kDa and 700 kDa, between 300 kDa and 600 kDa, between 400 kDa and 1,000 kDa, between 400 kDa and 800 kDa, between 400 kDa and 700 kDa or between 400 kDa and 600 kDa. In an embodiment, the activated serotypes 10A, 22F, 33F and 35B saccharides have a molecular weight between 100 kDa and 3,000 kDa, between 200 kDa and 2,000 kDa, between 250 kDa and 1,500 kDa, between 250 kDa and 1,000 kDa, between 250 kDa and 800 kDa, between 250 kDa and 700 kDa, between 250 kDa and 600 kDa, between 300 kDa and 1,000 kDa, between 300 kDa and 800 kDa, between 300 kDa and 700 kDa or between 300 kDa and 600 kDa.

In an embodiment, the activated serotypes 10A, 22F and 33F saccharides have a molecular weight between 300 kDa and 800 kDa. In a preferred embodiment, the activated serotypes 10A, 22F and 33F saccharides have a molecular weight between 400 kda and 600 kDa and a degree of oxidation between 10 and 25, between 10 and 20, between 12 and 20 or between 14 and 18. In a preferred embodiment, the activated serotypes 10A, 22F and 33F saccharides have a molecular weight between 400 kDa and 600 kDa and a degree of oxidation between 10 and 20. The activated polysaccharides and/or the carrier protein may be lyophilised (freeze-dried), either independently (discrete lyophilization) or together (co-lyophilized).

In an embodiment, the activated serotypes 10A, 22F and 33F saccharides are lyophilized, optionally in the presence of saccharide such as sucrose, trehalose, raffinose, stachyose, melezitose, dextran, mannitol, lactitol or palatinit. In a preferred embodiment, the saccharide is sucrose. In one embodiment, the lyophilized activated serotypes 10A, 22F and 33F saccharides are then compounded with a solution comprising the carrier protein.

In another embodiment the activated serotypes 10A, 22F and 33F saccharides and the carrier protein are co-lyophilised. In such embodiments, the activated serotypes 10A, 22F and 33F saccharides are compounded with the carrier protein and lyophilized, optionally in the presence of a saccharide such as sucrose, trehalose, raffinose, stachyose, melezitose, dextran, mannitol, lactitol and palatinit. In a preferred embodiment, the saccharide is sucrose. The co-lyophilized activated serotypes 10A, 22F and 33F saccharides and carrier protein can then be resuspended in solution and reacted with a reducing agent.

The second step of the conjugation process is the reduction of the activated saccharides and a carrier protein to form a conjugate (reductive amination), using a reducing agent. The activated serotypes 10A, 22F and 33F saccharides can be conjugated to a carrier protein by a process comprising the step of:

(c) compounding the activated serotypes 10A, 22F and 33F saccharides with a carrier protein; and
(d) reacting the compounded activated serotypes 10A, 22F and 33F saccharides and carrier protein with a reducing agent to form a serotypes 10A/22F/33F glycoconjugate.

In an embodiment, the reduction reaction is carried out in aqueous solvent. Preferably though, the reaction is carried out in aprotic solvent. In a preferred embodiment, the reduction reaction is carried out in DMSO (dimethylsulfoxide) or in DMF (dimethylformamide)) solvent. The DMSO or DMF solvent may be used to reconstitute the activated serotypes 10A, 22F and 33F saccharides and carrier protein which have been lyophilised.

The conjugation of activated serotypes 10A, 22F and 33F saccharides with a protein carrier by reductive amination in dimethylsulfoxide (DMSO) is suitable to preserve the O-acetyl content of the saccharides as compared, for example, to reductive amination in aqueous phase where the level of O-acetylation of the saccharides may be significantly reduced. Therefore in a preferred embodiment, step (c) and step (d) are carried out in DMSO.

In an embodiment, the reducing agent is sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^i$PrN—$BH_3$, benzylamine-$BH_3$ or 5-ethyl-2-methylpyridine borane (PEMB). In a preferred embodiment, the reducing agent is sodium cyanoborohydride.

At the end of the reduction reaction, there may be unreacted aldehyde groups remaining in the conjugates, these may be capped using a suitable capping agent. In one embodiment this capping agent is sodium borohydride ($NaBH_4$).

Following conjugation of serotypes 10A, 22F and 33F saccharides to the carrier protein, the glycoconjugate can be purified (enriched with respect to the amount of saccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration.

1.3.3.3 Glycoconjugates Comprising a Saccharide from *S. pneumoniae* Serotype 10A, a Saccharide from *S. pneumoniae* Serotype 22F and a Saccharide from *S. pneumoniae* Serotype 35B and Conjugated to a Carrier Protein In an embodiment the glycoconjugates of the invention comprises a saccharide from *S. pneumoniae* serotype 10A, a saccharide from *S. pneumoniae* serotype 22F and a saccharide from *S. pneumoniae* serotype 35B conjugated to the same carrier protein (herein after 'the serotypes 10A/22F/35B glycoconjugate'). In said embodiment, the carrier molecules have the three different capsular saccharides conjugated to them. Preferably, the glycoconjugates of this section (1.3.3.3) are therefore 3-valent glycoconjugates (i.e. they have serotypes 10A, 22F and 35B conjugated to the carrier protein and have no other polysaccharide antigens covalently attached to the carrier protein).

In some embodiments, the serotypes 10A/22F/35B glycoconjugate of the present invention comprise a serotype 10A saccharide having a molecular weight of between 10 kDa and 5,000 kDa. In other such embodiments, the serotype 10A saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 10A saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/22F/35B glycoconjugate of the present invention comprise a serotype 22F saccharide having a molecular weight of between 10 kDa and 5,000 kDa. In other such embodiments, the serotype 22F saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 22F saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/22F/35B glycoconjugate of the present invention comprise a serotype 35B saccharide having a molecular weight of between 10 kDa and 5,000 kDa. In other such embodiments, the serotype 35B saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 35B saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/22F/35B glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the serotypes 10A/22F/35B glycoconjugate has a molecular weight of between 500 kDa and 10,000 kDa. In other embodiments, the serotypes 10A/22F/35B glycoconjugate has a molecular weight of between 1,000 kDa and 8,000 kDa. In still other embodiments, the serotypes 10A/22F/35B glycoconjugate has a molecular weight of between 2,000 kDa and 8,000 kDa or between 3,000 kDa and 7,000 kDa. In further embodiments, the serotypes 10A/22F/35B glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa. In further embodiments, the serotypes 10A/22F/35B glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa.

In further embodiments, the serotypes 10A/22F/35B glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate is measured by SEC-MALLS. Any whole number integer within any of the above ranges is contemplated as an embodiment of the disclosure.

Another way to characterize the serotypes 10A/22F/35B glycoconjugate of the invention is by the number of lysine residues in the carrier protein (e.g., $CRM_{197}$) that become conjugated to the saccharides which can be characterized as a range of conjugated lysines (degree of conjugation). The evidence for lysine modification of the carrier protein, due to covalent linkages to the saccharides, can be obtained by amino acid analysis using routine methods known to those of skill in the art. Conjugation results in a reduction in the number of lysine residues recovered compared to the carrier protein starting material (e.g. $CRM_{197}$) used to generate the conjugate materials. In a preferred embodiment, the degree of conjugation of the serotypes 10A/22F/35B glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotypes 10A/22F/35B glycoconjugate of the invention is about 2, about 3, about 4, about 5, about 6, about 7, about 8, about 9, about 10, about 11, about 12, about 13, about 14 or about 15. In a preferred embodiment, the degree of conjugation of the serotypes 10A/22F/35B glycoconjugate of the invention is between 4 and 7. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/22F/35B glycoconjugate of the invention may also be characterized by the ratio (weight/weight) of saccharide to carrier protein. In some embodiments, the ratio of serotypes 10A, 22F and 35B saccharides to carrier protein in the glycoconjugate (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of serotypes 10A, 22F and 35B saccharides to carrier protein in the conjugate is between 0.9 and 1.1. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/22F/35B glycoconjugate of the invention may also be characterized by the ratio (weight/weight) of serotype 10A saccharide to serotype 22F saccharide in the glycoconjugate. In some embodiments, the ratio of serotype 10A saccharide to serotype 22F saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 10A saccharide to serotype 22F saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 10A saccharide to serotype 22F saccharide ratio (w/w) is between 0.8 and 1.2. In a preferred embodiment, the ratio of serotype 10A saccharide to serotype 22F saccharide in the conjugate is between 0.9 and 1.1, even more preferably the ratio of serotype 10A saccharide to serotype 22F saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/22F/35B glycoconjugate of the invention may also be characterized by the ratio (weight/weight) of serotype 10A saccharide to serotype 35B saccharide in the glycoconjugate. In some embodiments, the ratio of serotype 10A saccharide to serotype 35B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 10A saccharide to serotype 35B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 10A saccharide to serotype 35B saccharide ratio (w/w) is between 0.8 and 1.2. In a preferred embodiment, the ratio of serotype 10A saccharide to serotype 35B saccharide in the conjugate is between 0.9 and 1.1, even more preferably the ratio of serotype 10A saccharide to serotype 35B saccharide in the conjugate is about 1.0. In some such embodiments, the carrier protein is $CRM_{197}$. In other such embodiments, the carrier protein is DT. In other such embodiments, the carrier protein is TT. In other such embodiments the carrier protein is PD.

The serotypes 10A/22F/35B glycoconjugate of the invention may also be characterized by the ratio (weight/weight) of serotype 22F saccharide to serotype 35B saccharide in the glycoconjugate. In some embodiments, the ratio of serotype 22F saccharide to serotype 35B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 22F saccharide to serotype 35B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 22F saccharide to serotype 35B saccharide ratio (w/w) is between 0.8 and 1.2. In a preferred embodiment, the ratio of serotype 22F saccharide to serotype 35B saccharide in the conjugate is between 0.9 and 1.1, even more preferably the ratio of serotype 22F saccharide to serotype 35B saccharide in the conjugate is about 1.0. In some such embodiments, the carrier protein is $CRM_{197}$. In other such embodiments, the carrier protein is DT. In other such embodiments, the carrier protein is TT. In other such embodiments the carrier protein is PD.

The serotypes 10A/22F/35B glycoconjugate of the invention may also be characterized by the relative proportion (weight/weight) of serotypes 10A saccharide, serotypes 22F saccharide and serotype 35B saccharide in the glycoconjugate. In some embodiments, the relative proportion of serotype 10A saccharide, serotype 22F saccharide and serotype 35B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | K | l | m | n | o | p | q | r | s |
| 10A | 1 | 1 | 1 | 2 | 2 | 2 | 4 | 4 | 4 | 1 | 1 | 1 | 2 | 4 | 1 | 1 | 1 | 2 | 4 |
| 22F | 1 | 1 | 1 | 1 | 1 | 1 | 1 | 1 | 1 | 2 | 2 | 2 | 2 | 2 | 4 | 4 | 4 | 4 | 4 |
| 35B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 10A saccharide, serotypes 22F saccharide and serotype 35B saccharide in the glycoconjugate, for example column a is to be read as: in an embodiment the relative proportion of serotype 10A saccharide, serotype 22F saccharide and serotype 35B saccharide in the serotypes 10A/22F/35B glycoconjugate is respectively about 1:about 1:about 4 (about one 10A saccharide for about one 22F saccharide and for about four 35B saccharide (w/w)). Preferably, the mass of serotype 10A saccharide, serotype 22F saccharide and serotype 35B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

In an embodiment, the serotypes 10A/22F/35B glycoconjugate of the invention comprises at least 0.1, 0.2, 0.3, 0.4, 0.5, 0.6 or 0.7 or about 0.8 mM acetate per mM serotype 22F polysaccharide. In a preferred embodiment, the serotypes 10A/22F/35B glycoconjugate comprises at least 0.5, 0.6 or 0.7 mM acetate per mM serotype 22F polysaccharide. In a preferred embodiment, the serotypes 10A/22F/35B glycoconjugate comprises at least 0.6 mM acetate per mM serotype 22F polysaccharide. In a preferred embodiment, the serotypes 10A/22F/35B glycoconjugate comprises at least 0.7 mM acetate per mM serotype 22F polysaccharide.

In an embodiment, the serotypes 10A/22F/35B glycoconjugate of the invention comprises at least 0.1, 0.2, 0.3, 0.4, 0.5, 0.6, 0.7 or 0.8 mM acetate per mM serotype 35B capsular polysaccharide. In a preferred embodiment, the glycoconjugate comprises at least 0.5, 0.6 or 0.7 mM acetate per mM serotype 35B capsular polysaccharide. In a preferred embodiment, the glycoconjugate comprises at least 0.6 mM acetate per mM serotype 35B capsular polysaccharide. In a preferred embodiment, the glycoconjugate comprises at least 0.7 mM acetate per mM serotype 35B capsular polysaccharide. In a preferred embodiment, the presence of O-acetyl groups is determined by NMR analysis.

The serotypes 10A/22F/35B glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d$=0), and the fraction representing the maximum retention ($V_i$), ($K_d$=1). The fraction at which a specified sample attribute is reached ($V_e$), is related to $K_d$ by the expression, $K_d=(V_e-V_0)/(V_i-V_0)$.

In a preferred embodiment, at least 30% of the serotypes 10A/22F/35B glycoconjugate has a $K_d$ below or equal to 0.3 in a CL-4B column. In a preferred embodiment, at least 40% of the serotypes 10A/22F/35B glycoconjugate has a $K_d$ below or equal to 0.3 in a CL-4B column. In a preferred embodiment, at least 45%, 50%, 55%, 60%, 65%, 70%, 75%, 80%, or 85% of the serotypes 10A/22F/35B glycoconjugate has a $K_d$ below or equal to 0.3 in a CL-4B column. In a preferred embodiment, at least 60% of the serotypes 10A/22F/35B glycoconjugate has a $K_d$ below or equal to 0.3 in a CL-4B column. In a preferred embodiment, between 50% and 80% of the serotypes 10A/22F/35B glycoconjugate has a $K_d$ below or equal to 0.3 in a CL-4B column. In a preferred embodiment, between 65% and 80% of the serotypes 10A/22F/35B glycoconjugate has a $K_d$ below or equal to 0.3 in a CL-4B column.

The serotypes 10A/22F/35B glycoconjugate of the invention may contain free saccharide that is not covalently conjugated to the carrier protein, but is nevertheless present in the serotypes 10A/22F/35B glycoconjugate composition. The free saccharide may be noncovalently associated with (i.e., noncovalently bound to, adsorbed to, or entrapped in or with) the serotypes 10A/22F/35B glycoconjugate.

In a preferred embodiment, the serotypes 10A/22F/35B glycoconjugate comprises less than about 50%, 45%, 40%, 35%, 30%, 25%, 20% or 15% of free serotypes 10A, 22F and 35B saccharide compared to the total amount of serotypes 10A, 22F and 35B saccharide. In a preferred embodiment the serotypes 10A/22F/35B glycoconjugate comprises less than about 40% of free serotypes 10A, 22F and 35B saccharide compared to the total amount of serotypes 10A, 22F and 35B saccharide. In a preferred embodiment the serotypes 10A/22F/35B glycoconjugate comprises less than about 25% of free serotypes 10A, 22F and 35B saccharide compared to the total amount of serotypes 10A, 22F and 35B saccharide. In a preferred embodiment the serotypes 10A/22F/35B glycoconjugate comprises less than about 20% of free serotypes 10A, 22F and 35B saccharide compared to the total amount of serotypes 10A, 22F and 35B saccharide. In a preferred embodiment the serotypes 10A/22F/35B glycoconjugate comprises less than about 15% of free serotypes 10A, 22F and 35B saccharide compared to the total amount of serotypes 10A, 22F and 35B saccharide.

In preferred embodiments, the serotype 10A/22F/35B glycoconjugates of the invention are prepared using reductive amination.

Reductive amination involves two steps, (1) oxidation (activation) of the saccharide, (2) reduction of the activated saccharide and a carrier protein (e.g., $CRM_{197}$, DT, TT or PD) to form a conjugate. Before oxidation, sizing of the serotype 10A, 22F and/or 35B saccharide to a target molecular weight (MW) range can be performed. Mechanical or chemical hydrolysis may be employed. Chemical hydrolysis may be conducted using acetic acid. Advantageously, the size of the purified serotype 10A, 22F and/or 35B saccharide is reduced while preserving critical features of the structure of the saccharide such as for example the presence of O-acetyl groups. Therefore preferably, the size of the purified serotype 10A, 22F and/or 35B saccharide is reduced by mechanical homogenization.

In an embodiment, serotypes 10A, 22F and 35B saccharides are activated (oxidized) by a process comprising the step of:

(a) reacting a mixture of isolated serotypes 10A, 22F and 35B saccharides with an oxidizing agent. Said process can further comprise a quenching step.

Therefore in an embodiment, serotypes 10A, 22F and 35B saccharides are activated (oxidized) by a process comprising the step of:

(a) reacting a mixture of isolated serotypes 10A, 22F and 35B saccharides with an oxidizing agent;
(b) quenching the oxidation reaction by addition of a quenching agent resulting in activated serotypes 10A, 22F and 35B saccharides.

In these embodiments, the saccharides are therefore activated altogether as a mixture.

In another embodiment, serotypes 10A, 22F and 35B saccharides are activated (oxidized) separately and the activated saccharides are then mixed.

In said embodiment, serotypes 10A, 22F and 35B saccharides are activated (oxidized) by a process comprising the step of:

(a) individually reacting an isolated serotypes 10A, 22F and 35B saccharides with an oxidizing agent;
(b) mixing the activated serotypes 10A, 22F and 35B saccharides.

Said process can further comprise a quenching step.

Therefore in an embodiment, serotypes 10A, 22F and 35B saccharides are activated (oxidized) by a process comprising the step of:

(a) individually reacting an isolated serotypes 10A, 22F and 35B saccharides with an oxidizing agent;
(b) quenching the oxidation reactions by addition of a quenching agent resulting in activated serotypes 10A, 22F and 35B saccharides;
(b) mixing the activated serotypes 10A, 22F and 35B saccharides.

The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate).

In a preferred embodiment, the oxidizing agent is sodium periodate. In a preferred embodiment, the periodate used for the oxidation of serotypes 10A, 22F and 35B saccharides is metaperiodate. In a preferred embodiment the periodate used for the oxidation of serotypes 10A, 22F and 35B saccharides is sodium metaperiodate.

In one embodiment, the quenching agent is selected from vicinal diols, 1,2-aminoalcohols, amino acids, glutathione, sulfite, bisulfate, dithionite, metabisulfite, thiosulfate, phosphites, hypophosphites or phosphorous acid.

In one embodiment, the quenching agent is a 1,2-aminoalcohols of formula (I):

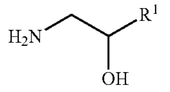

(I)

wherein $R^1$ is selected from H, methyl, ethyl, propyl or isopropyl.

In one embodiment, the quenching agent is selected from sodium and potassium salts of sulfite, bisulfate, dithionite, metabisulfite, thiosulfate, phosphites, hypophosphites or phosphorous acid.

In one embodiment, the quenching agent is a sulfite such as bisulfate, dithionite, metabisulfite, thiosulfate.

In one embodiment, the quenching agent is a compound comprising two vicinal hydroxyl groups (vicinal diols), i.e., two hydroxyl groups covalently linked to two adjacent carbon atoms. Preferably, the quenching agent is a compound of formula (II):

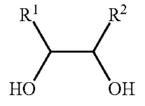

(II)

wherein $R^1$ and $R^2$ are each independently selected from H, methyl, ethyl, propyl or isopropyl. In a preferred embodiment, the quenching agent is glycerol, ethylene glycol, propan-1,2-diol, butan-1,2-diol or butan-2,3-diol, or ascorbic acid. In a preferred embodiment, the quenching agent is butan-2,3-diol.

In a preferred embodiment, the isolated serotypes 10A, 22F and 35B saccharides are activated by a process comprising the step of:

(a) reacting a mixture of isolated serotypes 10A, 22F and 35B saccharides with periodate;
(b) quenching the oxidation reaction by addition of butan-2,3-diol resulting in a mixture of activated serotypes 10A, 22F and 35B saccharides.

Following the oxidation step of the saccharides, the saccharides are said to be activated and is referred to as "activated saccharides" here below.

In a preferred embodiment, the activated serotypes 10A, 22F and 35B saccharides are purified. The activated serotypes 10A, 22F and 35B saccharides are purified according to methods known to the man skilled in the art such as gel permeation chromatography (GPC), dialysis or ultrafiltration/diafiltration. For example, the activated serotypes 10A, 22F and 35B saccharides are purified by concentration and diafiltration using an ultrafiltration device.

In a preferred embodiment the degree of oxidation of the activated serotypes 10A, 22F and 35B saccharides are between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25. In a preferred embodiment the degree of oxidation of the activated serotypes 10A, 22F and 35B saccharides are between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20.

In a preferred embodiment, the activated serotypes 10A, 22F and 35B saccharides have a molecular weight of between 10 kDa and 5,000 kDa; between 20 kDa and 4,000 kDa; between 50 kDa and 3,000 kDa; between 100 kDa and 2500 kDa; 100 kDa and 2,000 kDa; between 150 kDa and 2,000 kDa; between 150 kDa and 1,500 kDa; between 10 kDa and 2,000 kDa; between 20 kDa and 1,500 kDa; between 30 kDa and 1,250 kDa; between 50 kDa and 1,000 kDa; between 70 kDa and 900 kDa; between 100 kDa and 800 kDa; between 200 kDa to 600 kDa or between 400 kDa to 700 kDa.

In an embodiment, the activated serotypes 10A, 22F and 35B saccharides have a molecular weight between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In an embodiment, the activated serotypes 10A, 22F and 35B saccharides have a molecular weight between 25 kDa and 3,000 kDa, between 50 kDa and 2,000 kDa, between 100 kDa and 1,500 kDa, between 100 kDa and 1,000 kDa, between 300 kDa and 800 kDa, between 300 kDa and 700 kDa, between 300 kDa and 600 kDa, between 400 kDa and 1,000 kDa, between 400 kDa and 800 kDa, between 400 kDa and 700 kDa or between 400 kDa and 600 kDa. In an embodiment, the activated serotypes 10A, 22F and 35B saccharides have a molecular weight between 100 kDa and 3,000 kDa, between 200 kDa and 2,000 kDa, between 250 kDa and 1,500 kDa, between 250 kDa and 1,000 kDa, between 250 kDa and 800 kDa, between 250 kDa and 700 kDa, between 250 kDa and 600 kDa, between 300 kDa and 1,000 kDa, between 300 kDa and 800 kDa, between 300 kDa and 700 kDa or between 300 kDa and 600 kDa.

In an embodiment, the activated serotypes 10A, 22F and 35B saccharides have a molecular weight between 300 kDa and 800 kDa. In an embodiment, the activated serotypes 10A, 22F and 35B saccharides have a molecular weight between 400 kDa and 600 kDa. In a preferred embodiment, the activated serotypes 10A, 22F and 35B saccharides have a molecular weight between 400 kda and 600 kDa and a degree of oxidation between 10 and 25, between 10 and 20, between 12 and 20 or between 14 and 18. In a preferred embodiment, the activated serotypes 10A, 22F and 35B saccharides have a molecular weight between 400 kDa and 600 kDa and a degree of oxidation between 10 and 20.

The activated polysaccharides and/or the carrier protein may be lyophilised (freeze-dried), either independently (discrete lyophilization) or together (co-lyophilized).

In an embodiment, the activated serotypes 10A, 22F and 35B saccharides are lyophilized, optionally in the presence of saccharide such as sucrose, trehalose, raffinose, stachyose, melezitose, dextran, mannitol, lactitol or palatinit. In a preferred embodiment, the saccharide is sucrose. In one embodiment, the lyophilized activated serotypes 10A, 22F and 35B saccharides are then compounded with a solution comprising the carrier protein.

In another embodiment the activated serotypes 10A, 22F and 35B saccharides and the carrier protein are co-lyophilised. In such embodiments, the activated serotypes 10A, 22F and 35B saccharides are compounded with the carrier protein and lyophilized, optionally in the presence of a saccharide such as sucrose, trehalose, raffinose, stachyose, melezitose, dextran, mannitol, lactitol and palatinit. In a preferred embodiment, the saccharide is sucrose. The co-lyophilized activated serotypes 10A, 22F and 35B saccharides and carrier protein can then be resuspended in solution and reacted with a reducing agent.

The second step of the conjugation process is the reduction of the activated saccharides and a carrier protein to form a conjugate (reductive amination), using a reducing agent.

The activated serotypes 10A, 22F and 35B saccharides can be conjugated to a carrier protein by a process comprising the step of:

(c) compounding the activated serotypes 10A, 22F and 35B saccharides with a carrier protein; and (d) reacting the compounded activated serotypes 10A, 22F and 35B saccharides and carrier protein with a reducing agent to form a serotypes 10A/22F/35B glycoconjugate.

In an embodiment, the reduction reaction is carried out in aqueous solvent. Preferably though, the reaction is carried out in aprotic solvent. In a preferred embodiment, the reduction reaction is carried out in DMSO (dimethylsulfoxide) or in DMF (dimethylformamide)) solvent. The DMSO or DMF solvent may be used to reconstitute the activated serotypes 10A, 22F and 35B saccharides and carrier protein which have been lyophilised.

The conjugation of activated serotypes 10A, 22F and 35B saccharides with a protein carrier by reductive amination in dimethylsulfoxide (DMSO) is suitable to preserve the O-acetyl content of the saccharides as compared, for example, to reductive amination in aqueous phase where the level of O-acetylation of the saccharides may be significantly reduced. Therefore in a preferred embodiment, step (c) and step (d) are carried out in DMSO.

In an embodiment, the reducing agent is sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^i$PrN—$BH_3$, benzylamine-$BH_3$ or 5-ethyl-2-methylpyridine borane (PEMB). In a preferred embodiment, the reducing agent is sodium cyanoborohydride.

At the end of the reduction reaction, there may be unreacted aldehyde groups remaining in the conjugates, these may be capped using a suitable capping agent. In one embodiment this capping agent is sodium borohydride ($NaBH_4$).

Following conjugation of serotypes 10A, 22F and 35B saccharides to the carrier protein, the glycoconjugate can be purified (enriched with respect to the amount of saccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration.

1.3.3.4 Glycoconjugates Comprising a Saccharide from *S. pneumoniae* Serotype 10A, a Saccharide from *S. pneumoniae* Serotype 33F and a Saccharide from *S. pneumoniae* Serotype 35B and Conjugated to a Carrier Protein In an embodiment the glycoconjugates of the invention comprises a saccharide from *S. pneumoniae* serotype 10A, a saccharide from *S. pneumoniae* serotype 33F and a saccharide from *S. pneumoniae* serotype 35B conjugated to the same carrier protein (herein after 'the serotypes 10A/33F/35B glycoconjugate'). In said embodiment, the carrier molecules have the three different capsular saccharides conjugated to them. Preferably, the glycoconjugates of this section (1.3.3.4) are therefore 3-valent glycoconjugates (i.e. they have serotypes 10A, 33F and 35B conjugated to the carrier protein and have no other polysaccharide antigens covalently attached to the carrier protein).

In some embodiments, the serotypes 10A/33F/35B glycoconjugate of the present invention comprise a serotype 10A saccharide having a molecular weight of between 10 kDa and 5,000 kDa. In other such embodiments, the serotype 10A saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 10A saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/33F/35B glycoconjugate of the present invention comprise a serotype 33F saccharide having a molecular weight of between 10 kDa and 5,000 kDa. In other such embodiments, the serotype 33F saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharide has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 33F saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/33F/35B glycoconjugate of the present invention comprise a serotype 35B saccharide having a molecular weight of between 10 kDa and 5,000 kDa. In other such embodiments, the serotype 35B saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 35B saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/33F/35B glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the serotypes 10A/33F/35B glycoconjugate has a molecular weight of between 500 kDa and 10,000 kDa. In other embodiments, the serotypes 10A/33F/35B glycoconjugate has a molecular weight of between 1,000 kDa and 8,000 kDa. In still other embodiments, the serotypes 10A/33F/35B glycoconjugate has a molecular weight of between 2,000 kDa and 8,000 kDa or between 3,000 kDa and 7,000 kDa. In further embodiments, the serotypes 10A/33F/35B glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa. In further embodiments, the serotypes 10A/33F/35B glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa.

In further embodiments, the serotypes 10A/33F/35B glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate is measured by SEC-MALLS. Any whole number integer within any of the above ranges is contemplated as an embodiment of the disclosure.

Another way to characterize the serotypes 10A/33F/35B glycoconjugate of the invention is by the number of lysine residues in the carrier protein (e.g., $CRM_{197}$) that become conjugated to the saccharides which can be characterized as a range of conjugated lysines (degree of conjugation). The evidence for lysine modification of the carrier protein, due to covalent linkages to the saccharides, can be obtained by amino acid analysis using routine methods known to those of skill in the art. Conjugation results in a reduction in the number of lysine residues recovered compared to the carrier protein starting material (e.g. $CRM_{197}$) used to generate the conjugate materials. In a preferred embodiment, the degree of conjugation of the serotypes 10A/33F/35B glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotypes 10A/33F/35B glycoconjugate of the invention is about 2, about 3, about 4, about 5, about 6, about 7, about 8, about 9, about 10, about 11, about 12, about 13, about 14 or about 15. In a preferred embodiment, the degree of conjugation of the serotypes 10A/33F/35B glycoconjugate of the invention is between 4 and 7. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/33F/35B glycoconjugate of the invention may also be characterized by the ratio (weight/weight) of saccharide to carrier protein. In some embodiments, the ratio of serotypes 10A, 33F and 35B saccharides to carrier protein in the glycoconjugate (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of serotypes 10A, 33F and 35B saccharides to carrier protein in the conjugate is between 0.9 and 1.1. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/33F/35B glycoconjugate of the invention may also be characterized by the ratio (weight/weight) of serotype 10A saccharide to serotype 33F saccharide in the glycoconjugate. In some embodiments, the ratio of serotype 10A saccharide to serotype 33F saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 10A saccharide to serotype 33F saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 10A saccharide to serotype 33F saccharide ratio (w/w) is between 0.8 and 1.2. In a preferred embodiment, the ratio of serotype 10A saccharide to serotype 33F saccharide in the conjugate is between 0.9 and 1.1, even more preferably the ratio of serotype 10A saccharide to serotype 33F saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/33F/35B glycoconjugate of the invention may also be characterized by the ratio (weight/weight) of serotype 10A saccharide to serotype 35B saccharide in the glycoconjugate. In some embodiments, the ratio of serotype 10A saccharide to serotype 35B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 10A saccharide to serotype 35B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 10A saccharide to serotype 35B saccharide ratio (w/w) is between 0.8 and 1.2. In a preferred embodiment, the ratio of serotype 10A saccharide to serotype 35B saccharide in the conjugate is between 0.9 and 1.1, even more preferably the ratio of serotype 10A saccharide to serotype 35B saccharide in the conjugate is about 1.0. In some such embodiments, the carrier protein is $CRM_{197}$. In other such embodiments, the carrier protein is DT. In other such embodiments, the carrier protein is TT. In other such embodiments the carrier protein is PD.

The serotypes 10A/33F/35B glycoconjugate of the invention may also be characterized by the ratio (weight/weight) of serotype 33F saccharide to serotype 35B saccharide in the glycoconjugate. In some embodiments, the ratio of serotype 33F saccharide to serotype 35B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 33F saccharide to serotype 35B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 33F saccharide to serotype 35B saccharide ratio (w/w) is between 0.8 and 1.2. In a preferred embodiment, the ratio of serotype 33F saccharide to serotype 35B saccharide in the conjugate is between 0.9 and 1.1, even more preferably the ratio of serotype 33F saccharide to serotype 35B saccharide in the conjugate is about 1.0. In some such embodiments, the carrier protein is $CRM_{197}$. In other such embodiments, the carrier protein is DT. In other such embodiments, the carrier protein is TT. In other such embodiments the carrier protein is PD.

The serotypes 10A/33F/35B glycoconjugate of the invention may also be characterized by the relative proportion (weight/weight) of serotypes 10A saccharide, serotypes 33F saccharide and serotype 35B saccharide in the glycoconjugate. In some embodiments, the relative proportion of serotype 10A saccharide, serotype 33F saccharide and serotype 35B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | K | l | m | n | o | p | q | r | s |
| 10A | 1 | 1 | 1 | 2 | 2 | 2 | 4 | 4 | 4 | 1 | 1 | 1 | 2 | 4 | 1 | 1 | 1 | 2 | 4 |
| 33F | 1 | 1 | 1 | 1 | 1 | 1 | 1 | 1 | 1 | 2 | 2 | 2 | 2 | 2 | 4 | 4 | 4 | 4 | 4 |
| 35B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 10A saccharide, serotypes 33F saccharide and serotype 35B saccharide in the glycoconjugate, for example column a is to be read as: in an embodiment the relative proportion of serotype 10A saccharide, serotype 33F saccharide and serotype 35B saccharide in the serotypes 10A/33F/35B glycoconjugate is respectively about 1: about 1: about 4 (about one 10A saccharide for about one 33F saccharide and for about four 35B saccharide (w/w)). Preferably, the mass of serotype 10A saccharide, serotype 33F saccharide and serotype 35B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

In an embodiment, the serotypes 10A/33F/35B glycoconjugate of the invention comprises at least 0.1, 0.2, 0.3, 0.4, 0.5, 0.6 or 0.7 or about 0.8 mM acetate per mM serotype 33F polysaccharide. In a preferred embodiment, the serotypes 10A/33F/35B glycoconjugate comprises at least 0.5, 0.6 or 0.7 mM acetate per mM serotype 33F polysaccharide. In a preferred embodiment, the serotypes 10A/33F/35B glycoconjugate comprises at least 0.6 mM acetate per mM serotype 33F polysaccharide. In a preferred embodiment, the serotypes 10A/33F/35B glycoconjugate comprises at least 0.7 mM acetate per mM serotype 33F polysaccharide.

In an embodiment, the serotypes 10A/33F/35B glycoconjugate of the invention comprises at least 0.1, 0.2, 0.3, 0.4, 0.5, 0.6, 0.7 or 0.8 mM acetate per mM serotype 35B capsular polysaccharide. In a preferred embodiment, the glycoconjugate comprises at least 0.5, 0.6 or 0.7 mM acetate per mM serotype 35B capsular polysaccharide. In a preferred embodiment, the glycoconjugate comprises at least 0.6 mM acetate per mM serotype 35B capsular polysaccharide. In a preferred embodiment, the glycoconjugate comprises at least 0.7 mM acetate per mM serotype 35B capsular polysaccharide. In a preferred embodiment, the presence of O-acetyl groups is determined by NMR analysis.

The serotypes 10A/33F/35B glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d$=0), and the fraction representing the maximum retention ($V_i$), ($K_d$=1). The fraction at which a specified sample attribute is reached ($V_e$), is related to $K_d$ by the expression, $K_d=(V_e-V_0)/(V_i-V_0)$.

In a preferred embodiment, at least 30% of the serotypes 10A/33F/35B glycoconjugate has a $K_d$ below or equal to 0.3 in a CL-4B column. In a preferred embodiment, at least 40% of the serotypes 10A/33F/35B glycoconjugate has a $K_d$ below or equal to 0.3 in a CL-4B column. In a preferred embodiment, at least 45%, 50%, 55%, 60%, 65%, 70%, 75%, 80%, or 85% of the serotypes 10A/33F/35B glycoconjugate has a $K_d$ below or equal to 0.3 in a CL-4B column. In a preferred embodiment, at least 60% of the serotypes 10A/33F/35B glycoconjugate has a $K_d$ below or equal to 0.3 in a CL-4B column. In a preferred embodiment, between 50% and 80% of the serotypes 10A/33F/35B glycoconjugate has a $K_d$ below or equal to 0.3 in a CL-4B column. In a preferred embodiment, between 65% and 80% of the serotypes 10A/33F/35B glycoconjugate has a $K_d$ below or equal to 0.3 in a CL-4B column.

The serotypes 10A/33F/35B glycoconjugate of the invention may contain free saccharide that is not covalently conjugated to the carrier protein, but is nevertheless present in the serotypes 10A/33F/35B glycoconjugate composition. The free saccharide may be noncovalently associated with (i.e., noncovalently bound to, adsorbed to, or entrapped in or with) the serotypes 10A/33F/35B glycoconjugate.

In a preferred embodiment, the serotypes 10A/33F/35B glycoconjugate comprises less than about 50%, 45%, 40%, 35%, 30%, 25%, 20% or 15% of free serotypes 10A, 33F and 35B saccharide compared to the total amount of serotypes 10A, 33F and 35B saccharide. In a preferred embodiment the serotypes 10A/33F/35B glycoconjugate comprises less than about 40% of free serotypes 10A, 33F and 35B saccharide compared to the total amount of serotypes 10A, 33F and 35B saccharide. In a preferred embodiment the serotypes 10A/33F/35B glycoconjugate comprises less than about 25% of free serotypes 10A, 33F and 35B saccharide compared to the total amount of serotypes 10A, 33F and 35B saccharide. In a preferred embodiment the serotypes 10A/33F/35B glycoconjugate comprises less than about 20% of free serotypes 10A, 33F and 35B saccharide compared to the total amount of serotypes 10A, 33F and 35B saccharide. In a preferred embodiment the serotypes 10A/33F/35B glycoconjugate comprises less than about 15% of free serotypes 10A, 33F and 35B saccharide compared to the total amount of serotypes 10A, 33F and 35B saccharide.

In preferred embodiments, the serotype 10A/33F/35B glycoconjugates of the invention are prepared using reductive amination.

Reductive amination involves two steps, (1) oxidation (activation) of the saccharide, (2) reduction of the activated saccharide and a carrier protein (e.g., $CRM_{197}$, DT, TT or PD) to form a conjugate.

Before oxidation, sizing of the serotype 10A, 33F and/or 35B saccharide to a target molecular weight (MW) range can be performed. Mechanical or chemical hydrolysis may be employed. Chemical hydrolysis may be conducted using acetic acid. Advantageously, the size of the purified serotype 10A, 33F and/or 35B saccharide is reduced while preserving critical features of the structure of the saccharide such as for example the presence of O-acetyl groups. Therefore preferably, the size of the purified serotype 10A, 33F and/or 35B saccharide is reduced by mechanical homogenization.

In an embodiment, serotypes 10A, 33F and 35B saccharides are activated (oxidized) by a process comprising the step of:

(a) reacting a mixture of isolated serotypes 10A, 33F and 35B saccharides with an oxidizing agent.

Said process can further comprise a quenching step.

Therefore in an embodiment, serotypes 10A, 33F and 35B saccharides are activated (oxidized) by a process comprising the step of:

(a) reacting a mixture of isolated serotypes 10A, 33F and 35B saccharides with an oxidizing agent;
(b) quenching the oxidation reaction by addition of a quenching agent resulting in activated serotypes 10A, 33F and 35B saccharides.

In these embodiments, the saccharides are therefore activated altogether as a mixture.

In another embodiment, serotypes 10A, 33F and 35B saccharides are activated (oxidized) separately and the activated saccharides are then mixed.

In said embodiment, serotypes 10A, 33F and 35B saccharides are activated (oxidized) by a process comprising the step of:

(a) individually reacting an isolated serotypes 10A, 33F and 35B saccharides with an oxidizing agent;
(b) mixing the activated serotypes 10A, 33F and 35B saccharides.

Said process can further comprise a quenching step.

Therefore in an embodiment, serotypes 10A, 33F and 35B saccharides are activated (oxidized) by a process comprising the step of:

(a) individually reacting an isolated serotypes 10A, 33F and 35B saccharides with an oxidizing agent;
(b) quenching the oxidation reactions by addition of a quenching agent resulting in activated serotypes 10A, 33F and 35B saccharides;
(b) mixing the activated serotypes 10A, 33F and 35B saccharides.

The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate).

In a preferred embodiment, the oxidizing agent is sodium periodate. In a preferred embodiment, the periodate used for the oxidation of serotypes 10A, 33F and 35B saccharides is metaperiodate.

In a preferred embodiment the periodate used for the oxidation of serotypes 10A, 33F and 35B saccharides is sodium metaperiodate.

In one embodiment, the quenching agent is selected from vicinal diols, 1,2-aminoalcohols, amino acids, glutathione, sulfite, bisulfate, dithionite, metabisulfite, thiosulfate, phosphites, hypophosphites or phosphorous acid.

In one embodiment, the quenching agent is a 1,2-aminoalcohols of formula (I):

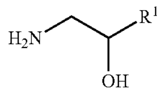

(I)

wherein $R^1$ is selected from H, methyl, ethyl, propyl or isopropyl.

In one embodiment, the quenching agent is selected from sodium and potassium salts of sulfite, bisulfate, dithionite, metabisulfite, thiosulfate, phosphites, hypophosphites or phosphorous acid.

In one embodiment, the quenching agent is an amino acid. In such embodiments, said amino acid may be selected from serine, threonine, cysteine, cystine, methionine, proline, hydroxyproline, tryptophan, tyrosine, and histidine.

In one embodiment, the quenching agent is a sulfite such as bisulfate, dithionite, metabisulfite, thiosulfate.

In one embodiment, the quenching agent is a compound comprising two vicinal hydroxyl groups (vicinal diols), i.e., two hydroxyl groups covalently linked to two adjacent carbon atoms.

Preferably, the quenching agent is a compound of formula (II):

(II)

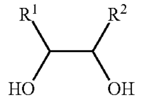

wherein $R^1$ and $R^2$ are each independently selected from H, methyl, ethyl, propyl or isopropyl. In a preferred embodiment, the quenching agent is glycerol, ethylene glycol, propan-1,2-diol, butan-1,2-diol or butan-2,3-diol, or ascorbic acid. In a preferred embodiment, the quenching agent is butan-2,3-diol.

In a preferred embodiment, the isolated serotypes 10A, 33F and 35B saccharides are activated by a process comprising the step of:

(a) reacting a mixture of isolated serotypes 10A, 33F and 35B saccharides with periodate;

(b) quenching the oxidation reaction by addition of butan-2,3-diol resulting in a mixture of activated serotypes 10A, 33F and 35B saccharides.

Following the oxidation step of the saccharides, the saccharides are said to be activated and is referred to as "activated saccharides" here below.

In a preferred embodiment, the activated serotypes 10A, 33F and 35B saccharides are purified. The activated serotypes 10A, 33F and 35B saccharides are purified according to methods known to the man skilled in the art such as gel permeation chromatography (GPC), dialysis or ultrafiltration/diafiltration. For example, the activated serotypes 10A, 33F and 35B saccharides are purified by concentration and diafiltration using an ultrafiltration device.

In a preferred embodiment the degree of oxidation of the activated serotypes 10A, 33F and 35B saccharides are between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25. In a preferred embodiment the degree of oxidation of the activated serotypes 10A, 33F and 35B saccharides are between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20.

In a preferred embodiment, the activated serotypes 10A, 33F and 35B saccharides have a molecular weight of between 10 kDa and 5,000 kDa; between 20 kDa and 4,000 kDa; between 50 kDa and 3,000 kDa; between 100 kDa and 2500 kDa; 100 kDa and 2,000 kDa; between 150 kDa and 2,000 kDa; between 150 kDa and 1,500 kDa; between 10 kDa and 2,000 kDa; between 20 kDa and 1,500 kDa; between 30 kDa and 1,250 kDa; between 50 kDa and 1,000 kDa; between 70 kDa and 900 kDa; between 100 kDa and 800 kDa; between 200 kDa to 600 kDa or between 400 kDa to 700 kDa.

In an embodiment, the activated serotypes 10A, 33F and 35B saccharides have a molecular weight between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In an embodiment, the activated serotypes 10A, 33F and 35B saccharides have a molecular weight between 25 kDa and 3,000 kDa, between 50 kDa and 2,000 kDa, between 100 kDa and 1,500 kDa, between 100 kDa and 1,000 kDa, between 300 kDa and 800 kDa, between 300 kDa and 700 kDa, between 300 kDa and 600 kDa, between 400 kDa and 1,000 kDa, between 400 kDa and 800 kDa, between 400 kDa and 700 kDa or between 400 kDa and 600 kDa. In an embodiment, the activated serotypes 10A, 33F and 35B saccharides have a molecular weight between 100 kDa and 3,000 kDa, between 200 kDa and 2,000 kDa, between 250 kDa and 1,500 kDa, between 250 kDa and 1,000 kDa, between 250 kDa and 800 kDa, between 250 kDa and 700 kDa, between 250 kDa and 600 kDa, between 300 kDa and 1,000 kDa, between 300 kDa and 800 kDa, between 300 kDa and 700 kDa or between 300 kDa and 600 kDa.

In an embodiment, the activated serotypes 10A, 33F and 35B saccharides have a molecular weight between 300 kDa and 800 kDa. In an embodiment, the activated serotypes 10A, 33F and 35B saccharides have a molecular weight between 400 kDa and 600 kDa. In a preferred embodiment, the activated serotypes 10A, 33F and 35B saccharides have a molecular weight between 400 kda and 600 kDa and a degree of oxidation between 10 and 25, between 10 and 20, between 12 and 20 or between 14 and 18. In a preferred embodiment, the activated serotypes 10A, 33F and 35B saccharides have a molecular weight between 400 kDa and 600 kDa and a degree of oxidation between 10 and 20.

The activated polysaccharides and/or the carrier protein may be lyophilised (freeze-dried), either independently (discrete lyophilization) or together (co-lyophilized).

In an embodiment, the activated serotypes 10A, 33F and 35B saccharides are lyophilized, optionally in the presence of saccharide such as sucrose, trehalose, raffinose, stachyose, melezitose, dextran, mannitol, lactitol or palatinit. In a preferred embodiment, the saccharide is sucrose. In one embodiment, the lyophilized activated serotypes 10A, 33F and 35B saccharides are then compounded with a solution comprising the carrier protein.

In another embodiment the activated serotypes 10A, 33F and 35B saccharides and the carrier protein are co-lyophilised. In such embodiments, the activated serotypes 10A, 33F and 35B saccharides are compounded with the carrier protein and lyophilized, optionally in the presence of a saccharide such as sucrose, trehalose, raffinose, stachyose, melezitose, dextran, mannitol, lactitol and palatinit. In a preferred embodiment, the saccharide is sucrose. The co-lyophilized activated serotypes 10A, 33F and 35B saccharides and carrier protein can then be resuspended in solution and reacted with a reducing agent.

The second step of the conjugation process is the reduction of the activated saccharides and a carrier protein to form a conjugate (reductive amination), using a reducing agent.

The activated serotypes 10A, 33F and 35B saccharides can be conjugated to a carrier protein by a process comprising the step of:

(c) compounding the activated serotypes 10A, 33F and 35B saccharides with a carrier protein; and (d) reacting the compounded activated serotypes 10A, 33F and 35B saccharides and carrier protein with a reducing agent to form a serotypes 10A/33F/35B glycoconjugate.

In an embodiment, the reduction reaction is carried out in aqueous solvent. Preferably though, the reaction is carried out in aprotic solvent. In a preferred embodiment, the reduction reaction is carried out in DMSO (dimethylsulfoxide) or in DMF (dimethylformamide)) solvent. The DMSO or DMF solvent may be used to reconstitute the activated serotypes 10A, 33F and 35B saccharides and carrier protein which have been lyophilised.

The conjugation of activated serotypes 10A, 33F and 35B saccharides with a protein carrier by reductive amination in dimethylsulfoxide (DMSO) is suitable to preserve the O-acetyl content of the saccharides as compared, for example, to reductive amination in aqueous phase where the level of O-acetylation of the saccharides may be significantly reduced. Therefore in a preferred embodiment, step (c) and step (d) are carried out in DMSO.

In an embodiment, the reducing agent is sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^{i}$PrN—$BH_3$, benzylamine-$BH_3$ or 5-ethyl-2-methylpyridine borane (PEMB). In a preferred embodiment, the reducing agent is sodium cyanoborohydride.

At the end of the reduction reaction, there may be unreacted aldehyde groups remaining in the conjugates, these may be capped using a suitable capping agent. In one embodiment this capping agent is sodium borohydride ($NaBH_4$).

Following conjugation of serotypes 10A, 33F and 35B saccharides to the carrier protein, the glycoconjugate can be purified (enriched with respect to the amount of saccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration.

1.3.3.5 Glycoconjugates Comprising a Saccharide from *S. pneumoniae* Serotype 22F, a Saccharide from *S. pneumoniae* Serotype 33F and a Saccharide from *S. pneumoniae* Serotype 35B and Conjugated to a Carrier Protein In an embodiment the glycoconjugates of the invention comprises a saccharide from *S. pneumoniae* serotype 22F, a saccharide from *S. pneumoniae* serotype 33F and a saccharide from *S. pneumoniae* serotype 35B conjugated to the same carrier protein (herein after 'the serotypes 22F/33F/35B glycoconjugate'). In said embodiment, the carrier molecules have the three different capsular saccharides conjugated to them. Preferably, the glycoconjugates of this section (1.3.3.5) are therefore 3-valent glycoconjugates (i.e. they have serotypes 22F, 33F and 35B conjugated to the carrier protein and have no other polysaccharide antigens covalently attached to the carrier protein).

In some embodiments, the serotypes 22F/33F/35B glycoconjugate of the present invention comprise a serotype 22F saccharide having a molecular weight of between 10 kDa and 5,000 kDa. In other such embodiments, the serotype 22F saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 22F saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 22F/33F/35B glycoconjugate of the present invention comprise a serotype 33F saccharide having a molecular weight of between 10 kDa and 5,000 kDa. In other such embodiments, the serotype 33F saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharide has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 33F saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 22F/33F/35B glycoconjugate of the present invention comprise a serotype 35B saccharide having a molecular weight of between 10 kDa and 5,000 kDa. In other such embodiments, the serotype 35B saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 35B saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 22F/33F/35B glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the serotypes 22F/33F/35B glycoconjugate has a molecular weight of between 500 kDa and 10,000 kDa. In other embodiments, the serotypes 22F/33F/35B glycoconjugate has a molecular weight of between 1,000 kDa and 8,000 kDa. In still other embodiments, the serotypes 22F/33F/35B glycoconjugate has a molecular weight of between 2,000 kDa and 8,000 kDa or between 3,000 kDa and 7,000 kDa. In further embodiments, the serotypes 22F/33F/35B glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa.

In further embodiments, the serotypes 22F/33F/35B glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa.

In further embodiments, the serotypes 22F/33F/35B glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate is measured by SEC-MALLS. Any whole number integer within any of the above ranges is contemplated as an embodiment of the disclosure.

Another way to characterize the serotypes 22F/33F/35B glycoconjugate of the invention is by the number of lysine residues in the carrier protein (e.g., $CRM_{197}$) that become conjugated to the saccharides which can be characterized as a range of conjugated lysines (degree of conjugation). The evidence for lysine modification of the carrier protein, due to covalent linkages to the saccharides, can be obtained by amino acid analysis using routine methods known to those of skill in the art. Conjugation results in a reduction in the number of lysine residues recovered compared to the carrier protein starting material (e.g. $CRM_{197}$) used to generate the conjugate materials. In a preferred embodiment, the degree of conjugation of the serotypes 22F/33F/35B glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotypes 22F/33F/35B glycoconjugate of the invention is about 2, about 3, about 4, about 5, about 6, about 7, about 8, about 9, about 10, about 11, about 12, about 13, about 14 or about 15.

In a preferred embodiment, the degree of conjugation of the serotypes 22F/33F/35B glycoconjugate of the invention is between 4 and 7. In some such embodiments, the carrier protein is $CRM_{197}$. In other such embodiments, the carrier protein is DT. In other such embodiments, the carrier protein is TT. In other such embodiments, the carrier protein is PD.

The serotypes 22F/33F/35B glycoconjugate of the invention may also be characterized by the ratio (weight/weight) of saccharide to carrier protein. In some embodiments, the ratio of serotypes 22F, 33F and 35B saccharides to carrier protein in the glycoconjugate (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of serotypes 22F, 33F and 35B saccharides to carrier protein in the conjugate is between 0.9 and 1.1. In some such embodiments, the carrier protein is $CRM_{197}$. In other such embodiments, the carrier protein is DT. In other such embodiments, the carrier protein is TT. In other such embodiments, the carrier protein is PD.

The serotypes 22F/33F/35B glycoconjugate of the invention may also be characterized by the ratio (weight/weight) of serotype 22F saccharide to serotype 33F saccharide in the glycoconjugate. In some embodiments, the ratio of serotype 22F saccharide to serotype 33F saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 22F saccharide to serotype 33F saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 22F saccharide to serotype 33F saccharide ratio (w/w) is between 0.8 and 1.2. In a preferred embodiment, the ratio of serotype 22F saccharide to serotype 33F saccharide in the conjugate is between 0.9 and 1.1, even more preferably the ratio of serotype 22F saccharide to serotype 33F saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

The serotypes 22F/33F/35B glycoconjugate of the invention may also be characterized by the ratio (weight/weight) of serotype 22F saccharide to serotype 35B saccharide in the glycoconjugate. In some embodiments, the ratio of serotype 22F saccharide to serotype 35B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 22F saccharide to serotype 35B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 22F saccharide to serotype 35B saccharide ratio (w/w) is between 0.8 and 1.2. In a preferred embodiment, the ratio of serotype 22F saccharide to serotype 35B saccharide in the conjugate is between 0.9 and 1.1, even more preferably the ratio of serotype 22F saccharide to serotype 35B saccharide in the conjugate is about 1.0. In some such embodiments, the carrier protein is $CRM_{197}$. In other such embodiments, the carrier protein is DT. In other such embodiments, the carrier protein is TT. In other such embodiments the carrier protein is PD.

The serotypes 22F/33F/35B glycoconjugate of the invention may also be characterized by the ratio (weight/weight) of serotype 33F saccharide to serotype 35B saccharide in the glycoconjugate. In some embodiments, the ratio of serotype 33F saccharide to serotype 35B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 33F saccharide to serotype 35B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 33F saccharide to serotype 35B saccharide ratio (w/w) is between 0.8 and 1.2. In a preferred embodiment, the ratio of serotype 33F saccharide to serotype 35B saccharide in the conjugate is between 0.9 and 1.1, even more preferably the ratio of serotype 33F saccharide to serotype 35B saccharide in the conjugate is about 1.0. In some such embodiments, the carrier protein is $CRM_{197}$. In other such embodiments, the carrier protein is DT. In other such embodiments, the carrier protein is TT. In other such embodiments the carrier protein is PD.

The serotypes 22F/33F/35B glycoconjugate of the invention may also be characterized by the relative proportion (weight/weight) of serotypes 22F saccharide, serotypes 33F saccharide and serotype 35B saccharide in the glycoconjugate. In some embodiments, the relative proportion of serotype 22F saccharide, serotype 33F saccharide and serotype 35B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | K | l | m | n | O | p | q | r | s |
| 22F | 1 | 1 | 1 | 2 | 2 | 2 | 4 | 4 | 4 | 1 | 1 | 1 | 2 | 4 | 1 | 1 | 1 | 2 | 4 |
| 33F | 1 | 1 | 1 | 1 | 1 | 1 | 1 | 1 | 1 | 2 | 2 | 2 | 2 | 2 | 4 | 4 | 4 | 4 | 4 |
| 35B | 4 | 2 | 1 | 4 | 2 | 1 | 4 | 2 | 1 | 4 | 2 | 1 | 1 | 1 | 4 | 2 | 1 | 1 | 1 |

Each column a to s of the above table provides the relative proportion of serotypes 22F saccharide, serotypes 33F saccharide and serotype 35B saccharide in the glycoconjugate, for example column a is to be read as: in an embodiment the relative proportion of serotype 22F saccharide, serotype 33F saccharide and serotype 35B saccharide in the serotypes 22F/33F/35B glycoconjugate is respectively about 1: about 1: about 4 (about one 22F saccharide for about one 33F saccharide and for about four 35B saccharide (w/w)). Preferably, the mass of serotype 22F saccharide, serotype 33F saccharide and serotype 35B saccharide in the glycoconjugate is about the same for each saccharide (ratio of about 1:1:1 (w/w)).

In some such embodiments, the carrier protein is $CRM_{197}$. In other such embodiments, the carrier protein is DT. In other such embodiments, the carrier protein is TT. In other such embodiments the carrier protein is PD.

In an embodiment, the serotypes 22F/33F/35B glycoconjugate of the invention comprises at least 0.1, 0.2, 0.3, 0.4, 0.5, 0.6 or 0.7 or about 0.8 mM acetate per mM serotype 33F polysaccharide. In a preferred embodiment, the serotypes 22F/33F/35B glycoconjugate comprises at least 0.5, 0.6 or 0.7 mM acetate per mM serotype 33F polysaccharide. In a preferred embodiment, the serotypes 22F/33F/35B glycoconjugate comprises at least 0.6 mM acetate per mM serotype 33F polysaccharide. In a preferred embodiment, the serotypes 22F/33F/35B glycoconjugate comprises at least 0.7 mM acetate per mM serotype 33F polysaccharide.

In an embodiment, the serotypes 22F/33F/35B glycoconjugate of the invention comprises at least 0.1, 0.2, 0.3, 0.4, 0.5, 0.6, 0.7 or 0.8 mM acetate per mM serotype 35B capsular polysaccharide. In a preferred embodiment, the glycoconjugate comprises at least 0.5, 0.6 or 0.7 mM acetate per mM serotype 35B capsular polysaccharide. In a preferred embodiment, the glycoconjugate comprises at least 0.6 mM acetate per mM serotype 35B capsular polysaccharide. In a preferred embodiment, the glycoconjugate comprises at least 0.7 mM acetate per mM serotype 35B capsular polysaccharide. In a preferred embodiment, the presence of O-acetyl groups is determined by NMR analysis.

The serotypes 22F/33F/35B glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d$=0), and the fraction representing the maximum retention ($V_i$), ($K_d$=1). The fraction at which a specified sample attribute is reached ($V_e$), is related to $K_d$ by the expression, $K_d=(V_e-V_0)/(V_i-V_0)$.

In a preferred embodiment, at least 30% of the serotypes 22F/33F/35B glycoconjugate has a $K_d$ below or equal to 0.3 in a CL-4B column. In a preferred embodiment, at least 40% of the serotypes 22F/33F/35B glycoconjugate has a $K_d$ below or equal to 0.3 in a CL-4B column. In a preferred embodiment, at least 45%, 50%, 55%, 60%, 65%, 70%, 75%, 80%, or 85% of the serotypes 22F/33F/35B glycoconjugate has a $K_d$ below or equal to 0.3 in a CL-4B column. In a preferred embodiment, at least 60% of the serotypes 22F/33F/35B glycoconjugate has a $K_d$ below or equal to 0.3 in a CL-4B column. In a preferred embodiment, between 50% and 80% of the serotypes 22F/33F/35B glycoconjugate has a $K_d$ below or equal to 0.3 in a CL-4B column. In a preferred embodiment, between 65% and 80% of the serotypes 22F/33F/35B glycoconjugate has a $K_d$ below or equal to 0.3 in a CL-4B column.

The serotypes 22F/33F/35B glycoconjugate of the invention may contain free saccharide that is not covalently conjugated to the carrier protein, but is nevertheless present in the serotypes 22F/33F/35B glycoconjugate composition. The free saccharide may be noncovalently associated with (i.e., noncovalently bound to, adsorbed to, or entrapped in or with) the serotypes 22F/33F/35B glycoconjugate.

In a preferred embodiment, the serotypes 22F/33F/35B glycoconjugate comprises less than about 50%, 45%, 40%, 35%, 30%, 25%, 20% or 15% of free serotypes 22F, 33F and 35B saccharide compared to the total amount of serotypes 22F, 33F and 35B saccharide. In a preferred embodiment the serotypes 22F/33F/35B glycoconjugate comprises less than about 40% of free serotypes 22F, 33F and 35B saccharide compared to the total amount of serotypes 22F, 33F and 35B saccharide. In a preferred embodiment the serotypes 22F/33F/35B glycoconjugate comprises less than about 25% of free serotypes 22F, 33F and 35B saccharide compared to the total amount of serotypes 22F, 33F and 35B saccharide. In a preferred embodiment the serotypes 22F/33F/35B glycoconjugate comprises less than about 20% of free serotypes 22F, 33F and 35B saccharide compared to the total amount of serotypes 22F, 33F and 35B saccharide. In a preferred embodiment the serotypes 22F/33F/35B glycoconjugate comprises less than about 15% of free serotypes 22F, 33F and 35B saccharide compared to the total amount of serotypes 22F, 33F and 35B saccharide.

In preferred embodiments, the serotype 22F/33F/35B glycoconjugates of the invention are prepared using reductive amination.

Reductive amination involves two steps, (1) oxidation (activation) of the saccharide, (2) reduction of the activated saccharide and a carrier protein (e.g., $CRM_{197}$, DT, TT or PD) to form a conjugate. Before oxidation, sizing of the serotype 22F, 33F and/or 35B saccharide to a target molecular weight (MW) range can be performed. Mechanical or chemical hydrolysis may be employed. Chemical hydrolysis may be conducted using acetic acid. Advantageously, the size of the purified serotype 22F, 33F and/or 35B saccharide is reduced while preserving critical features of the structure of the saccharide such as for example the presence of O-acetyl groups. Therefore preferably, the size of the purified serotype 22F, 33F and/or 35B saccharide is reduced by mechanical homogenization.

In an embodiment, serotypes 22F, 33F and 35B saccharides are activated (oxidized) by a process comprising the step of:

(a) reacting a mixture of isolated serotypes 22F, 33F and 35B saccharides with an oxidizing agent. Said process can further comprise a quenching step.

Therefore, in an embodiment, serotypes 22F, 33F and 35B saccharides are activated (oxidized) by a process comprising the step of:

(a) reacting a mixture of isolated serotypes 22F, 33F and 35B saccharides with an oxidizing agent;
(b) quenching the oxidation reaction by addition of a quenching agent resulting in activated serotypes 22F, 33F and 35B saccharides.

In these embodiments, the saccharides are therefore activated altogether as a mixture.

In another embodiment, serotypes 22F, 33F and 35B saccharides are activated (oxidized) separately and the activated saccharides are then mixed.

In said embodiment, serotypes 22F, 33F and 35B saccharides are activated (oxidized) by a process comprising the step of:

(a) individually reacting an isolated serotypes 22F, 33F and 35B saccharides with an oxidizing agent;

(b) mixing the activated serotypes 22F, 33F and 35B saccharides.

Said process can further comprise a quenching step.

Therefore in an embodiment, serotypes 22F, 33F and 35B saccharides are activated (oxidized) by a process comprising the step of:

(a) individually reacting an isolated serotypes 22F, 33F and 35B saccharides with an oxidizing agent;

(b) quenching the oxidation reactions by addition of a quenching agent resulting in activated serotypes 22F, 33F and 35B saccharides;

(b) mixing the activated serotypes 22F, 33F and 35B saccharides.

The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate).

In a preferred embodiment, the oxidizing agent is sodium periodate. In a preferred embodiment, the periodate used for the oxidation of serotypes 22F, 33F and 35B saccharides is metaperiodate. In a preferred embodiment the periodate used for the oxidation of serotypes 22F, 33F and 35B saccharides is sodium metaperiodate.

In one embodiment, the quenching agent is selected from vicinal diols, 1,2-aminoalcohols, amino acids, glutathione, sulfite, bisulfate, dithionite, metabisulfite, thiosulfate, phosphites, hypophosphites or phosphorous acid.

In one embodiment, the quenching agent is a 1,2-aminoalcohols of formula (I):

(I)

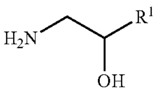

wherein $R^1$ is selected from H, methyl, ethyl, propyl or isopropyl.

In one embodiment, the quenching agent is selected from sodium and potassium salts of sulfite, bisulfate, dithionite, metabisulfite, thiosulfate, phosphites, hypophosphites or phosphorous acid. In one embodiment, the quenching agent is an amino acid. In such embodiments, said amino acid may be selected from serine, threonine, cysteine, cystine, methionine, proline, hydroxyproline, tryptophan, tyrosine, and histidine.

In one embodiment, the quenching agent is a sulfite such as bisulfate, dithionite, metabisulfite, thiosulfate.

In one embodiment, the quenching agent is a compound comprising two vicinal hydroxyl groups (vicinal diols), i.e., two hydroxyl groups covalently linked to two adjacent carbon atoms.

Preferably, the quenching agent is a compound of formula (II):

(II)

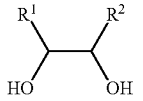

wherein $R^1$ and $R^2$ are each independently selected from H, methyl, ethyl, propyl or isopropyl. In a preferred embodiment, the quenching agent is glycerol, ethylene glycol, propan-1,2-diol, butan-1,2-diol or butan-2,3-diol, or ascorbic acid. In a preferred embodiment, the quenching agent is butan-2,3-diol.

In a preferred embodiment, the isolated serotypes 22F, 33F and 35B saccharides are activated by a process comprising the step of:

(a) reacting a mixture of isolated serotypes 22F, 33F and 35B saccharides with periodate;

(b) quenching the oxidation reaction by addition of butan-2,3-diol resulting in a mixture of activated serotypes 22F, 33F and 35B saccharides.

Following the oxidation step of the saccharides, the saccharides are said to be activated and is referred to as "activated saccharides" here below.

In a preferred embodiment, the activated serotypes 22F, 33F and 35B saccharides are purified. The activated serotypes 22F, 33F and 35B saccharides are purified according to methods known to the man skilled in the art such as gel permeation chromatography (GPC), dialysis or ultrafiltration/diafiltration. For example, the activated serotypes 22F, 33F and 35B saccharides are purified by concentration and diafiltration using an ultrafiltration device.

In a preferred embodiment the degree of oxidation of the activated serotypes 22F, 33F and 35B saccharides are between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25. In a preferred embodiment the degree of oxidation of the activated serotypes 22F, 33F and 35B saccharides are between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20.

In a preferred embodiment, the activated serotypes 22F, 33F and 35B saccharides have a molecular weight of between 10 kDa and 5,000 kDa; between 20 kDa and 4,000 kDa; between 50 kDa and 3,000 kDa; between 100 kDa and 2500 kDa; 100 kDa and 2,000 kDa; between 150 kDa and 2,000 kDa; between 150 kDa and 1,500 kDa; between 10 kDa and 2,000 kDa; between 20 kDa and 1,500 kDa; between 30 kDa and 1,250 kDa; between 50 kDa and 1,000 kDa; between 70 kDa and 900 kDa; between 100 kDa and 800 kDa; between 200 kDa to 600 kDa or between 400 kDa to 700 kDa.

In an embodiment, the activated serotypes 22F, 33F and 35B saccharides have a molecular weight between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In an embodiment, the activated serotypes 22F, 33F and 35B saccharides have a molecular weight between 25 kDa and 3,000 kDa, between 50 kDa and 2,000 kDa, between 100 kDa and 1,500 kDa, between 100 kDa and 1,000 kDa, between 300 kDa and 800 kDa, between 300 kDa and 700 kDa, between 300 kDa and 600 kDa, between 400 kDa and 1,000 kDa, between 400 kDa and 800 kDa, between 400 kDa and 700 kDa or between 400 kDa and 600 kDa. In an embodiment, the activated serotypes 22F, 33F and 35B saccharides have a molecular weight between 100 kDa and 3,000 kDa, between 200 kDa and 2,000 kDa, between 250 kDa and 1,500 kDa, between 250 kDa and 1,000 kDa, between 250 kDa and 800 kDa, between 250 kDa and 700 kDa, between 250 kDa and 600 kDa, between 300 kDa and 1,000 kDa, between 300 kDa and 800 kDa, between 300 kDa and 700 kDa or between 300 kDa and 600 kDa.

In an embodiment, the activated serotypes 22F, 33F and 35B saccharides have a molecular weight between 300 kDa and 800 kDa. In an embodiment, the activated serotypes 22F, 33F and 35B saccharides have a molecular weight between 400 kDa and 600 kDa. In a preferred embodiment, the activated serotypes 22F, 33F and 35B saccharides have a molecular weight between 400 kda and 600 kDa and a degree of oxidation between 10 and 25, between 10 and 20, between 12 and 20 or between 14 and 18. In a preferred embodiment, the activated serotypes 22F, 33F and 35B saccharides have a molecular weight between 400 kDa and 600 kDa and a degree of oxidation between 10 and 20.

The activated polysaccharides and/or the carrier protein may be lyophilised (freeze-dried), either independently (discrete lyophilization) or together (co-lyophilized).

In an embodiment, the activated serotypes 22F, 33F and 35B saccharides are lyophilized, optionally in the presence of saccharide such as sucrose, trehalose, raffinose, stachyose, melezitose, dextran, mannitol, lactitol or palatinit. In a preferred embodiment, the saccharide is sucrose. In one embodiment, the lyophilized activated serotypes 22F, 33F and 35B saccharides are then compounded with a solution comprising the carrier protein.

In another embodiment the activated serotypes 22F, 33F and 35B saccharides and the carrier protein are co-lyophilised. In such embodiments, the activated serotypes 22F, 33F and 35B saccharides are compounded with the carrier protein and lyophilized, optionally in the presence of a saccharide such as sucrose, trehalose, raffinose, stachyose, melezitose, dextran, mannitol, lactitol and palatinit. In a preferred embodiment, the saccharide is sucrose. The co-lyophilized activated serotypes 22F, 33F and 35B saccharides and carrier protein can then be resuspended in solution and reacted with a reducing agent.

The second step of the conjugation process is the reduction of the activated saccharides and a carrier protein to form a conjugate (reductive amination), using a reducing agent.

The activated serotypes 22F, 33F and 35B saccharides can be conjugated to a carrier protein by a process comprising the step of:

(c) compounding the activated serotypes 22F, 33F and 35B saccharides with a carrier protein; and (d) reacting the compounded activated serotypes 22F, 33F and 35B saccharides and carrier protein with a reducing agent to form a serotypes 22F/33F/35B glycoconjugate.

In an embodiment, the reduction reaction is carried out in aqueous solvent. Preferably though, the reaction is carried out in aprotic solvent. In a preferred embodiment, the reduction reaction is carried out in DMSO (dimethylsulfoxide) or in DMF (dimethylformamide)) solvent. The DMSO or DMF solvent may be used to reconstitute the activated serotypes 22F, 33F and 35B saccharides and carrier protein which have been lyophilised.

The conjugation of activated serotypes 22F, 33F and 35B saccharides with a protein carrier by reductive amination in dimethylsulfoxide (DMSO) is suitable to preserve the O-acetyl content of the saccharides as compared, for example, to reductive amination in aqueous phase where the level of O-acetylation of the saccharides may be significantly reduced. Therefore, in a preferred embodiment, step (c) and step (d) are carried out in DMSO.

In an embodiment, the reducing agent is sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^i$PrN—$BH_3$, benzylamine-$BH_3$ or 5-ethyl-2-methylpyridine borane (PEMB). In a preferred embodiment, the reducing agent is sodium cyanoborohydride.

At the end of the reduction reaction, there may be unreacted aldehyde groups remaining in the conjugates, these may be capped using a suitable capping agent. In one embodiment this capping agent is sodium borohydride ($NaBH_4$).

Following conjugation of serotypes 22F, 33F and 35B saccharides to the carrier protein, the glycoconjugate can be purified (enriched with respect to the amount of saccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration.

1.3.3.6 Glycoconjugates Comprising a Saccharide from *S. pneumoniae* Serotype 10A and a Saccharide from *S. pneumoniae* Serotype 22F Conjugated to a Carrier Protein In an embodiment the glycoconjugates of the invention comprises a saccharide from *S. pneumoniae* serotype 10A and a saccharide from *S. pneumoniae* serotype 22F conjugated to the same carrier protein (herein after 'the serotypes 10A/22F glycoconjugate'). In said embodiment, the carrier molecules have the two different capsular saccharides conjugated to them. Preferably, the glycoconjugates of this section (1.3.3.6) are therefore 2-valent glycoconjugates (i.e. they have serotypes 10A and 22F conjugated to the carrier protein and have no other polysaccharide antigens covalently attached to the carrier protein).

In some embodiments, the serotypes 10A/22F glycoconjugate of the present invention comprise a serotype 10A saccharide having a molecular weight of between 10 kDa and 5,000 kDa. In other such embodiments, the serotype 10A saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 10A saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/22F glycoconjugate of the present invention comprise a serotype 22F saccharide having a molecular weight of between 10 kDa and 5,000 kDa. In other such embodiments, the serotype 22F saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 22F saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/22F glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the serotypes 10A/22F glycoconjugate has a molecular weight of between 500 kDa and 10,000 kDa. In other embodiments, the serotypes 10A/22F glycoconjugate has a molecular weight of between 1,000 kDa and 8,000 kDa. In still other embodiments, the serotypes 10A/22F glycoconjugate has a molecular weight of between 2,000 kDa and 8,000 kDa or between 3,000 kDa and 7,000 kDa. In further embodiments, the serotypes 10A/22F glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa.

In further embodiments, the serotypes 10A/22F glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa.

In further embodiments, the serotypes 10A/22F glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate is measured by SEC-MALLS. Any whole number integer within any of the above ranges is contemplated as an embodiment of the disclosure.

Another way to characterize the serotypes 10A/22F glycoconjugate of the invention is by the number of lysine residues in the carrier protein (e.g., $CRM_{197}$) that become conjugated to the saccharides which can be characterized as a range of conjugated lysines (degree of conjugation). The evidence for lysine modification of the carrier protein, due to covalent linkages to the saccharides, can be obtained by amino acid analysis using routine methods known to those of skill in the art. Conjugation results in a reduction in the number of lysine residues recovered compared to the carrier protein starting material (e.g. $CRM_{197}$) used to generate the conjugate materials. In a preferred embodiment, the degree of conjugation of the serotypes 10A/22F glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotypes 10A/22F glycoconjugate of the invention is about 2, about 3, about 4, about 5, about 6, about 7, about 8, about 9, about 10, about 11, about 12, about 13, about 14 or about 15. In a preferred embodiment, the degree of conjugation of the serotypes 10A/22F glycoconjugate of the invention is between 4 and 7. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/22F glycoconjugate of the invention may also be characterized by the ratio (weight/weight) of saccharide to carrier protein. In some embodiments, the ratio of serotypes 10A and 22F saccharides to carrier protein in the glycoconjugate (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of serotypes 10A and 22F saccharides to carrier protein in the conjugate is between 0.9 and 1.1. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/22F glycoconjugate of the invention may also be characterized by the ratio (weight/weight) of serotype 10A saccharide to serotype 22F saccharide in the glycoconjugate. In some embodiments, the ratio of serotype 10A saccharide to serotype 22F saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 10A saccharide to serotype 22F saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 10A saccharide to serotype 22F saccharide ratio (w/w) is between 0.8 and 1.2. In a preferred embodiment, the ratio of serotype 10A saccharide to serotype 22F saccharide in the conjugate is between 0.9 and 1.1, even more preferably the ratio of serotype 10A saccharide to serotype 22F saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

In an embodiment, the serotypes 10A/22F glycoconjugate of the invention comprises at least 0.1, 0.2, 0.3, 0.4, 0.5, 0.6 or 0.7 or about 0.8 mM acetate per mM serotype 22F polysaccharide. In a preferred embodiment, the serotypes 10A/22F glycoconjugate comprises at least 0.5, 0.6 or 0.7 mM acetate per mM serotype 22F polysaccharide. In a preferred embodiment, the serotypes 10A/22F glycoconjugate comprises at least 0.6 mM acetate per mM serotype 22F polysaccharide. In a preferred embodiment, the serotypes 10A/22F glycoconjugate comprises at least 0.7 mM acetate per mM serotype 22F polysaccharide.

The serotypes 10A/22F glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d$=0), and the fraction representing the maximum retention ($V_i$), ($K_d$=1). The fraction at which a specified sample attribute is reached ($V_e$), is related to $K_d$ by the expression, $K_d=(V_e-V_0)/(V_i-V_0)$.

In a preferred embodiment, at least 30% of the serotypes 10A/22F glycoconjugate has a $K_d$ below or equal to 0.3 in a CL-4B column. In a preferred embodiment, at least 40% of the serotypes 10A/22F glycoconjugate has a $K_d$ below or equal to 0.3 in a CL-4B column. In a preferred embodiment, at least 45%, 50%, 55%, 60%, 65%, 70%, 75%, 80%, or 85% of the serotypes 10A/22F glycoconjugate has a $K_d$ below or equal to 0.3 in a CL-4B column. In a preferred embodiment, at least 60% of the serotypes 10A/22F glycoconjugate has a $K_d$ below or equal to 0.3 in a CL-4B column. In a preferred embodiment, between 50% and 80% of the serotypes 10A/22F glycoconjugate has a $K_d$ below or equal to 0.3 in a CL-4B column. In a preferred embodiment, between 65% and 80% of the serotypes 10A/22F glycoconjugate has a $K_d$ below or equal to 0.3 in a CL-4B column.

The serotypes 10A/22F glycoconjugate of the invention may contain free saccharide that is not covalently conjugated to the carrier protein, but is nevertheless present in the serotypes 10A/22F glycoconjugate composition. The free saccharide may be noncovalently associated with (i.e., noncovalently bound to, adsorbed to, or entrapped in or with) the serotypes 10A/22F glycoconjugate.

In a preferred embodiment, the serotypes 10A/22F glycoconjugate comprises less than about 50%, 45%, 40%, 35%, 30%, 25%, 20% or 15% of free serotypes 10A and 22F saccharide compared to the total amount of serotypes 10A and 22F saccharide. In a preferred embodiment the serotypes 10A/22F glycoconjugate comprises less than about 40% of free serotypes 10A and 22F saccharide compared to the total amount of serotypes 10A and 22F saccharide. In a preferred embodiment the serotypes 10A/22F glycoconjugate comprises less than about 25% of free serotypes 10A and 22F saccharide compared to the total amount of serotypes 10A and 22F saccharide. In a preferred embodiment the serotypes 10A/22F glycoconjugate comprises less than about 20% of free serotypes 10A and 22F saccharide compared to the total amount of serotypes 10A and 22F saccharide. In a preferred embodiment the serotypes 10A/22F glycoconjugate comprises less than about 15% of free serotypes 10A and 22F saccharide compared to the total amount of serotypes 10A and 22F saccharide.

In preferred embodiments, the serotype 10A/22F glycoconjugates of the invention are prepared using reductive amination.

Reductive amination involves two steps, (1) oxidation (activation) of the saccharide, (2) reduction of the activated saccharide and a carrier protein (e.g., $CRM_{197}$, DT, TT or PD) to form a conjugate. Before oxidation, sizing of the serotype 10A and/or 22F saccharide to a target molecular weight (MW) range can be performed. Mechanical or chemical hydrolysis may be employed. Chemical hydrolysis may be conducted using acetic acid. Advantageously, the size of the purified serotype 10A and/or 22F saccharide is reduced while preserving critical features of the structure of the saccharide such as for example the presence of O-acetyl groups. Therefore preferably, the size of the purified serotype 10A and/or 22F saccharide is reduced by mechanical homogenization.

In an embodiment, serotypes 10A and 22F saccharides are activated (oxidized) by a process comprising the step of:

(a) reacting a mixture of isolated serotypes 10A and 22F saccharides with an oxidizing agent. Said process can further comprise a quenching step.

Therefore, in an embodiment, serotypes 10A and 22F saccharides are activated (oxidized) by a process comprising the step of:

(a) reacting a mixture of isolated serotypes 10A and 22F saccharides with an oxidizing agent;

(b) quenching the oxidation reaction by addition of a quenching agent resulting in activated serotypes 10A and 22F saccharides.

In these embodiments, the saccharides are therefore activated altogether as a mixture.

In another embodiment, serotypes 10A and 22F saccharides are activated (oxidized) separately and the activated saccharides are then mixed.

In said embodiment, serotypes 10A and 22F saccharides are activated (oxidized) by a process comprising the step of:

(a) individually reacting an isolated serotypes 10A and 22F saccharides with an oxidizing agent;

(b) mixing the activated serotypes 10A and 22F saccharides.

Said process can further comprise a quenching step.

Therefore in an embodiment, serotypes 10A and 22F saccharides are activated (oxidized) by a process comprising the step of:

(a) individually reacting an isolated serotypes 10A and 22F saccharides with an oxidizing agent;

(b) quenching the oxidation reactions by addition of a quenching agent resulting in activated serotypes 10A and 22F saccharides;

(b) mixing the activated serotypes 10A and 22F saccharides.

The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate).

In a preferred embodiment, the oxidizing agent is sodium periodate. In a preferred embodiment, the periodate used for the oxidation of serotypes 10A and 22F saccharides is metaperiodate. In a preferred embodiment the periodate used for the oxidation of serotypes 10A and 22F saccharides is sodium metaperiodate.

In one embodiment, the quenching agent is selected from vicinal diols, 1,2-aminoalcohols, amino acids, glutathione, sulfite, bisulfate, dithionite, metabisulfite, thiosulfate, phosphites, hypophosphites or phosphorous acid.

In one embodiment, the quenching agent is a 1,2-aminoalcohols of formula (I):

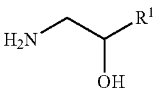

(I)

wherein $R^1$ is selected from H, methyl, ethyl, propyl or isopropyl.

In one embodiment, the quenching agent is selected from sodium and potassium salts of sulfite, bisulfate, dithionite, metabisulfite, thiosulfate, phosphites, hypophosphites or phosphorous acid. In one embodiment, the quenching agent is an amino acid. In such embodiments, said amino acid may be selected from serine, threonine, cysteine, cystine, methionine, proline, hydroxyproline, tryptophan, tyrosine, and histidine.

In one embodiment, the quenching agent is a sulfite such as bisulfate, dithionite, metabisulfite, thiosulfate.

In one embodiment, the quenching agent is a compound comprising two vicinal hydroxyl groups (vicinal diols), i.e., two hydroxyl groups covalently linked to two adjacent carbon atoms.

Preferably, the quenching agent is a compound of formula (II):

(II)

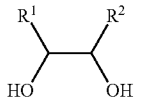

wherein $R^1$ and $R^2$ are each independently selected from H, methyl, ethyl, propyl or isopropyl.

In a preferred embodiment, the quenching agent is glycerol, ethylene glycol, propan-1,2-diol, butan-1,2-diol or butan-2,3-diol, or ascorbic acid. In a preferred embodiment, the quenching agent is butan-2,3-diol.

In a preferred embodiment, the isolated serotypes 10A and 22F saccharides are activated by a process comprising the step of:

(a) reacting a mixture of isolated serotypes 10A and 22F saccharides with periodate;

(b) quenching the oxidation reaction by addition of butan-2,3-diol resulting in a mixture of activated serotypes 10A and 22F saccharides.

Following the oxidation step of the saccharides, the saccharides are said to be activated and is referred to as "activated saccharides" here below.

In a preferred embodiment, the activated serotypes 10A and 22F saccharides are purified. The activated serotypes 10A and 22F saccharides are purified according to methods known to the man skilled in the art such as gel permeation chromatography (GPC), dialysis or ultrafiltration/diafiltration. For example, the activated serotypes 10A and 22F saccharides are purified by concentration and diafiltration using an ultrafiltration device.

In a preferred embodiment the degree of oxidation of the activated serotypes 10A and 22F saccharides are between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25. In a preferred embodiment the degree of oxidation of the activated serotype 10A and 22F polysaccharide is between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20.

In a preferred embodiment, the activated serotypes 10A and 22F saccharides have a molecular weight of between 10 kDa and 5,000 kDa; between 20 kDa and 4,000 kDa; between 50 kDa and 3,000 kDa; between 100 kDa and 2500 kDa; 100 kDa and 2,000 kDa; between 150 kDa and 2,000 kDa; between 150 kDa and 1,500 kDa; between 10 kDa and 2,000 kDa; between 20 kDa and 1,500 kDa; between 30 kDa and 1,250 kDa; between 50 kDa and 1,000 kDa; between 70 kDa and 900 kDa; between 100 kDa and 800 kDa; between 200 kDa to 600 kDa or between 400 kDa to 700 kDa.

In an embodiment, the activated serotypes 10A and 22F saccharides have a molecular weight between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In an embodiment, the activated serotypes 10A and 22F saccharides have a molecular weight between 25 kDa and 3,000 kDa, between 50 kDa and 2,000 kDa, between 100 kDa and 1,500 kDa, between 100 kDa and 1,000 kDa, between 300 kDa and 800 kDa, between 300 kDa and 700 kDa, between 300 kDa and 600 kDa, between 400 kDa and 1,000 kDa, between 400 kDa and 800 kDa, between 400 kDa and 700 kDa or between 400 kDa and 600 kDa. In an embodiment, the activated serotypes 10A and 22F saccharides have a molecular weight between 100 kDa and 3,000 kDa, between 200 kDa and 2,000 kDa, between 250 kDa and 1,500 kDa, between 250 kDa and 1,000 kDa, between 250 kDa and 800 kDa, between 250 kDa and 700 kDa, between 250 kDa and 600 kDa, between 300 kDa and 1,000 kDa, between 300 kDa and 800 kDa, between 300 kDa and 700 kDa or between 300 kDa and 600 kDa.

In an embodiment, the activated serotypes 10A and 22F saccharides have a molecular weight between 300 kDa and 800 kDa. In an embodiment, the activated serotypes 10A and 22F saccharides have a molecular weight between 400 kDa and 600 kDa.

In a preferred embodiment, the activated serotypes 10A and 22F saccharides have a molecular weight between 400 kda and 600 kDa and a degree of oxidation between 10 and 25, between 10 and 20, between 12 and 20 or between 14 and 18. In a preferred embodiment, the activated serotypes 10A and 22F saccharides have a molecular weight between 400 kDa and 600 kDa and a degree of oxidation between 10 and 20.

The activated polysaccharides and/or the carrier protein may be lyophilised (freeze-dried), either independently (discrete lyophilization) or together (co-lyophilized).

In an embodiment, the activated serotypes 10A and 22F saccharides are lyophilized, optionally in the presence of saccharide such as sucrose, trehalose, raffinose, stachyose, melezitose, dextran, mannitol, lactitol or palatinit. In a preferred embodiment, the saccharide is sucrose. In one embodiment, the lyophilized activated serotypes 10A and 22F saccharides are then compounded with a solution comprising the carrier protein.

In another embodiment the activated serotypes 10A and 22F saccharides and the carrier protein are co-lyophilised. In such embodiments, the activated serotypes 10A and 22F saccharides are compounded with the carrier protein and lyophilized, optionally in the presence of a saccharide such as sucrose, trehalose, raffinose, stachyose, melezitose, dextran, mannitol, lactitol and palatinit. In a preferred embodiment, the saccharide is sucrose. The co-lyophilized activated serotypes 10A and 22F saccharides and carrier protein can then be resuspended in solution and reacted with a reducing agent.

The second step of the conjugation process is the reduction of the activated saccharides and a carrier protein to form a conjugate (reductive amination), using a reducing agent.

The activated serotypes 10A and 22F saccharides can be conjugated to a carrier protein by a process comprising the step of:

(c) compounding the activated serotypes 10A and 22F saccharides with a carrier protein; and
(d) reacting the compounded activated serotypes 10A and 22F saccharides and carrier protein with a reducing agent to form a serotypes 10A/22F glycoconjugate.

In an embodiment, the reduction reaction is carried out in aqueous solvent. Preferably though, the reaction is carried out in aprotic solvent. In a preferred embodiment, the reduction reaction is carried out in DMSO (dimethylsulfoxide) or in DMF (dimethylformamide)) solvent. The DMSO or DMF solvent may be used to reconstitute the activated serotypes 10A and 22F saccharides and carrier protein which have been lyophilised.

The conjugation of activated serotypes 10A and 22F saccharides with a protein carrier by reductive amination in dimethylsulfoxide (DMSO) is suitable to preserve the O-acetyl content of the saccharides as compared, for example, to reductive amination in aqueous phase where the level of O-acetylation of the saccharides may be significantly reduced. Therefore in a preferred embodiment, step (c) and step (d) are carried out in DMSO.

In an embodiment, the reducing agent is sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^i$PrN—$BH_3$, benzylamine-$BH_3$ or 5-ethyl-2-methylpyridine borane (PEMB). In a preferred embodiment, the reducing agent is sodium cyanoborohydride.

At the end of the reduction reaction, there may be unreacted aldehyde groups remaining in the conjugates, these may be capped using a suitable capping agent. In one embodiment this capping agent is sodium borohydride ($NaBH_4$).

Following conjugation of serotypes 10A and 22F saccharides to the carrier protein, the glycoconjugate can be purified (enriched with respect to the amount of saccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration.

1.3.3.7 Glycoconjugates Comprising a Saccharide from *S. pneumoniae* Serotype 10A and a Saccharide from *S. pneumoniae* Serotype 33F Conjugated to a Carrier Protein In an embodiment the glycoconjugates of the invention comprises a saccharide from *S. pneumoniae* serotype 10A and a saccharide from *S. pneumoniae* serotype 33F conjugated to the same carrier protein (herein after 'the serotypes 10A/33F glycoconjugate'). In said embodiment, the carrier molecules have the two different capsular saccharides conjugated to them. Preferably, the glycoconjugates of this section (1.3.3.7) are therefore 2-valent glycoconjugates (i.e. they have serotypes 10A and 33F conjugated to the carrier protein and have no other polysaccharide antigens covalently attached to the carrier protein).

In some embodiments, the serotypes 10A/33F glycoconjugate of the present invention comprise a serotype 10A saccharide having a molecular weight of between 10 kDa and 5,000 kDa. In other such embodiments, the serotype 10A saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharide has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 10A saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/33F glycoconjugate of the present invention comprise a serotype 33F saccharide having a molecular weight of between 10 kDa and 5,000 kDa. In other such embodiments, the serotype 33F saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharide has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa.

In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 33F saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/33F glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the serotypes 10A/33F glycoconjugate has a molecular weight of between 500 kDa and 10,000 kDa. In other embodiments, the serotypes 10A/33F glycoconjugate has a molecular weight of between 1,000 kDa and 8,000 kDa. In still other embodiments, the serotypes 10A/33F glycoconjugate has a molecular weight of between 2,000 kDa and 8,000 kDa or between 3,000 kDa and 7,000 kDa. In further embodiments, the serotypes 10A/33F glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa.

In further embodiments, the serotypes 10A/33F glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa.

In further embodiments, the serotypes 10A/33F glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate is measured by SEC-MALLS. Any whole number integer within any of the above ranges is contemplated as an embodiment of the disclosure.

Another way to characterize the serotypes 10A/33F glycoconjugate of the invention is by the number of lysine residues in the carrier protein (e.g., $CRM_{197}$) that become conjugated to the saccharides which can be characterized as a range of conjugated lysines (degree of conjugation).

The evidence for lysine modification of the carrier protein, due to covalent linkages to the saccharides, can be obtained by amino acid analysis using routine methods known to those of skill in the art. Conjugation results in a reduction in the number of lysine residues recovered compared to the carrier protein starting material (e.g. $CRM_{197}$) used to generate the conjugate materials. In a preferred embodiment, the degree of conjugation of the serotypes 10A/33F glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotypes 10A/33F glycoconjugate of the invention is about 2, about 3, about 4, about 5, about 6, about 7, about 8, about 9, about 10, about 11, about 12, about 13, about 14 or about 15. In a preferred embodiment, the degree of conjugation of the serotypes 10A/33F glycoconjugate of the invention is between 4 and 7. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/33F glycoconjugate of the invention may also be characterized by the ratio (weight/weight) of saccharide to carrier protein. In some embodiments, the ratio of serotypes 10A and 33F saccharides to carrier protein in the glycoconjugate (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of serotypes 10A and 33F saccharides to carrier protein in the conjugate is between 0.9 and 1.1. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/33F glycoconjugate of the invention may also be characterized by the ratio (weight/weight) of serotype 10A saccharide to serotype 33F saccharide in the glycoconjugate. In some embodiments, the ratio of serotype 10A saccharide to serotype 33F saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 10A saccharide to serotype 33F saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 10A saccharide to serotype 33F saccharide ratio (w/w) is between 0.8 and 1.2. In a preferred embodiment, the ratio of serotype 10A saccharide to serotype 33F saccharide in the conjugate is between 0.9 and 1.1, even more preferably the ratio of serotype 10A saccharide to serotype 33F saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

In an embodiment, the serotypes 10A/33F glycoconjugate of the invention comprises at least 0.1, 0.2, 0.3, 0.4, 0.5, 0.6 or 0.7 or about 0.8 mM acetate per mM serotype 33F polysaccharide. In a preferred embodiment, the serotypes 10A/33F glycoconjugate comprises at least 0.5, 0.6 or 0.7 mM acetate per mM serotype 33F polysaccharide. In a preferred embodiment, the serotypes 10A/33F glycoconjugate comprises at least 0.6 mM acetate per mM serotype 33F polysaccharide. In a preferred embodiment, the serotypes 10A/33F glycoconjugate comprises at least 0.7 mM acetate per mM serotype 33F polysaccharide.

The serotypes 10A/33F glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d$=0), and the fraction representing the maximum retention ($V_i$), ($K_d$=1). The fraction at which a specified sample attribute is reached ($V_e$), is related to $K_d$ by the expression, $K_d=(V_e-V_0)/(V_i-V_0)$.

In a preferred embodiment, at least 30% of the serotypes 10A/33F glycoconjugate has a $K_d$ below or equal to 0.3 in a CL-4B column. In a preferred embodiment, at least 40% of the serotypes 10A/33F glycoconjugate has a $K_d$ below or equal to 0.3 in a CL-4B column. In a preferred embodiment, at least 45%, 50%, 55%, 60%, 65%, 70%, 75%, 80%, or 85% of the serotypes 10A/33F glycoconjugate has a $K_d$ below or equal to 0.3 in a CL-4B column. In a preferred embodiment, at least 60% of the serotypes 10A/33F glycoconjugate has a $K_d$ below or equal to 0.3 in a CL-4B column. In a preferred embodiment, between 50% and 80% of the serotypes 10A/33F glycoconjugate has a $K_d$ below or equal to 0.3 in a CL-4B column. In a preferred embodiment, between 65% and 80% of the serotypes 10A/33F glycoconjugate has a $K_d$ below or equal to 0.3 in a CL-4B column.

The serotypes 10A/33F glycoconjugate of the invention may contain free saccharide that is not covalently conjugated to the carrier protein, but is nevertheless present in the serotypes 10A/33F glycoconjugate composition. The free saccharide may be noncovalently associated with (i.e., noncovalently bound to, adsorbed to, or entrapped in or with) the serotypes 10A/33F glycoconjugate.

In a preferred embodiment, the serotypes 10A/33F glycoconjugate comprises less than about 50%, 45%, 40%, 35%, 30%, 25%, 20% or 15% of free serotypes 10A and 33F saccharide compared to the total amount of serotypes 10A and 33F saccharide. In a preferred embodiment the serotypes 10A/33F glycoconjugate comprises less than about 40% of free serotypes 10A and 33F saccharide compared to the total amount of serotypes 10A and 33F saccharide. In a preferred embodiment the serotypes 10A/33F glycoconjugate comprises less than about 25% of free serotypes 10A and 33F saccharide compared to the total amount of serotypes 10A and 33F saccharide. In a preferred embodiment the serotypes 10A/33F glycoconjugate comprises less than about 20% of free serotypes 10A and 33F saccharide compared to the total amount of serotypes 10A and 33F saccharide. In a preferred embodiment the serotypes 10A/33F glycoconjugate comprises less than about 15% of free serotypes 10A and 33F saccharide compared to the total amount of serotypes 10A and 33F saccharide.

In preferred embodiments, the serotype 10A/33F glycoconjugates of the invention are prepared using reductive amination.

Reductive amination involves two steps, (1) oxidation (activation) of the saccharide, (2) reduction of the activated saccharide and a carrier protein (e.g., $CRM_{197}$, DT, TT or PD) to form a conjugate. Before oxidation, sizing of the serotype 10A and/or 33F saccharide to a target molecular weight (MW) range can be performed. Mechanical or chemical hydrolysis may be employed. Chemical hydrolysis may be conducted using acetic acid. Advantageously, the size of the purified serotype 10A and/or 33F saccharide is reduced while preserving critical features of the structure of the saccharide such as for example the presence of O-acetyl groups. Therefore preferably, the size of the purified serotype 10A and/or 33F saccharide is reduced by mechanical homogenization. In an embodiment, serotypes 10A and 33F saccharides are activated (oxidized) by a process comprising the step of:

(a) reacting a mixture of isolated serotypes 10A and 33F saccharides with an oxidizing agent. Said process can further comprise a quenching step.

Therefore, in an embodiment, serotypes 10A and 33F saccharides are activated (oxidized) by a process comprising the step of:

(a) reacting a mixture of isolated serotypes 10A and 33F saccharides with an oxidizing agent;
(b) quenching the oxidation reaction by addition of a quenching agent resulting in activated serotypes 10A and 33F saccharides.

In these embodiments, the saccharides are therefore activated altogether as a mixture.

In another embodiment, serotypes 10A and 33F saccharides are activated (oxidized) separately and the activated saccharides are then mixed.

In said embodiment, serotypes 10A and 33F saccharides are activated (oxidized) by a process comprising the step of:

(a) individually reacting an isolated serotypes 10A and 33F saccharides with an oxidizing agent;
(b) mixing the activated serotypes 10A and 33F saccharides.

Said process can further comprise a quenching step.

Therefore, in an embodiment, serotypes 10A and 33F saccharides are activated (oxidized) by a process comprising the step of:

(a) individually reacting an isolated serotypes 10A and 33F saccharides with an oxidizing agent;
(b) quenching the oxidation reactions by addition of a quenching agent resulting in activated serotypes 10A and 33F saccharides;
(b) mixing the activated serotypes 10A and 33F saccharides.

The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate).

In a preferred embodiment, the oxidizing agent is sodium periodate. In a preferred embodiment, the periodate used for the oxidation of serotypes 10A and 33F saccharides is metaperiodate. In a preferred embodiment the periodate used for the oxidation of serotypes 10A and 33F saccharides is sodium metaperiodate.

In one embodiment, the quenching agent is selected from vicinal diols, 1,2-aminoalcohols, amino acids, glutathione, sulfite, bisulfate, dithionite, metabisulfite, thiosulfate, phosphites, hypophosphites or phosphorous acid.

In one embodiment, the quenching agent is a 1,2-aminoalcohols of formula (I):

(I)

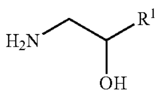

wherein $R^1$ is selected from H, methyl, ethyl, propyl or isopropyl.

In one embodiment, the quenching agent is selected from sodium and potassium salts of sulfite, bisulfate, dithionite, metabisulfite, thiosulfate, phosphites, hypophosphites or phosphorous acid.

In one embodiment, the quenching agent is a sulfite such as bisulfate, dithionite, metabisulfite, thiosulfate.

In one embodiment, the quenching agent is a compound comprising two vicinal hydroxyl groups (vicinal diols), i.e., two hydroxyl groups covalently linked to two adjacent carbon atoms.

Preferably, the quenching agent is a compound of formula (II):

(II)

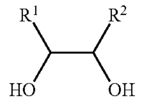

wherein $R^1$ and $R^2$ are each independently selected from H, methyl, ethyl, propyl or isopropyl.

In a preferred embodiment, the quenching agent is glycerol, ethylene glycol, propan-1,2-diol, butan-1,2-diol or butan-2,3-diol, or ascorbic acid. In a preferred embodiment, the quenching agent is butan-2,3-diol.

In a preferred embodiment, the isolated serotypes 10A and 33F saccharides are activated by a process comprising the step of:

(a) reacting a mixture of isolated serotypes 10A and 33F saccharides with periodate;
(b) quenching the oxidation reaction by addition of butan-2,3-diol resulting in a mixture of activated serotypes 10A and 33F saccharides.

Following the oxidation step of the saccharides, the saccharides are said to be activated and is referred to as "activated saccharides" here below.

In a preferred embodiment, the activated serotypes 10A and 33F saccharides are purified. The activated serotypes 10A and 33F saccharides are purified according to methods known to the man skilled in the art such as gel permeation chromatography (GPC), dialysis or ultrafiltration/diafiltration. For example, the activated serotypes 10A and 33F saccharides are purified by concentration and diafiltration using an ultrafiltration device.

In a preferred embodiment the degree of oxidation of the activated serotypes 10A and 33F saccharides are between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25. In a preferred embodiment the degree of oxidation of the activated serotype 10A and 33F polysaccharide is between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20.

In a preferred embodiment, the activated serotypes 10A and 33F saccharides have a molecular weight of between 10 kDa and 5,000 kDa; between 20 kDa and 4,000 kDa; between 50 kDa and 3,000 kDa; between 100 kDa and 2500 kDa; 100 kDa and 2,000 kDa; between 150 kDa and 2,000 kDa; between 150 kDa and 1,500 kDa; between 10 kDa and 2,000 kDa; between 20 kDa and 1,500 kDa; between 30 kDa and 1,250 kDa; between 50 kDa and 1,000 kDa; between 70 kDa and 900 kDa; between 100 kDa and 800 kDa; between 200 kDa to 600 kDa or between 400 kDa to 700 kDa.

In an embodiment, the activated serotypes 10A and 33F saccharides have a molecular weight between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In an embodiment, the activated serotypes 10A and 33F saccharides have a molecular weight between 25 kDa and 3,000 kDa, between 50 kDa and 2,000 kDa, between 100 kDa and 1,500 kDa, between 100 kDa and 1,000 kDa, between 300 kDa and 800 kDa, between 300 kDa and 700 kDa, between 300 kDa and 600 kDa, between 400 kDa and 1,000 kDa, between 400 kDa and 800 kDa, between 400 kDa and 700 kDa or between 400 kDa and 600 kDa. In an embodiment, the activated serotypes 10A and 33F saccharides have a molecular weight between 100 kDa and 3,000 kDa, between 200 kDa and 2,000 kDa, between 250 kDa and 1,500 kDa, between 250 kDa and 1,000 kDa, between 250 kDa and 800 kDa, between 250 kDa and 700 kDa, between 250 kDa and 600 kDa, between 300 kDa and 1,000 kDa, between 300 kDa and 800 kDa, between 300 kDa and 700 kDa or between 300 kDa and 600 kDa.

In an embodiment, the activated serotypes 10A and 33F saccharides have a molecular weight between 300 kDa and 800 kDa. In an embodiment, the activated serotypes 10A and 33F saccharides have a molecular weight between 400 kDa and 600 kDa.

In a preferred embodiment, the activated serotypes 10A and 33F saccharides have a molecular weight between 400 kda and 600 kDa and a degree of oxidation between 10 and 25, between 10 and 20, between 12 and 20 or between 14 and 18. In a preferred embodiment, the activated serotypes 10A and 33F saccharides have a molecular weight between 400 kDa and 600 kDa and a degree of oxidation between 10 and 20.

The activated polysaccharides and/or the carrier protein may be lyophilised (freeze-dried), either independently (discrete lyophilization) or together (co-lyophilized).

In an embodiment, the activated serotypes 10A and 33F saccharides are lyophilized, optionally in the presence of saccharide such as sucrose, trehalose, raffinose, stachyose, melezitose, dextran, mannitol, lactitol or palatinit. In a preferred embodiment, the saccharide is sucrose. In one embodiment, the lyophilized activated serotypes 10A and 33F saccharides are then compounded with a solution comprising the carrier protein.

In another embodiment the activated serotypes 10A and 33F saccharides and the carrier protein are co-lyophilised. In such embodiments, the activated serotypes 10A and 33F saccharides are compounded with the carrier protein and lyophilized, optionally in the presence of a saccharide such as sucrose, trehalose, raffinose, stachyose, melezitose, dextran, mannitol, lactitol and palatinit. In a preferred embodiment, the saccharide is sucrose. The co-lyophilized activated serotypes 10A and 33F saccharides and carrier protein can then be resuspended in solution and reacted with a reducing agent.

The second step of the conjugation process is the reduction of the activated saccharides and a carrier protein to form a conjugate (reductive amination), using a reducing agent.

The activated serotypes 10A and 33F saccharides can be conjugated to a carrier protein by a process comprising the step of:

(c) compounding the activated serotypes 10A and 33F saccharides with a carrier protein; and (d) reacting the compounded activated serotypes 10A and 33F saccharides and carrier protein with a reducing agent to form a serotypes 10A/33F glycoconjugate.

In an embodiment, the reduction reaction is carried out in aqueous solvent. Preferably though, the reaction is carried out in aprotic solvent. In a preferred embodiment, the reduction reaction is carried out in DMSO (dimethylsulfoxide) or in DMF (dimethylformamide)) solvent. The DMSO or DMF solvent may be used to reconstitute the activated serotypes 10A and 33F saccharides and carrier protein which have been lyophilised.

The conjugation of activated serotypes 10A and 33F saccharides with a protein carrier by reductive amination in dimethylsulfoxide (DMSO) is suitable to preserve the O-acetyl content of the saccharides as compared, for example, to reductive amination in aqueous phase where the level of O-acetylation of the saccharides may be significantly reduced. Therefore in a preferred embodiment, step (c) and step (d) are carried out in DMSO.

In an embodiment, the reducing agent is sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^i$PrN—$BH_3$, benzylamine-$BH_3$ or 5-ethyl-2-methylpyridine borane (PEMB). In a preferred embodiment, the reducing agent is sodium cyanoborohydride.

At the end of the reduction reaction, there may be unreacted aldehyde groups remaining in the conjugates, these may be capped using a suitable capping agent. In one embodiment this capping agent is sodium borohydride ($NaBH_4$).

Following conjugation of serotypes 10A and 33F saccharides to the carrier protein, the glycoconjugate can be purified (enriched with respect to the amount of saccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration.

1.3.3.8 Glycoconjugates Comprising a Saccharide from *S. pneumoniae* Serotype 10A and a Saccharide from *S. pneumoniae* Serotype 35B Conjugated to a Carrier Protein In an embodiment the glycoconjugates of the invention comprises a saccharide from *S. pneumoniae* serotype 10A and a saccharide from *S. pneumoniae* serotype 35B conjugated to the same carrier protein (herein after 'the serotypes 10A/35B glycoconjugate'). In said embodiment, the carrier molecules have the two different capsular saccharides conjugated to them. Preferably, the glycoconjugates of this section (1.3.3.8) are therefore 2-valent glycoconjugates (i.e. they have serotypes 10A and 35B conjugated to the carrier protein and have no other polysaccharide antigens covalently attached to the carrier protein).

In some embodiments, the serotypes 10A/35B glycoconjugate of the present invention comprise a serotype 10A saccharide having a molecular weight of between 10 kDa and 5,000 kDa. In other such embodiments, the serotype 10A saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 10A saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/35B glycoconjugate of the present invention comprise a serotype 35B saccharide having a molecular weight of between 10 kDa and 5,000 kDa. In other such embodiments, the serotype 35B saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa.

In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 35B saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 10A/35B glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the serotypes 10A/22F glycoconjugate has a molecular weight of between 500 kDa and 10,000 kDa. In other embodiments, the serotypes 10A/22F glycoconjugate has a molecular weight of between 1,000 kDa and 8,000 kDa. In still other embodiments, the serotypes 10A/22F glycoconjugate has a molecular weight of between 2,000 kDa and 8,000 kDa or between 3,000 kDa and 7,000 kDa. In further embodiments, the serotypes 10A/35B glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa.

In further embodiments, the serotypes 10A/35B glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa.

In further embodiments, the serotypes 10A/35B glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate is measured by SEC-MALLS. Any whole number integer within any of the above ranges is contemplated as an embodiment of the disclosure.

Another way to characterize the serotypes 10A/35B glycoconjugate of the invention is by the number of lysine residues in the carrier protein (e.g., $CRM_{197}$) that become conjugated to the saccharides which can be characterized as a range of conjugated lysines (degree of conjugation).

The evidence for lysine modification of the carrier protein, due to covalent linkages to the saccharides, can be obtained by amino acid analysis using routine methods known to those of skill in the art. Conjugation results in a reduction in the number of lysine residues recovered compared to the carrier protein starting material (e.g. $CRM_{197}$) used to generate the conjugate materials. In a preferred embodiment, the degree of conjugation of the serotypes 10A/35B glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotypes 10A/35B glycoconjugate of the invention is about 2, about 3, about 4, about 5, about 6, about 7, about 8, about 9, about 10, about 11, about 12, about 13, about 14 or about 15. In a preferred embodiment, the degree of conjugation of the serotypes 10A/35B glycoconjugate of the invention is between 4 and 7. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/35B glycoconjugate of the invention may also be characterized by the ratio (weight/weight) of saccharide to carrier protein. In some embodiments, the ratio of serotypes 10A and 35B saccharides to carrier protein in the glycoconjugate (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of serotypes 10A and 35B saccharides to carrier protein in the conjugate is between 0.9 and 1.1. In some such embodiments, the carrier protein is $CRM_{197}$. In other such embodiments, the carrier protein is DT. In other such embodiments, the carrier protein is TT. In other such embodiments, the carrier protein is PD.

The serotypes 10A/35B glycoconjugate of the invention may also be characterized by the ratio (weight/weight) of serotype 10A saccharide to serotype 35B saccharide in the glycoconjugate. In some embodiments, the ratio of serotype 10A saccharide to serotype 35B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 10A saccharide to serotype 35B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 10A saccharide to serotype 35B saccharide ratio (w/w) is between 0.8 and 1.2. In a preferred embodiment, the ratio of serotype 10A saccharide to serotype 35B saccharide in the conjugate is between 0.9 and 1.1, even more preferably the ratio of serotype 10A saccharide to serotype 35B saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

In an embodiment, the serotypes 10A/35B glycoconjugate of the invention comprises at least 0.1, 0.2, 0.3, 0.4, 0.5, 0.6 or 0.7 or about 0.8 mM acetate per mM serotype 35B polysaccharide. In a preferred embodiment, the serotypes 10A/35B glycoconjugate comprises at least 0.5, 0.6 or 0.7 mM acetate per mM serotype 35B polysaccharide. In a preferred embodiment, the serotypes 10A/35B glycoconjugate comprises at least 0.6 mM acetate per mM serotype 35B polysaccharide. In a preferred embodiment, the serotypes 10A/35B glycoconjugate comprises at least 0.7 mM acetate per mM serotype 35B polysaccharide.

The serotypes 10A/35B glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d$=0), and the fraction representing the maximum retention ($V_i$), ($K_d$=1). The fraction at which a specified sample attribute is reached ($V_e$), is related to $K_d$ by the expression, $K_d=(V_e-V_0)/(V_i-V_0)$.

In a preferred embodiment, at least 30% of the serotypes 10A/35B glycoconjugate has a $K_d$ below or equal to 0.3 in a CL-4B column. In a preferred embodiment, at least 40% of the serotypes 10A/35B glycoconjugate has a $K_d$ below or equal to 0.3 in a CL-4B column. In a preferred embodiment, at least 45%, 50%, 55%, 60%, 65%, 70%, 75%, 80%, or 85% of the serotypes 10A/35B glycoconjugate has a $K_d$ below or equal to 0.3 in a CL-4B column. In a preferred embodiment, at least 60% of the serotypes 10A/35B glycoconjugate has a $K_d$ below or equal to 0.3 in a CL-4B column. In a preferred embodiment, between 50% and 80% of the serotypes 10A/35B glycoconjugate has a $K_d$ below or equal to 0.3 in a CL-4B column. In a preferred embodiment, between 65% and 80% of the serotypes 10A/35B glycoconjugate has a $K_d$ below or equal to 0.3 in a CL-4B column.

The serotypes 10A/35B glycoconjugate of the invention may contain free saccharide that is not covalently conjugated to the carrier protein, but is nevertheless present in the serotypes 10A/35B glycoconjugate composition. The free saccharide may be noncovalently associated with (i.e., non-covalently bound to, adsorbed to, or entrapped in or with) the serotypes 10A/35B glycoconjugate.

In a preferred embodiment, the serotypes 10A/35B glycoconjugate comprises less than about 50%, 45%, 40%, 35%, 30%, 25%, 20% or 15% of free serotypes 10A and 35B saccharide compared to the total amount of serotypes 10A and 35B saccharide. In a preferred embodiment the serotypes 10A/35B glycoconjugate comprises less than about 40% of free serotypes 10A and 35B saccharide compared to the total amount of serotypes 10A and 35B saccharide. In a preferred embodiment the serotypes 10A/35B glycoconjugate comprises less than about 25% of free serotypes 10A and 35B saccharide compared to the total amount of serotypes 10A and 35B saccharide. In a preferred embodiment the serotypes 10A/35B glycoconjugate comprises less than about 20% of free serotypes 10A and 35B saccharide compared to the total amount of serotypes 10A and 35B saccharide. In a preferred embodiment the serotypes 10A/35B glycoconjugate comprises less than about 15% of free serotypes 10A and 35B saccharide compared to the total amount of serotypes 10A and 35B saccharide.

In preferred embodiments, the serotype 10A/35B glycoconjugates of the invention are prepared using reductive amination.

Reductive amination involves two steps, (1) oxidation (activation) of the saccharide, (2) reduction of the activated saccharide and a carrier protein (e.g., $CRM_{197}$, DT, TT or PD) to form a conjugate. Before oxidation, sizing of the serotype 10A and/or 35B saccharide to a target molecular weight (MW) range can be performed. Mechanical or chemical hydrolysis may be employed. Chemical hydrolysis may be conducted using acetic acid. Advantageously, the size of the purified serotype 10A and/or 35B saccharide is reduced while preserving critical features of the structure of the saccharide such as for example the presence of O-acetyl groups. Therefore preferably, the size of the purified serotype 10A and/or 35B saccharide is reduced by mechanical homogenization. In an embodiment, serotypes 10A and 35B saccharides are activated (oxidized) by a process comprising the step of:

(a) reacting a mixture of isolated serotypes 10A and 35B saccharides with an oxidizing agent. Said process can further comprise a quenching step.

Therefore, in an embodiment, serotypes 10A and 35B saccharides are activated (oxidized) by a process comprising the step of:

(a) reacting a mixture of isolated serotypes 10A and 35B saccharides with an oxidizing agent;
(b) quenching the oxidation reaction by addition of a quenching agent resulting in activated serotypes 10A and 35B saccharides.

In these embodiments, the saccharides are therefore activated altogether as a mixture.

In another embodiment, serotypes 10A and 35B saccharides are activated (oxidized) separately and the activated saccharides are then mixed.

In said embodiment, serotypes 10A and 35B saccharides are activated (oxidized) by a process comprising the step of:

(a) individually reacting an isolated serotypes 10A and 35B saccharides with an oxidizing agent;
(b) mixing the activated serotypes 10A and 35B saccharides.

Said process can further comprise a quenching step.

Therefore in an embodiment, serotypes 10A and 35B saccharides are activated (oxidized) by a process comprising the step of:

(a) individually reacting an isolated serotypes 10A and 35B saccharides with an oxidizing agent;
(b) quenching the oxidation reactions by addition of a quenching agent resulting in activated serotypes 10A and 35B saccharides;
(b) mixing the activated serotypes 10A and 35B saccharides.

The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate).

In a preferred embodiment, the oxidizing agent is sodium periodate. In a preferred embodiment, the periodate used for the oxidation of serotypes 10A and 35B saccharides is metaperiodate. In a preferred embodiment the periodate used for the oxidation of serotypes 10A and 35B saccharides is sodium metaperiodate.

In one embodiment, the quenching agent is selected from vicinal diols, 1,2-aminoalcohols, amino acids, glutathione, sulfite, bisulfate, dithionite, metabisulfite, thiosulfate, phosphites, hypophosphites or phosphorous acid.

In one embodiment, the quenching agent is a 1,2-aminoalcohols of formula (I):

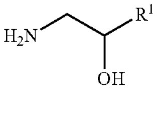

(I)

wherein $R^1$ is selected from H, methyl, ethyl, propyl or isopropyl.

In one embodiment, the quenching agent is selected from sodium and potassium salts of sulfite, bisulfate, dithionite, metabisulfite, thiosulfate, phosphites, hypophosphites or phosphorous acid.

In one embodiment, the quenching agent is an amino acid. In such embodiments, said amino acid may be selected from serine, threonine, cysteine, cystine, methionine, proline, hydroxyproline, tryptophan, tyrosine, and histidine.

In one embodiment, the quenching agent is a sulfite such as bisulfate, dithionite, metabisulfite, thiosulfate.

In one embodiment, the quenching agent is a compound comprising two vicinal hydroxyl groups (vicinal diols), i.e., two hydroxyl groups covalently linked to two adjacent carbon atoms.

Preferably, the quenching agent is a compound of formula (II):

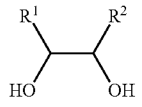

(II)

wherein $R^1$ and $R^2$ are each independently selected from H, methyl, ethyl, propyl or isopropyl. In a preferred embodiment, the quenching agent is glycerol, ethylene glycol, propan-1,2-diol, butan-1,2-diol or butan-2,3-diol, or ascorbic acid. In a preferred embodiment, the quenching agent is butan-2,3-diol.

In a preferred embodiment, the isolated serotypes 10A and 35B saccharides are activated by a process comprising the step of:

(a) reacting a mixture of isolated serotypes 10A and 35B saccharides with periodate;
(b) quenching the oxidation reaction by addition of butan-2,3-diol resulting in a mixture of activated serotypes 10A and 35B saccharides.

Following the oxidation step of the saccharides, the saccharides are said to be activated and is referred to as "activated saccharides" here below.

In a preferred embodiment, the activated serotypes 10A and 35B saccharides are purified. The activated serotypes 10A and 35B saccharides are purified according to methods known to the man skilled in the art such as gel permeation chromatography (GPC), dialysis or ultrafiltration/diafiltration. For example, the activated serotypes 10A and 35B saccharides are purified by concentration and diafiltration using an ultrafiltration device.

In a preferred embodiment the degree of oxidation of the activated serotypes 10A and 35B saccharides are between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25. In a preferred embodiment the degree of oxidation of the activated serotype 10A and 35B polysaccharide is between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20.

In a preferred embodiment, the activated serotypes 10A and 35B saccharides have a molecular weight of between 10 kDa and 5,000 kDa; between 20 kDa and 4,000 kDa; between 50 kDa and 3,000 kDa; between 100 kDa and 2500 kDa; 100 kDa and 2,000 kDa; between 150 kDa and 2,000 kDa; between 150 kDa and 1,500 kDa; between 10 kDa and 2,000 kDa; between 20 kDa and 1,500 kDa; between 30 kDa and 1,250 kDa; between 50 kDa and 1,000 kDa; between 70 kDa and 900 kDa; between 100 kDa and 800 kDa; between 200 kDa to 600 kDa or between 400 kDa to 700 kDa.

In an embodiment, the activated serotypes 10A and 35B saccharides have a molecular weight between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In an embodiment, the activated serotypes 10A and 35B saccharides have a molecular weight between 25 kDa and 3,000 kDa, between 50 kDa and 2,000 kDa, between 100 kDa and 1,500 kDa, between 100 kDa and 1,000 kDa, between 300 kDa and 800 kDa, between 300 kDa and 700 kDa, between 300 kDa and 600 kDa, between 400 kDa and 1,000 kDa, between 400 kDa and 800 kDa, between 400 kDa and 700 kDa or between 400 kDa and 600 kDa. In an embodiment, the activated serotypes 10A and 35B saccharides have a molecular weight between 100 kDa and 3,000 kDa, between 200 kDa and 2,000 kDa, between 250 kDa and 1,500 kDa, between 250 kDa and 1,000 kDa, between 250 kDa and 800 kDa, between 250 kDa and 700 kDa, between 250 kDa and 600 kDa, between 300 kDa and 1,000 kDa, between 300 kDa and 800 kDa, between 300 kDa and 700 kDa or between 300 kDa and 600 kDa.

In an embodiment, the activated serotypes 10A and 35B saccharides have a molecular weight between 300 kDa and 800 kDa. In an embodiment, the activated serotypes 10A and 35B saccharides have a molecular weight between 400 kDa and 600 kDa.

In a preferred embodiment, the activated serotypes 10A and 35B saccharides have a molecular weight between 400 kda and 600 kDa and a degree of oxidation between 10 and 25, between 10 and 20, between 12 and 20 or between 14 and 18. In a preferred embodiment, the activated serotypes 10A and 35B saccharides have a molecular weight between 400 kDa and 600 kDa and a degree of oxidation between 10 and 20.

The activated polysaccharides and/or the carrier protein may be lyophilised (freeze-dried), either independently (discrete lyophilization) or together (co-lyophilized).

In an embodiment, the activated serotypes 10A and 35B saccharides are lyophilized, optionally in the presence of saccharide such as sucrose, trehalose, raffinose, stachyose, melezitose, dextran, mannitol, lactitol or palatinit. In a preferred embodiment, the saccharide is sucrose. In one embodiment, the lyophilized activated serotypes 10A and 35B saccharides are then compounded with a solution comprising the carrier protein.

In another embodiment the activated serotypes 10A and 35B saccharides and the carrier protein are co-lyophilised. In such embodiments, the activated serotypes 10A and 35B saccharides are compounded with the carrier protein and lyophilized, optionally in the presence of a saccharide such as sucrose, trehalose, raffinose, stachyose, melezitose, dextran, mannitol, lactitol and palatinit. In a preferred embodiment, the saccharide is sucrose. The co-lyophilized activated serotypes 10A and 35B saccharides and carrier protein can then be resuspended in solution and reacted with a reducing agent.

The second step of the conjugation process is the reduction of the activated saccharides and a carrier protein to form a conjugate (reductive amination), using a reducing agent.

The activated serotypes 10A and 35B saccharides can be conjugated to a carrier protein by a process comprising the step of:

(c) compounding the activated serotypes 10A and 35B saccharides with a carrier protein; and (d) reacting the compounded activated serotypes 10A and 35B saccharides and carrier protein with a reducing agent to form a serotypes 10A/35B glycoconjugate.

In an embodiment, the reduction reaction is carried out in aqueous solvent. Preferably though, the reaction is carried out in aprotic solvent. In a preferred embodiment, the reduction reaction is carried out in DMSO (dimethylsulfoxide) or in DMF (dimethylformamide)) solvent. The DMSO or DMF solvent may be used to reconstitute the activated serotypes 10A and 35B saccharides and carrier protein which have been lyophilised.

The conjugation of activated serotypes 10A and 35B saccharides with a protein carrier by reductive amination in dimethylsulfoxide (DMSO) is suitable to preserve the O-acetyl content of the saccharides as compared, for example, to reductive amination in aqueous phase where the level of O-acetylation of the saccharides may be significantly reduced. Therefore in a preferred embodiment, step (c) and step (d) are carried out in DMSO.

In an embodiment, the reducing agent is sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^i$PrN—$BH_3$, benzylamine-$BH_3$ or 5-ethyl-2-methylpyridine borane (PEMB). In a preferred embodiment, the reducing agent is sodium cyanoborohydride.

At the end of the reduction reaction, there may be unreacted aldehyde groups remaining in the conjugates, these may be capped using a suitable capping agent. In one embodiment this capping agent is sodium borohydride ($NaBH_4$).

Following conjugation of serotypes 10A and 35B saccharides to the carrier protein, the glycoconjugate can be purified (enriched with respect to the amount of saccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration.

1.3.3.9 Glycoconjugates Comprising a Saccharide from *S. pneumoniae* Serotype 22F and a Saccharide from *S. pneumoniae* Serotype 33F Conjugated to a Carrier Protein In an embodiment the glycoconjugates of the invention comprises a saccharide from *S. pneumoniae* serotype 22F and a saccharide from *S. pneumoniae* serotype 33F conjugated to the same carrier protein (herein after 'the serotypes 22F/33F glycoconjugate'). In said embodiment, the carrier molecules have the two different capsular saccharides conjugated to them. Preferably, the glycoconjugates of this section (1.3.3.9) are therefore 2-valent glycoconjugates (i.e. they have serotypes 22F and 33F conjugated to the carrier protein and have no other polysaccharide antigens covalently attached to the carrier protein).

In some embodiments, the serotypes 22F/33F glycoconjugate of the present invention comprise a serotype 22F saccharide having a molecular weight of between 10 kDa and 5,000 kDa. In other such embodiments, the serotype 22F saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 22F saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 22F/33F glycoconjugate of the present invention comprise a serotype 33F saccharide having a molecular weight of between 10 kDa and 5,000 kDa. In other such embodiments, the serotype 33F saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharide has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 33F saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 22F/33F glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the serotypes 22F/33F glycoconjugate has a molecular weight of between 500 kDa and 10,000 kDa. In other embodiments, the serotypes 22F/33F glycoconjugate has a molecular weight of between 1,000 kDa and 8,000 kDa. In still other embodiments, the serotypes 22F/33F glycoconjugate has a molecular weight of between 2,000 kDa and 8,000 kDa or between 3,000 kDa and 7,000 kDa. In further embodiments, the serotypes 22F/33F glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa.

In further embodiments, the serotypes 22F/33F glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa.

In further embodiments, the serotypes 22F/33F glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate is measured by SEC-MALLS. Any whole number integer within any of the above ranges is contemplated as an embodiment of the disclosure.

Another way to characterize the serotypes 22F/33F glycoconjugate of the invention is by the number of lysine residues in the carrier protein (e.g., $CRM_{197}$) that become conjugated to the saccharides which can be characterized as a range of conjugated lysines (degree of conjugation). The evidence for lysine modification of the carrier protein, due to covalent linkages to the saccharides, can be obtained by amino acid analysis using routine methods known to those of skill in the art. Conjugation results in a reduction in the number of lysine residues recovered compared to the carrier protein starting material (e.g. $CRM_{197}$) used to generate the conjugate materials. In a preferred embodiment, the degree of conjugation of the serotypes 22F/33F glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotypes 22F/33F glycoconjugate of the invention is about 2, about 3, about 4, about 5, about 6, about 7, about 8, about 9, about 10, about 11, about 12, about 13, about 14 or about 15. In a preferred embodiment, the degree of conjugation of the serotypes 22F/33F glycoconjugate of the invention is between 4 and 7. In some such embodiments, the carrier protein is $CRM_{197}$. In other such embodiments, the carrier protein is DT. In other such embodiments, the carrier protein is TT. In other such embodiments, the carrier protein is PD.

The serotypes 22F/33F glycoconjugate of the invention may also be characterized by the ratio (weight/weight) of saccharide to carrier protein. In some embodiments, the ratio of serotypes 22F and 33F saccharides to carrier protein in the glycoconjugate (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of serotypes 22F and 33F saccharides to carrier protein in the conjugate is between 0.9 and 1.1. In some such embodiments, the carrier protein is $CRM_{197}$. In other such embodiments, the carrier protein is DT. In other such embodiments, the carrier protein is TT. In other such embodiments, the carrier protein is PD.

The serotypes 22F/33F glycoconjugate of the invention may also be characterized by the ratio (weight/weight) of serotype 22F saccharide to serotype 33F saccharide in the glycoconjugate. In some embodiments, the ratio of serotype 22F saccharide to serotype 33F saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 22F saccharide to serotype 33F saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 22F saccharide to serotype 33F saccharide ratio (w/w) is between 0.8 and 1.2. In a preferred embodiment, the ratio of serotype 22F saccharide to serotype 33F saccharide in the conjugate is between 0.9 and 1.1, even more preferably the ratio of serotype 22F saccharide to serotype 33F saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

In an embodiment, the serotypes 22F/33F glycoconjugate of the invention comprises at least 0.1, 0.2, 0.3, 0.4, 0.5, 0.6 or 0.7 or about 0.8 mM acetate per mM serotype 22F polysaccharide. In a preferred embodiment, the serotypes 22F/33F glycoconjugate comprises at least 0.5, 0.6 or 0.7 mM acetate per mM serotype 22F polysaccharide. In a preferred embodiment, the serotypes 22F/33F glycoconjugate comprises at least 0.6 mM acetate per mM serotype 22F polysaccharide. In a preferred embodiment, the serotypes 22F/33F glycoconjugate comprises at least 0.7 mM acetate per mM serotype 22F polysaccharide.

In an embodiment, the serotypes 22F/33F glycoconjugate of the invention comprises at least 0.1, 0.2, 0.3, 0.4, 0.5, 0.6 or 0.7 or about 0.8 mM acetate per mM serotype 33F polysaccharide. In a preferred embodiment, the serotypes 22F/33F glycoconjugate comprises at least 0.5, 0.6 or 0.7 mM acetate per mM serotype 33F polysaccharide. In a preferred embodiment, the serotypes 22F/33F glycoconjugate comprises at least 0.6 mM acetate per mM serotype 33F polysaccharide. In a preferred embodiment, the serotypes 22F/33F glycoconjugate comprises at least 0.7 mM acetate per mM serotype 33F polysaccharide.

The serotypes 22F/33F glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d$=0), and the fraction representing the maximum retention ($V_i$), ($K_d$=1). The fraction at which a specified sample attribute is reached ($V_e$), is related to $K_d$ by the expression, $K_d=(V_e-V_0)/(V_i-V_0)$.

In a preferred embodiment, at least 30% of the serotypes 22F/33F glycoconjugate has a $K_d$ below or equal to 0.3 in a CL-4B column. In a preferred embodiment, at least 40% of the serotypes 22F/33F glycoconjugate has a $K_d$ below or equal to 0.3 in a CL-4B column. In a preferred embodiment, at least 45%, 50%, 55%, 60%, 65%, 70%, 75%, 80%, or 85% of the serotypes 22F/33F glycoconjugate has a $K_d$ below or equal to 0.3 in a CL-4B column. In a preferred embodiment, at least 60% of the serotypes 22F/33F glycoconjugate has a $K_d$ below or equal to 0.3 in a CL-4B column. In a preferred embodiment, between 50% and 80% of the serotypes 22F/33F glycoconjugate has a $K_d$ below or equal to 0.3 in a CL-4B column. In a preferred embodiment, between 65% and 80% of the serotypes 22F/33F glycoconjugate has a $K_d$ below or equal to 0.3 in a CL-4B column.

The serotypes 22F/33F glycoconjugate of the invention may contain free saccharide that is not covalently conjugated to the carrier protein, but is nevertheless present in the serotypes 22F/33F glycoconjugate composition. The free saccharide may be noncovalently associated with (i.e., noncovalently bound to, adsorbed to, or entrapped in or with) the serotypes 22F/33F glycoconjugate.

In a preferred embodiment, the serotypes 22F/33F glycoconjugate comprises less than about 50%, 45%, 40%, 35%, 30%, 25%, 20% or 15% of free serotypes 22F and 33F saccharide compared to the total amount of serotypes 22F and 33F saccharide. In a preferred embodiment the serotypes 22F/33F glycoconjugate comprises less than about 40% of free serotypes 22F and 33F saccharide compared to the total amount of serotypes 22F and 33F saccharide. In a preferred embodiment the serotypes 22F/33F glycoconjugate comprises less than about 25% of free serotypes 22F and 33F saccharide compared to the total amount of serotypes 22F and 33F saccharide. In a preferred embodiment the serotypes 22F/33F glycoconjugate comprises less than about 20% of free serotypes 22F and 33F saccharide compared to the total amount of serotypes 22F and 33F saccharide. In a preferred embodiment the serotypes 22F/33F glycoconjugate comprises less than about 15% of free serotypes 22F and 33F saccharide compared to the total amount of serotypes 22F and 33F saccharide.

In preferred embodiments, the serotype 22F/33F glycoconjugates of the invention are prepared using reductive amination.

Reductive amination involves two steps, (1) oxidation (activation) of the saccharide, (2) reduction of the activated saccharide and a carrier protein (e.g., $CRM_{197}$, DT, TT or PD) to form a conjugate. Before oxidation, sizing of the serotype 22F and/or 33F saccharide to a target molecular weight (MW) range can be performed. Mechanical or chemical hydrolysis may be employed. Chemical hydrolysis may be conducted using acetic acid. Advantageously, the size of the purified serotype 22F and/or 33F saccharide is reduced while preserving critical features of the structure of the saccharide such as for example the presence of O-acetyl groups. Therefore preferably, the size of the purified serotype 22F and/or 33F saccharide is reduced by mechanical homogenization.

In an embodiment, serotypes 22F and 33F saccharides are activated (oxidized) by a process comprising the step of:

(a) reacting a mixture of isolated serotypes 22F and 33F saccharides with an oxidizing agent.

Said process can further comprise a quenching step.

Therefore, in an embodiment, serotypes 22F and 33F saccharides are activated (oxidized) by a process comprising the step of:

(a) reacting a mixture of isolated serotypes 22F and 33F saccharides with an oxidizing agent;
(b) quenching the oxidation reaction by addition of a quenching agent resulting in activated serotypes 22F and 33F saccharides.

In these embodiments, the saccharides are therefore activated altogether as a mixture.

In another embodiment, serotypes 22F and 33F saccharides are activated (oxidized) separately and the activated saccharides are then mixed.

In said embodiment, serotypes 22F and 33F saccharides are activated (oxidized) by a process comprising the step of:

(a) individually reacting an isolated serotypes 22F and 33F saccharides with an oxidizing agent;
(b) mixing the activated serotypes 22F and 33F saccharides.

Said process can further comprise a quenching step.

Therefore, in an embodiment, serotypes 22F and 33F saccharides are activated (oxidized) by a process comprising the step of:

(a) individually reacting an isolated serotypes 22F and 33F saccharides with an oxidizing agent;
(b) quenching the oxidation reactions by addition of a quenching agent resulting in activated serotypes 22F and 33F saccharides;
(b) mixing the activated serotypes 22F and 33F saccharides.

The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate).

In a preferred embodiment, the oxidizing agent is sodium periodate. In a preferred embodiment, the periodate used for the oxidation of serotypes 22F and 33F saccharides is metaperiodate. In a preferred embodiment the periodate used for the oxidation of serotypes 22F and 33F saccharides is sodium metaperiodate.

In one embodiment, the quenching agent is selected from vicinal diols, 1,2-aminoalcohols, amino acids, glutathione, sulfite, bisulfate, dithionite, metabisulfite, thiosulfate, phosphites, hypophosphites or phosphorous acid.

In one embodiment, the quenching agent is a 1,2-aminoalcohols of formula (I):

(I)

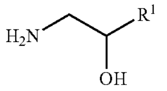

wherein $R^1$ is selected from H, methyl, ethyl, propyl or isopropyl.

In one embodiment, the quenching agent is selected from sodium and potassium salts of sulfite, bisulfate, dithionite, metabisulfite, thiosulfate, phosphites, hypophosphites or phosphorous acid. In one embodiment, the quenching agent is an amino acid. In such embodiments, said amino acid may be selected from serine, threonine, cysteine, cystine, methionine, proline, hydroxyproline, tryptophan, tyrosine, and histidine.

In one embodiment, the quenching agent is a sulfite such as bisulfate, dithionite, metabisulfite, thiosulfate.

In one embodiment, the quenching agent is a compound comprising two vicinal hydroxyl groups (vicinal diols), i.e., two hydroxyl groups covalently linked to two adjacent carbon atoms.

Preferably, the quenching agent is a compound of formula (II):

(II)

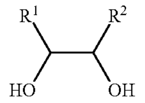

wherein $R^1$ and $R^2$ are each independently selected from H, methyl, ethyl, propyl or isopropyl.

In a preferred embodiment, the quenching agent is glycerol, ethylene glycol, propan-1,2-diol, butan-1,2-diol or butan-2,3-diol, or ascorbic acid. In a preferred embodiment, the quenching agent is butan-2,3-diol.

In a preferred embodiment, the isolated serotypes 22F and 33F saccharides are activated by a process comprising the step of:

(a) reacting a mixture of isolated serotypes 22F and 33F saccharides with periodate;
(b) quenching the oxidation reaction by addition of butan-2,3-diol resulting in a mixture of activated serotypes 22F and 33F saccharides.

Following the oxidation step of the saccharides, the saccharides are said to be activated and is referred to as "activated saccharides" here below.

In a preferred embodiment, the activated serotypes 22F and 33F saccharides are purified. The activated serotypes 22F and 33F saccharides are purified according to methods known to the man skilled in the art such as gel permeation chromatography (GPC), dialysis or ultrafiltration/diafiltration. For example, the activated serotypes 22F and 33F saccharides are purified by concentration and diafiltration using an ultrafiltration device.

In a preferred embodiment the degree of oxidation of the activated serotypes 22F and 33F saccharides are between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25. In a preferred embodiment the degree of oxidation of the activated serotype 22F and 33F polysaccharide is between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20.

In a preferred embodiment, the activated serotypes 22F and 33F saccharides have a molecular weight of between 10 kDa and 5,000 kDa; between 20 kDa and 4,000 kDa; between 50 kDa and 3,000 kDa; between 100 kDa and 2500 kDa; 100 kDa and 2,000 kDa; between 150 kDa and 2,000 kDa; between 150 kDa and 1,500 kDa; between 10 kDa and 2,000 kDa; between 20 kDa and 1,500 kDa; between 30 kDa and 1,250 kDa; between 50 kDa and 1,000 kDa; between 70 kDa and 900 kDa; between 100 kDa and 800 kDa; between 200 kDa to 600 kDa or between 400 kDa to 700 kDa.

In an embodiment, the activated serotypes 22F and 33F saccharides have a molecular weight between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In an embodiment, the activated serotypes 22F and 33F saccharides have a molecular weight between 25 kDa and 3,000 kDa, between 50 kDa and 2,000 kDa, between 100 kDa and 1,500 kDa, between 100 kDa and 1,000 kDa, between 300 kDa and 800 kDa, between 300 kDa and 700 kDa, between 300 kDa and 600 kDa, between 400 kDa and 1,000 kDa, between 400 kDa and 800 kDa, between 400 kDa and 700 kDa or between 400 kDa and 600 kDa. In an embodiment, the activated serotypes 22F and 33F saccharides have a molecular weight between 100 kDa and 3,000 kDa, between 200 kDa and 2,000 kDa, between 250 kDa and 1,500 kDa, between 250 kDa and 1,000 kDa, between 250 kDa and 800 kDa, between 250 kDa and 700 kDa, between 250 kDa and 600 kDa, between 300 kDa and 1,000 kDa, between 300 kDa and 800 kDa, between 300 kDa and 700 kDa or between 300 kDa and 600 kDa.

In an embodiment, the activated serotypes 22F and 33F saccharides have a molecular weight between 300 kDa and 800 kDa. In an embodiment, the activated serotypes 22F and 33F saccharides have a molecular weight between 400 kDa and 600 kDa.

In a preferred embodiment, the activated serotypes 22F and 33F saccharides have a molecular weight between 400 kda and 600 kDa and a degree of oxidation between 10 and 25, between 10 and 20, between 12 and 20 or between 14 and 18. In a preferred embodiment, the activated serotypes 22F and 33F saccharides have a molecular weight between 400 kDa and 600 kDa and a degree of oxidation between 10 and 20.

The activated polysaccharides and/or the carrier protein may be lyophilised (freeze-dried), either independently (discrete lyophilization) or together (co-lyophilized).

In an embodiment, the activated serotypes 22F and 33F saccharides are lyophilized, optionally in the presence of saccharide such as sucrose, trehalose, raffinose, stachyose, melezitose, dextran, mannitol, lactitol or palatinit. In a preferred embodiment, the saccharide is sucrose. In one embodiment, the lyophilized activated serotypes 22F and 33F saccharides are then compounded with a solution comprising the carrier protein.

In another embodiment the activated serotypes 22F and 33F saccharides and the carrier protein are co-lyophilised. In such embodiments, the activated serotypes 22F and 33F saccharides are compounded with the carrier protein and lyophilized, optionally in the presence of a saccharide such as sucrose, trehalose, raffinose, stachyose, melezitose, dextran, mannitol, lactitol and palatinit. In a preferred embodiment, the saccharide is sucrose. The co-lyophilized activated serotypes 22F and 33F saccharides and carrier protein can then be resuspended in solution and reacted with a reducing agent.

The second step of the conjugation process is the reduction of the activated saccharides and a carrier protein to form a conjugate (reductive amination), using a reducing agent.

The activated serotypes 22F and 33F saccharides can be conjugated to a carrier protein by a process comprising the step of:

(c) compounding the activated serotypes 22F and 33F saccharides with a carrier protein; and (d) reacting the compounded activated serotypes 22F and 33F saccharides and carrier protein with a reducing agent to form a serotypes 22F/33F glycoconjugate.

In an embodiment, the reduction reaction is carried out in aqueous solvent. Preferably though, the reaction is carried out in aprotic solvent. In a preferred embodiment, the reduction reaction is carried out in DMSO (dimethylsulfoxide) or in DMF (dimethylformamide)) solvent. The DMSO or DMF solvent may be used to reconstitute the activated serotypes 22F and 33F saccharides and carrier protein which have been lyophilised.

The conjugation of activated serotypes 22F and 33F saccharides with a protein carrier by reductive amination in dimethylsulfoxide (DMSO) is suitable to preserve the O-acetyl content of the saccharides as compared, for example, to reductive amination in aqueous phase where the level of O-acetylation of the saccharides may be significantly reduced. Therefore in a preferred embodiment, step (c) and step (d) are carried out in DMSO.

In an embodiment, the reducing agent is sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^i$PrN—$BH_3$, benzylamine-$BH_3$ or 5-ethyl-2-methylpyridine borane (PEMB). In a preferred embodiment, the reducing agent is sodium cyanoborohydride.

At the end of the reduction reaction, there may be unreacted aldehyde groups remaining in the conjugates, these may be capped using a suitable capping agent. In one embodiment this capping agent is sodium borohydride ($NaBH_4$).

Following conjugation of serotypes 22F and 33F saccharides to the carrier protein, the glycoconjugate can be purified (enriched with respect to the amount of saccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration.

1.3.3.10 Glycoconjugates Comprising a Saccharide from *S. pneumoniae* Serotype 22F and a Saccharide from *S. pneumoniae* Serotype 35B Conjugated to a Carrier Protein In an embodiment the glycoconjugates of the invention comprises a saccharide from *S. pneumoniae* serotype 22F and a saccharide from *S. pneumoniae* serotype 35B conjugated to the same carrier protein (herein after 'the serotypes 22F/35B glycoconjugate'). In said embodiment, the carrier molecules have the two different capsular saccharides conjugated to them. Preferably, the glycoconjugates of this section (1.3.3.10) are therefore 2-valent glycoconjugates (i.e. they have serotypes 22F and 35B conjugated to the carrier protein and have no other polysaccharide antigens covalently attached to the carrier protein).

In some embodiments, the serotypes 22F/35B glycoconjugate of the present invention comprise a serotype 22F saccharide having a molecular weight of between 10 kDa and 5,000 kDa. In other such embodiments, the serotype 22F saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 22F saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 22F/35B glycoconjugate of the present invention comprise a serotype 35B saccharide having a molecular weight of between 10 kDa and 5,000 kDa. In other such embodiments, the serotype 35B saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 35B saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 22F/35B glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the serotypes 22F/35B glycoconjugate has a molecular weight of between 500 kDa and 10,000 kDa. In other embodiments, the serotypes 22F/35B glycoconjugate has a molecular weight of between 1,000 kDa and 8,000 kDa. In still other embodiments, the serotypes 22F/35B glycoconjugate has a molecular weight of between 2,000 kDa and 8,000 kDa or between 3,000 kDa and 7,000 kDa. In further embodiments, the serotypes 22F/35B glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa.

In further embodiments, the serotypes 22F/35B glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa.

In further embodiments, the serotypes 22F/35B glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate is measured by SEC-MALLS. Any whole number integer within any of the above ranges is contemplated as an embodiment of the disclosure.

Another way to characterize the serotypes 22F/35B glycoconjugate of the invention is by the number of lysine residues in the carrier protein (e.g., $CRM_{197}$) that become conjugated to the saccharides which can be characterized as a range of conjugated lysines (degree of conjugation). The evidence for lysine modification of the carrier protein, due to covalent linkages to the saccharides, can be obtained by amino acid analysis using routine methods known to those of skill in the art. Conjugation results in a reduction in the number of lysine residues recovered compared to the carrier protein starting material (e.g. $CRM_{197}$) used to generate the conjugate materials. In a preferred embodiment, the degree of conjugation of the serotypes 22F/35B glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotypes 22F/35B glycoconjugate of the invention is about 2, about 3, about 4, about 5, about 6, about 7, about 8, about 9, about 10, about 11, about 12, about 13, about 14 or about 15. In a preferred embodiment, the degree of conjugation of the serotypes 22F/35B glycoconjugate of the invention is between 4 and 7. In some such embodiments, the carrier protein is $CRM_{197}$. In other such embodiments, the carrier protein is DT. In other such embodiments, the carrier protein is TT. In other such embodiments, the carrier protein is PD.

The serotypes 22F/35B glycoconjugate of the invention may also be characterized by the ratio (weight/weight) of saccharide to carrier protein. In some embodiments, the ratio of serotypes 22F and 35B saccharides to carrier protein in the glycoconjugate (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of serotypes 22F and 35B saccharides to carrier protein in the conjugate is between 0.9 and 1.1. In some such embodiments, the carrier protein is $CRM_{197}$. In other such embodiments, the carrier protein is DT. In other such embodiments, the carrier protein is TT. In other such embodiments, the carrier protein is PD.

The serotypes 22F/35B glycoconjugate of the invention may also be characterized by the ratio (weight/weight) of serotype 22F saccharide to serotype 35B saccharide in the glycoconjugate. In some embodiments, the ratio of serotype 22F saccharide to serotype 35B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 22F saccharide to serotype 35B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 22F saccharide to serotype 35B saccharide ratio (w/w) is between 0.8 and 1.2. In a preferred embodiment, the ratio of serotype 22F saccharide to serotype 35B saccharide in the conjugate is between 0.9 and 1.1, even more preferably the ratio of serotype 22F saccharide to serotype 35B saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

In an embodiment, the serotypes 22F/35B glycoconjugate of the invention comprises at least 0.1, 0.2, 0.3, 0.4, 0.5, 0.6 or 0.7 or about 0.8 mM acetate per mM serotype 22F polysaccharide. In a preferred embodiment, the serotypes 22F/35B glycoconjugate comprises at least 0.5, 0.6 or 0.7 mM acetate per mM serotype 22F polysaccharide. In a preferred embodiment, the serotypes 22F/35B glycoconjugate comprises at least 0.6 mM acetate per mM serotype 22F polysaccharide. In a preferred embodiment, the serotypes 22F/35B glycoconjugate comprises at least 0.7 mM acetate per mM serotype 22F polysaccharide.

In an embodiment, the serotypes 22F/35B glycoconjugate of the invention comprises at least 0.1, 0.2, 0.3, 0.4, 0.5, 0.6 or 0.7 or about 0.8 mM acetate per mM serotype 35B polysaccharide. In a preferred embodiment, the serotypes 22F/35B glycoconjugate comprises at least 0.5, 0.6 or 0.7 mM acetate per mM serotype 35B polysaccharide. In a preferred embodiment, the serotypes 22F/35B glycoconjugate comprises at least 0.6 mM acetate per mM serotype 35B polysaccharide. In a preferred embodiment, the serotypes 22F/35B glycoconjugate comprises at least 0.7 mM acetate per mM serotype 35B polysaccharide.

The serotypes 22F/35B glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d$=0), and the fraction representing the maximum retention ($V_i$), ($K_d$=1). The fraction at which a specified sample attribute is reached ($V_e$), is related to $K_d$ by the expression, $K_d=(V_e-V_0)/(V_i-V_0)$.

In a preferred embodiment, at least 30% of the serotypes 22F/35B glycoconjugate has a $K_d$ below or equal to 0.3 in a CL-4B column. In a preferred embodiment, at least 40% of the serotypes 22F/35B glycoconjugate has a $K_d$ below or equal to 0.3 in a CL-4B column. In a preferred embodiment, at least 45%, 50%, 55%, 60%, 65%, 70%, 75%, 80%, or 85% of the serotypes 22F/35B glycoconjugate has a $K_d$ below or equal to 0.3 in a CL-4B column. In a preferred embodiment, at least 60% of the serotypes 22F/35B glycoconjugate has a $K_d$ below or equal to 0.3 in a CL-4B column. In a preferred embodiment, between 50% and 80% of the serotypes 22F/35B glycoconjugate has a $K_d$ below or equal to 0.3 in a CL-4B column. In a preferred embodiment, between 65% and 80% of the serotypes 22F/35B glycoconjugate has a $K_d$ below or equal to 0.3 in a CL-4B column.

The serotypes 22F/35B glycoconjugate of the invention may contain free saccharide that is not covalently conjugated to the carrier protein, but is nevertheless present in the serotypes 22F/35B glycoconjugate composition. The free saccharide may be noncovalently associated with (i.e., noncovalently bound to, adsorbed to, or entrapped in or with) the serotypes 22F/35B glycoconjugate.

In a preferred embodiment, the serotypes 22F/35B glycoconjugate comprises less than about 50%, 45%, 40%, 35%, 30%, 25%, 20% or 15% of free serotypes 22F and 35B saccharide compared to the total amount of serotypes 22F and 35B saccharide. In a preferred embodiment the serotypes 22F/35B glycoconjugate comprises less than about 40% of free serotypes 22F and 35B saccharide compared to the total amount of serotypes 22F and 35B saccharide. In a preferred embodiment the serotypes 22F/35B glycoconjugate comprises less than about 25% of free serotypes 22F and 35B saccharide compared to the total amount of serotypes 22F and 35B saccharide. In a preferred embodiment the serotypes 22F/35B glycoconjugate comprises less than about 20% of free serotypes 22F and 35B saccharide compared to the total amount of serotypes 22F and 35B saccharide. In a preferred embodiment the serotypes 22F/35B glycoconjugate comprises less than about 15% of free serotypes 22F and 35B saccharide compared to the total amount of serotypes 22F and 35B saccharide.

In preferred embodiments, the serotype 22F/35B glycoconjugates of the invention are prepared using reductive amination.

Reductive amination involves two steps, (1) oxidation (activation) of the saccharide, (2) reduction of the activated saccharide and a carrier protein (e.g., $CRM_{197}$, DT, TT or PD) to form a conjugate. Before oxidation, sizing of the serotype 22F and/or 35B saccharide to a target molecular weight (MW) range can be performed. Mechanical or chemical hydrolysis may be employed. Chemical hydrolysis may be conducted using acetic acid. Advantageously, the size of the purified serotype 22F and/or 35B saccharide is reduced while preserving critical features of the structure of the saccharide such as for example the presence of O-acetyl groups. Therefore preferably, the size of the purified serotype 22F and/or 35B saccharide is reduced by mechanical homogenization.

In an embodiment, serotypes 22F and 35B saccharides are activated (oxidized) by a process comprising the step of:

(a) reacting a mixture of isolated serotypes 22F and 35B saccharides with an oxidizing agent. Said process can further comprise a quenching step.

Therefore, in an embodiment, serotypes 22F and 35B saccharides are activated (oxidized) by a process comprising the step of:

(a) reacting a mixture of isolated serotypes 22F and 35B saccharides with an oxidizing agent;

(b) quenching the oxidation reaction by addition of a quenching agent resulting in activated serotypes 22F and 35B saccharides.

In these embodiments, the saccharides are therefore activated altogether as a mixture.

In another embodiment, serotypes 22F and 35B saccharides are activated (oxidized) separately and the activated saccharides are then mixed.

In said embodiment, serotypes 22F and 35B saccharides are activated (oxidized) by a process comprising the step of:

(a) individually reacting an isolated serotypes 22F and 35B saccharides with an oxidizing agent;

(b) mixing the activated serotypes 22F and 35B saccharides.

Said process can further comprise a quenching step.

Therefore, in an embodiment, serotypes 22F and 35B saccharides are activated (oxidized) by a process comprising the step of:

(a) individually reacting an isolated serotypes 22F and 35B saccharides with an oxidizing agent;

(b) quenching the oxidation reactions by addition of a quenching agent resulting in activated serotypes 22F and 35B saccharides;

(b) mixing the activated serotypes 22F and 35B saccharides.

The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate).

In a preferred embodiment, the oxidizing agent is sodium periodate. In a preferred embodiment, the periodate used for the oxidation of serotypes 22F and 35B saccharides is metaperiodate. In a preferred embodiment the periodate used for the oxidation of serotypes 22F and 35B saccharides is sodium metaperiodate.

In one embodiment, the quenching agent is selected from vicinal diols, 1,2-aminoalcohols, amino acids, glutathione, sulfite, bisulfate, dithionite, metabisulfite, thiosulfate, phosphites, hypophosphites or phosphorous acid.

In one embodiment, the quenching agent is a 1,2-aminoalcohols of formula (I):

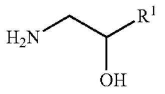

(I)

wherein $R^1$ is selected from H, methyl, ethyl, propyl or isopropyl.

In one embodiment, the quenching agent is selected from sodium and potassium salts of sulfite, bisulfate, dithionite, metabisulfite, thiosulfate, phosphites, hypophosphites or phosphorous acid. In one embodiment, the quenching agent is an amino acid. In such embodiments, said amino acid may be selected from serine, threonine, cysteine, cystine, methionine, proline, hydroxyproline, tryptophan, tyrosine, and histidine.

In one embodiment, the quenching agent is a sulfite such as bisulfate, dithionite, metabisulfite, thiosulfate.

In one embodiment, the quenching agent is a compound comprising two vicinal hydroxyl groups (vicinal diols), i.e., two hydroxyl groups covalently linked to two adjacent carbon atoms. Preferably, the quenching agent is a compound of formula (II):

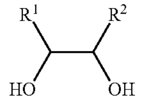

(II)

wherein $R^1$ and $R^2$ are each independently selected from H, methyl, ethyl, propyl or isopropyl.

In a preferred embodiment, the quenching agent is glycerol, ethylene glycol, propan-1,2-diol, butan-1,2-diol or butan-2,3-diol, or ascorbic acid. In a preferred embodiment, the quenching agent is butan-2,3-diol.

In a preferred embodiment, the isolated serotypes 22F and 35B saccharides are activated by a process comprising the step of:

(a) reacting a mixture of isolated serotypes 22F and 35B saccharides with periodate;

(b) quenching the oxidation reaction by addition of butan-2,3-diol resulting in a mixture of activated serotypes 22F and 35B saccharides.

Following the oxidation step of the saccharides, the saccharides are said to be activated and is referred to as "activated saccharides" here below.

In a preferred embodiment, the activated serotypes 22F and 35B saccharides are purified. The activated serotypes 22F and 35B saccharides are purified according to methods known to the man skilled in the art such as gel permeation chromatography (GPC), dialysis or ultrafiltration/diafiltration. For example, the activated serotypes 22F and 35B saccharides are purified by concentration and diafiltration using an ultrafiltration device.

In a preferred embodiment the degree of oxidation of the activated serotypes 22F and 35B saccharides are between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25. In a preferred embodiment the degree of oxidation of the activated serotype 22F and 35B polysaccharide is between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20.

In a preferred embodiment, the activated serotypes 22F and 35B saccharides have a molecular weight of between 10 kDa and 5,000 kDa; between 20 kDa and 4,000 kDa; between 50 kDa and 3,000 kDa; between 100 kDa and 2500 kDa; 100 kDa and 2,000 kDa; between 150 kDa and 2,000 kDa; between 150 kDa and 1,500 kDa; between 10 kDa and 2,000 kDa; between 20 kDa and 1,500 kDa; between 30 kDa and 1,250 kDa; between 50 kDa and 1,000 kDa; between 70 kDa and 900 kDa; between 100 kDa and 800 kDa; between 200 kDa to 600 kDa or between 400 kDa to 700 kDa.

In an embodiment, the activated serotypes 22F and 35B saccharides have a molecular weight between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In an embodiment, the activated serotypes 22F and 35B saccharides have a molecular weight between 25 kDa and 3,000 kDa, between 50 kDa and 2,000 kDa, between 100 kDa and 1,500 kDa, between 100 kDa and 1,000 kDa, between 300 kDa and 800 kDa, between 300 kDa and 700 kDa, between 300 kDa and 600 kDa, between 400 kDa and 1,000 kDa, between 400 kDa and 800 kDa, between 400 kDa and 700 kDa or between 400 kDa and 600 kDa. In an embodiment, the activated serotypes 22F and 35B saccharides have a molecular weight between 100 kDa and 3,000 kDa, between 200 kDa and 2,000 kDa, between 250 kDa and 1,500 kDa, between 250 kDa and 1,000 kDa, between 250 kDa and 800 kDa, between 250 kDa and 700 kDa, between 250 kDa and 600 kDa, between 300 kDa and 1,000 kDa, between 300 kDa and 800 kDa, between 300 kDa and 700 kDa or between 300 kDa and 600 kDa.

In an embodiment, the activated serotypes 22F and 35B saccharides have a molecular weight between 300 kDa and 800 kDa. In an embodiment, the activated serotypes 22F and 35B saccharides have a molecular weight between 400 kDa and 600 kDa.

In a preferred embodiment, the activated serotypes 22F and 35B saccharides have a molecular weight between 400 kda and 600 kDa and a degree of oxidation between 10 and 25, between 10 and 20, between 12 and 20 or between 14 and 18. In a preferred embodiment, the activated serotypes 22F and 35B saccharides have a molecular weight between 400 kDa and 600 kDa and a degree of oxidation between 10 and 20.

The activated polysaccharides and/or the carrier protein may be lyophilised (freeze-dried), either independently (discrete lyophilization) or together (co-lyophilized).

In an embodiment, the activated serotypes 22F and 35B saccharides are lyophilized, optionally in the presence of saccharide such as sucrose, trehalose, raffinose, stachyose, melezitose, dextran, mannitol, lactitol or palatinit. In a preferred embodiment, the saccharide is sucrose. In one embodiment, the lyophilized activated serotypes 22F and 35B saccharides are then compounded with a solution comprising the carrier protein.

In another embodiment the activated serotypes 22F and 35B saccharides and the carrier protein are co-lyophilised. In such embodiments, the activated serotypes 22F and 35B saccharides are compounded with the carrier protein and lyophilized, optionally in the presence of a saccharide such as sucrose, trehalose, raffinose, stachyose, melezitose, dextran, mannitol, lactitol and palatinit. In a preferred embodiment, the saccharide is sucrose. The co-lyophilized activated serotypes 22F and 35B saccharides and carrier protein can then be resuspended in solution and reacted with a reducing agent.

The second step of the conjugation process is the reduction of the activated saccharides and a carrier protein to form a conjugate (reductive amination), using a reducing agent.

The activated serotypes 22F and 35B saccharides can be conjugated to a carrier protein by a process comprising the step of:

(c) compounding the activated serotypes 22F and 35B saccharides with a carrier protein; and (d) reacting the compounded activated serotypes 22F and 35B saccharides and carrier protein with a reducing agent to form a serotypes 22F/35B glycoconjugate.

In an embodiment, the reduction reaction is carried out in aqueous solvent. Preferably though, the reaction is carried out in aprotic solvent. In a preferred embodiment, the reduction reaction is carried out in DMSO (dimethylsulfoxide) or in DMF (dimethylformamide)) solvent. The DMSO or DMF solvent may be used to reconstitute the activated serotypes 22F and 35B saccharides and carrier protein which have been lyophilised.

The conjugation of activated serotypes 22F and 35B saccharides with a protein carrier by reductive amination in dimethylsulfoxide (DMSO) is suitable to preserve the O-acetyl content of the saccharides as compared, for example, to reductive amination in aqueous phase where the level of O-acetylation of the saccharides may be significantly reduced. Therefore in a preferred embodiment, step (c) and step (d) are carried out in DMSO.

In an embodiment, the reducing agent is sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^i$PrN—$BH_3$, benzylamine-$BH_3$ or 5-ethyl-2-methylpyridine borane (PEMB). In a preferred embodiment, the reducing agent is sodium cyanoborohydride.

At the end of the reduction reaction, there may be unreacted aldehyde groups remaining in the conjugates, these may be capped using a suitable capping agent. In one embodiment this capping agent is sodium borohydride ($NaBH_4$).

Following conjugation of serotypes 22F and 35B saccharides to the carrier protein, the glycoconjugate can be purified (enriched with respect to the amount of saccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration.

1.3.3.11 Glycoconjugates Comprising a Saccharide from *S. pneumoniae* Serotype 33F and a Saccharide from *S. pneumoniae* Serotype 35B Conjugated to a Carrier Protein In an embodiment the glycoconjugates of the invention comprises a saccharide from *S. pneumoniae* serotype 33F and a saccharide from *S. pneumoniae* serotype 35B are conjugated to the same carrier protein (herein after 'the serotypes 33F/35B glycoconjugate'). In said embodiment, the carrier molecules have the two different capsular saccharides conjugated to them. Preferably, the glycoconjugates of this section (1.3.3.11) are therefore 2-valent glycoconjugates (i.e. they have serotypes 33F and 35B conjugated to the carrier protein and have no other polysaccharide antigens covalently attached to the carrier protein).

In some embodiments, the serotypes 33F/35B glycoconjugate of the present invention comprise a serotype 33F saccharide having a molecular weight of between 10 kDa and 5,000 kDa. In other such embodiments, the serotype 33F saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharide has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 33F saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 33F/35B glycoconjugate of the present invention comprise a serotype 35B saccharide having a molecular weight of between 10 kDa and 5,000 kDa. In other such embodiments, the serotype 35B saccharide has a molecular weight of between 20 kDa and 4,000 kDa. In other such embodiments, the saccharide has a molecular weight of between 50 kDa and 3,000 kDa. In other such embodiments, the saccharide has a molecular weight of between 100 kDa and 2500 kDa. In other such embodiments, the saccharide has a molecular weight of between 100 kDa and 2,000 kDa. In other such embodiments, the saccharide has a molecular weight of between 150 kDa and 2,000 kDa. In other such embodiments, the saccharide has a molecular weight of between 150 kDa and 1,500 kDa. In some embodiments, the saccharides has a molecular weight of between 10 kDa and 2,000 kDa. In other such embodiments, the saccharide has a molecular weight of between 20 kDa and 1,500 kDa. In another embodiment, the saccharide has a molecular weight of between 30 kDa and 1,250 kDa. In another embodiment, the saccharide has a molecular weight of between 50 kDa and 1,000 kDa. In another embodiment, the saccharide has a molecular weight of between 70 kDa and 900 kDa. In another embodiment, the saccharide has a molecular weight of between 100 kDa and 800 kDa. In another embodiment, the saccharide has a molecular weight of between 200 kDa to 600 kDa. In another embodiment, the saccharide has a molecular weight of between 400 kDa to 700 kDa.

In further such embodiments, the serotype 35B saccharide has a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In some embodiments, the serotypes 33F/35B glycoconjugate of the invention has a molecular weight of between 400 kDa and 15,000 kDa; between 500 kDa and 10,000 kDa; between 2,000 kDa and 10,000 kDa; between 3,000 kDa and 8,000 kDa; or between 3,000 kDa and 5,000 kDa. In other embodiments, the serotypes 33F/35B glycoconjugate has a molecular weight of between 500 kDa and 10,000 kDa. In other embodiments, the serotypes 33F/35B glycoconjugate has a molecular weight of between 1,000 kDa and 8,000 kDa. In still other embodiments, the serotypes 33F/35B glycoconjugate has a molecular weight of between 2,000 kDa and 8,000 kDa or between 3,000 kDa and 7,000 kDa. In further embodiments, the serotypes 33F/35B glycoconjugate of the invention has a molecular weight of between 200 kDa and 20,000 kDa; between 200 kDa and 15,000 kDa; between 200 kDa and 10,000 kDa; between 200 kDa and 7,500 kDa; between 200 kDa and 5,000 kDa; between 200 kDa and 3,000 kDa; between 200 kDa and 1,000 kDa; between 500 kDa and 20,000 kDa; between 500 kDa and 15,000 kDa; between 500 kDa and 12,500 kDa; between 500 kDa and 10,000 kDa; between 500 kDa and 7,500 kDa; between 500 kDa and 6,000 kDa; between 500 kDa and 5,000 kDa; between 500 kDa and 4,000 kDa; between 500 kDa and 3,000 kDa; between 500 kDa and 2,000 kDa; between 500 kDa and 1,500 kDa; between 500 kDa and 1,000 kDa; between 750 kDa and 20,000 kDa; between 750 kDa and 15,000 kDa; between 750 kDa and 12,500 kDa; between 750 kDa and 10,000 kDa; between 750 kDa and 7,500 kDa; between 750 kDa and 6,000 kDa; between 750 kDa and 5,000 kDa; between 750 kDa and 4,000 kDa; between 750 kDa and 3,000 kDa; between 750 kDa and 2,000 kDa; between 750 kDa and 1,500 kDa; between 1,000 kDa and 15,000 kDa; between 1,000 kDa and 12,500 kDa; between 1,000 kDa and 10,000 kDa; between 1,000 kDa and 7,500 kDa; between 1,000 kDa and 6,000 kDa; between 1,000 kDa and 5,000 kDa; between 1,000 kDa and 4,000 kDa; between 1,000 kDa and 2,500 kDa; between 2,000 kDa and 15,000 kDa; between 2,000 kDa and 12,500 kDa; between 2,000 kDa and 10,000 kDa; between 2,000 kDa and 7,500 kDa; between 2,000 kDa and 6,000 kDa; between 2,000 kDa and 5,000 kDa; between 2,000 kDa and 4,000 kDa; or between 2,000 kDa and 3,000 kDa.

In further embodiments, the serotypes 33F/35B glycoconjugate of the invention has a molecular weight of between 3,000 kDa and 20,000 kDa; between 3,000 kDa and 15,000 kDa; between 3,000 kDa and 10,000 kDa; between 3,000 kDa and 7,500 kDa; between 3,000 kDa and 5,000 kDa; between 4,000 kDa and 20,000 kDa; between 4,000 kDa and 15,000 kDa; between 4,000 kDa and 12,500 kDa; between 4,000 kDa and 10,000 kDa; between 4,000 kDa and 7,500 kDa; between 4,000 kDa and 6,000 kDa; or between 4,000 kDa and 5,000 kDa.

In further embodiments, the serotypes 33F/35B glycoconjugate of the invention has a molecular weight of between 5,000 kDa and 20,000 kDa; between 5,000 kDa and 15,000 kDa; between 5,000 kDa and 10,000 kDa; between 5,000 kDa and 7,500 kDa; between 6,000 kDa and 20,000 kDa; between 6,000 kDa and 15,000 kDa; between 6,000 kDa and 12,500 kDa; between 6,000 kDa and 10,000 kDa or between 6,000 kDa and 7,500 kDa.

The molecular weight of the glycoconjugate is measured by SEC-MALLS. Any whole number integer within any of the above ranges is contemplated as an embodiment of the disclosure.

Another way to characterize the serotypes 33F/35B glycoconjugate of the invention is by the number of lysine residues in the carrier protein (e.g., $CRM_{197}$) that become conjugated to the saccharides which can be characterized as a range of conjugated lysines (degree of conjugation). The evidence for lysine modification of the carrier protein, due to covalent linkages to the saccharides, can be obtained by amino acid analysis using routine methods known to those of skill in the art. Conjugation results in a reduction in the number of lysine residues recovered compared to the carrier protein starting material (e.g. $CRM_{197}$) used to generate the conjugate materials. In a preferred embodiment, the degree of conjugation of the serotypes 33F/35B glycoconjugate of the invention is between 2 and 15, between 2 and 13, between 2 and 10, between 2 and 8, between 2 and 6, between 2 and 5, between 2 and 4, between 3 and 15, between 3 and 13, between 3 and 10, between 3 and 8, between 3 and 6, between 3 and 5, between 3 and 4, between 5 and 15, between 5 and 10, between 8 and 15, between 8 and 12, between 10 and 15 or between 10 and 12. In an embodiment, the degree of conjugation of the serotypes 33F/35B glycoconjugate of the invention is about 2, about 3, about 4, about 5, about 6, about 7, about 8, about 9, about 10, about 11, about 12, about 13, about 14 or about 15. In a preferred embodiment, the degree of conjugation of the serotypes 33F/35B glycoconjugate of the invention is between 4 and 7. In some such embodiments, the carrier protein is $CRM_{197}$. In other such embodiments, the carrier protein is DT. In other such embodiments, the carrier protein is TT. In other such embodiments, the carrier protein is PD.

The serotypes 33F/35B glycoconjugate of the invention may also be characterized by the ratio (weight/weight) of saccharide to carrier protein. In some embodiments, the ratio of serotypes 33F and 35B saccharides to carrier protein in the glycoconjugate (w/w) is between 0.5 and 3.0 (e.g., about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0). In other embodiments, the saccharide to carrier protein ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the saccharide to carrier protein ratio (w/w) is between 0.8 and 1.2. In a preferred embodiment, the ratio of serotypes 33F and 35B saccharides to carrier protein in the conjugate is between 0.9 and 1.1. In some such embodiments, the carrier protein is $CRM_{197}$. In other such embodiments, the carrier protein is DT. In other such embodiments, the carrier protein is TT. In other such embodiments, the carrier protein is PD.

The serotypes 33F/35B glycoconjugate of the invention may also be characterized by the ratio (weight/weight) of serotype 33F saccharide to serotype 35B saccharide in the glycoconjugate. In some embodiments, the ratio of serotype 33F saccharide to serotype 35B saccharide in the glycoconjugate (w/w) is between 0.25 and 4.0 (e.g., about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0). In other embodiments, the serotype 33F saccharide to serotype 35B saccharide ratio (w/w) is between 0.5 and 2.0, between 0.5 and 1.5, between 0.8 and 1.2, between 0.5 and 1.0, between 1.0 and 1.5 or between 1.0 and 2.0. In further embodiments, the serotype 33F saccharide to serotype 35B saccharide ratio (w/w) is between 0.8 and 1.2. In a preferred embodiment, the ratio of serotype 33F saccharide to serotype 35B saccharide in the conjugate is between 0.9 and 1.1, even more preferably the ratio of serotype 33F saccharide to serotype 35B saccharide in the conjugate is about 1.0. In some such embodiments, the carrier protein is $CRM_{197}$. In other such embodiments, the carrier protein is DT. In other such embodiments, the carrier protein is TT. In other such embodiments, the carrier protein is PD.

In an embodiment, the serotypes 33F/35B glycoconjugate of the invention comprises at least 0.1, 0.2, 0.3, 0.4, 0.5, 0.6 or 0.7 or about 0.8 mM acetate per mM serotype 33F polysaccharide. In a preferred embodiment, the serotypes 33F/35B glycoconjugate comprises at least 0.5, 0.6 or 0.7 mM acetate per mM serotype 33F polysaccharide. In a preferred embodiment, the serotypes 33F/35B glycoconjugate comprises at least 0.6 mM acetate per mM serotype 33F polysaccharide. In a preferred embodiment, the serotypes 33F/35B glycoconjugate comprises at least 0.7 mM acetate per mM serotype 33F polysaccharide.

In an embodiment, the serotypes 33F/35B glycoconjugate of the invention comprises at least 0.1, 0.2, 0.3, 0.4, 0.5, 0.6 or 0.7 or about 0.8 mM acetate per mM serotype 35B polysaccharide. In a preferred embodiment, the serotypes 33F/35B glycoconjugate comprises at least 0.5, 0.6 or 0.7 mM acetate per mM serotype 35B polysaccharide. In a preferred embodiment, the serotypes 33F/35B glycoconjugate comprises at least 0.6 mM acetate per mM serotype 35B polysaccharide. In a preferred embodiment, the serotypes 33F/35B glycoconjugate comprises at least 0.7 mM acetate per mM serotype 35B polysaccharide.

The serotypes 33F/35B glycoconjugates may also be characterized by their molecular size distribution ($K_d$). Size exclusion chromatography media (CL-4B) can be used to determine the relative molecular size distribution of the conjugate. Size Exclusion Chromatography (SEC) is used in gravity fed columns to profile the molecular size distribution of conjugates. Large molecules excluded from the pores in the media elute more quickly than small molecules. Fraction collectors are used to collect the column eluate. The fractions are tested colorimetrically by saccharide assay. For the determination of $K_d$, columns are calibrated to establish the fraction at which molecules are fully excluded ($V_0$), ($K_d$=0), and the fraction representing the maximum retention ($V_i$), ($K_d$=1). The fraction at which a specified sample attribute is reached ($V_e$), is related to $K_d$ by the expression, $K_d=(V_e-V_0)/(V_i-V_0)$.

In a preferred embodiment, at least 30% of the serotypes 33F/35B glycoconjugate has a $K_d$ below or equal to 0.3 in a CL-4B column. In a preferred embodiment, at least 40% of the serotypes 33F/35B glycoconjugate has a $K_d$ below or equal to 0.3 in a CL-4B column. In a preferred embodiment, at least 45%, 50%, 55%, 60%, 65%, 70%, 75%, 80%, or 85% of the serotypes 33F/35B glycoconjugate has a $K_d$ below or equal to 0.3 in a CL-4B column. In a preferred embodiment, at least 60% of the serotypes 33F/35B glycoconjugate has a $K_d$ below or equal to 0.3 in a CL-4B column. In a preferred embodiment, between 50% and 80% of the serotypes 33F/35B glycoconjugate has a $K_d$ below or equal to 0.3 in a CL-4B column. In a preferred embodiment, between 65% and 80% of the serotypes 33F/35B glycoconjugate has a $K_d$ below or equal to 0.3 in a CL-4B column.

The serotypes 33F/35B glycoconjugate of the invention may contain free saccharide that is not covalently conjugated to the carrier protein but is nevertheless present in the serotypes 33F/35B glycoconjugate composition. The free saccharide may be noncovalently associated with (i.e., noncovalently bound to, adsorbed to, or entrapped in or with) the serotypes 33F/35B glycoconjugate.

In a preferred embodiment, the serotypes 33F/35B glycoconjugate comprises less than about 50%, 45%, 40%, 35%, 30%, 25%, 20% or 15% of free serotypes 33F and 35B saccharide compared to the total amount of serotypes 33F and 35B saccharide. In a preferred embodiment the serotypes 33F/35B glycoconjugate comprises less than about 40% of free serotypes 33F and 35B saccharide compared to the total amount of serotypes 33F and 35B saccharide. In a preferred embodiment the serotypes 33F/35B glycoconjugate comprises less than about 25% of free serotypes 33F and 35B saccharide compared to the total amount of serotypes 33F and 35B saccharide. In a preferred embodiment the serotypes 33F/35B glycoconjugate comprises less than about 20% of free serotypes 33F and 35B saccharide compared to the total amount of serotypes 33F and 35B saccharide. In a preferred embodiment the serotypes 33F/35B glycoconjugate comprises less than about 15% of free serotypes 33F and 35B saccharide compared to the total amount of serotypes 33F and 35B saccharide.

In preferred embodiments, the serotype 33F/35B glycoconjugates of the invention are prepared using reductive amination.

Reductive amination involves two steps, (1) oxidation (activation) of the saccharide, (2) reduction of the activated saccharide and a carrier protein (e.g., $CRM_{197}$, DT, TT or PD) to form a conjugate. Before oxidation, sizing of the serotype 33F and/or 35B saccharide to a target molecular weight (MW) range can be performed. Mechanical or chemical hydrolysis may be employed. Chemical hydrolysis may be conducted using acetic acid. Advantageously, the size of the purified serotype 33F and/or 35B saccharide is reduced while preserving critical features of the structure of the saccharide such as for example the presence of O-acetyl groups. Therefore preferably, the size of the purified serotype 33F and/or 35B saccharide is reduced by mechanical homogenization.

In an embodiment, serotypes 33F and 35B saccharides are activated (oxidized) by a process comprising the step of:

(a) reacting a mixture of isolated serotypes 33F and 35B saccharides with an oxidizing agent. Said process can further comprise a quenching step.

Therefore, in an embodiment, serotypes 33F and 35B saccharides are activated (oxidized) by a process comprising the step of:

(a) reacting a mixture of isolated serotypes 33F and 35B saccharides with an oxidizing agent;
(b) quenching the oxidation reaction by addition of a quenching agent resulting in activated serotypes 33F and 35B saccharides.

In these embodiments, the saccharides are therefore activated altogether as a mixture.

In another embodiment, serotypes 33F and 35B saccharides are activated (oxidized) separately and the activated saccharides are then mixed.

In said embodiment, serotypes 33F and 35B saccharides are activated (oxidized) by a process comprising the step of:

(a) individually reacting an isolated serotypes 33F and 35B saccharides with an oxidizing agent;
(b) mixing the activated serotypes 33F and 35B saccharides.

Said process can further comprise a quenching step.

Therefore, in an embodiment, serotypes 33F and 35B saccharides are activated (oxidized) by a process comprising the step of:

(a) individually reacting an isolated serotypes 33F and 35B saccharides with an oxidizing agent;
(b) quenching the oxidation reactions by addition of a quenching agent resulting in activated serotypes 33F and 35B saccharides;
(b) mixing the activated serotypes 33F and 35B saccharides.

The oxidation step may involve reaction with periodate. For the purpose of the present invention, the term "periodate" includes both periodate and periodic acid; the term also includes both metaperiodate ($IO_4^-$) and orthoperiodate ($IO_6^{5-}$) and the various salts of periodate (e.g., sodium periodate and potassium periodate).

In a preferred embodiment, the oxidizing agent is sodium periodate. In a preferred embodiment, the periodate used for the oxidation of serotypes 33F and 35B saccharides is metaperiodate. In a preferred embodiment the periodate used for the oxidation of serotypes 33F and 35B saccharides is sodium metaperiodate.

In one embodiment, the quenching agent is selected from vicinal diols, 1,2-aminoalcohols, amino acids, glutathione, sulfite, bisulfate, dithionite, metabisulfite, thiosulfate, phosphites, hypophosphites or phosphorous acid.

In one embodiment, the quenching agent is a 1,2-aminoalcohols of formula (I):

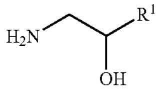

(I)

wherein $R^1$ is selected from H, methyl, ethyl, propyl or isopropyl.

In one embodiment, the quenching agent is selected from sodium and potassium salts of sulfite, bisulfate, dithionite, metabisulfite, thiosulfate, phosphites, hypophosphites or phosphorous acid.

In one embodiment, the quenching agent is an amino acid. In such embodiments, said amino acid may be selected from serine, threonine, cysteine, cystine, methionine, proline, hydroxyproline, tryptophan, tyrosine, and histidine.

In one embodiment, the quenching agent is a sulfite such as bisulfate, dithionite, metabisulfite, thiosulfate.

In one embodiment, the quenching agent is a compound comprising two vicinal hydroxyl groups (vicinal diols), i.e., two hydroxyl groups covalently linked to two adjacent carbon atoms.

Preferably, the quenching agent is a compound of formula (II):

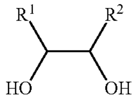

(II)

wherein $R^1$ and $R^2$ are each independently selected from H, methyl, ethyl, propyl or isopropyl.

In a preferred embodiment, the quenching agent is glycerol, ethylene glycol, propan-1,2-diol, butan-1,2-diol or butan-2,3-diol, or ascorbic acid. In a preferred embodiment, the quenching agent is butan-2,3-diol.

In a preferred embodiment, the isolated serotypes 33F and 35B saccharides are activated by a process comprising the step of:

(a) reacting a mixture of isolated serotypes 33F and 35B saccharides with periodate;
(b) quenching the oxidation reaction by addition of butan-2,3-diol resulting in a mixture of activated serotypes 33F and 35B saccharides.

Following the oxidation step of the saccharides, the saccharides are said to be activated and is referred to as "activated saccharides" here below.

In a preferred embodiment, the activated serotypes 33F and 35B saccharides are purified. The activated serotypes 33F and 35B saccharides are purified according to methods known to the man skilled in the art such as gel permeation chromatography (GPC), dialysis or ultrafiltration/diafiltration. For example, the activated serotypes 33F and 35B saccharides are purified by concentration and diafiltration using an ultrafiltration device.

In a preferred embodiment the degree of oxidation of the activated serotypes 33F and 35B saccharides are between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25. In a preferred embodiment the degree of oxidation of the activated serotype 33F and 35B polysaccharide is between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20.

In a preferred embodiment, the activated serotypes 33F and 35B saccharides have a molecular weight of between 10 kDa and 5,000 kDa; between 20 kDa and 4,000 kDa; between 50 kDa and 3,000 kDa; between 100 kDa and 2500 kDa; 100 kDa and 2,000 kDa; between 150 kDa and 2,000 kDa; between 150 kDa and 1,500 kDa; between 10 kDa and 2,000 kDa; between 20 kDa and 1,500 kDa; between 30 kDa and 1,250 kDa; between 50 kDa and 1,000 kDa; between 70 kDa and 900 kDa; between 100 kDa and 800 kDa; between 200 kDa to 600 kDa or between 400 kDa to 700 kDa.

In an embodiment, the activated serotypes 33F and 35B saccharides have a molecular weight between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa. Any whole number integer within any of the above ranges is contemplated as an embodiment of the disclosure.

In an embodiment, the activated serotypes 33F and 35B saccharides have a molecular weight between 25 kDa and 3,000 kDa, between 50 kDa and 2,000 kDa, between 100 kDa and 1,500 kDa, between 100 kDa and 1,000 kDa, between 300 kDa and 800 kDa, between 300 kDa and 700 kDa, between 300 kDa and 600 kDa, between 400 kDa and 1,000 kDa, between 400 kDa and 800 kDa, between 400 kDa and 700 kDa or between 400 kDa and 600 kDa. In an embodiment, the activated serotypes 33F and 35B saccharides have a molecular weight between 100 kDa and 3,000 kDa, between 200 kDa and 2,000 kDa, between 250 kDa and 1,500 kDa, between 250 kDa and 1,000 kDa, between 250 kDa and 800 kDa, between 250 kDa and 700 kDa, between 250 kDa and 600 kDa, between 300 kDa and 1,000 kDa, between 300 kDa and 800 kDa, between 300 kDa and 700 kDa or between 300 kDa and 600 kDa.

In an embodiment, the activated serotypes 33F and 35B saccharides have a molecular weight between 300 kDa and 800 kDa. In an embodiment, the activated serotypes 33F and 35B saccharides have a molecular weight between 400 kDa and 600 kDa.

In a preferred embodiment, the activated serotypes 33F and 35B saccharides have a molecular weight between 400 kda and 600 kDa and a degree of oxidation between 10 and 25, between 10 and 20, between 12 and 20 or between 14 and 18. In a preferred embodiment, the activated serotypes 33F and 35B saccharides have a molecular weight between 400 kDa and 600 kDa and a degree of oxidation between 10 and 20.

The activated polysaccharides and/or the carrier protein may be lyophilised (freeze-dried), either independently (discrete lyophilization) or together (co-lyophilized).

In an embodiment, the activated serotypes 33F and 35B saccharides are lyophilized, optionally in the presence of saccharide such as sucrose, trehalose, raffinose, stachyose, melezitose, dextran, mannitol, lactitol or palatinit. In a preferred embodiment, the saccharide is sucrose. In one embodiment, the lyophilized activated serotypes 33F and 35B saccharides are then compounded with a solution comprising the carrier protein.

In another embodiment the activated serotypes 33F and 35B saccharides and the carrier protein are co-lyophilised. In such embodiments, the activated serotypes 33F and 35B saccharides are compounded with the carrier protein and lyophilized, optionally in the presence of a saccharide such as sucrose, trehalose, raffinose, stachyose, melezitose, dextran, mannitol, lactitol and palatinit. In a preferred embodiment, the saccharide is sucrose. The co-lyophilized activated serotypes 33F and 35B saccharides and carrier protein can then be resuspended in solution and reacted with a reducing agent.

The second step of the conjugation process is the reduction of the activated saccharides and a carrier protein to form a conjugate (reductive amination), using a reducing agent.

The activated serotypes 33F and 35B saccharides can be conjugated to a carrier protein by a process comprising the step of:

(c) compounding the activated serotypes 33F and 35B saccharides with a carrier protein; and (d) reacting the compounded activated serotypes 33F and 35B saccharides and carrier protein with a reducing agent to form a serotypes 33F/35B glycoconjugate.

In an embodiment, the reduction reaction is carried out in aqueous solvent. Preferably though, the reaction is carried out in aprotic solvent. In a preferred embodiment, the reduction reaction is carried out in DMSO (dimethylsulfoxide) or in DMF (dimethylformamide)) solvent. The DMSO or DMF solvent may be used to reconstitute the activated serotypes 33F and 35B saccharides and carrier protein which have been lyophilised.

The conjugation of activated serotypes 33F and 35B saccharides with a protein carrier by reductive amination in dimethylsulfoxide (DMSO) is suitable to preserve the O-acetyl content of the saccharides as compared, for example, to reductive amination in aqueous phase where the level of O-acetylation of the saccharides may be significantly reduced. Therefore, in a preferred embodiment, step (c) and step (d) are carried out in DMSO.

In an embodiment, the reducing agent is sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^i$PrN—$BH_3$, benzylamine-$BH_3$ or 5-ethyl-2-methylpyridine borane (PEMB). In a preferred embodiment, the reducing agent is sodium cyanoborohydride.

At the end of the reduction reaction, there may be unreacted aldehyde groups remaining in the conjugates, these may be capped using a suitable capping agent. In one embodiment this capping agent is sodium borohydride ($NaBH_4$).

Following conjugation of serotypes 33F and 35B saccharides to the carrier protein, the glycoconjugate can be purified (enriched with respect to the amount of saccharide-protein conjugate) by a variety of techniques known to the skilled person. These techniques include dialysis, concentration/diafiltration operations, tangential flow filtration precipitation/elution, column chromatography (DEAE or hydrophobic interaction chromatography), and depth filtration.

2 IMMUNOGENIC COMPOSITIONS OF THE INVENTION

2.1 Immunogenic Compositions Comprising at Least One Glycoconjugate as Disclosed at Section 1 Above The immunogenic compositions of the present invention will typically comprise at least one glycoconjugate as disclosed at section 1 above.

In an embodiment, the immunogenic composition of the present invention comprises one of the glycoconjugates disclosed at section 1 above. In another embodiment, the immunogenic composition of the present invention comprises two of the glycoconjugates disclosed at section 1 above. In an embodiment, the immunogenic composition of the present invention comprises three or more of the glycoconjugates disclosed at section 1 above.

In an embodiment, the immunogenic composition of the present invention comprises one serotypes 8/15A/15B glycoconjugate and one serotypes 23A/23B glycoconjugate.

In an embodiment, the immunogenic composition of the present invention comprises one serotypes 8/15A/23A glycoconjugate and one serotypes 15B/23B glycoconjugate.

In an embodiment, the immunogenic composition of the present invention comprises one serotypes 8/15A/23B glycoconjugate and one serotypes 15B/23A glycoconjugate.

In an embodiment, the immunogenic composition of the present invention comprises one serotypes 8/15B/23A glycoconjugate and one serotypes 15A/23B glycoconjugate.

In an embodiment, the immunogenic composition of the present invention comprises one serotypes 8/15B/23B glycoconjugate and one serotypes 15A/23A glycoconjugate.

In an embodiment, the immunogenic composition of the present invention comprises one serotypes 8/23A/23B glycoconjugate and one serotypes 15A/15B glycoconjugate.

In an embodiment, the immunogenic composition of the present invention comprises one serotypes 15A/15B/23A glycoconjugate and one serotypes 8/23B glycoconjugate.

In an embodiment, the immunogenic composition of the present invention comprises one serotypes 15A/15B/23B glycoconjugate and one serotypes 8/23A glycoconjugate.

In an embodiment, the immunogenic composition of the present invention comprises one serotypes 15A/23A/23B glycoconjugate and one serotypes 8/15B glycoconjugate.

In an embodiment, the immunogenic composition of the present invention comprises one serotypes 15B/23A/23B glycoconjugate and one serotypes 8/15A glycoconjugate.

In an embodiment, the immunogenic composition of the present invention comprises one serotypes 8/15A glycoconjugate and one serotypes 15B/23A, 15B/23B or 23A/23B glycoconjugate.

In an embodiment, the immunogenic composition of the present invention comprises one serotypes 8/15B glycoconjugate and one serotypes 15A/23A, 15A/23B or 23A/23B glycoconjugate.

In an embodiment, the immunogenic composition of the present invention comprises one serotypes 8/23A glycoconjugate and one serotypes 15A/23B, 15B/23B or 15A/15B glycoconjugate.

In an embodiment, the immunogenic composition of the present invention comprises one serotypes 8/23B glycoconjugate and one serotypes 15A/23A, 15B/23A or 15A/15B glycoconjugate.

In an embodiment, the immunogenic composition of the present invention comprises one serotypes 15A/15B glycoconjugate and one serotypes 8/23A, 8/23B or 23A/23B glycoconjugate.

In an embodiment, the immunogenic composition of the present invention comprises one serotypes 15A/23A glycoconjugate and one serotypes 8/15B, 8/23B or 15B/23B glycoconjugate.

In an embodiment, the immunogenic composition of the present invention comprises one serotypes 15A/23B glycoconjugate and one serotypes 8/15B, 8/23A or 15B/23A glycoconjugate.

In an embodiment, the immunogenic composition of the present invention comprises one serotypes 15B/23A glycoconjugate and one serotypes 8/15A, 8/23B or 15A/23B glycoconjugate.

In an embodiment, the immunogenic composition of the present invention comprises one serotypes 15B/23B glycoconjugate and one serotypes 8/15A, 8/23A or 15A/23A glycoconjugate.

In an embodiment, the immunogenic composition of the present invention comprises one serotypes 23A/23B glycoconjugate and one serotypes 8/15A, 8/15B or 15A/15B glycoconjugate.

In an embodiment, the immunogenic composition of the present invention comprises one serotypes 8/11A/12F glycoconjugate and one serotypes 23A/23B glycoconjugate.

In an embodiment, the immunogenic composition of the present invention comprises one serotypes 8/11A/23A glycoconjugate and one serotypes 12F/23B glycoconjugate.

In an embodiment, the immunogenic composition of the present invention comprises one serotypes 8/11A/23B glycoconjugate and one serotypes 12F/23A glycoconjugate.

In an embodiment, the immunogenic composition of the present invention comprises one serotypes 8/12F/23A glycoconjugate and one serotypes 11A/23B glycoconjugate.

In an embodiment, the immunogenic composition of the present invention comprises one serotypes 8/12F/23B glycoconjugate and one serotypes 11A/23A glycoconjugate.

In an embodiment, the immunogenic composition of the present invention comprises one serotypes 8/23A/23B glycoconjugate and one serotypes 11A/12F glycoconjugate.

In an embodiment, the immunogenic composition of the present invention comprises one serotypes 11A/12F/23A glycoconjugate and one serotypes 8/23B glycoconjugate.

In an embodiment, the immunogenic composition of the present invention comprises one serotypes 11A/12F/23B glycoconjugate and one serotypes 8/23A glycoconjugate.

In an embodiment, the immunogenic composition of the present invention comprises one serotypes 11A/23A/23B glycoconjugate and one serotypes 8/12F glycoconjugate.

In an embodiment, the immunogenic composition of the present invention comprises one serotypes 12F/23A/23B glycoconjugate and one serotypes 8/11A glycoconjugate.

In an embodiment, the immunogenic composition of the present invention comprises one serotypes 8/11A glycoconjugate and one serotypes 12F/23A, 12F/23B or 23A/23B glycoconjugate.

In an embodiment, the immunogenic composition of the present invention comprises one serotypes 8/12F glycoconjugate and one serotypes 11A/23A, 11A/23B or 23A/23B glycoconjugate.

In an embodiment, the immunogenic composition of the present invention comprises one serotypes 8/23A glycoconjugate and one serotypes 11A/23B, 12F/23B or 11A/12F glycoconjugate.

In an embodiment, the immunogenic composition of the present invention comprises one serotypes 8/23B glycoconjugate and one serotypes 11A/23A, 12F/23A or 11A/12F glycoconjugate.

In an embodiment, the immunogenic composition of the present invention comprises one serotypes 11A/12F glycoconjugate and one serotypes 8/23A, 8/23B or 23A/23B glycoconjugate.

In an embodiment, the immunogenic composition of the present invention comprises one serotypes 11A/23A glycoconjugate and one serotypes 8/12F, 8/23B or 12F/23B glycoconjugate.

In an embodiment, the immunogenic composition of the present invention comprises one serotypes 11A/23B glycoconjugate and one serotypes 8/12F, 8/23A or 12F/23A glycoconjugate.

In an embodiment, the immunogenic composition of the present invention comprises one serotypes 12F/23A glycoconjugate and one serotypes 8/11A, 8/23B or 11A/23B glycoconjugate.

In an embodiment, the immunogenic composition of the present invention comprises one serotypes 12F/23B glycoconjugate and one serotypes 8/11A, 8/23A or 11A/23A glycoconjugate.

In an embodiment, the immunogenic composition of the present invention comprises one serotypes 23A/23B glycoconjugate and one serotypes 8/11A, 8/12F or 11A/12F glycoconjugate.

In an embodiment, the immunogenic composition of the present invention comprises one serotypes 10A/22F glycoconjugate (such as the one disclosed at section 1.3.3.6 above) and one serotypes 33F/35B glycoconjugate such as the one disclosed at section 1.3.3.11 above).

In an embodiment, the immunogenic composition of the present invention comprises one serotypes 10A/33F glycoconjugate (such as the one disclosed at section 1.3.3.7 above) and one serotypes 22F/35B glycoconjugate such as the one disclosed at section 1.3.3.10 above).

In an embodiment, the immunogenic composition of the present invention comprises one serotypes 10A/35B glycoconjugate (such as the one disclosed at section 1.3.3.8 above) and one serotypes 22F/33F glycoconjugate (such as the one disclosed at section 1.3.3.9 above).

2.2 Immunogenic Composition of the Invention Comprising Further Glycoconjugates

In an embodiment, the immunogenic composition of the invention, in particular the immunogenic composition of section 2.1 can comprise further glycoconjugates. In an embodiment any of the immunogenic composition of section 2.1 further comprises at least one glycoconjugate selected from the group consisting of a glycoconjugate from *S. pneumoniae* serotype 1, 3, 4, 5, 6A, 6B, 7F, 8, 9V, 10A, 11A, 12F, 14, 15A, 15B, 18C, 19A, 19F, 22F, 23A, 23B, 23F and 33F. Preferably, said additional glycoconjugates are individually conjugated glycoconjugates (i.e. the capsular saccharides are separately conjugated to the carrier protein and each molecule of the protein carrier only carry one type of saccharide conjugated to it). In said embodiment, the capsular saccharides are said to be individually conjugated to the carrier protein.

Capsular polysaccharides from serotypes 1, 3, 4, 5, 6A, 6B, 7F, 8, 9V, 10A, 11A, 12F, 14, 15A, 15B, 18C, 19A, 19F, 22F, 23A, 23B, 23F and 33F of *S. pneumoniae* are prepared by standard techniques known to those of ordinary skill in the art (see for example WO 2006/110381, WO 2008/118752, WO 2006/110352, WO2015/110941 and U.S. Patent App. Pub. Nos. 2006/0228380, 2006/0228381, 2008/0102498 and 2008/0286838).

In an embodiment, the polysaccharides are activated with 1-cyano-4-dimethylamino pyridinium tetrafluoroborate (CDAP) to form a cyanate ester. The activated polysaccharide is then coupled directly or via a spacer (linker) group to an amino group on the carrier protein (such as the one of section 1.2, preferably $CRM_{197}$). For example, the spacer could be cystamine or cysteamine to give a thiolated polysaccharide which could be coupled to the carrier via a thioether linkage obtained after reaction with a maleimide-activated carrier protein (for example using N-[γ-maleimidobutyrloxy]succinimide ester (GMBS)) or a haloacetylated carrier protein (for example using iodoacetimide, N-succinimidyl bromoacetate (SBA; SIB), N-succinimidyl(4-iodoacetyl)aminobenzoate (SIAB), sulfosuccinimidyl(4-iodoacetyl)aminobenzoate (sulfo-SIAB), N-succinimidyl iodoacetate (SIA) or succinimidyl 3-[bromoacetamido]proprionate (SBAP)). Preferably, the cyanate ester (optionally made by CDAP chemistry) is coupled with hexane diamine or adipic acid dihydrazide (ADH) and the amino-derivatised saccharide is conjugated to the carrier protein (e.g., $CRM_{197}$) using carbodiimide (e.g., EDAC or EDC) chemistry via a carboxyl group on the protein carrier. Such conjugates are described for example in WO 93/15760, WO 95/08348 and WO 96/129094.

Other suitable techniques for conjugation use carbodiimides, hydrazides, active esters, norborane, p-nitrobenzoic acid, N-hydroxysuccinimide, S—NHS, EDC, TSTU. Many are described in International Patent Application Publication No. WO 98/42721. Conjugation may involve a carbonyl linker which may be formed by reaction of a free hydroxyl group of the saccharide with 1,1'-carbonyldiimidazole (CDI) (see Bethell et al. (1979) J. Biol. Chem. 254:2572-2574; Hearn et al. (1981) J. Chromatogr. 218:509-518) followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

In a preferred embodiment, at least one of capsular polysaccharides from serotypes 1, 3, 4, 5, 6A, 6B, 7F, 8, 9V, 10A, 11A, 12F, 14, 15A, 15B, 18C, 19A, 19F, 22F, 23A, 23B, 23F and 33F of *S. pneumoniae* is conjugated to the carrier protein (such as the one of section 1.2, preferably $CRM_{197}$) by reductive amination (such as described in U.S. Patent Appl. Pub. Nos. 2006/0228380, 2007/0231340, 2007/0184071 and 2007/0184072, WO 2006/110381, WO 2008/079653, and WO 2008/143709). In a preferred embodiment, the capsular polysaccharides from serotypes 1, 3, 4, 5, 6A, 6B, 7F, 8, 9V, 10A, 11A, 12F, 14, 15B, 18C, 19A, 19F, 22F and 23F of *S. pneumoniae* are conjugated to the carrier protein (such as the one of section 1.2, preferably $CRM_{197}$) by reductive amination. In an embodiment, the capsular polysaccharides from serotypes 1, 3, 4, 5, 6A, 6B, 7F, 8, 9V, 10A, 11A, 12F, 14, 15B, 18C, 19A, 19F, 22F, 23F and 33F of *S. pneumoniae* are conjugated to the carrier protein (such as the one of section 1.2, preferably $CRM_{197}$) by reductive amination.

In an embodiment any of the immunogenic compositions of section 2.1 further comprises glycoconjugates from *S. pneumoniae* serotypes 4, 6B, 9V, 14, 18C, 19F and 23F (such as the glycoconjugates of section 1.3.1 of WO2015/110941).

In an embodiment any of the immunogenic compositions above comprise in addition glycoconjugates from *S. pneumoniae* serotypes 1, 5 and 7F (such as the glycoconjugates of section 1.3.1 of WO2015/110941).

In an embodiment any of the immunogenic compositions above comprise in addition glycoconjugates from *S. pneumoniae* serotypes 6A and 19A (such as the glycoconjugates of section 1.3.1 of WO2015/110941).

In an embodiment any of the immunogenic compositions above comprise in addition a glycoconjugate from *S. pneumoniae* serotype 3 (such as the glycoconjugates of section 1.3.1 of WO2015/110941).

In an embodiment any of the immunogenic compositions above comprise in addition a glycoconjugate from *S. pneumoniae* serotype 22F (such as the glycoconjugates of section 1.3.2 of WO2015/110941).

In an embodiment any of the immunogenic compositions above comprise in addition a glycoconjugate from *S. pneumoniae* serotype 33F (such as the glycoconjugates of section 1.3.3 of WO2015/110941).

In an embodiment any of the immunogenic compositions above comprise in addition a glycoconjugate from *S. pneumoniae* serotype 15B (such as the glycoconjugates of section 1.3.4 of WO2015/110941).

In an embodiment any of the immunogenic compositions above comprise in addition a glycoconjugate from *S. pneumoniae* serotype 12F (such as the glycoconjugates of section 1.3.5 of WO2015/110941).

In an embodiment any of the immunogenic compositions above comprise in addition a glycoconjugate from *S. pneumoniae* serotype 10A (such as the glycoconjugates of section 1.3.6 of WO2015/110941).

In an embodiment any of the immunogenic compositions above comprise in addition a glycoconjugate from *S. pneumoniae* serotype 11A (such as the glycoconjugates of section 1.3.7 of WO2015/110941).

In an embodiment any of the immunogenic compositions above comprise in addition a glycoconjugate from *S. pneumoniae* serotype 8 (such as the glycoconjugates of section 1.3.8 of WO2015/110941).

In an embodiment the immunogenic composition of the invention comprise at least one glycoconjugate of each of the two *S. pneumoniae* serotypes selected from the group consisting of: 22F and 33F, 22F and 12F, 22F and 10A, 22F and 11A, 33F and 12F, 33F and 10A, 33F and 11A, 12F and 10A, 12F and 11A and 10A and 11A.

In an embodiment the immunogenic composition of the invention comprises at least one glycoconjugate of each of the three following *S. pneumoniae* serotypes:

22F and 33F and 12F,
22F and 33F and 10A,
22F and 33F and 11A,
22F and 12F and 10A,
22F and 12F and 11A,
22F and 10A and 11A,
33F and 12F and 10A,
33F and 12F and 11A,
33F and 10A and 11A, or
12F and 10A and 11A.

In an embodiment the immunogenic composition of the invention comprises at least one glycoconjugate of each of the four following *S. pneumoniae* serotypes:

22F and 33F and 12F and 10A,
22F and 33F and 12F and 11A,
22F and 33F and 10A and 11A,
22F and 12F and 10A and 11A, or
33F and 12F and 10A and 11A.

In an embodiment the immunogenic composition of the invention comprises at least one glycoconjugate of each of the five following *S. pneumoniae* serotypes: 22F and 33F and 12F and 10A and 11A.

In an embodiment any of the immunogenic compositions above comprise in addition a glycoconjugate from *S. pneumoniae* serotype 8 (such as the glycoconjugates of section 1.3.8 of WO2015/110941).

In an embodiment any of the immunogenic compositions above comprise in addition a glycoconjugate from *S. pneumoniae* serotype 15B (such as the glycoconjugates of section 1.3.4 of WO2015/110941).

Preferably, all the additional glycoconjugates of the above immunogenic compositions (in section 2.2.1) are individually conjugated to the carrier protein.

In an embodiment of any of the above immunogenic compositions, the glycoconjugates from *S. pneumoniae* serotype 22F is conjugated to $CRM_{197}$. In an embodiment of any of the above immunogenic compositions, the glycoconjugates from *S. pneumoniae* serotype 33F is conjugated to $CRM_{197}$. In an embodiment of any of the above immunogenic compositions, the glycoconjugates from *S. pneumoniae* serotype 15B is conjugated to $CRM_{197}$. In an embodiment of any of the above immunogenic compositions, the glycoconjugates from *S. pneumoniae* serotype 12F is conjugated to $CRM_{197}$. In an embodiment of any of the above immunogenic compositions, the glycoconjugates from *S. pneumoniae* serotype 10A is conjugated to $CRM_{197}$. In an embodiment of any of the above immunogenic compositions, the glycoconjugates from *S. pneumoniae* serotype 11A is conjugated to $CRM_{197}$. In an embodiment of any of the above immunogenic compositions, the glycoconjugates from *S. pneumoniae* serotype 8 is conjugated to $CRM_{197}$. In an embodiment of any of the above immunogenic compositions, the glycoconjugates from *S. pneumoniae* serotypes 4, 6B, 9V, 14, 18C, 19F and 23F are conjugated to $CRM_{197}$. In an embodiment of any of the above immunogenic compositions, the glycoconjugates from *S. pneumoniae* serotypes 1, 5 and 7F are conjugated to $CRM_{197}$. In an embodiment of any of the above immunogenic compositions, the glycoconjugates from *S. pneumoniae* serotypes 6A and 19A are conjugated to $CRM_{197}$. In an embodiment of any of the above immunogenic compositions, the glycoconjugates from *S. pneumoniae* serotype 3 is conjugated to $CRM_{197}$.

In an embodiment, the further glycoconjugates of any of the above immunogenic compositions of this section are all individually conjugated to $CRM_{197}$.

In an embodiment, the further glycoconjugates from *S. pneumoniae* serotypes 1, 4, 5, 6B, 7F, 9V, 14 and/or 23F of any of the above immunogenic compositions of this section are individually conjugated to PD.

In an embodiment, the further glycoconjugate from *S. pneumoniae* serotype 18C of any of the above immunogenic compositions of this section is conjugated to TT.

In an embodiment, the further glycoconjugate from *S. pneumoniae* serotype 19F of any of the above immunogenic compositions of this section is conjugated to DT.

In an embodiment, the further glycoconjugates from *S. pneumoniae* serotypes 1, 4, 5, 6B, 7F, 9V, 14 and/or 23F of any of the above immunogenic compositions of this section are individually conjugated to PD, the further glycoconjugate from *S. pneumoniae* serotype 18C is conjugated to TT and the further glycoconjugate from *S. pneumoniae* serotype 19F is conjugated to DT.

In an embodiment the above immunogenic compositions comprise from 2 to 20 different serotypes of *S. pneumoniae*. In one embodiment the above immunogenic compositions comprise saccharides from 2, 3, 4, 5, 6, 7, 8, 9, 10, 11, 12, 13, 14, 15, 16, 17, 18, 19 or 20 different serotypes of *S. pneumoniae*.

In an embodiment the above immunogenic compositions are 2, 3, 4, 5, 6, 7, 8, 9, 10, 11, 12, 13, 14, 15, 16, 17, 18, 19 or 20-valent pneumococcal conjugate compositions (valency being defined by the number of different serotypes of *S. pneumoniae* contained in the composition, a mono-valent glycoconjugate counting for 1, a 2-valent glycoconjugatre counting for 2 etc. . . . ). In an embodiment the above immunogenic compositions are 2, 3, 4 or 5-valent pneumococcal conjugate compositions. In an embodiment the above immunogenic compositions are 6, 7, 8, 9, 10, 11, 12, 13, 14, 15, 16, 17, 18, 19, 20, 21, 22 or 23-valent pneumococcal conjugate compositions. In an embodiment the above immunogenic compositions are 18-valent pneumococcal conjugate compositions. In an embodiment the above immunogenic compositions are 20-valent pneumococcal conjugate compositions. In an embodiment the above immunogenic compositions are 23-valent pneumococcal conjugate compositions.

After conjugation of the capsular polysaccharide to the carrier protein, the glycoconjugates are purified (enriched with respect to the amount of polysaccharide-protein conjugate) by a variety of techniques. These techniques include concentration/diafiltration operations, precipitation/elution, column chromatography, and depth filtration (see for example U.S. Patent App. Pub. No. 2007/0184072 or WO 2008/079653). After the individual glycoconjugates are purified, they are compounded to formulate the immunogenic composition of the present invention.

3 DOSAGE OF THE IMMUNOGENIC COMPOSITIONS

The amount of glycoconjugate(s) in each dose is selected as an amount which induces an immunoprotective response without significant, adverse side effects in typical vaccinees. Such amount will vary depending upon which specific immunogen is employed and how it is presented.

3.1 Glycoconjugate Amount

The amount of a particular glycoconjugate in an immunogenic composition can be calculated based on total saccharide for that conjugate (conjugated and non-conjugated). For example, a glycoconjugate with 20% free saccharide will have about 80 μg of conjugated saccharide and about 20 μg of nonconjugated saccharide in a 100 μg saccharide dose. The amount of glycoconjugate can vary depending upon the pneumococcal serotype. The saccharide concentration can be determined by the uronic acid assay.

The "immunogenic amount" of the different saccharide components in the immunogenic composition, may diverge and each may comprise about 1 μg, about 2 μg, about 3 μg, about 4 μg, about 5 μg, about 6 μg, about 7 μg, about 8 μg, about 9 μg, about 10 μg, about 15 μg, about 20 μg, about 30 μg, about 40 μg, about 50 μg, about 60 μg, about 70 μg, about 80 μg, about 90 μg, or about 100 μg of any particular saccharide antigen.

Generally, each dose will comprise 0.1 μg to 100 μg of saccharide for a given serotype, particularly 0.5 μg to 20 μg, more particularly 1.0 μg to 10 μg, and even more more particularly 2.0 μg to 5.0 μg. Any whole number integer within any of the above ranges is contemplated as an embodiment of the disclosure.

3.2 Carrier Amount

Generally, each dose will comprise 10 μg to 150 μg of carrier protein, particularly 15 μg to 100 μg of carrier protein, more particularly 25 μg to 75 μg of carrier protein, and even more particularly 40 μg to 60 μg of carrier protein. In an embodiment, said carrier protein is $CRM_{197}$. In an embodiment, each dose will comprise about 25 μg, about 26 μg, about 27 μg, about 28 μg, about 29 μg, about 30 μg, about 31 μg, about 32 μg, about 33 μg, about 34 μg, about 35 μg, about 36 μg, about 37 μg, about 38 μg, about 39 μg, about 40 μg, about 41 μg, about 42 μg, about 43 μg, about 44 μg, about 45 μg, about 46 μg, about 47 μg, about 48 μg, about 49 μg, about 50 μg, about 51 μg, about 52 μg, about 53 μg, about 54 μg, about 55 μg, about 56 μg, about 57 μg, about 58 μg, about 59 μg, about 60 μg, about 61 μg, about 62 μg, about 63 μg, about 64 μg, about 65 μg, about 66 μg, about 67 μg, about 68 μg, about 69 μg, about 70 μg, about 71 μg, about 72 μg, about 73 μg, about 74 μg or about 75 μg of carrier protein. In an embodiment, said carrier protein is $CRM_{197}$.

4 Further Antigens

Immunogenic compositions of the invention comprise conjugated *S. pneumoniae* saccharide antigens (glycoconjugates). They may also further include antigens from other pathogens, particularly from bacteria and/or viruses. Preferred further antigens are selected from: a diphtheria toxoid (D), a tetanus toxoid (T), a pertussis antigen (P), which is typically acellular (Pa), a hepatitis B virus (HBV) surface antigen (HBsAg), a hepatitis A virus (HAV) antigen, a conjugated *Haemophilus influenzae* type b capsular saccharide (Hib), inactivated poliovirus vaccine (IPV).

In an embodiment, the immunogenic compositions of the invention comprise D-T-Pa. In an embodiment, the immunogenic compositions of the invention comprise D-T-Pa-Hib, D-T-Pa-IPV or D-T-Pa-HBsAg. In an embodiment, the immunogenic compositions of the invention comprise D-T-Pa-HBsAg-IPV or D-T-Pa-HBsAg-Hib. In an embodiment, the immunogenic compositions of the invention comprise D-T-Pa-HBsAg-IPV-Hib.

Pertussis antigens: *Bordetella pertussis* causes whooping cough. Pertussis antigens in vaccines are either cellular (whole cell, in the form of inactivated *B. pertussis* cells) or acellular. Preparation of cellular pertussis antigens is well documented (e.g., it may be obtained by heat inactivation of phase I culture of *B. pertussis*). Preferably, however, the invention uses acellular antigens. Where acellular antigens are used, it is preferred to use one, two or (preferably) three of the following antigens: (1) detoxified pertussis toxin (pertussis toxoid, or PT); (2) filamentous hemagglutinin (FHA); (3) pertactin (also known as the 69 kiloDalton outer membrane protein). FHA and pertactin may be treated with formaldehyde prior to use according to the invention. PT is preferably detoxified by treatment with formaldehyde and/or glutaraldehyde. Acellular pertussis antigens are preferably adsorbed onto one or more aluminum salt adjuvants. As an alternative, they may be added in an unadsorbed state. Where pertactin is added then it is preferably already adsorbed onto an aluminum hydroxide adjuvant. PT and FHA may be adsorbed onto an aluminum hydroxide adjuvant or an aluminum phosphate. Adsorption of all of PT, FHA and pertactin to aluminum hydroxide is most preferred.

Inactivated poliovirus vaccine: Poliovirus causes poliomyelitis. Rather than use oral poliovirus vaccine, preferred embodiments of the invention use IPV. Prior to administration to patients, polioviruses must be inactivated, and this can be achieved by treatment with formaldehyde. Poliomyelitis can be caused by one of three types of poliovirus. The three types are similar and cause identical symptoms, but they are antigenically different and infection by one type does not protect against infection by others. It is therefore preferred to use three poliovirus antigens in the invention: poliovirus Type 1 (e.g., Mahoney strain), poliovirus Type 2 (e.g., MEF-1 strain), and poliovirus Type 3 (e.g., Saukett strain). The viruses are preferably grown, purified and inactivated individually, and are then combined to give a bulk trivalent mixture for use with the invention. Diphtheria toxoid: *Corynebacterium diphtheriae* causes diphtheria. Diphtheria toxin can be treated (e.g., using formalin or formaldehyde) to remove toxicity while retaining the ability to induce specific anti-toxin antibodies after injection. These diphtheria toxoids are used in diphtheria vaccines. Preferred diphtheria toxoids are those prepared by formaldehyde treatment. The diphtheria toxoid can be obtained by growing *C. diphtheriae* in growth medium, followed by formaldehyde treatment, ultrafiltration and precipitation. The toxoided material may then be treated by a process comprising sterile filtration and/or dialysis. The diphtheria toxoid is preferably adsorbed onto an aluminum hydroxide adjuvant.

Tetanus toxoid: *Clostridium tetani* causes tetanus. Tetanus toxin can be treated to give a protective toxoid. The toxoids are used in tetanus vaccines. Preferred tetanus toxoids are those prepared by formaldehyde treatment. The tetanus toxoid can be obtained by growing *C. tetani* in growth medium, followed by formaldehyde treatment, ultrafiltration and precipitation. The material may then be treated by a process comprising sterile filtration and/or dialysis.

Hepatitis A virus antigens: Hepatitis A virus (HAV) is one of the known agents which causes viral hepatitis. A preferred HAV component is based on inactivated virus, and inactivation can be achieved by formalin treatment.

Hepatitis B virus (HBV) is one of the known agents which causes viral hepatitis. The major component of the capsid is a protein known as HBV surface antigen or, more commonly, HBsAg, which is typically a 226-amino acid polypeptide with a molecular weight of −24 kDa. All existing hepatitis B vaccines contain HBsAg, and when this antigen is administered to a normal vaccinee it stimulates the production of anti-HBsAg antibodies which protect against HBV infection.

For vaccine manufacture, HBsAg has been made in two ways: purification of the antigen in particulate form from the plasma of chronic hepatitis B carriers or expression of the protein by recombinant DNA methods (e.g., recombinant expression in yeast cells). Unlike native HBsAg (i.e., as in the plasma-purified product), yeast-expressed HBsAg is generally non-glycosylated, and this is the most preferred form of HBsAg for use with the invention.

Conjugated *Haemophilus influenzae* type b antigens: *Haemophilus influenzae* type b (Hib) causes bacterial meningitis. Hib vaccines are typically based on the capsular saccharide antigen, the preparation of which is well documented. The Hib saccharide can be conjugated to a carrier protein in order to enhance its immunogenicity, especially in children. Typical carrier proteins are tetanus toxoid, diphtheria toxoid, $CRM_{197}$, *H. influenzae* protein D, and an outer membrane protein complex from serogroup B meningococcus. The saccharide moiety of the conjugate may comprise full-length polyribosylribitol phosphate (PRP) as prepared from Hib bacteria, and/or fragments of full-length PRP. Hib conjugates may or may not be adsorbed to an aluminum salt adjuvant.

In an embodiment the immunogenic compositions of the invention further include a conjugated *N. meningitidis* serogroup Y capsular saccharide (MenY), and/or a conjugated *N. meningitidis* serogroup C capsular saccharide (MenC).

In an embodiment the immunogenic compositions of the invention further include a conjugated *N. meningitidis* serogroup A capsular saccharide (MenA), a conjugated *N. meningitidis* serogroup W135 capsular saccharide (MenW135), a conjugated *N. meningitidis* serogroup Y capsular saccharide (MenY), and/or a conjugated *N. meningitidis* serogroup C capsular saccharide (MenC).

In an embodiment the immunogenic compositions of the invention further include a conjugated *N. meningitidis* serogroup W135 capsular saccharide (MenW135), a conjugated *N. meningitidis* serogroup Y capsular saccharide (MenY), and/or a conjugated *N. meningitidis* serogroup C capsular saccharide (MenC).

4 ADJUVANT(S)

In some embodiments, the immunogenic compositions disclosed herein may further comprise at least one, two or three adjuvants. The term "adjuvant" refers to a compound or mixture that enhances the immune response to an antigen. Antigens may act primarily as a delivery system, primarily as an immune modulator or have strong features of both. Suitable adjuvants include those suitable for use in mammals, including humans.

Examples of known suitable delivery-system type adjuvants that can be used in humans include, but are not limited to, alum (e.g., aluminum phosphate, aluminum sulfate or aluminum hydroxide), calcium phosphate, liposomes, oil-in-water emulsions such as MF59 (4.3% w/v squalene, 0.5% w/v polysorbate 80 (Tween 80), 0.5% w/v sorbitan trioleate (Span 85)), water-in-oil emulsions such as Montanide, and poly(D,L-lactide-co-glycolide) (PLG) microparticles or nanoparticles.

In an embodiment, the immunogenic compositions disclosed herein comprise aluminum salts (alum) as adjuvant (e.g., aluminum phosphate, aluminum sulfate or aluminum hydroxide). In a preferred embodiment, the immunogenic compositions disclosed herein comprise aluminum phosphate or aluminum hydroxide as adjuvant. In an embodiment, the immunogenic compositions disclosed herein comprise from 0.1 mg/mL to 1 mg/mL or from 0.2 mg/mL to 0.3 mg/mL of elemental aluminum in the form of aluminum phosphate. In an embodiment, the immunogenic compositions disclosed herein comprise about 0.25 mg/mL of elemental aluminum in the form of aluminum phosphate.

Examples of known suitable immune modulatory type adjuvants that can be used in humans include, but are not limited to, saponin extracts from the bark of the Aquilla tree (QS21, Quil A), TLR4 agonists such as MPL (Monophosphoryl Lipid A), 3DMPL (3-O-deacylated MPL) or GLA-AQ, LT/CT mutants, cytokines such as the various interleukins (e.g., IL-2, IL-12) or GM-CSF, and the like.

Examples of known suitable immune modulatory type adjuvants with both delivery and immune modulatory features that can be used in humans include, but are not limited to, ISCOMS (see, e.g., Sjölander et al. (1998) J. Leukocyte Biol. 64:713; WO 90/03184, WO 96/11711, WO 00/48630, WO 98/36772, WO 00/41720, WO 2006/134423 and WO 2007/026190) or GLA-EM which is a combination of a TLR4 agonist and an oil-in-water emulsion.

For veterinary applications including but not limited to animal experimentation, one can use Complete Freund's Adjuvant (CFA), Freund's Incomplete Adjuvant (IFA), Emulsigen, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further exemplary adjuvants to enhance effectiveness of the pneumococcal vaccines as disclosed herein include, but are not limited to: (1) oil-in-water emulsion formulations (with or without other specific immunostimulating agents such as muramyl peptides (see below) or bacterial cell wall components), such as for example (a) SAF, containing 10% Squalane, 0.4% Tween 80, 5% pluronic-blocked polymer L121, and thr-MDP either microfluidized into a submicron emulsion or vortexed to generate a larger particle size emulsion, and (b) RIBI™ adjuvant system (RAS), (Ribi Immunochem, Hamilton, MT) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (DETOX™); (2) saponin adjuvants, such as QS21, STIMULON™ (Cambridge Bioscience, Worcester, MA), ABISCO® (Isconova, Sweden), or ISCOMATRIX® (Commonwealth Serum Laboratories, Australia), may be used or particles generated therefrom such as ISCOMs (immunostimulating complexes), which ISCOMS may be devoid of additional detergent (e.g., WO 00/07621); (3) Complete Freund's Adjuvant (CFA) and Incomplete Freund's Adjuvant (IFA); (4) cytokines, such as interleukins (e.g., IL-1, IL-2, IL-4, IL-5, IL-6, IL-7, IL-12 (e.g., WO 99/44636)), interferons (e.g., gamma interferon), macrophage colony stimulating factor (M-CSF), tumor necrosis factor (TNF), etc.; (5) monophosphoryl lipid A (MPL) or 3-O-deacylated MPL (3dMPL) (see, e.g., GB-2220221, EP0689454), optionally in the substantial absence of alum when used with pneumococcal saccharides (see, e.g., WO 00/56358); (6) combinations of 3dMPL with, for example, QS21 and/or oil-in-water emulsions (see, e.g., EP0835318, EP0735898, EP0761231); (7) a polyoxyethylene ether or a polyoxyethylene ester (see, e.g., WO 99/52549); (8) a polyoxyethylene sorbitan ester surfactant in combination with an octoxynol (e.g., WO 01/21207) or a polyoxyethylene alkyl ether or ester surfactant in combination with at least one additional non-ionic surfactant such as an octoxynol (e.g., WO 01/21152); (9) a saponin and an immunostimulatory oligonucleotide (e.g., a CpG oligonucleotide) (e.g., WO 00/62800); (10) an immunostimulant and a particle of metal salt (see, e.g., WO 00/23105); (11) a saponin and an oil-in-water emulsion (e.g., WO 99/11241); (12) a saponin (e.g., QS21)+3dMPL+IM2 (optionally+a sterol) (e.g., WO 98/57659); (13) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc.

In an embodiment of the present invention, the immunogenic compositions as disclosed herein comprise a CpG Oligonucleotide as adjuvant. A CpG oligonucleotide as used herein refers to an immunostimulatory CpG oligodeoxynucleotide (CpG ODN), and accordingly these terms are used interchangeably unless otherwise indicated. Immunostimulatory CpG oligodeoxynucleotides contain one or more immunostimulatory CpG motifs that are unmethylated cytosine-guanine dinucleotides, optionally within certain preferred base contexts. The methylation status of the CpG immunostimulatory motif generally refers to the cytosine residue in the dinucleotide. An immunostimulatory oligonucleotide containing at least one unmethylated CpG dinucleotide is an oligonucleotide which contains a 5' unmethylated cytosine linked by a phosphate bond to a 3' guanine, and which activates the immune system through binding to Toll-like receptor 9 (TLR-9). In another embodiment the immunostimulatory oligonucleotide may contain one or more methylated CpG dinucleotides, which will activate the immune system through TLR9 but not as strongly as if the CpG motif(s) was/were unmethylated. CpG immunostimulatory oligonucleotides may comprise one or more palindromes that in turn may encompass the CpG dinucleotide. CpG oligonucleotides have been described in a number of issued patents, published patent applications, and other publications, including U.S. Pat. Nos. 6,194,388; 6,207,646; 6,214,806; 6,218,371; 6,239,116; and 6,339,068.

In an embodiment of the present invention, the immunogenic compositions as disclosed herein comprise any of the CpG Oligonucleotide described at page 3, line 22, to page 12, line 36, of WO 2010/125480 or page 107 lines 29 to page 113 line 2 of WO2015/110941.

In some embodiments of the invention, CpG-containing nucleic acids might be simply mixed with immunogenic carriers according to methods known to those skilled in the art (see, e.g., WO 03/024480).

In a particular embodiment of the present invention, any of the immunogenic compositions disclosed herein comprise from 2 μg to 100 mg of CpG oligonucleotide, preferably from 0.1 mg to 50 mg CpG oligonucleotide, preferably from 0.2 mg to 10 mg CpG oligonucleotide, preferably from 0.3 mg to 5 mg CpG oligonucleotide, preferably from 0.3 mg to 5 mg CpG oligonucleotide, even preferably from 0.5 to 2 mg CpG oligonucleotide, even preferably from 0.75 to 1.5 mg CpG oligonucleotide. In a preferred embodiment, any of the immunogenic composition disclosed herein comprises about 1 mg CpG oligonucleotide.

5 FORMULATION

The immunogenic compositions of the invention may be formulated in liquid form (i.e., solutions or suspensions) or in a lyophilized form. Liquid formulations may advantageously be administered directly from their packaged form and are thus ideal for injection without the need for reconstitution in aqueous medium as otherwise required for lyophilized compositions of the invention.

Formulation of the immunogenic composition of the present invention can be accomplished using art-recognized methods. For instance, the individual pneumococcal conjugates can be formulated with a physiologically acceptable vehicle to prepare the composition. Examples of such vehicles include, but are not limited to, water, buffered saline, polyols (e.g., glycerol, propylene glycol, liquid polyethylene glycol) and dextrose solutions.

The present disclosure provides an immunogenic composition comprising any of combination of glycoconjugates disclosed herein and a pharmaceutically acceptable excipient, carrier, or diluent.

In an embodiment, the immunogenic composition of the invention is in liquid form, preferably in aqueous liquid form.

Immunogenic compositions of the disclosure may comprise one or more of a buffer, a salt, a divalent cation, a non-ionic detergent, a cryoprotectant such as a sugar, and an anti-oxidant such as a free radical scavenger or chelating agent, or any multiple combinations thereof.

In an embodiment, the immunogenic compositions of the invention comprise a buffer. In an embodiment, said buffer has a pKa of about 3.5 to about 7.5. In some embodiments, the buffer is phosphate, succinate, histidine or citrate. In certain embodiments, the buffer is succinate at a final concentration of 1 mM to 10 mM. In one particular embodiment, the final concentration of the succinate buffer is about 5 mM.

In an embodiment, the immunogenic compositions of the invention comprise a salt. In some embodiments, the salt is selected from the groups consisting of magnesium chloride, potassium chloride, sodium chloride and a combination thereof. In one particular embodiment, the salt is sodium chloride. In one particular embodiment, the immunogenic compositions of the invention comprise sodium chloride at 150 mM.

In an embodiment, the immunogenic compositions of the invention comprise a surfactant. In an embodiment, the surfactant is selected from the group consisting of polysorbate 20 (TWEEN™20), polysorbate 40 (TWEEN™40), polysorbate 60 (TWEEN™60), polysorbate 65 (TWEEN™65), polysorbate 80 (TWEEN™80), polysorbate 85 (TWEEN™85), TRITON™ N-101, TRITON™ X-100, oxtoxynol 40, nonoxynol-9, triethanolamine, triethanolamine polypeptide oleate, polyoxyethylene-660 hydroxystearate (PEG-15, Solutol H 15), polyoxyethylene-35-ricinoleate (CREMOPHOR® EL), soy lecithin and a poloxamer.

In one particular embodiment, the surfactant is a polysorbate. In some said embodiment, the final concentration of polysorbate in the formulation is at least 0.0001% to 10% polysorbate weight to weight (w/w). In some said embodiments, the final concentration of polysorbate in the formulation is at least 0.001% to 1% polysorbate weight to weight (w/w). In some said embodiments, the final concentration of polysorbate in the formulation is at least 0.01% to 1% polysorbate weight to weight (w/w). In other embodiments, the final concentration of polysorbate in the formulation is 0.01%, 0.02%, 0.03%, 0.04%, 0.05%, 0.06%, 0.07%, 0.08%, 0.09% or 0.1% polysorbate (w/w). In another embodiment, the final concentration of the polysorbate in the formulation is 1% polysorbate (w/w).

In one particular embodiment, the surfactant is polysorbate 20, polysorbate 40, polysorbate 60, polysorbate 65, polysorbate 80 or polysorbate 85. In some said embodiment, the final concentration of polysorbate in the formulation is at least 0.0001% to 10% polysorbate weight to weight (w/w). In some said embodiments, the final concentration of polysorbate in the formulation is at least 0.001% to 1% polysorbate weight to weight (w/w). In some said embodiments, the final concentration of polysorbate in the formulation is at least 0.01% to 1% polysorbate weight to weight (w/w). In other embodiments, the final concentration of polysorbate in the formulation is 0.01%, 0.02%, 0.03%, 0.04%, 0.05%, 0.06%, 0.07%, 0.08%, 0.09% or 0.1% polysorbate (w/w). In another embodiment, the final concentration of the polysorbate in the formulation is 1% polysorbate (w/w).

In one particular embodiment, the surfactant is polysorbate 20. In some said embodiment, the final concentration of polysorbate 20 in the formulation is at least 0.0001% to 10% polysorbate 20 weight to weight (w/w). In some said embodiments, the final concentration of polysorbate 20 in the formulation is at least 0.001% to 1% polysorbate 20 weight to weight (w/w). In some said embodiments, the final concentration of polysorbate 20 in the formulation is at least 0.01% to 1% polysorbate 20 weight to weight (w/w). In other embodiments, the final concentration of polysorbate 20 in the formulation is 0.01%, 0.02%, 0.03%, 0.04%, 0.05%, 0.06%, 0.07%, 0.08%, 0.09% or 0.1% polysorbate 20 (w/w). In another embodiment, the final concentration of the polysorbate 20 in the formulation is 1% polysorbate 20 (w/w).

In one particular embodiment, the surfactant is polysorbate 80. In some said embodiment, the final concentration of polysorbate 80 in the formulation is at least 0.0001% to 10% polysorbate 80 weight to weight (w/w). In some said embodiments, the final concentration of polysorbate 80 in the formulation is at least 0.001% to 1% polysorbate 80 weight to weight (w/w). In some said embodiments, the final concentration of polysorbate 80 in the formulation is at least 0.01% to 1% polysorbate 80 weight to weight (w/w). In other embodiments, the final concentration of polysorbate 80 in the formulation is 0.01%, 0.02%, 0.03%, 0.04%, 0.05%, 0.06%, 0.07%, 0.08%, 0.09% or 0.1% polysorbate 80 (w/w). In another embodiment, the final concentration of the polysorbate 80 in the formulation is 1% polysorbate 80 (w/w).

In certain embodiments, the immunogenic composition of the invention has a pH of 5.5 to 7.5, more preferably a pH of 5.6 to 7.0, even more preferably a pH of 5.8 to 6.0.

In one embodiment, the present invention provides a container filled with any of the immunogenic compositions disclosed herein. In one embodiment, the container is selected from the group consisting of a vial, a syringe, a flask, a fermentor, a bioreactor, a bag, a jar, an ampoule, a cartridge and a disposable pen. In certain embodiments, the container is siliconized.

In an embodiment, the container of the present invention is made of glass, metals (e.g., steel, stainless steel, aluminum, etc.) and/or polymers (e.g., thermoplastics, elastomers, thermoplastic-elastomers). In an embodiment, the container of the present invention is made of glass.

In one embodiment, the present invention provides a syringe filled with any of the immunogenic compositions disclosed herein. In certain embodiments, the syringe is siliconized and/or is made of glass.

A typical dose of the immunogenic composition of the invention for injection has a volume of 0.1 mL to 2 mL, more preferably 0.2 mL to 1 mL, even more preferably a volume of about 0.5 mL.

Therefore the container or syringe as defined above is filed with a volume of 0.1 mL to 2 mL, more preferably 0.2 mL to 1 mL, even more preferably a volume of about 0.5 mL of any of the immunogenic compositions defined herein.

6 USES OF THE IMMUNOGENIC COMPOSITIONS OF THE INVENTION

In an embodiment, the immunogenic compositions disclosed herein are for use as a medicament. The immunogenic compositions described herein may be used in various therapeutic or prophylactic methods for preventing, treating or ameliorating a bacterial infection, disease or condition in a subject. In particular, immunogenic compositions described herein may be used to prevent, treat or ameliorate a *S. pneumoniae* infection, disease or condition in a subject.

Thus in one aspect, the invention provides a method of preventing, treating or ameliorating an infection, disease or condition associated with *S. pneumoniae* in a subject, comprising administering to the subject an immunologically effective amount of an immunogenic composition of the invention.

In some such embodiments, the infection, disease or condition is selected from the group consisting of pneumonia, sinusitis, otitis media, acute otitis media, meningitis, bacteremia, sepsis, pleural empyema, conjunctivitis, osteomyelitis, septic arthritis, endocarditis, peritonitis, pericarditis, mastoiditis, cellulitis, soft tissue infection and brain abscess.

In an embodiment, the invention provides a method of inducing an immune response to *S. pneumoniae* in a subject comprising administering to the subject an immunologically effective amount of an immunogenic composition of the invention In an embodiment, the immunogenic compositions disclosed herein are for use as a vaccine. In such embodiments the immunogenic compositions described herein may be used to prevent a *S. pneumoniae* infection in a subject. Thus in one aspect, the invention provides a method of preventing an infection by *S. pneumoniae* in a subject comprising administering to the subject an immunologically effective amount of an immunogenic composition of the invention. In some such embodiments, the infection is selected from the group consisting of pneumonia, sinusitis, otitis media, acute otitis media, meningitis, bacteremia, sepsis, pleural empyema, conjunctivitis, osteomyelitis, septic arthritis, endocarditis, peritonitis, pericarditis, mastoiditis, cellulitis, soft tissue infection and brain abscess. In one aspect, the subject to be vaccinated is a mammal, such as a human, cat, sheep, pig, horse, bovine or dog.

In one aspect, the immunogenic compositions disclosed herein are for use in a method of preventing, treating or ameliorating an infection, disease or condition associated with *S. pneumoniae* in a subject. In some such embodiments, the infection, disease or condition is selected from the group consisting of pneumonia, sinusitis, otitis media, acute otitis media, meningitis, bacteremia, sepsis, pleural empyema, conjunctivitis, osteomyelitis, septic arthritis, endocarditis, peritonitis, pericarditis, mastoiditis, cellulitis, soft tissue infection and brain abscess.

In an embodiment, the immunogenic compositions disclosed herein are for use as a vaccine. In such embodiments the immunogenic compositions described herein may be used to prevent a *S. pneumoniae* infection in a subject. Thus in one aspect, the immunogenic compositions disclosed herein are for use in a method of preventing, an infection by *S. pneumoniae* in a subject. In some such embodiments, the infection is selected from the group consisting of pneumonia, sinusitis, otitis media, acute otitis media, meningitis, bacteremia, sepsis, pleural empyema, conjunctivitis, osteomyelitis, septic arthritis, endocarditis, peritonitis, pericarditis, mastoiditis, cellulitis, soft tissue infection and brain abscess. In one aspect, the subject to be vaccinated is a mammal, such as a human, cat, sheep, pig, horse, bovine or dog.

The immunogenic compositions of the present invention can be used to protect or treat a human susceptible to pneumococcal infection, by means of administering the immunogenic compositions via a systemic or mucosal route. In an embodiment, the immunogenic compositions disclosed herein are administered by intramuscular, intraperitoneal, intradermal or subcutaneous routes. In an embodiment, the immunogenic compositions disclosed herein are administered by intramuscular, intraperitoneal, intradermal or subcutaneous injection. In an embodiment, the immunogenic compositions disclosed herein are administered by intramuscular or subcutaneous injection.

7 SUBJECT TO BE TREATED WITH THE IMMUNOGENIC COMPOSITIONS OF THE INVENTION

As disclosed herein, the immunogenic compositions described herein may be used in various therapeutic or prophylactic methods for preventing, treating or ameliorating a bacterial infection, disease or condition in a subject.

In a preferred embodiment, said subject is a human. In a most preferred embodiment, said subject is a newborn (i.e., under three months of age), an infant (i.e., from 3 months to one year of age) or a toddler (i.e., from one year to four years of age).

In an embodiment, the immunogenic compositions disclosed herein are for use as a vaccine.

In such embodiment, the subject to be vaccinated may be less than 1 year of age. For example, the subject to be vaccinated can be about 1, about 2, about 3, about 4, about 5, about 6, about 7, about 8, about 9, about 10, about 11 or about 12 months of age. In an embodiment, the subject to be vaccinated is about 2, about 4 or about 6 months of age. In another embodiment, the subject to be vaccinated is less than 2 years of age. For example the subject to be vaccinated can be about 12 to about 15 months of age. In some cases, as little as one dose of the immunogenic composition according to the invention is needed, but under some circumstances, a second, third or fourth dose may be given (see section 8 below).

In an embodiment of the present invention, the subject to be vaccinated is a human adult 50 years of age or older, more preferably a human adult 55 years of age or older. In an embodiment, the subject to be vaccinated is a human adult 65 years of age or older, 70 years of age or older, 75 years of age or older or 80 years of age or older.

In an embodiment the subject to be vaccinated is an immunocompromised individual, in particular a human. An immunocompromised individual is generally defined as a person who exhibits an attenuated or reduced ability to mount a normal humoral or cellular defense to challenge by infectious agents.

In an embodiment of the present invention, the immunocompromised subject to be vaccinated suffers from a disease or condition that impairs the immune system and results in an antibody response that is insufficient to protect against or treat pneumococcal disease.

In an embodiment, said disease is a primary immunodeficiency disorder. Preferably, said primary immunodeficiency disorder is selected from the group consisting of: combined T- and B-cell immunodeficiencies, antibody deficiencies, well-defined syndromes, immune dysregulation diseases, phagocyte disorders, innate immunity deficiencies, autoinflammatory disorders, and complement deficiencies. In an embodiment, said primary immunodeficiency disorder is selected from the one disclosed on page 24, line 11, to page 25, line 19, of WO 2010/125480.

In a particular embodiment of the present invention, the immunocompromised subject to be vaccinated suffers from a disease selected from the groups consisting of: HIV-infection, acquired immunodeficiency syndrome (AIDS), cancer, chronic heart or lung disorders, congestive heart failure, diabetes mellitus, chronic liver disease, alcoholism, cirrhosis, spinal fluid leaks, cardiomyopathy, chronic bronchitis, emphysema, chronic obstructive pulmonary disease (COPD), spleen dysfunction (such as sickle cell disease), lack of spleen function (asplenia), blood malignancy, leukemia, multiple myeloma, Hodgkin's disease, lymphoma, kidney failure, nephrotic syndrome and asthma.

In an embodiment of the present invention, the immunocompromised subject to be vaccinated suffers from malnutrition.

In a particular embodiment of the present invention, the immunocompromised subject to be vaccinated is taking a drug or treatment that lowers the body's resistance to infection. In an embodiment, said drug is selected from the one disclosed on page 26, line 33, to page 26, line 4, of WO 2010/125480.

In a particular embodiment of the present invention, the immunocompromised subject to be vaccinated is a smoker.

In a particular embodiment of the present invention, the immunocompromised subject to be vaccinated has a white blood cell count (leukocyte count) below $5\times10^9$ cells per liter, or below $4\times10^9$ cells per liter, or below $3\times10^9$ cells per liter, or below $2\times10^9$ cells per liter, or below $1\times10^9$ cells per liter, or below $0.5\times10^9$ cells per liter, or below $0.3\times10^9$ cells per liter, or below $0.1\times10^9$ cells per liter.

White blood cell count (leukocyte count): The number of white blood cells (WBC) in the blood. The WBC is usually measured as part of the CBC (complete blood count). White blood cells are the infection-fighting cells in the blood and are distinct from the red (oxygen-carrying) blood cells known as erythrocytes. There are different types of white blood cells, including neutrophils (polymorphonuclear leukocytes; PMN), band cells (slightly immature neutrophils), T-type lymphocytes (T-cells), B-type lymphocytes (B-cells), monocytes, eosinophils, and basophils. All the types of white blood cells are reflected in the white blood cell count. The normal range for the white blood cell count is usually between 4,300 and 10,800 cells per cubic millimeter of blood. This can also be referred to as the leukocyte count and can be expressed in international units as $4.3\text{-}10.8\times10^9$ cells per liter.

In a particular embodiment of the present invention, the immunocompromised subject to be vaccinated suffers from neutropenia. In a particular embodiment of the present invention, the immunocompromised subject to be vaccinated has a neutrophil count below $2\times10^9$ cells per liter, or below $1\times10^9$ cells per liter, or below $0.5\times10^9$ cells per liter, or below $0.1\times10^9$ cells per liter, or below $0.05\times10^9$ cells per liter.

A low white blood cell count or "neutropenia" is a condition characterized by abnormally low levels of neutrophils in the circulating blood. Neutrophils are a specific kind of white blood cell that help to prevent and fight infections. The most common reason that cancer patients experience neutropenia is as a side effect of chemotherapy. Chemotherapy-induced neutropenia increases a patient's risk of infection and disrupts cancer treatment.

In a particular embodiment of the present invention, the immunocompromised subject to be vaccinated has a CD4+ cell count below $500/mm^3$, or CD4+ cell count below $300/mm^3$, or CD4+ cell count below $200/mm^3$, CD4+ cell count below $100/mm^3$, CD4+ cell count below $75/mm^3$, or CD4+ cell count below $50/mm^3$.

CD4 cell tests are normally reported as the number of cells in $mm^3$. Normal CD4 counts are between 500 and 1,600, and CD8 counts are between 375 and 1,100. CD4 counts drop dramatically in people with HIV.

In an embodiment of the invention, any of the immunocompromised subjects disclosed herein is a human male or a human female.

8 REGIMEN

In some cases, as little as one dose of the immunogenic composition according to the invention is needed, but under some circumstances, such as conditions of greater immune deficiency, a second, third or fourth dose may be given. Following an initial vaccination, subjects can receive one or several booster immunizations adequately spaced.

In an embodiment, the schedule of vaccination of the immunogenic composition according to the invention is a single dose. In a particular embodiment, said single dose schedule is for healthy persons being at least 2 years of age.

In an embodiment, the schedule of vaccination of the immunogenic composition according to the invention is a multiple dose schedule. In a particular embodiment, said multiple dose schedule consists of a series of 2 doses separated by an interval of about 1 month to about 2 months. In a particular embodiment, said multiple dose schedule consists of a series of 2 doses separated by an interval of about 1 month, or a series of 2 doses separated by an interval of about 2 months. In another embodiment, said multiple dose schedule consists of a series of 3 doses separated by an interval of about 1 month to about 2 months. In another embodiment, said multiple dose schedule consists of a series of 3 doses separated by an interval of about 1 month, or a series of 3 doses separated by an interval of about 2 months.

In another embodiment, said multiple dose schedule consists of a series of 3 doses separated by an interval of about 1 month to about 2 months followed by a fourth dose about 10 months to about 13 months after the first dose. In another embodiment, said multiple dose schedule consists of a series of 3 doses separated by an interval of about 1 month followed by a fourth dose about 10 months to about 13 months after the first dose, or a series of 3 doses separated by an interval of about 2 months followed by a fourth dose about 10 months to about 13 months after the first dose.

In an embodiment, the multiple dose schedule consists of at least one dose (e.g., 1, 2 or 3 doses) in the first year of age followed by at least one toddler dose.

In an embodiment, the multiple dose schedule consists of a series of 2 or 3 doses separated by an interval of about 1 month to about 2 months (for example 28-56 days between doses), starting at 2 months of age, and followed by a toddler dose at 12-18 months of age. In an embodiment, said multiple dose schedule consists of a series of 3 doses separated by an interval of about 1 month to about 2 months (for example 28-56 days between doses), starting at 2 months of age, and followed by a toddler dose at 12-15 months of age. In another embodiment, said multiple dose schedule consists of a series of 2 doses separated by an interval of about 2 months, starting at 2 months of age, and followed by a toddler dose at 12-18 months of age.

In an embodiment, the multiple dose schedule consists of a 4-dose series of vaccine at 2, 4, 6, and 12-15 months of age.

In an embodiment, a prime dose is given at day 0 and one or more boosts are given at intervals that range from about 2 to about 24 weeks, preferably with a dosing interval of 4-8 weeks. In an embodiment, a prime dose is given at day 0 and a boost is given about 3 months later.

Particular embodiments of the invention are set forth in the following numbered paragraphs:

1. A glycoconjugate comprising at least two saccharides selected from the group consisting of a saccharide from *S. pneumoniae* serotype 8, a saccharide from *S. pneumoniae* serotype 15A, a saccharide from *S. pneumoniae* serotype 15B, a saccharide from *S. pneumoniae* serotype 23B and a saccharide from *S. pneumoniae* serotype 23B, conjugated to the same carrier protein.
2. The glycoconjugate of paragraph 1, which is a 2, 3, 4 or a 5-valent glycoconjugate.
3. The glycoconjugate of paragraph 1 or 2 selected from a group consisting of a serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugate.
4. The glycoconjugate of paragraph 2 or 3 which is a serotypes 8/15A/15B/23A/23B, 8/15A/15B/23A, 8/15A/15B/23B, 8/15A/23A/23B, 8/15B/23A/23B, 8/15A/15B, 8/15A/23A, 8/15A/23B, 8/15B/23A, 8/15B/23B, 8/23A/23B, 8/15A, 8/15B, 8/23A or 8/23B glycoconjugate and comprises a serotype 8 saccharide having a molecular weight of between 10 kDa and 5,000 kDa.
5. The glycoconjugate of paragraph 2 or 3 which is a serotypes 8/15A/15B/23A/23B, 8/15A/15B/23A, 8/15A/15B/23B, 8/15A/23A/23B, 15A/15B/23A/23B, 8/15A/15B, 8/15A/23A, 8/15A/23B, 15A/15B/23A, 15A/15B/23B, 15A/23A/23B, 8/15A, 15A/15B, 15A/23A or 15A/23B glycoconjugate and comprises a serotype 15A saccharide having a molecular weight of between 10 kDa and 5,000 kDa.
6. The glycoconjugate of paragraph 2 or 3 which is a serotypes 8/15A/15B/23A/23B, 8/15A/15B/23A, 8/15A/15B/23B, 8/15B/23A/23B, 15A/15B/23A/23B, 8/15A/15B, 8/15B/23A, 8/15B/23B, 15A/15B/23A, 15A/15B/23B, 15B/23A/23B, 8/15B, 15A/15B, 15B/23A or 15B/23B glycoconjugate and comprises a serotype 15B saccharide having a molecular weight of between 10 kDa and 5,000 kDa.
7. The glycoconjugate of paragraph 2 or 3 which is a serotypes 8/15A/15B/23A/23B, 8/15A/15B/23A, 8/15A/23A/23B, 8/15B/23A/23B, 15A/15B/23A/23B, 8/15A/23A, 8/15B/23A, 8/23A/23B, 15A/15B/23A, 15A/23A/23B, 15B/23A/23B, 8/23A, 15A/23A, 15B/23A or 23A/23B glycoconjugate and comprises a serotype 23A saccharide having a molecular weight of between 10 kDa and 5,000 kDa.
8. The glycoconjugate of paragraph 2 or 3 which is a serotypes 8/15A/15B/23A/23B, 8/15A/15B/23B, 8/15A/23A/23B, 8/15B/23A/23B, 15A/15B/23A/23B, 8/15A/23B, 8/15B/23B, 8/23A/23B, 15A/15B/23B, 15A/23A/23B, 15B/23A/23B, 8/23B, 15A/23B, 15B/23B or 23A/23B glycoconjugate and comprises a serotype 23B saccharide having a molecular weight of between 10 kDa and 5,000 kDa.
9. The glycoconjugate of anyone of paragraphs 1 to 8 having a molecular weight of between 400 kDa and 15,000 kDa.
10. The glycoconjugate of anyone of paragraphs 1 to 9 having a degree of conjugation of between 2 and 15.
11. The glycoconjugate of anyone of paragraphs 1 to 10 wherein the ratio of saccharides to carrier protein in the glycoconjugate (w/w) is between 0.5 and 3.0.
12. The glycoconjugate of any one of paragraphs 1 to 11 which is a serotypes 8/15A/15B/23A/23B, 8/15A/15B/23A, 8/15A/15B/23B, 8/15A/23A/23B, 8/15A/15B, 8/15A/23A, 8/15A/23B or 8/15A glycoconjugate wherien the ratio of serotype 8 saccharide to serotype 15A saccharide in the glycoconjugate (w/w) is between 0.25 and 4.0.
13. The glycoconjugate of any one of paragraphs 1 to 12 which is a serotypes 8/15A/15B/23A/23B, 8/15A/15B/23A, 8/15A/15B/23B, 8/15B/23A/23B, 8/15A/15B, 8/15B/23A, 8/15B/23B or 8/15B glycoconjugate wherein the ratio of serotype 8 saccharide to serotype 15B saccharide in the glycoconjugate (w/w) is between 0.25 and 4.0.
14. The glycoconjugate of any one of paragraphs 1 to 13 which is a serotypes 8/15A/15B/23A/23B, 8/15A/15B/23A, 8/15A/23A/23B, 8/15B/23A/23B, 8/15A/23A, 8/15B/23A, 8/23A/23B or 8/23A glycoconjugate wherein the ratio of serotype 8 saccharide to serotype 23A saccharide in the glycoconjugate (w/w) is between 0.25 and 4.0.
15. The glycoconjugate of any one of paragraphs 1 to 14 which is a serotypes 8/15A/15B/23A/23B, 8/15A/15B/23B, 8/15A/23A/23B, 8/15B/23A/23B, 8/15A/23B, 8/15B/23B, 8/23A/23B or 8/23B glycoconjugate wherein the ratio of serotype 8 saccharide to serotype 23B saccharide in the glycoconjugate (w/w) is between 0.25 and 4.0.

16. The glycoconjugate of any one of paragraphs 1 to 15 which is a 8/15A/15B/23A/23B, 8/15A/15B/23A, 8/15A/15B/23B, 15A/15B/23A/23B, 8/15A/15B, 15A/15B/23A, 15A/15B/23B or 15A/15B glycoconjugate wherein the ratio of serotype 15A saccharide to serotype 15B saccharide in the glycoconjugate (w/w) is between 0.25 and 4.0.

17. The glycoconjugate of any one of paragraphs 1 to 16 which is a serotypes 8/15A/15B/23A/23B, 8/15A/15B/23A, 8/15A/23A/23B, 15A/15B/23A/23B, 8/15A/23A, 15A/15B/23A, 15A/23A/23B or 15A/23A glycoconjugate wherein the ratio of serotype 15A saccharide to serotype 23A saccharide in the glycoconjugate (w/w) is between 0.25 and 4.0.

18. The glycoconjugate of any one of paragraphs 1 to 17 which is a serotypes 8/15A/15B/23A/23B, 8/15A/15B/23B, 8/15A/23A/23B, 15A/15B/23A/23B, 8/15A/23B, 15A/15B/23B, 15A/23A/23B or 15A/23B glycoconjugate wherein the ratio of serotype 15A saccharide to serotype 23B saccharide in the glycoconjugate (w/w) is between 0.25 and 4.0.

19. The glycoconjugate of any one of paragraphs 1 to 18 which is a serotypes 8/15A/15B/23A/23B, 8/15A/15B/23A, 8/15B/23A/23B, 15A/15B/23A/23B, 8/15B/23A, 15A/15B/23A, 15B/23A/23B or 15B/23A glycoconjugate wherein the ratio of serotype 15B saccharide to serotype 23A saccharide in the glycoconjugate (w/w) is between 0.25 and 4.0.

20. The glycoconjugate of any one of paragraphs 1 to 19 which is a serotypes 8/15A/15B/23A/23B, 8/15A/15B/23B, 8/15B/23A/23B, 15A/15B/23A/23B, 8/15B/23B, 15A/15B/23B, 15B/23A/23B or 15B/23B glycoconjugate wherein the ratio of serotype 15B saccharide to serotype 23B saccharide in the glycoconjugate (w/w) is between 0.25 and 4.0.

21. The glycoconjugate of any one of paragraphs 1 to 20 which is a serotypes 8/15A/15B/23A/23B, 8/15A/23A/23B, 8/15B/23A/23B, 15A/15B/23A/23B, 8/23A/23B, 15A/23A/23B, 15B/23A/23B or 23A/23B glycoconjugate wherein the ratio of serotype 23A saccharide to serotype 23B saccharide in the glycoconjugate (w/w) is between 0.25 and 4.0.

22. The glycoconjugate of any one of paragraphs 1 to 21 which is a 8/15A/15B/23A/23B, 8/15A/15B/23A, 8/15A/15B/23B, or 8/15A/15B glycoconjugate wherein the relative proportion of serotype 8 saccharide, serotype 15A saccharide and serotype 15B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 15B | 4 | 2 | 1 | 4 | 2 | 1 | 4 | 2 | 1 | 4 | 2 | 1 | 1 | 1 | 4 | 2 | 1 | 1 | 1 |

23. The glycoconjugate of any one of paragraphs 1 to 22 which is a serotypes 8/15A/15B/23A/23B, 8/15A/15B/23A, 8/15A/23A/23B, or 8/15A/23A glycoconjugate wherein the relative proportion of serotype 8 saccharide, serotype 15A saccharide and serotype 23A saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 23A | 4 | 2 | 1 | 4 | 2 | 1 | 4 | 2 | 1 | 4 | 2 | 1 | 1 | 1 | 4 | 2 | 1 | 1 | 1 |

24. The glycoconjugate of any one of paragraphs 1 to 23 which is a serotypes 8/15A/15B/23A/23B, 8/15A/15B/23B, 8/15A/23A/23B or 8/15A/23B glycoconjugate wherein the relative proportion of serotype 8 saccharide, serotype 15A saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

25. The glycoconjugate of any one of paragraphs 1 to 24 which is a serotypes 8/15A/15B/23A/23B, 8/15A/15B/23A, 8/15B/23A/23B or 8/15B/23A glycoconjugate wherein the relative proportion of serotype 8 saccharide, serotype 15B saccharide and serotype 23A saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 15B | 1 | 1 | 1 | 1 | 1 | 1 | 1 | 1 | 1 | 2 | 2 | 2 | 2 | 2 | 4 | 4 | 4 | 4 | 4 |
| 23A | 4 | 2 | 1 | 4 | 2 | 1 | 4 | 2 | 1 | 4 | 2 | 1 | 1 | 1 | 4 | 2 | 1 | 1 | 1 |

26. The glycoconjugate of any one of paragraphs 1 to 25 which is a serotypes 8/15A/15B/23A/23B, 8/15A/15B/23B, 8/15B/23A/23B or 8/15B/23B glycoconjugate wherein the relative proportion of serotype 8 saccharide, serotype 15B saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 15B | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

27. The glycoconjugate of any one of paragraphs 1 to 26 which is a serotypes 8/15A/15B/23A/23B, 8/15A/23A/23B, 8/15B/23A/23B or 8/23A/23B glycoconjugate wherein the relative proportion of serotype 8 saccharide, serotype 23A saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 23A | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

28. The glycoconjugate of any one of paragraphs 1 to 27 which is a serotypes 8/15A/15B/23A/23B, 8/15A/15B/23A, 15A/15B/23A/23B or 15A/15B/23A glycoconjugate wherein the relative proportion of serotype 15A saccharide, serotype 15B saccharide and serotype 23A saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 15A | 1 | 1 | 1 | 2 | 2 | 2 | 4 | 4 | 4 | 1 | 1 | 1 | 2 | 4 | 1 | 1 | 1 | 2 | 4 |
| 15B | 1 | 1 | 1 | 1 | 1 | 1 | 1 | 1 | 1 | 2 | 2 | 2 | 2 | 2 | 4 | 4 | 4 | 4 | 4 |
| 23A | 4 | 2 | 1 | 4 | 2 | 1 | 4 | 2 | 1 | 4 | 2 | 1 | 1 | 1 | 4 | 2 | 1 | 1 | 1 |

29. The glycoconjugate of any one of paragraphs 1 to 28 which is a serotypes 8/15A/15B/23A/23B, 8/15A/15B/23B, 15A/15B/23A/23B or 15A/15B/23B glycoconjugate wherein the relative proportion of serotype 15A saccharide, serotype 15B saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 15A | 1 | 1 | 1 | 2 | 2 | 2 | 4 | 4 | 4 | 1 | 1 | 1 | 2 | 4 | 1 | 1 | 1 | 2 | 4 |
| 15B | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

30. The glycoconjugate of any one of paragraphs 1 to 29 which is a serotypes 8/15A/15B/23A/23B, 8/15A/23A/23B, 15A/15B/23A/23B or 15A/23A/23B glycoconjugate wherein the relative proportion of serotype 15A saccharide, serotype 23A saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 15A | 1 | 1 | 1 | 2 | 2 | 2 | 4 | 4 | 4 | 1 | 1 | 1 | 2 | 4 | 1 | 1 | 1 | 2 | 4 |
| 23A | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

31. The glycoconjugate of any one of paragraphs 1 to 30 which is a serotypes 8/15A/15B/23A/23B, 8/15B/23A/23B, 15A/15B/23A/23B or 15B/23A/23B glycoconjugate wherein the relative proportion of serotype 15B saccharide, serotype 23A saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 15B | 1 | 1 | 1 | 2 | 2 | 2 | 4 | 4 | 4 | 1 | 1 | 1 | 2 | 4 | 1 | 1 | 1 | 2 | 4 |
| 23A | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

32. The glycoconjugate of any one of paragraphs 1 to 31 which is a serotypes 8/15A/15B/23A/23B or 8/15A/15B/23A glycoconjugate wherein the relative proportion of serotype 8 saccharide, serotype 15A saccharide, serotype 15B saccharide and serotype 23A saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 15A | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 15B | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23A | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 15B | 2 | 2 | 2 | 2 | 2 | 2 | 2 | 2 | 2 | 2 | 2 | 2 | 2 | 2 | 2 | 2 | 2 | 2 | 2 |
| 23A | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 15B | 4 | 4 | 4 | 4 | 4 | 4 | 4 | 4 | 4 | 4 | 4 | 4 | 4 | 4 | 4 | 4 | 4 | 4 | 4 |
| 23A | 1 | 2 | 4 | 1 | 2 | 4 | 1 | 2 | 4 | 1 | 2 | 4 | 1 | 1 | 1 | 2 | 4 | 1 | 1 |

33. The glycoconjugate of any one of paragraphs 1 to 32 which is a serotypes 8/15A/15B/23A/23B or 8/15A/15B/23B glycoconjugate wherein the relative proportion of serotype 8 saccharide, serotype 15A saccharide, serotype 15B saccharide and serotype 23B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 15A | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 15B | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 15B | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 15B | 4 | 4 | 4 | 4 | 4 | 4 | 4 | 4 | 4 | 4 | 4 | 4 | 4 | 4 | 4 | 4 | 4 | 4 | 4 |
| 23B | 1 | 2 | 4 | 1 | 2 | 4 | 1 | 2 | 4 | 1 | 2 | 4 | 1 | 1 | 1 | 2 | 4 | 1 | 1 |

34. The glycoconjugate of any one of paragraphs 1 to 33 which is a serotypes 8/15A/15B/23A/23B or 8/15A/23A/23B glycoconjugate wherein the relative proportion of serotype 8 saccharide, serotype 15A saccharide, serotype 23A saccharide and serotype 23B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 15A | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 23A | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 15A | 1 | 1 | 1 | 1 | 1 | 1 | 1 | 1 | 1 | 2 | 2 | 2 | 2 | 2 | 4 | 4 | 4 | 4 | 4 |
| 23A | 4 | 4 | 4 | 4 | 4 | 4 | 4 | 4 | 4 | 4 | 4 | 4 | 4 | 4 | 4 | 4 | 4 | 4 | 4 |
| 23B | 1 | 2 | 4 | 1 | 2 | 4 | 1 | 2 | 4 | 1 | 2 | 4 | 1 | 1 | 1 | 2 | 4 | 1 | 1 |

35. The glycoconjugate of any one of paragraphs 1 to 34 which is a serotypes 8/15A/15B/23A/23B or 8/15B/23A/23B glycoconjugate wherein the relative proportion of serotype 8 saccharide, serotype 15B saccharide, serotype 23A saccharide and serotype 23B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 15B | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 15B | 1 | 1 | 1 | 1 | 1 | 1 | 1 | 1 | 1 | 2 | 2 | 2 | 2 | 2 | 4 | 4 | 4 | 4 | 4 |
| 23A | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 15B | 1 | 1 | 1 | 1 | 1 | 1 | 1 | 1 | 1 | 2 | 2 | 2 | 2 | 2 | 4 | 4 | 4 | 4 | 4 |
| 23A | 4 | 4 | 4 | 4 | 4 | 4 | 4 | 4 | 4 | 4 | 4 | 4 | 4 | 4 | 4 | 4 | 4 | 4 | 4 |
| 23B | 1 | 2 | 4 | 1 | 2 | 4 | 1 | 2 | 4 | 1 | 2 | 4 | 1 | 1 | 1 | 2 | 4 | 1 | 1 |

36. The glycoconjugate of any one of paragraphs 1 to 35 which is a serotypes 8/15A/15B/23A/23B or 15A/15B/23A/23B glycoconjugate wherein the relative proportion of serotype 15A saccharide, serotype 15B saccharide, serotype 23A saccharide and serotype 23B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 15A | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 15B | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 15A | 1 | 1 | 1 | 2 | 2 | 2 | 4 | 4 | 4 | 1 | 1 | 1 | 2 | 4 | 1 | 1 | 1 | 2 | 4 |
| 15B | 1 | 1 | 1 | 1 | 1 | 1 | 1 | 1 | 1 | 2 | 2 | 2 | 2 | 2 | 4 | 4 | 4 | 4 | 4 |
| 23A | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 15A | 1 | 1 | 1 | 2 | 2 | 2 | 4 | 4 | 4 | 1 | 1 | 1 | 2 | 4 | 1 | 1 | 1 | 2 | 4 |
| 15B | 1 | 1 | 1 | 1 | 1 | 1 | 1 | 1 | 1 | 2 | 2 | 2 | 2 | 2 | 4 | 4 | 4 | 4 | 4 |
| 23A | 4 | 4 | 4 | 4 | 4 | 4 | 4 | 4 | 4 | 4 | 4 | 4 | 4 | 4 | 4 | 4 | 4 | 4 | 4 |
| 23B | 1 | 2 | 4 | 1 | 2 | 4 | 1 | 2 | 4 | 1 | 2 | 4 | 1 | 1 | 1 | 2 | 4 | 1 | 1 |

37. The glycoconjugate of any one of paragraphs 1 to 36 which is a serotypes 8/15A/15B/23A/23B glycoconjugate wherein the relative proportion of serotype 8 saccharide, serotype 15A saccharide, serotype 15B saccharide, serotype 23A saccharide and serotype 23B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 15A | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 15B | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at | au |
|---|---|---|---|---|---|---|---|---|---|---|---|---|---|---|---|---|---|---|---|---|
| 8 | 1 | 1 | 1 | 1 | 1 | 1 | 1 | 1 | 1 | 1 | 1 | 1 | 1 | 1 | 1 | 1 | 1 | 1 | 1 | 1 |
| 15A | 1 | 1 | 1 | 2 | 2 | 2 | 4 | 4 | 4 | 1 | 1 | 1 | 2 | 2 | 2 | 4 | 4 | 4 | 1 | 1 |
| 15B | 1 | 1 | 1 | 1 | 1 | 1 | 1 | 1 | 1 | 2 | 2 | 2 | 2 | 2 | 2 | 2 | 2 | 2 | 4 | 4 |
| 23A | 2 | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 2 | 4 | 1 | 2 | 4 | 1 | 2 |

| | av | aw | ax | ay | az | ba | bb | bc | bd | be | bf | bg | bh | bi | bj | bk | bl | bm | bn |
|---|---|---|---|---|---|---|---|---|---|---|---|---|---|---|---|---|---|---|---|
| 8 | 1 | 1 | 1 | 1 | 1 | 1 | 1 | 1 | 1 | 1 | 1 | 1 | 1 | 1 | 1 | 1 | 1 | 1 | 1 |
| 15A | 1 | 2 | 2 | 2 | 4 | 4 | 4 | 1 | 1 | 1 | 2 | 2 | 2 | 4 | 4 | 4 | 1 | 1 | 1 |
| 15B | 4 | 4 | 4 | 4 | 4 | 4 | 4 | 1 | 1 | 1 | 1 | 1 | 1 | 1 | 1 | 1 | 2 | 2 | 2 |
| 23A | 2 | 2 | 2 | 2 | 2 | 2 | 2 | 4 | 4 | 4 | 4 | 4 | 4 | 4 | 4 | 4 | 4 | 4 | 4 |
| 23B | 4 | 1 | 2 | 4 | 1 | 2 | 4 | 1 | 2 | 4 | 1 | 2 | 4 | 1 | 2 | 4 | 1 | 2 | 4 |

| | bo | bp | bq | br | bs | bt | bu | bv | bw | bx | by | bz | ca | cb | cd | ce | cf | cg | ch | ci |
|---|---|---|---|---|---|---|---|---|---|---|---|---|---|---|---|---|---|---|---|---|
| 8 | 1 | 1 | 1 | 1 | 1 | 1 | 1 | 1 | 1 | 1 | 1 | 1 | 1 | 1 | 1 | 2 | 2 | 2 | 2 | 2 |
| 15A | 2 | 2 | 2 | 4 | 4 | 4 | 1 | 1 | 1 | 2 | 2 | 2 | 4 | 4 | 4 | 1 | 1 | 1 | 2 | 2 |
| 15B | 2 | 2 | 2 | 2 | 2 | 2 | 4 | 4 | 4 | 4 | 4 | 4 | 4 | 4 | 4 | 1 | 1 | 1 | 1 | 1 |
| 23A | 4 | 4 | 4 | 4 | 4 | 4 | 4 | 4 | 4 | 4 | 4 | 4 | 4 | 4 | 4 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 |

| | cj | ck | cl | cm | en | co | cp | eq | cr | cs | ct | cu | cv | cw | cx | cy | cz | da |
|---|---|---|---|---|---|---|---|---|---|---|---|---|---|---|---|---|---|---|
| 8 | 2 | 2 | 2 | 2 | 2 | 2 | 2 | 2 | 2 | 2 | 2 | 2 | 2 | 2 | 2 | 2 | 2 | 2 |
| 15A | 2 | 4 | 4 | 4 | 1 | 1 | 1 | 2 | 2 | 2 | 4 | 4 | 4 | 1 | 1 | 1 | 2 | 2 |
| 15B | 1 | 1 | 1 | 1 | 2 | 2 | 2 | 2 | 2 | 2 | 2 | 2 | 2 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 |
| 23B | 4 | 1 | 2 | 4 | 1 | 2 | 4 | 1 | 2 | 4 | 1 | 2 | 4 | 1 | 2 | 4 | 1 | 2 |

| | db | dc | dd | de | df | dg | dh | di | dj | dk | dl | dm | dn | do | dp | dq | dr | ds | dt |
|---|---|---|---|---|---|---|---|---|---|---|---|---|---|---|---|---|---|---|---|
| 8 | 2 | 2 | 2 | 2 | 2 | 2 | 2 | 2 | 2 | 2 | 2 | 2 | 2 | 2 | 2 | 2 | 2 | 2 | 2 |
| 15A | 2 | 4 | 4 | 4 | 1 | 1 | 1 | 2 | 2 | 2 | 4 | 4 | 4 | 1 | 1 | 1 | 2 | 4 | 1 |
| 15B | 4 | 4 | 4 | 4 | 1 | 1 | 1 | 1 | 1 | 1 | 1 | 1 | 1 | 2 | 2 | 2 | 2 | 2 | 4 |
| 23A | 1 | 1 | 1 | 1 | 2 | 2 | 2 | 2 | 2 | 2 | 2 | 2 | 2 | 2 | 2 | 2 | 2 | 2 | 2 |
| 23B | 4 | 1 | 2 | 4 | 1 | 2 | 4 | 1 | 2 | 4 | 1 | 2 | 4 | 1 | 2 | 4 | 1 | 1 | 1 |

| | du | dv | dw | dx | dy | dz | ea | eb | ec | ed | ee | ef | eg | eh | ei | ej | ek | el | em | en | eo |
|---|---|---|---|---|---|---|---|---|---|---|---|---|---|---|---|---|---|---|---|---|---|
| 8 | 2 | 2 | 2 | 2 | 2 | 2 | 2 | 2 | 2 | 2 | 2 | 2 | 2 | 2 | 2 | 2 | 2 | 2 | 2 | 2 | 2 |
| 15A | 1 | 1 | 2 | 4 | 1 | 1 | 1 | 2 | 2 | 2 | 4 | 4 | 4 | 1 | 1 | 1 | 2 | 4 | 1 | 1 | 1 |

-continued

| | du | dv | dw | dx | dy | dz | ea | eb | ec | ed | ee | ef | eg | eh | ei | ej | ek | el | em | en | eo |
|---|---|---|---|---|---|---|---|---|---|---|---|---|---|---|---|---|---|---|---|---|---|
| 15B | 4 | 4 | 4 | 4 | 1 | 1 | 1 | 1 | 1 | 1 | 1 | 1 | 1 | 2 | 2 | 2 | 2 | 2 | 4 | 4 | 4 |
| 23A | 2 | 2 | 2 | 2 | 4 | 4 | 4 | 4 | 4 | 4 | 4 | 4 | 4 | 4 | 4 | 4 | 4 | 4 | 4 | 4 | 4 |
| 23B | 2 | 4 | 1 | 1 | 1 | 2 | 4 | 1 | 2 | 4 | 1 | 2 | 4 | 1 | 2 | 4 | 1 | 1 | 1 | 2 | 4 |

| | ep | eq | er | es | et | eu | ev | ew | ex | ey | ez | fa | fb | fc | fd | fe | ff | fg | fh | fi | fj | fk |
|---|---|---|---|---|---|---|---|---|---|---|---|---|---|---|---|---|---|---|---|---|---|---|
| 8 | 2 | 2 | 4 | 4 | 4 | 4 | 4 | 4 | 4 | 4 | 4 | 4 | 4 | 4 | 4 | 4 | 4 | 4 | 4 | 4 | 4 | 4 |
| 15A | 2 | 4 | 1 | 1 | 2 | 2 | 2 | 4 | 4 | 4 | 1 | 1 | 1 | 2 | 2 | 2 | 4 | 4 | 4 | 1 | 1 | 1 |
| 15B | 4 | 4 | 1 | 1 | 1 | 1 | 1 | 1 | 1 | 1 | 2 | 2 | 2 | 2 | 2 | 2 | 2 | 2 | 2 | 4 | 4 | 4 |
| 23A | 4 | 4 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 1 | 2 | 4 | 1 | 2 | 4 | 1 | 2 | 4 | 1 | 2 | 4 | 1 | 2 | 4 | 1 | 2 | 4 | 1 | 2 | 4 |

| | fl | fm | fn | fo | fp | fq | fr | fs | ft | fu | fv | fw | fx | fy | fz | ga | gb | gc | gd |
|---|---|---|---|---|---|---|---|---|---|---|---|---|---|---|---|---|---|---|---|
| 8 | 4 | 4 | 4 | 4 | 4 | 4 | 4 | 4 | 4 | 4 | 4 | 4 | 4 | 4 | 4 | 4 | 4 | 4 | 4 |
| 15A | 2 | 2 | 2 | 4 | 4 | 4 | 1 | 1 | 1 | 2 | 2 | 2 | 4 | 4 | 4 | 1 | 1 | 1 | 2 |
| 15B | 4 | 4 | 4 | 4 | 4 | 4 | 1 | 1 | 1 | 1 | 1 | 1 | 1 | 1 | 1 | 2 | 2 | 2 | 2 |
| 23A | 1 | 1 | 1 | 1 | 1 | 1 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 2 | 4 | 1 | 2 | 4 | 1 |

| | ge | gf | gg | gh | gi | gj | gk | gl | gl | gn | go | gp | gq | gr | gs | gt | gu | gv | gw | gx | gy | gz |
|---|---|---|---|---|---|---|---|---|---|---|---|---|---|---|---|---|---|---|---|---|---|---|
| 8 | 4 | 4 | 4 | 4 | 4 | 4 | 4 | 4 | 4 | 4 | 4 | 4 | 4 | 4 | 4 | 4 | 4 | 4 | 4 | 4 | 4 | 4 |
| 15A | 4 | 1 | 1 | 1 | 2 | 4 | 1 | 1 | 1 | 2 | 2 | 2 | 4 | 4 | 4 | 1 | 1 | 1 | 2 | 4 | 1 | 1 |
| 15B | 2 | 4 | 4 | 4 | 4 | 4 | 1 | 1 | 1 | 1 | 1 | 1 | 1 | 1 | 1 | 2 | 2 | 2 | 2 | 2 | 4 | 4 |
| 23A | 2 | 2 | 2 | 2 | 2 | 2 | 4 | 4 | 4 | 4 | 4 | 4 | 4 | 4 | 4 | 4 | 4 | 4 | 4 | 4 | 4 | 4 |
| 23B | 1 | 1 | 2 | 4 | 1 | 1 | 1 | 2 | 4 | 1 | 2 | 4 | 1 | 2 | 4 | 1 | 2 | 4 | 1 | 1 | 1 | 2 |

| | ha | hb | hc |
|---|---|---|---|
| 8 | 4 | 4 | 4 |
| 15A | 1 | 2 | 4 |
| 15B | 4 | 4 | 4 |
| 23A | 4 | 4 | 4 |
| 23B | 4 | 1 | 1 |

38. The glycoconjugate of any one of paragraphs 1 to 37 which is a serotypes 8/15A/15B/23A/23B, 8/15A/15B/23A, 8/15A/15B/23B, 8/15A/23A/23B, 15A/15B/23A/23B, 8/15A/15B, 8/15A/23A, 8/15A/23B, 15A/15B/23A, 15A/15B/23B, 15A/23A/23B, 8/15A, 15A/15B, 15A/23A or 15A/23B glycoconjugate comprising 0.1 to 1.0 mM acetate per mM serotype 15A saccharide.

39. The glycoconjugate of any one of paragraphs 1 to 38 which is a serotypes 8/15A/15B/23A/23B, 8/15A/15B/23A, 8/15A/15B/23B, 8/15B/23A/23B, 15A/15B/23A/23B, 8/15A/15B, 8/15B/23A, 8/15B/23B, 15A/15B/23A, 15A/15B/23B, 15B/23A/23B, 8/15B, 15A/15B, 15B/23A or 15B/23B glycoconjugate comprising 0.1 to 1.0 mM acetate per mM serotype 15B saccharide.

40. The glycoconjugate of any one of paragraphs 1 to 39 which is a serotypes 8/15A/15B/23A/23B, 8/15A/15B/23A, 8/15A/15B/23B, 8/15A/23A/23B, 15A/15B/23A/23B, 8/15A/15B, 8/15A/23A, 8/15A/23B, 15A/15B/23A, 15A/15B/23B, 15A/23A/23B, 8/15A, 15A/15B, 15A/23A or 15A/23B glycoconjugate comprising 0.1 to 1.0 mM glycerol per mM serotype 15A saccharide.

41. The glycoconjugate of any one of paragraphs 1 to 40 which is a serotypes 8/15A/15B/23A/23B, 8/15A/15B/23A, 8/15A/15B/23B, 8/15B/23A/23B, 15A/15B/23A/23B, 8/15A/15B, 8/15B/23A, 8/15B/23B, 15A/15B/23A, 15A/15B/23B, 15B/23A/23B, 8/15B, 15A/15B, 15B/23A or 15B/23B glycoconjugate comprising 0.1 to 1.0 mM glycerol per mM serotype 15B saccharide.

42. The glycoconjugate of any one of paragraphs 1 to 41 which is a serotypes 8/15A/15B/23A/23B, 8/15A/15B/23A, 8/15A/23A/23B, 8/15B/23A/23B, 15A/15B/23A/23B, 8/15A/23A, 8/15B/23A, 8/23A/23B, 15A/15B/23A, 15A/23A/23B, 15B/23A/23B, 8/23A, 15A/23A, 15B/23A, or 23A/23B glycoconjugate comprising 0.1 to 1.0 mM glycerol per mM serotype 23A saccharide.

43. The glycoconjugate of any one of paragraphs 1 to 42 which is a serotypes 8/15A/15B/23A/23B, 8/15A/15B/23B, 8/15A/23A/23B, 8/15B/23A/23B, 15A/15B/23A/23B, 8/15A/23B, 8/15B/23B, 8/23A/23B, 15A/15B/23B, 15A/23A/23B, 15B/23A/23B, 8/23B, 15A/23B, 15B/23B or 23A/23B glycoconjugate comprising 0.1 to 1.0 mM glycerol per mM serotype 23B saccharide.

44. The glycoconjugate of any one of paragraphs 1 to 43 wherein at least 30% of the glycoconjugate has a $K_d$ below or equal to 0.3 in a CL-4B column.

45. The glycoconjugate of any one of paragraphs 1 to 44 comprising less than about 50%, of free saccharide compared to the total amount of saccharide.

46. The glycoconjugate of any one of paragraphs 1 to 45 wherein the carrier protein is selected in the group consisting of: TT, DT, DT mutants (such as $CRM_{197}$), *H. influenzae* protein D, PhtX, PhtD, PhtDE fusions, detoxified pneumolysin, PorB, N19 protein, PspA, OMPC, toxin A or B of *C. difficile* and PsaA.

47. The glycoconjugate of any one of paragraphs 1 to 45 wherein the carrier protein is DT (Diphtheria toxoid).
48. The glycoconjugate of any one of paragraphs 1 to 45 wherein the carrier protein is TT (tetanus toxid).
49. The glycoconjugate of any one of paragraphs 1 to 45 wherein the carrier protein is PD (*H. influenzae* protein D).
50. The glycoconjugate of any one of paragraphs 1 to 45 wherein the carrier protein is detoxified pneumolysin or a mutant nontoxic form of pneumolysin.
51. The glycoconjugate of any one of paragraphs 1 to 45 wherein the carrier protein is $CRM_{197}$.
52. The glycoconjugate of any one of paragraphs 1 to 45 wherein the carrier protein is the A chain of $CRM_{197}$.
53. An immunogenic composition comprising at least one glycoconjugate of any one of paragraphs 1 to 52.
54. An immunogenic composition comprising one, two or three glycoconjugate(s) as defined at any one of paragraphs 1 to 52.
55. An immunogenic composition comprising one serotypes 8/15A/15B glycoconjugate and one serotypes 23A/23B glycoconjugate.
56. An immunogenic composition comprising one serotypes 8/15A/23A glycoconjugate and one serotypes 15B/23B glycoconjugate.
57. An immunogenic composition comprising one serotypes 8/15A/23B glycoconjugate and one serotypes 15B/23A glycoconjugate.
58. An immunogenic composition comprising one serotypes 8/15B/23A glycoconjugate and one serotypes 15A/23B glycoconjugate.
59. An immunogenic composition comprising one serotypes 8/15B/23B glycoconjugate and one serotypes 15A/23A glycoconjugate.
60. An immunogenic composition comprising one serotypes 8/23A/23B glycoconjugate and one serotypes 15A/15B glycoconjugate.
61. An immunogenic composition comprising one serotypes 15A/15B/23A glycoconjugate and one serotypes 8/23B glycoconjugate.
62. An immunogenic composition comprising one serotypes 15A/15B/23B glycoconjugate and one serotypes 8/23A glycoconjugate.
63. An immunogenic composition comprising one serotypes 15A/23A/23B glycoconjugate and one serotypes 8/15B glycoconjugate.
64. An immunogenic composition comprising one serotypes 15B/23A/23B glycoconjugate and one serotypes 8/15A glycoconjugate.
65. An immunogenic composition comprising one serotypes 8/15A glycoconjugate and one serotypes 15B/23A, 15B/23B or 23A/23B glycoconjugate.
66. An immunogenic composition comprising one serotypes 8/15B glycoconjugate and one serotypes 15A/23A, 15A/23B or 23A/23B glycoconjugate.
67. An immunogenic composition comprising one serotypes 8/23A glycoconjugate and one serotypes 15A/23B, 15B/23B or 15A/15B glycoconjugate.
68. An immunogenic composition comprising one serotypes 8/23B glycoconjugate and one serotypes 15A/23A, 15B/23A or 15A/15B glycoconjugate.
69. An immunogenic composition comprising one serotypes 15A/15B glycoconjugate and one serotypes 8/23A, 8/23B or 23A/23B glycoconjugate.
70. An immunogenic composition comprising one serotypes 15A/23A glycoconjugate and one serotypes 8/15B, 8/23B or 15B/23B glycoconjugate.

71. An immunogenic composition comprising one serotypes 15A/23B glycoconjugate and one serotypes 8/15B, 8/23A or 15B/23A glycoconjugate.
72. An immunogenic composition comprising one serotypes 15B/23A glycoconjugate and one serotypes 8/15A, 8/23B or 15A/23B glycoconjugate.
73. An immunogenic composition comprising one serotypes 15B/23B glycoconjugate and one serotypes 8/15A, 8/23A or 15A/23A glycoconjugate.
74. An immunogenic composition comprising one serotypes 23A/23B glycoconjugate and one serotypes 8/15A, 8/15B or 15A/15B glycoconjugate.
75. The immunogenic composition of any one of paragraphs 53-74, further comprising at least one glycoconjugate selected from the group consisting of a glycoconjugate from *S. pneumoniae* serotype 1, 3, 4, 5, 6A, 6B, 7F, 8, 9V, 10A, 11A, 12F, 14, 15A, 15B, 18C, 19A, 19F, 22F, 23A, 23B, 23F and 33F.
76. The immunogenic composition of paragraph 75, wherein said additional glycoconjugate(s) is/are individually conjugated glycoconjugate(s).
77. The immunogenic composition of any one of paragraphs 75-76, wherein said additional glycoconjugate(s) is/are conjugated to the carrier protein by reductive amination.
78. The immunogenic composition of any one of paragraphs 75-77 wherein said additional glycoconjugate(s) carrier protein is $CRM_{197}$.
79. The immunogenic composition of any one of paragraphs 53-74, further comprising glycoconjugates from *S. pneumoniae* serotypes 4, 6B, 9V, 14, 18C, 19F and 23F.
80. The immunogenic composition of any one of paragraphs 53-74 or 79, further comprising glycoconjugates from *S. pneumoniae* serotypes 1, 5 and 7F.
81. The immunogenic composition of any one of paragraphs 53-74 or 79-80, further comprising glycoconjugates from *S. pneumoniae* serotypes 6A and 19A.
82. The immunogenic composition of any one of paragraphs 53-74 or 79-81, further comprising a glycoconjugate from *S. pneumoniae* serotype 3.
83. The immunogenic composition of any one of paragraphs 53-74 or 79-82, further comprising a glycoconjugate from *S. pneumoniae* serotype 22F.
84. The immunogenic composition of any one of paragraphs 53-74 or 79-83, further comprising a glycoconjugate from *S. pneumoniae* serotype 33F.
85. The immunogenic composition of any one of paragraphs 53-74 or 79-84, further comprising a glycoconjugate from *S. pneumoniae* serotype 15B.
86. The immunogenic composition of any one of paragraphs 53-74 or 79-85, further comprising a glycoconjugate from *S. pneumoniae* serotype 12F.
87. The immunogenic composition of any one of paragraphs 53-74 or 79-86, further comprising a glycoconjugate from *S. pneumoniae* serotype 10A.
88. The immunogenic composition of any one of paragraphs 53-74 or 79-87, further comprising a glycoconjugate from *S. pneumoniae* serotype 11A.
89. The immunogenic composition of any one of paragraphs 53-74 or 79-88, further comprising a glycoconjugate from *S. pneumoniae* serotype 8.
90. The immunogenic composition of any one of paragraphs 53-74 or 79-82 further comprising at least one glycoconjugate of each of the two *S. pneumoniae* serotypes selected from the group consisting of: 22F and 33F, 22F and 12F, 22F and 10A, 22F and 11A, 33F and 12F, 33F and 10A, 33F and 11A, 12F and 10A, 12F and 11A and 10A and 11A.

91. The immunogenic composition of any one of paragraphs 53-74 or 79-82 further comprising at least one glycoconjugate of each of the three following *S. pneumoniae* serotypes:
   22F and 33F and 12F,
   22F and 33F and 10A,
   22F and 33F and 11A,
   22F and 12F and 10A,
   22F and 12F and 11A,
   22F and 10A and 11A,
   33F and 12F and 10A,
   33F and 12F and 11A,
   33F and 10A and 11A, or
   12F and 10A and 11A.
92. The immunogenic composition of any one of paragraphs 53-74 or 79-82 further comprising at least one glycoconjugate of each of the four following *S. pneumoniae* serotypes:
   22F and 33F and 12F and 10A,
   22F and 33F and 12F and 11A,
   22F and 33F and 10A and 11A,
   22F and 12F and 10A and 11A, or
   33F and 12F and 10A and 11A.
93. The immunogenic composition of any one of paragraphs 53-74 or 79-82 further comprising at least one glycoconjugate of each of the five following *S. pneumoniae* serotypes: 22F and 33F and 12F and 10A and 11A.
94. The immunogenic composition of any one of paragraphs 53-74 or 79-82 further comprising a glycoconjugate from *S. pneumoniae* serotype 8.
95. The immunogenic composition of any one of paragraphs 53-74, 79-82 or 94 further comprising a glycoconjugate from *S. pneumoniae* serotype 15B.
96. The immunogenic composition of any one of paragraphs 75-95 wherein said additional glycoconjugate(s) is/are individually conjugated to the carrier protein.
97. The immunogenic composition of any one of paragraphs 75-96 wherein said additional glycoconjugate(s) is/are conjugated to $CRM_{197}$.
98. The immunogenic composition of any one of paragraphs 79-96 wherein the glycoconjugates from *S. pneumoniae* serotypes 4, 6B, 9V, 14, 18C, 19F and 23F are conjugated to $CRM_{197}$.
99. The immunogenic composition of any one of paragraphs 80-96 or 98 wherein the glycoconjugates from *S. pneumoniae* serotypes 1, 5 and 7F are conjugated to $CRM_{197}$.
100. The immunogenic composition of any one of paragraphs 80-96 or 98-99 wherein the glycoconjugates from *S. pneumoniae* serotypes 6A and 19A are conjugated to $CRM_{197}$.
101. The immunogenic composition of any one of paragraphs 80-96 or 98-100 wherein the glycoconjugates from *S. pneumoniae* serotype 3 is conjugated to $CRM_{197}$.
102. The immunogenic composition of any one of paragraphs 79-96 wherein the glycoconjugates from *S. pneumoniae* serotypes 1, 4, 5, 6B, 7F, 9V, 14 and 23F are individually conjugated to PD.
103. The immunogenic composition of any one of paragraphs 79-96 or 102 wherein the glycoconjugate from *S. pneumoniae* serotype 18C is conjugated to TT.
104. The immunogenic composition of any one of paragraphs 79-96 or 102-103 wherein the glycoconjugate from *S. pneumoniae* serotype 19F is conjugated to DT.
105. The immunogenic composition of any one of paragraphs 79-96 or 102-103 wherein the glycoconjugates from *S. pneumoniae* serotypes 1, 4, 5, 6B, 7F, 9V, 14 and 23F are individually conjugated to PD, the glycoconjugate from *S. pneumoniae* serotype 18C is individually conjugated to TT and the glycoconjugate from *S. pneumoniae* serotype 19F is individually conjugated to DT.
106. The immunogenic composition of any one of paragraphs 53-105 which is a 2, 3, 4, 5, 6, 7, 8, 9, 10, 11, 12, 13, 14, 15, 16, 17, 18, 19, 20, 21, 22 or 23-valent pneumococcal conjugate composition.
107. The immunogenic composition of any one of paragraphs 53-106 further comprising at least one, two or three adjuvants.
108. The immunogenic composition of any one of paragraphs 53-106 further comprising any of the adjuvant of section 4 of the present document.
109. The immunogenic composition of any one of paragraphs 53-106 further comprising an adjuvant selected from the group consisting of alum, calcium phosphate, liposomes, an oil-in-water emulsions, a water-in-oil emulsion, and poly(D,L-lactide-co-glycolide) microparticles or nanoparticles.
110. The immunogenic composition of any one of paragraphs 53-106 further comprising aluminum phosphate, aluminum sulfate or aluminum hydroxide as adjuvant.
111. The immunogenic composition of any one of paragraphs 53-106 further comprising aluminum phosphate as adjuvant.
112. The immunogenic composition of any one of paragraphs 53-111 formulated in liquid form, preferably in aqueous liquid form.
113. The immunogenic composition of any one of paragraphs 53-111 formulated in a lyophilized form.
114. The immunogenic composition of any one of paragraphs 53-113 formulated with a physiologically acceptable vehicle.
115. The immunogenic composition of any one of paragraphs 53-113 formulated in a pharmaceutically acceptable excipient, carrier, or diluent.
116. The immunogenic composition of any one of paragraphs 53-113 comprising one or more of a buffer, a salt, a divalent cation, a non-ionic detergent, a cryoprotectant such as a sugar, and an anti-oxidant such as a free radical scavenger or chelating agent, or any multiple combinations thereof.
117. The glycoconjugate of any one of paragraphs 1-52 or the immunogenic composition of any one of paragraphs 53-116 for use as a medicament.
118. The glycoconjugate of any one of paragraphs 1-52 or the immunogenic composition of any one of paragraphs 53-116 for use as a vaccine.
119. The glycoconjugate of any one of paragraphs 1-52 or the immunogenic composition of any one of paragraphs 53-116 for use in a method of preventing, treating or ameliorating a *S. pneumoniae* infection, disease or condition in a subject.
120. A method of preventing, treating or ameliorating an infection, disease or condition associated with *S. pneumoniae* in a subject, comprising administering to the subject an immunologically effective amount of a glycoconjugate of any one of paragraphs 1-52 or an immunologically effective amount of an immunogenic composition of any one of paragraphs 53-116.

121. A method of inducing an immune response to *S. pneumoniae* in a subject comprising administering to the subject an immunologically effective amount of a glycoconjugate of any one of paragraphs 1-52 or an immunologically effective amount of an immunogenic composition of any one of paragraphs 53-116.

122. The glycoconjugate of any one of paragraphs 1-52 or the immunogenic composition of any one of paragraphs 53-116 for use in a method of preventing a *S. pneumoniae* infection in a subject.

123. A method of preventing an infection by *S. pneumoniae* in a subject comprising administering to the subject an immunologically effective amount of an immunologically effective amount of a glycoconjugate of any one of paragraphs 1-52 or an immunologically effective amount of an immunogenic composition of any one of paragraphs 53-116.

124. A serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B glycoconjugate prepared using reductive amination.

125. The glycoconjugate of any one of paragraphs 1-52 wherien said glycoconjugate is prepared using reductive amination 126. A process for the production of activated *S. pneumoniae* serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides comprising the step of (a) reacting a mixture of isolated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides with an oxidizing agent.

127. The process of paragraph 126 further comprising (b) quenching the oxidation reaction by addition of a quenching agent resulting in activated saccharides.

128. A process for the production of activated *S. pneumoniae* serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B comprising the step of (a) individually reacting an isolated serotype 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharide with an oxidizing agent and (b) mixing the activated serotypes 8/15A/15B/23A/23B, 8/15A/15B/23A, 8/15A/15B/23B, 8/15A/23A/23B, 8/15B/23A/23B, 15A/15B/23A/23B, 8/15A/15B, 8/15A/23A, 8/15A/23B, 8/15B/23A, 8/15B/23B, 8/23A/23B, 15A/15B/23A, 15A/15B/23B, 15A/23A/23B, 15B/23A/23B, 8/15A, 8/15B, 8/23A, 8/23B, 15A/15B, 15A/23A, 15A/23B, 15B/23A, 15B/23B or 23A/23B saccharides.

129. The process of paragraph 128 further comprising quenching the oxidation reaction by addition of a quenching agent.

130. The process of anyone of paragraphs 126-129 wherien said oxidizing agent is periodate.

131. The process of anyone of paragraphs 126-129 wherien said oxidizing agent is metaperiodate or orthoperiodate.

132. The process of anyone of paragraphs 126-129 wherien said oxidizing agent is sodium periodate or potassium periodate.

133. The process of anyone of paragraphs 126-132 wherein if present the quenching agent is any of the one disclosed herein.

134. The process of anyone of paragraphs 126-133 wherein the activated saccharides are purified.

135. The process of anyone of paragraphs 126-134 wherein the activated saccharides are purified according to any on the methods disclosed herein.

136. The process of anyone of paragraphs 126-135 wherein the degree of oxidation of the activated saccharides are between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25.

137. The process of anyone of paragraphs 126-135 wherein the degree of oxidation of the activated saccharides are between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25.

138. The process of anyone of paragraphs 126-135 wherein the degree of oxidation of the activated saccharides are between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20.

139. The process of anyone of paragraphs 126-138 wherein the activated saccharides have a molecular weight of between 10 kDa and 5,000 kDa; between 20 kDa and 4,000 kDa; between 50 kDa and 3,000 kDa; between 100 kDa and 2500 kDa; 100 kDa and 2,000 kDa; between 150 kDa and 2,000 kDa; between 150 kDa and 1,500 kDa; between 10 kDa and 2,000 kDa; between 20 kDa and 1,500 kDa; between 30 kDa and 1,250 kDa; between 50 kDa and 1,000 kDa; between 70 kDa and 900 kDa; between 100 kDa and 800 kDa; between 200 kDa to 600 kDa or between 400 kDa to 700 kDa.

140. The process of anyone of paragraphs 126-138 wherein the activated saccharides have a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa.

141. The process of anyone of paragraphs 126-138 wherein the mixture of saccharides have a molecular weight between 25 kDa and 1,000 kDa, between 100 kDa and 1,000 kDa, between 300 kDa and 800 kDa, between 300 kDa and 700 kDa, between 300 kDa and 600 kDa, between 400 kDa and 1,000 kDa, between 400 kDa and 800 kDa, between 400 kDa and 700 kDa or between 400 kDa and 600 kDa.

142. The process of anyone of paragraphs 126-138 wherein the mixture of saccharides have a molecular weight between 300 kDa and 800 kDa. or between 400 kDa and 600 kDa.

143. The process of anyone of paragraphs 126-142 wherein the activated saccharides are lyophilised.

144. The process of anyone of paragraphs 126-142 wherein the activated saccharides are lyophilised. in the presence of saccharide such as sucrose, trehalose, raffinose, stachyose, melezitose, dextran, mannitol, lactitol or palatinit 145. A conjugation process comprising activating saccharides according to any one of paragraphs 126-144.

146. A conjugation process comprising activating saccharides according to any one of paragraphs 126-144, (c) compounding said activated saccharides with a carrier protein and (d) reacting the compounded activated saccharides and carrier protein with a reducing agent to form a glycoconjugate.

147. The conjugation process of paragraph 146 wherein said compounding between the activated saccharides and the carrier protein is conducted using co-lyophilization.

148. The conjugation process of paragraph 146 wherein said compounding between the activated saccharides and the carrier protein is conducted using co-lyophilization in the presence of a saccharide such as sucrose, trehalose, raffinose, stachyose, melezitose, dextran, mannitol, lactitol and palatinit.

149. The conjugation process of any one of paragraphs 145-148 wherein the reduction reaction is carried out in aqueous solvent.

150. The conjugation process of any one of paragraphs 145-148 wherein the reduction reaction is carried out in aprotic solvent.

151. The conjugation process of any one of paragraphs 145-148 wherein the reduction reaction is carried out in DMSO (dimethylsulfoxide) or in DMF (dimethylformamide)) solvent.

152. The conjugation process of any one of paragraphs 145-148 wherein step (c) and step (d) are carried out in aprotic solvent.

153. The conjugation process of any one of paragraphs 145-148 wherein step (c) and step (d) are carried out in DMSO (dimethylsulfoxide) or in DMF (dimethylformamide)) solvent.

154. The conjugation process of any one of paragraphs 145-148 wherein step (c) and step (d) are carried out in DMSO (dimethylsulfoxide).

155. The conjugation process of any one of paragraphs 145-154 wherein the reducing agent is selected from the group consisting of sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^{i}$PrN—$BH_3$, benzylamine-$BH_3$ or 5-ethyl-2-methylpyridine borane (PEMB).

156. The conjugation process of any one of paragraphs 145-154 wherein the reducing agent is sodium cyanoborohydride.

157. The conjugation process of any one of paragraphs 145-156 wherein unreacted aldehyde groups are capped.

158. The conjugation process of any one of paragraphs 145-156 wherein unreacted aldehyde groups are capped using a capping agent.

159. The conjugation process of any one of paragraphs 145-156 wherein unreacted aldehyde groups are capped using a capping agent using sodium borohydride ($NaBH_4$).

160. The conjugation process of any one of paragraphs 145-156 wherein the glycoconjugate are purified.

161. A mixture of activated saccharides obtained or obtainable according to the process of any one of paragraphs 126-144.

162. A glycoconjugate obtained or obtainable according to the process of any one of paragraphs 145-160.

Particular embodiments of the invention are set forth in the following numbered paragraphs:

1. A glycoconjugate comprising at least two saccharides selected from the group consisting of a saccharide from *S. pneumoniae* serotype 8, a saccharide from *S. pneumoniae* serotype 11A, a saccharide from *S. pneumoniae* serotype 12F, a saccharide from *S. pneumoniae* serotype 23B and a saccharide from *S. pneumoniae* serotype 23B, conjugated to the same carrier protein.
2. The glycoconjugate of paragraph 1, which is a 2, 3, 4 or a 5-valent glycoconjugate.
3. The glycoconjugate of paragraph 1 or 2 selected from a group consisting of a serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugate.
4. The glycoconjugate of paragraph 2 or 3 which is a serotypes 8/11A/12F/23A/23B, 8/11A/12F/23A, 8/11A/12F/23B, 8/11A/23A/23B, 8/12F/23A/23B, 8/11A/12F, 8/11A/23A, 8/11A/23B, 8/12F/23A, 8/12F/23B, 8/23A/23B, 8/11A, 8/12F, 8/23A or 8/23B glycoconjugate and comprises a serotype 8 saccharide having a molecular weight of between 10 kDa and 5,000 kDa.
5. The glycoconjugate of paragraph 2 or 3 which is a serotypes 8/11A/12F/23A/23B, 8/11A/12F/23A, 8/11A/12F/23B, 8/11A/23A/23B, 11A/12F/23A/23B, 8/11A/12F, 8/11A/23A, 8/11A/23B, 11A/12F/23A, 11A/12F/23B, 11A/23A/23B, 8/11A, 11A/12F, 11A/23A or 11A/23B glycoconjugate and comprises a serotype 11A saccharide having a molecular weight of between 10 kDa and 5,000 kDa.
6. The glycoconjugate of paragraph 2 or 3 which is a serotypes 8/11A/12F/23A/23B, 8/11A/12F/23A, 8/11A/12F/23B, 8/12F/23A/23B, 11A/12F/23A/23B, 8/11A/12F, 8/12F/23A, 8/12F/23B, 11A/12F/23A, 11A/12F/23B, 12F/23A/23B, 8/12F, 11A/12F, 12F/23A or 12F/23B glycoconjugate and comprises a serotype 12F saccharide having a molecular weight of between 10 kDa and 5,000 kDa.
7. The glycoconjugate of paragraph 2 or 3 which is a serotypes 8/11A/12F/23A/23B, 8/11A/12F/23A, 8/11A/23A/23B, 8/12F/23A/23B, 11A/12F/23A/23B, 8/11A/23A, 8/12F/23A, 8/23A/23B, 11A/12F/23A, 11A/23A/23B, 12F/23A/23B, 8/23A, 11A/23A, 12F/23A or 23A/23B glycoconjugate and comprises a serotype 23A saccharide having a molecular weight of between 10 kDa and 5,000 kDa.
8. The glycoconjugate of paragraph 2 or 3 which is a serotypes 8/11A/12F/23A/23B, 8/11A/12F/23B, 8/11A/23A/23B, 8/12F/23A/23B, 11A/12F/23A/23B, 8/11A/23B, 8/12F/23B, 8/23A/23B, 11A/12F/23B, 11A/23A/23B, 12F/23A/23B, 8/23B, 11A/23B, 12F/23B or 23A/23B glycoconjugate and comprises a serotype 23B saccharide having a molecular weight of between 10 kDa and 5,000 kDa.
9. The glycoconjugate of anyone of paragraphs 1 to 8 having a molecular weight of between 400 kDa and 15,000 kDa.
10. The glycoconjugate of anyone of paragraphs 1 to 9 having a degree of conjugation of between 2 and 15.
11. The glycoconjugate of anyone of paragraphs 1 to 10 wherein the ratio of saccharides to carrier protein in the glycoconjugate (w/w) is between 0.5 and 3.0.
12. The glycoconjugate of any one of paragraphs 1 to 11 which is a serotypes 8/11A/12F/23A/23B, 8/11A/12F/23A, 8/11A/12F/23B, 8/11A/23A/23B, 8/11A/12F, 8/11A/23A, 8/11A/23B or 8/11A glycoconjugate wherien the ratio of serotype 8 saccharide to serotype 11A saccharide in the glycoconjugate (w/w) is between 0.25 and 4.0.
13. The glycoconjugate of any one of paragraphs 1 to 12 which is a serotypes 8/11A/12F/23A/23B, 8/11A/12F/23A, 8/11A/12F/23B, 8/12F/23A/23B, 8/11A/12F, 8/12F/23A, 8/12F/23B or 8/12F glycoconjugate wherein the ratio of serotype 8 saccharide to serotype 12F saccharide in the glycoconjugate (w/w) is between 0.25 and 4.0.
14. The glycoconjugate of any one of paragraphs 1 to 13 which is a serotypes 8/11A/12F/23A/23B, 8/11A/12F/23A, 8/11A/23A/23B, 8/12F/23A/23B, 8/11A/23A, 8/12F/23A, 8/23A/23B or 8/23A glycoconjugate wherein the ratio of serotype 8 saccharide to serotype 23A saccharide in the glycoconjugate (w/w) is between 0.25 and 4.0.
15. The glycoconjugate of any one of paragraphs 1 to 14 which is a serotypes 8/11A/12F/23A/23B, 8/11A/12F/23B, 8/11A/23A/23B, 8/12F/23A/23B, 8/11A/23B, 8/12F/23B, 8/23A/23B or 8/23B glycoconjugate wherein the ratio of serotype 8 saccharide to serotype 23B saccharide in the glycoconjugate (w/w) is between 0.25 and 4.0.
16. The glycoconjugate of any one of paragraphs 1 to 15 which is a 8/11A/12F/23A/23B, 8/11A/12F/23A, 8/11A/12F/23B, 11A/12F/23A/23B, 8/11A/12F, 11A/12F/23A, 11A/12F/23B or 11A/12F glycoconjugate wherein the ratio of serotype 11A saccharide to serotype 12F saccharide in the glycoconjugate (w/w) is between 0.25 and 4.0.
17. The glycoconjugate of any one of paragraphs 1 to 16 which is a serotypes 8/11A/12F/23A/23B, 8/11A/12F/23A, 8/11A/23A/23B, 11A/12F/23A/23B, 8/11A/23A, 11A/12F/23A, 11A/23A/23B or 11A/23A glycoconjugate wherein the ratio of serotype 11A saccharide to serotype 23A saccharide in the glycoconjugate (w/w) is between 0.25 and 4.0.
18. The glycoconjugate of any one of paragraphs 1 to 17 which is a serotypes 8/11A/12F/23A/23B, 8/11A/12F/23B, 8/11A/23A/23B, 11A/12F/23A/23B, 8/11A/23B, 11A/12F/23B, 11A/23A/23B or 11A/23B glycoconjugate wherein the ratio of serotype 11A saccharide to serotype 23B saccharide in the glycoconjugate (w/w) is between 0.25 and 4.0.
19. The glycoconjugate of any one of paragraphs 1 to 18 which is a serotypes 8/11A/12F/23A/23B, 8/11A/12F/23A, 8/12F/23A/23B, 11A/12F/23A/23B, 8/12F/23A, 11A/12F/23A, 12F/23A/23B or 12F/23A glycoconjugate wherein the ratio of serotype 12F saccharide to serotype 23A saccharide in the glycoconjugate (w/w) is between 0.25 and 4.0.
20. The glycoconjugate of any one of paragraphs 1 to 19 which is a serotypes 8/11A/12F/23A/23B, 8/11A/12F/23B, 8/12F/23A/23B, 11A/12F/23A/23B, 8/12F/23B, 11A/12F/23B, 12F/23A/23B or 12F/23B glycoconjugate wherein the ratio of serotype 12F saccharide to serotype 23B saccharide in the glycoconjugate (w/w) is between 0.25 and 4.0.

21. The glycoconjugate of any one of paragraphs 1 to 20 which is a serotypes 8/11A/12F/23A/23B, 8/11A/23A/23B, 8/12F/23A/23B, 11A/12F/23A/23B, 8/23A/23B, 11A/23A/23B, 12F/23A/23B or 23A/23B glycoconjugate wherein the ratio of serotype 23A saccharide to serotype 23B saccharide in the glycoconjugate (w/w) is between 0.25 and 4.0.

22. The glycoconjugate of any one of paragraphs 1 to 21 which is a 8/11A/12F/23A/23B, 8/11A/12F/23A, 8/11A/12F/23B, or 8/11A/12F glycoconjugate wherein the relative proportion of serotype 8 saccharide, serotype 11A saccharide and serotype 12F saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 12F | 4 | 2 | 1 | 4 | 2 | 1 | 4 | 2 | 1 | 4 | 2 | 1 | 1 | 1 | 4 | 2 | 1 | 1 | 1 |

23. The glycoconjugate of any one of paragraphs 1 to 22 which is a serotypes 8/11A/12F/23A/23B, 8/11A/12F/23A, 8/11A/23A/23B, or 8/11A/23A glycoconjugate wherein the relative proportion of serotype 8 saccharide, serotype 11A saccharide and serotype 23A saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 23A | 4 | 2 | 1 | 4 | 2 | 1 | 4 | 2 | 1 | 4 | 2 | 1 | 1 | 1 | 4 | 2 | 1 | 1 | 1 |

24. The glycoconjugate of any one of paragraphs 1 to 23 which is a serotypes 8/11A/12F/23A/23B, 8/11A/12F/23B, 8/11A/23A/23B or 8/11A/23B glycoconjugate wherein the relative proportion of serotype 8 saccharide, serotype 11A saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

25. The glycoconjugate of any one of paragraphs 1 to 24 which is a serotypes 8/11A/12F/23A/23B, 8/11A/12F/23A, 8/12F/23A/23B or 8/12F/23A glycoconjugate wherein the relative proportion of serotype 8 saccharide, serotype 12F saccharide and serotype 23A saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 12F | 1 | 1 | 1 | 1 | 1 | 1 | 1 | 1 | 1 | 2 | 2 | 2 | 2 | 2 | 4 | 4 | 4 | 4 | 4 |
| 23A | 4 | 2 | 1 | 4 | 2 | 1 | 4 | 2 | 1 | 4 | 2 | 1 | 1 | 1 | 4 | 2 | 1 | 1 | 1 |

26. The glycoconjugate of any one of paragraphs 1 to 25 which is a serotypes 8/11A/12F/23A/23B, 8/11A/12F/23B, 8/12F/23A/23B or 8/12F/23B glycoconjugate wherein the relative proportion of serotype 8 saccharide, serotype 12F saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 12F | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

27. The glycoconjugate of any one of paragraphs 1 to 26 which is a serotypes 8/11A/12F/23A/23B, 8/11A/23A/23B, 8/12F/23A/23B or 8/23A/23B glycoconjugate wherein the relative proportion of serotype 8 saccharide, serotype 23A saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 8 | 1 | 1 | 1 | 2 | 2 | 2 | 4 | 4 | 4 | 1 | 1 | 1 | 2 | 4 | 1 | 1 | 1 | 2 | 4 |
| 23A | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

28. The glycoconjugate of any one of paragraphs 1 to 27 which is a serotypes 8/11A/12F/23A/23B, 8/11A/12F/23A, 11A/12F/23A/23B or 11A/12F/23A glycoconjugate wherein the relative proportion of serotype 11A saccharide, serotype 12F saccharide and serotype 23A saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 11A | 1 | 1 | 1 | 2 | 2 | 2 | 4 | 4 | 4 | 1 | 1 | 1 | 2 | 4 | 1 | 1 | 1 | 2 | 4 |
| 12F | 1 | 1 | 1 | 1 | 1 | 1 | 1 | 1 | 1 | 2 | 2 | 2 | 2 | 2 | 4 | 4 | 4 | 4 | 4 |
| 23A | 4 | 2 | 1 | 4 | 2 | 1 | 4 | 2 | 1 | 4 | 2 | 1 | 1 | 1 | 4 | 2 | 1 | 1 | 1 |

29. The glycoconjugate of any one of paragraphs 1 to 28 which is a serotypes 8/11A/12F/23A/23B, 8/11A/12F/23B, 11A/12F/23A/23B or 11A/12F/23B glycoconjugate wherein the relative proportion of serotype 11A saccharide, serotype 12F saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 11A | 1 | 1 | 1 | 2 | 2 | 2 | 4 | 4 | 4 | 1 | 1 | 1 | 2 | 4 | 1 | 1 | 1 | 2 | 4 |
| 12F | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

30. The glycoconjugate of any one of paragraphs 1 to 29 which is a serotypes 8/11A/12F/23A/23B, 8/11A/23A/23B, 11A/12F/23A/23B or 11A/23A/23B glycoconjugate wherein the relative proportion of serotype 11A saccharide, serotype 23A saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 11A | 1 | 1 | 1 | 2 | 2 | 2 | 4 | 4 | 4 | 1 | 1 | 1 | 2 | 4 | 1 | 1 | 1 | 2 | 4 |
| 23A | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

31. The glycoconjugate of any one of paragraphs 1 to 30 which is a serotypes 8/11A/12F/23A/23B, 8/12F/23A/23B, 11A/12F/23A/23B or 12F/23A/23B glycoconjugate wherein the relative proportion of serotype 12F saccharide, serotype 23A saccharide and serotype 23B saccharide in the glycoconjugate (w/w) is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 12F | 1 | 1 | 1 | 2 | 2 | 2 | 4 | 4 | 4 | 1 | 1 | 1 | 2 | 4 | 1 | 1 | 1 | 2 | 4 |
| 23A | 1 | 1 | 1 | 1 | 1 | 1 | 1 | 1 | 1 | 2 | 2 | 2 | 2 | 2 | 4 | 4 | 4 | 4 | 4 |
| 23B | 4 | 2 | 1 | 4 | 2 | 1 | 4 | 2 | 1 | 4 | 2 | 1 | 1 | 1 | 4 | 2 | 1 | 1 | 1 |

32. The glycoconjugate of any one of paragraphs 1 to 31 which is a serotypes 8/11A/12F/23A/23B or 8/11A/12F/23A glycoconjugate wherein the relative proportion of serotype 8 saccharide, serotype 11A saccharide, serotype 12F saccharide and serotype 23A saccharide in the glycoconjugate (w/w) is according to any of the one of the below tables:

| | a | b | c | d | e | f | g | h | i | j | k | l | m | n | o |
|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 2 | 2 |
| 11A | 1 | 1 | 1 | 1 | 1 | 1 | 1 | 1 | 1 | 2 | 2 | 2 | 2 | 2 | 2 |
| 12F | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 |

| | p | q | r | s | t | u | v | w | x | y | z | aa |
|---|---|---|---|---|---|---|---|---|---|---|---|---|
| 8 | 4 | 4 | 4 | 1 | 1 | 1 | 2 | 2 | 2 | 4 | 4 | 4 |
| 11A | 2 | 2 | 2 | 4 | 4 | 4 | 4 | 4 | 4 | 4 | 4 | 4 |
| 12F | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 12F | 2 | 2 | 2 | 2 | 2 | 2 | 2 | 2 | 2 | 2 | 2 | 2 | 2 | 2 | 2 | 2 | 2 | 2 | 2 |
| 23A | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 12F | 4 | 4 | 4 | 4 | 4 | 4 | 4 | 4 | 4 | 4 | 4 | 4 | 4 | 4 | 4 | 4 | 4 | 4 | 4 |
| 23A | 1 | 2 | 4 | 1 | 2 | 4 | 1 | 2 | 4 | 1 | 2 | 4 | 1 | 1 | 1 | 2 | 4 | 1 | 1 |

33. The glycoconjugate of any one of paragraphs 1 to 32 which is a serotypes 8/11A/12F/23A/23B or 8/11A/12F/23B glycoconjugate wherein the relative proportion of serotype 8 saccharide, serotype 11A saccharide, serotype 12F saccharide and serotype 23B saccharide in the glycoconjugate (w/w) is according to any of the one of the below tables:

| | a | b | c | d | e | f | g | h | i | j | k | l | m | n | o |
|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 2 | 2 |
| 11A | 1 | 1 | 1 | 1 | 1 | 1 | 1 | 1 | 1 | 2 | 2 | 2 | 2 | 2 | 2 |

-continued

| | | | | | | | | | | | | | | | |
|---|---|---|---|---|---|---|---|---|---|---|---|---|---|---|---|
| 12F | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 |

| | p | q | r | s | t | u | v | w | x | y | z | aa |
|---|---|---|---|---|---|---|---|---|---|---|---|---|
| 8 | 4 | 4 | 4 | 1 | 1 | 1 | 2 | 2 | 2 | 4 | 4 | 4 |
| 11A | 2 | 2 | 2 | 4 | 4 | 4 | 4 | 4 | 4 | 4 | 4 | 4 |
| 12F | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 12F | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 12F | 4 | 4 | 4 | 4 | 4 | 4 | 4 | 4 | 4 | 4 | 4 | 4 | 4 | 4 | 4 | 4 | 4 | 4 | 4 |
| 23B | 1 | 2 | 4 | 1 | 2 | 4 | 1 | 2 | 4 | 1 | 2 | 4 | 1 | 1 | 1 | 2 | 4 | 1 | 1 |

34. The glycoconjugate of any one of paragraphs 1 to 33 which is a serotypes 8/11A/12F/23A/23B or 8/11A/23A/23B glycoconjugate wherein the relative proportion of serotype 8 saccharide, serotype 11A saccharide, serotype 23A saccharide and serotype 23B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 11A | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 23A | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 11A | 1 | 1 | 1 | 1 | 1 | 1 | 1 | 1 | 1 | 2 | 2 | 2 | 2 | 2 | 4 | 4 | 4 | 4 | 4 |
| 23A | 4 | 4 | 4 | 4 | 4 | 4 | 4 | 4 | 4 | 4 | 4 | 4 | 4 | 4 | 4 | 4 | 4 | 4 | 4 |
| 23B | 1 | 2 | 4 | 1 | 2 | 4 | 1 | 2 | 4 | 1 | 2 | 4 | 1 | 1 | 1 | 2 | 4 | 1 | 1 |

35. The glycoconjugate of any one of paragraphs 1 to 34 which is a serotypes 8/11A/12F/23A/23B or 8/12F/23A/23B glycoconjugate wherein the relative proportion of serotype 8 saccharide, serotype 12F saccharide, serotype 23A saccharide and serotype 23B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 12F | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 12F | 1 | 1 | 1 | 1 | 1 | 1 | 1 | 1 | 1 | 2 | 2 | 2 | 2 | 2 | 4 | 4 | 4 | 4 | 4 |
| 23A | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 8 | 1 | 1 | 1 | 2 | 2 | 2 | 4 | 4 | 4 | 1 | 1 | 1 | 2 | 4 | 1 | 1 | 1 | 2 | 4 |
| 12F | 1 | 1 | 1 | 1 | 1 | 1 | 1 | 1 | 1 | 2 | 2 | 2 | 2 | 2 | 4 | 4 | 4 | 4 | 4 |
| 23A | 4 | 4 | 4 | 4 | 4 | 4 | 4 | 4 | 4 | 4 | 4 | 4 | 4 | 4 | 4 | 4 | 4 | 4 | 4 |
| 23B | 1 | 2 | 4 | 1 | 2 | 4 | 1 | 2 | 4 | 1 | 2 | 4 | 1 | 1 | 1 | 2 | 4 | 1 | 1 |

36. The glycoconjugate of any one of paragraphs 1 to 35 which is a serotypes 8/11A/12F/23A/23B or 11A/12F/23A/23B glycoconjugate wherein the relative proportion of serotype 11A saccharide, serotype 12F saccharide, serotype 23A saccharide and serotype 23B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 11A | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 12F | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 11A | 1 | 1 | 1 | 2 | 2 | 2 | 4 | 4 | 4 | 1 | 1 | 1 | 2 | 4 | 1 | 1 | 1 | 2 | 4 |
| 12F | 1 | 1 | 1 | 1 | 1 | 1 | 1 | 1 | 1 | 2 | 2 | 2 | 2 | 2 | 4 | 4 | 4 | 4 | 4 |
| 23A | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 11A | 1 | 1 | 1 | 2 | 2 | 2 | 4 | 4 | 4 | 1 | 1 | 1 | 2 | 4 | 1 | 1 | 1 | 2 | 4 |
| 12F | 1 | 1 | 1 | 1 | 1 | 1 | 1 | 1 | 1 | 2 | 2 | 2 | 2 | 2 | 4 | 4 | 4 | 4 | 4 |
| 23A | 4 | 4 | 4 | 4 | 4 | 4 | 4 | 4 | 4 | 4 | 4 | 4 | 4 | 4 | 4 | 4 | 4 | 4 | 4 |
| 23B | 1 | 2 | 4 | 1 | 2 | 4 | 1 | 2 | 4 | 1 | 2 | 4 | 1 | 1 | 1 | 2 | 4 | 1 | 1 |

37. The glycoconjugate of any one of paragraphs 1 to 36 which is a serotypes 8/11A/12F/23A/23B glycoconjugate wherein the relative proportion of serotype 8 saccharide, serotype 11A saccharide, serotype 12F saccharide, serotype 23A saccharide and serotype 23B saccharide in the glycoconjugate (w/w) is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 8 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 11A | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 12F | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at | au |
|---|---|---|---|---|---|---|---|---|---|---|---|---|---|---|---|---|---|---|---|---|
| 8 | 1 | 1 | 1 | 1 | 1 | 1 | 1 | 1 | 1 | 1 | 1 | 1 | 1 | 1 | 1 | 1 | 1 | 1 | 1 | 1 |
| 11A | 1 | 1 | 1 | 2 | 2 | 2 | 4 | 4 | 4 | 1 | 1 | 1 | 2 | 2 | 2 | 4 | 4 | 4 | 1 | 1 |
| 12F | 1 | 1 | 1 | 1 | 1 | 1 | 1 | 1 | 1 | 2 | 2 | 2 | 2 | 2 | 2 | 2 | 2 | 2 | 4 | 4 |
| 23A | 2 | 2 | 2 | 2 | 2 | 2 | 2 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 2 | 4 | 1 | 2 | 4 | 1 | 2 |

| | ay | aw | ax | ay | az | ba | bb | be | bd | be | bf | bg | bh | bi | bj | bk | bl | bm | bn |
|---|---|---|---|---|---|---|---|---|---|---|---|---|---|---|---|---|---|---|---|
| 8 | 1 | 1 | 1 | 1 | 1 | 1 | 1 | 1 | 1 | 1 | 1 | 1 | 1 | 1 | 1 | 1 | 1 | 1 | 1 |
| 11A | 1 | 2 | 2 | 2 | 4 | 4 | 4 | 1 | 1 | 1 | 2 | 2 | 2 | 4 | 4 | 4 | 1 | 1 | 1 |
| 12F | 4 | 4 | 4 | 4 | 4 | 4 | 4 | 1 | 1 | 1 | 1 | 1 | 1 | 1 | 1 | 1 | 2 | 2 | 2 |
| 23A | 2 | 2 | 2 | 2 | 2 | 2 | 2 | 4 | 4 | 4 | 4 | 4 | 4 | 4 | 4 | 4 | 4 | 4 | 4 |
| 23B | 4 | 1 | 2 | 4 | 1 | 2 | 4 | 1 | 2 | 4 | 1 | 2 | 4 | 1 | 2 | 4 | 1 | 2 | 4 |

| | bo | bp | bq | br | bs | bt | bu | bv | bw | bx | by | bz | ca | cb | cd | ce | cf | cg | ch | ci |
|---|---|---|---|---|---|---|---|---|---|---|---|---|---|---|---|---|---|---|---|---|
| 8 | 1 | 1 | 1 | 1 | 1 | 1 | 1 | 1 | 1 | 1 | 1 | 1 | 1 | 1 | 1 | 2 | 2 | 2 | 2 | 2 |
| 11A | 2 | 2 | 2 | 4 | 4 | 4 | 1 | 1 | 1 | 2 | 2 | 2 | 4 | 4 | 4 | 1 | 1 | 1 | 2 | 2 |
| 12F | 2 | 2 | 2 | 2 | 2 | 2 | 4 | 4 | 4 | 4 | 4 | 4 | 4 | 4 | 4 | 1 | 1 | 1 | 1 | 1 |
| 23A | 4 | 4 | 4 | 4 | 4 | 4 | 4 | 4 | 4 | 4 | 4 | 4 | 4 | 4 | 4 | 1 | 1 | 1 | 1 | 1 |
| 23B | 1 | 2 | 4 | 1 | 2 | 4 | 1 | 2 | 4 | 1 | 2 | 4 | 1 | 2 | 4 | 1 | 2 | 4 | 1 | 2 |

| | cj | ck | cl | cm | en | co | cp | eq | cr | cs | ct | cu | cv | cw | cx | cy | cz | da |
|---|---|---|---|---|---|---|---|---|---|---|---|---|---|---|---|---|---|---|
| 8 | 2 | 2 | 2 | 2 | 2 | 2 | 2 | 2 | 2 | 2 | 2 | 2 | 2 | 2 | 2 | 2 | 2 | 2 |
| 11A | 2 | 4 | 4 | 4 | 1 | 1 | 1 | 2 | 2 | 2 | 4 | 4 | 4 | 1 | 1 | 1 | 2 | 2 |
| 12F | 1 | 1 | 1 | 1 | 2 | 2 | 2 | 2 | 2 | 2 | 2 | 2 | 2 | 4 | 4 | 4 | 4 | 4 |
| 23A | 1 | 1 | 1 | 1 | 1 | 1 | 1 | 1 | 1 | 1 | 1 | 1 | 1 | 1 | 1 | 1 | 1 | 1 |
| 23B | 4 | 1 | 2 | 4 | 1 | 2 | 4 | 1 | 2 | 4 | 1 | 2 | 4 | 1 | 2 | 4 | 1 | 2 |

| | db | dc | dd | de | df | dg | dh | di | dj | dk | dl | dm | dn | do | dp | dq | dr | ds | dt |
|---|---|---|---|---|---|---|---|---|---|---|---|---|---|---|---|---|---|---|---|
| 8 | 2 | 2 | 2 | 2 | 2 | 2 | 2 | 2 | 2 | 2 | 2 | 2 | 2 | 2 | 2 | 2 | 2 | 2 | 2 |
| 11A | 2 | 4 | 4 | 4 | 1 | 1 | 1 | 2 | 2 | 2 | 4 | 4 | 4 | 1 | 1 | 1 | 2 | 4 | 1 |
| 12F | 4 | 4 | 4 | 4 | 1 | 1 | 1 | 1 | 1 | 1 | 1 | 1 | 1 | 2 | 2 | 2 | 2 | 2 | 4 |
| 23A | 1 | 1 | 1 | 1 | 2 | 2 | 2 | 2 | 2 | 2 | 2 | 2 | 2 | 2 | 2 | 2 | 2 | 2 | 2 |
| 23B | 4 | 1 | 2 | 4 | 1 | 2 | 4 | 1 | 2 | 4 | 1 | 2 | 4 | 1 | 2 | 4 | 1 | 1 | 1 |

| | du | dv | dw | dx | dy | dz | ea | eb | ec | ed | ee | ef | eg | eh | ei | ej | ek | el | em | en | eo |
|---|---|---|---|---|---|---|---|---|---|---|---|---|---|---|---|---|---|---|---|---|---|
| 8 | 2 | 2 | 2 | 2 | 2 | 2 | 2 | 2 | 2 | 2 | 2 | 2 | 2 | 2 | 2 | 2 | 2 | 2 | 2 | 2 | 2 |
| 11A | 1 | 1 | 2 | 4 | 1 | 1 | 1 | 2 | 2 | 2 | 4 | 4 | 4 | 1 | 1 | 1 | 2 | 4 | 1 | 1 | 1 |

-continued

| | du | dv | dw | dx | dy | dz | ea | eb | ec | ed | ee | ef | eg | eh | ei | ej | ek | el | em | en | eo |
|---|---|---|---|---|---|---|---|---|---|---|---|---|---|---|---|---|---|---|---|---|---|
| 12F | 4 | 4 | 4 | 4 | 1 | 1 | 1 | 1 | 1 | 1 | 1 | 1 | 1 | 2 | 2 | 2 | 2 | 2 | 4 | 4 | 4 |
| 23A | 2 | 2 | 2 | 2 | 4 | 4 | 4 | 4 | 4 | 4 | 4 | 4 | 4 | 4 | 4 | 4 | 4 | 4 | 4 | 4 | 4 |
| 23B | 2 | 4 | 1 | 1 | 1 | 2 | 4 | 1 | 2 | 4 | 1 | 2 | 4 | 1 | 2 | 4 | 1 | 1 | 1 | 2 | 4 |

| | ep | eq | er | es | et | eu | ev | ew | ex | ey | ez | fa | fb | fc | fd | fe | ff | fg | fh | fi | fj | fk |
|---|---|---|---|---|---|---|---|---|---|---|---|---|---|---|---|---|---|---|---|---|---|---|
| 8 | 2 | 2 | 4 | 4 | 4 | 4 | 4 | 4 | 4 | 4 | 4 | 4 | 4 | 4 | 4 | 4 | 4 | 4 | 4 | 4 | 4 | 4 |
| 11A | 2 | 4 | 1 | 1 | 2 | 2 | 2 | 4 | 4 | 4 | 1 | 1 | 1 | 2 | 2 | 2 | 4 | 4 | 4 | 1 | 1 | 1 |
| 12F | 4 | 4 | 1 | 1 | 1 | 1 | 1 | 1 | 1 | 1 | 2 | 2 | 2 | 2 | 2 | 2 | 2 | 2 | 2 | 4 | 4 | 4 |
| 23A | 4 | 4 | 1 | 1 | 1 | 1 | 1 | 1 | 1 | 1 | 1 | 1 | 1 | 1 | 1 | 1 | 1 | 1 | 1 | 1 | 1 | 1 |
| 23B | 1 | 1 | 2 | 4 | 1 | 2 | 4 | 1 | 2 | 4 | 1 | 2 | 4 | 1 | 2 | 4 | 1 | 2 | 4 | 1 | 2 | 4 |

| | fl | fm | fn | fo | fp | fq | fr | fs | ft | fu | fv | fw | fx | fy | fz | ga | gb | gc | gd |
|---|---|---|---|---|---|---|---|---|---|---|---|---|---|---|---|---|---|---|---|
| 8 | 4 | 4 | 4 | 4 | 4 | 4 | 4 | 4 | 4 | 4 | 4 | 4 | 4 | 4 | 4 | 4 | 4 | 4 | 4 |
| 11A | 2 | 2 | 2 | 4 | 4 | 4 | 1 | 1 | 1 | 2 | 2 | 2 | 4 | 4 | 4 | 1 | 1 | 1 | 2 |
| 12F | 4 | 4 | 4 | 4 | 4 | 4 | 1 | 1 | 1 | 1 | 1 | 1 | 1 | 1 | 1 | 2 | 2 | 2 | 2 |
| 23A | 1 | 1 | 1 | 1 | 1 | 1 | 2 | 2 | 2 | 2 | 2 | 2 | 2 | 2 | 2 | 2 | 2 | 2 | 2 |
| 23B | 1 | 2 | 4 | 1 | 2 | 4 | 1 | 2 | 4 | 1 | 2 | 4 | 1 | 2 | 4 | 1 | 2 | 4 | 1 |

| | ge | gf | gg | gh | gi | gj | gk | gl | gl | gn | go | gp | gq | gr | gs | gt | gu | gv | gw | gx | gy | gz |
|---|---|---|---|---|---|---|---|---|---|---|---|---|---|---|---|---|---|---|---|---|---|---|
| 8 | 4 | 4 | 4 | 4 | 4 | 4 | 4 | 4 | 4 | 4 | 4 | 4 | 4 | 4 | 4 | 4 | 4 | 4 | 4 | 4 | 4 | 4 |
| 11A | 4 | 1 | 1 | 1 | 2 | 4 | 1 | 1 | 1 | 2 | 2 | 2 | 4 | 4 | 4 | 1 | 1 | 1 | 2 | 4 | 1 | 1 |
| 12F | 2 | 4 | 4 | 4 | 4 | 4 | 1 | 1 | 1 | 1 | 1 | 1 | 1 | 1 | 1 | 2 | 2 | 2 | 2 | 2 | 4 | 4 |
| 23A | 2 | 2 | 2 | 2 | 2 | 2 | 4 | 4 | 4 | 4 | 4 | 4 | 4 | 4 | 4 | 4 | 4 | 4 | 4 | 4 | 4 | 4 |
| 23B | 1 | 1 | 2 | 4 | 1 | 1 | 1 | 2 | 4 | 1 | 2 | 4 | 1 | 2 | 4 | 1 | 2 | 4 | 1 | 1 | 1 | 2 |

| | ha | hb | hc |
|---|---|---|---|
| 8 | 4 | 4 | 4 |
| 11A | 1 | 2 | 1 |
| 12F | 4 | 4 | 4 |
| 23A | 4 | 4 | 4 |
| 23B | 4 | 1 | 1 |

38. The glycoconjugate of any one of paragraphs 1 to 37 which is a serotypes 8/11A/12F/23A/23B, 8/11A/12F/23A, 8/11A/12F/23B, 8/11A/23A/23B, 11A/12F/23A/23B, 8/11A/12F, 8/11A/23A, 8/11A/23B, 11A/12F/23A, 11A/12F/23B, 11A/23A/23B, 8/11A, 11A/12F, 11A/23A or 11A/23B glycoconjugate comprising 0.1 to 5.0 mM acetate per mM serotype 11A saccharide.
39. The glycoconjugate of any one of paragraphs 1 to 38 which is a serotypes 8/11A/12F/23A/23B, 8/11A/12F/23A, 8/11A/12F/23B, 8/12F/23A/23B, 11A/12F/23A/23B, 8/11A/12F, 8/12F/23A, 8/12F/23B, 11A/12F/23A, 11A/12F/23B, 12F/23A/23B, 8/12F, 11A/12F, 12F/23A or 12F/23B glycoconjugate comprising 0.1 to 1.0 mM acetate per mM serotype 12F saccharide.
40. The glycoconjugate of any one of paragraphs 1 to 39 which is a serotypes 8/11A/12F/23A/23B, 8/11A/12F/23A, 8/11A/12F/23B, 8/11A/23A/23B, 11A/12F/23A/23B, 8/11A/12F, 8/11A/23A, 8/11A/23B, 11A/12F/23A, 11A/12F/23B, 11A/23A/23B, 8/11A, 11A/12F, 11A/23A or 11A/23B glycoconjugate comprising 0.1 to 1.0 mM glycerol per mM serotype 11A saccharide.
41. The glycoconjugate of any one of paragraphs 1 to 40 which is a serotypes 8/11A/12F/23A/23B, 8/11A/12F/23A, 8/11A/12F/23B, 8/12F/23A/23B, 11A/12F/23A/23B, 8/11A/12F, 8/12F/23A, 8/12F/23B, 11A/12F/23A, 11A/12F/23B, 12F/23A/23B, 8/12F, 11A/12F, 12F/23A or 12F/23B glycoconjugate comprising 0.1 to 1.0 mM glycerol per mM serotype 12F saccharide.
42. The glycoconjugate of any one of paragraphs 1 to 41 which is a serotypes 8/11A/12F/23A/23B, 8/11A/12F/23A, 8/11A/23A/23B, 8/12F/23A/23B, 11A/12F/23A/23B, 8/11A/23A, 8/12F/23A, 8/23A/23B, 11A/12F/23A, 11A/23A/23B, 12F/23A/23B, 8/23A, 11A/23A, 12F/23A, or 23A/23B glycoconjugate comprising 0.1 to 1.0 mM glycerol per mM serotype 23A saccharide.
43. The glycoconjugate of any one of paragraphs 1 to 42 which is a serotypes 8/11A/12F/23A/23B, 8/11A/12F/23B, 8/11A/23A/23B, 8/12F/23A/23B, 11A/12F/23A/23B, 8/11A/23B, 8/12F/23B, 8/23A/23B, 11A/12F/23B, 11A/23A/23B, 12F/23A/23B, 8/23B, 11A/23B, 12F/23B or 23A/23B glycoconjugate comprising 0.1 to 1.0 mM glycerol per mM serotype 23B saccharide.
44. The glycoconjugate of any one of paragraphs 1 to 43 wherein at least 30% of the glycoconjugate has a $K_d$ below or equal to 0.3 in a CL-4B column.
45. The glycoconjugate of any one of paragraphs 1 to 44 comprising less than about 50%, of free saccharide compared to the total amount of saccharide.
46. The glycoconjugate of any one of paragraphs 1 to 45 wherein the carrier protein is selected in the group consisting of: TT, DT, DT mutants (such as $CRM_{197}$), *H. influenzae* protein D, PhtX, PhtD, PhtDE fusions, detoxified pneumolysin, PorB, N19 protein, PspA, OMPC, toxin A or B of *C. difficile* and PsaA.

47. The glycoconjugate of any one of paragraphs 1 to 45 wherein the carrier protein is DT (Diphtheria toxoid).
48. The glycoconjugate of any one of paragraphs 1 to 45 wherein the carrier protein is TT (tetanus toxid).
49. The glycoconjugate of any one of paragraphs 1 to 45 wherein the carrier protein is PD (*H. influenzae* protein D).
50. The glycoconjugate of any one of paragraphs 1 to 45 wherein the carrier protein is detoxified pneumolysin or a mutant nontoxic form of pneumolysin.
51. The glycoconjugate of any one of paragraphs 1 to 45 wherein the carrier protein is $CRM_{197}$.
52. The glycoconjugate of any one of paragraphs 1 to 45 wherein the carrier protein is the A chain of $CRM_{197}$.
53. An immunogenic composition comprising at least one glycoconjugate of any one of paragraphs 1 to 52.
54. An immunogenic composition comprising one, two or three glycoconjugate(s) as defined at any one of paragraphs 1 to 52.
55. An immunogenic composition comprising one serotypes 8/11A/12F glycoconjugate and one serotypes 23A/23B glycoconjugate.
56. An immunogenic composition comprising one serotypes 8/11A/23A glycoconjugate and one serotypes 12F/23B glycoconjugate.
57. An immunogenic composition comprising one serotypes 8/11A/23B glycoconjugate and one serotypes 12F/23A glycoconjugate.
58. An immunogenic composition comprising one serotypes 8/12F/23A glycoconjugate and one serotypes 11A/23B glycoconjugate.
59. An immunogenic composition comprising one serotypes 8/12F/23B glycoconjugate and one serotypes 11A/23A glycoconjugate.
60. An immunogenic composition comprising one serotypes 8/23A/23B glycoconjugate and one serotypes 11A/12F glycoconjugate.
61. An immunogenic composition comprising one serotypes 11A/12F/23A glycoconjugate and one serotypes 8/23B glycoconjugate.
62. An immunogenic composition comprising one serotypes 11A/12F/23B glycoconjugate and one serotypes 8/23A glycoconjugate.
63. An immunogenic composition comprising one serotypes 11A/23A/23B glycoconjugate and one serotypes 8/12F glycoconjugate.
64. An immunogenic composition comprising one serotypes 12F/23A/23B glycoconjugate and one serotypes 8/11A glycoconjugate.
65. An immunogenic composition comprising one serotypes 8/11A glycoconjugate and one serotypes 12F/23A, 12F/23B or 23A/23B glycoconjugate.
66. An immunogenic composition comprising one serotypes 8/12F glycoconjugate and one serotypes 11A/23A, 11A/23B or 23A/23B glycoconjugate.
67. An immunogenic composition comprising one serotypes 8/23A glycoconjugate and one serotypes 11A/23B, 12F/23B or 11A/12F glycoconjugate.
68. An immunogenic composition comprising one serotypes 8/23B glycoconjugate and one serotypes 11A/23A, 12F/23A or 11A/12F glycoconjugate.
69. An immunogenic composition comprising one serotypes 11A/12F glycoconjugate and one serotypes 8/23A, 8/23B or 23A/23B glycoconjugate.
70. An immunogenic composition comprising one serotypes 11A/23A glycoconjugate and one serotypes 8/12F, 8/23B or 12F/23B glycoconjugate.
71. An immunogenic composition comprising one serotypes 11A/23B glycoconjugate and one serotypes 8/12F, 8/23A or 12F/23A glycoconjugate.
72. An immunogenic composition comprising one serotypes 12F/23A glycoconjugate and one serotypes 8/11A, 8/23B or 11A/23B glycoconjugate.
73. An immunogenic composition comprising one serotypes 12F/23B glycoconjugate and one serotypes 8/11A, 8/23A or 11A/23A glycoconjugate.
74. An immunogenic composition comprising one serotypes 23A/23B glycoconjugate and one serotypes 8/11A, 8/12F or 11A/12F glycoconjugate.
75. The immunogenic composition of any one of paragraphs 53-74, further comprising at least one glycoconjugate selected from the group consisting of a glycoconjugate from *S. pneumoniae* serotype 1, 3, 4, 5, 6A, 6B, 7F, 8, 9V, 10A, 11A, 12F, 14, 15A, 15B, 18C, 19A, 19F, 22F, 23A, 23B, 23F and 33F.
76. The immunogenic composition of paragraph 75, wherein said additional glycoconjugate(s) is/are individually conjugated glycoconjugate(s).
77. The immunogenic composition of any one of paragraphs 75-76, wherein said additional glycoconjugate(s) is/are conjugated to the carrier protein by reductive amination.
78. The immunogenic composition of any one of paragraphs 75-77 wherein said additional glycoconjugate(s) carrier protein is $CRM_{197}$.
79. The immunogenic composition of any one of paragraphs 53-74, further comprising glycoconjugates from *S. pneumoniae* serotypes 4, 6B, 9V, 14, 18C, 19F and 23F.
80. The immunogenic composition of any one of paragraphs 53-74 or 79, further comprising glycoconjugates from *S. pneumoniae* serotypes 1, 5 and 7F.
81. The immunogenic composition of any one of paragraphs 53-74 or 79-80, further comprising glycoconjugates from *S. pneumoniae* serotypes 6A and 19A.
82. The immunogenic composition of any one of paragraphs 53-74 or 79-81, further comprising a glycoconjugate from *S. pneumoniae* serotype 3.
83. The immunogenic composition of any one of paragraphs 53-74 or 79-82, further comprising a glycoconjugate from *S. pneumoniae* serotype 22F.
84. The immunogenic composition of any one of paragraphs 53-74 or 79-83, further comprising a glycoconjugate from *S. pneumoniae* serotype 33F.
85. The immunogenic composition of any one of paragraphs 53-74 or 79-84, further comprising a glycoconjugate from *S. pneumoniae* serotype 15B.
86. The immunogenic composition of any one of paragraphs 53-74 or 79-85, further comprising a glycoconjugate from *S. pneumoniae* serotype 12F.
87. The immunogenic composition of any one of paragraphs 53-74 or 79-86, further comprising a glycoconjugate from *S. pneumoniae* serotype 10A.
88. The immunogenic composition of any one of paragraphs 53-74 or 79-87, further comprising a glycoconjugate from *S. pneumoniae* serotype 11A.
89. The immunogenic composition of any one of paragraphs 53-74 or 79-88, further comprising a glycoconjugate from *S. pneumoniae* serotype 8.
90. The immunogenic composition of any one of paragraphs 53-74 or 79-82 further comprising at least one glycoconjugate of each of the two *S. pneumoniae* serotypes selected from the group consisting of: 22F and 33F, 22F and 12F, 22F and 10A, 22F and 11A, 33F and 12F, 33F and 10A, 33F and 11A, 12F and 10A, 12F and 11A and 10A and 11A.

91. The immunogenic composition of any one of paragraphs 53-74 or 79-82 further comprising at least one glycoconjugate of each of the three following *S. pneumoniae* serotypes:
22F and 33F and 12F,
22F and 33F and 10A,
22F and 33F and 11A,
22F and 12F and 10A,
22F and 12F and 11A,
22F and 10A and 11A,
33F and 12F and 10A,
33F and 12F and 11A,
33F and 10A and 11A, or
12F and 10A and 11A.

92. The immunogenic composition of any one of paragraphs 53-74 or 79-82 further comprising at least one glycoconjugate of each of the four following *S. pneumoniae* serotypes:
22F and 33F and 12F and 10A,
22F and 33F and 12F and 11A,
22F and 33F and 10A and 11A,
22F and 12F and 10A and 11A, or
33F and 12F and 10A and 11A.

93. The immunogenic composition of any one of paragraphs 53-74 or 79-82 further comprising at least one glycoconjugate of each of the five following *S. pneumoniae* serotypes: 22F and 33F and 12F and 10A and 11A.

94. The immunogenic composition of any one of paragraphs 53-74 or 79-82 further comprising a glycoconjugate from *S. pneumoniae* serotype 8.

95. The immunogenic composition of any one of paragraphs 53-74, 79-82 or 94 further comprising a glycoconjugate from *S. pneumoniae* serotype 15B.

96. The immunogenic composition of any one of paragraphs 75-95 wherein said additional glycoconjugate(s) is/are individually conjugated to the carrier protein.

97. The immunogenic composition of any one of paragraphs 75-96 wherein said additional glycoconjugate(s) is/are conjugated to $CRM_{197}$.

98. The immunogenic composition of any one of paragraphs 79-96 wherein the glycoconjugates from *S. pneumoniae* serotypes 4, 6B, 9V, 14, 18C, 19F and 23F are conjugated to $CRM_{197}$.

99. The immunogenic composition of any one of paragraphs 80-96 or 98 wherein the glycoconjugates from *S. pneumoniae* serotypes 1, 5 and 7F are conjugated to $CRM_{197}$.

100. The immunogenic composition of any one of paragraphs 80-96 or 98-99 wherein the glycoconjugates from *S. pneumoniae* serotypes 6A and 19A are conjugated to $CRM_{197}$.

101. The immunogenic composition of any one of paragraphs 80-96 or 98-100 wherein the glycoconjugates from *S. pneumoniae* serotype 3 is conjugated to $CRM_{197}$.

102. The immunogenic composition of any one of paragraphs 79-96 wherein the glycoconjugates from *S. pneumoniae* serotypes 1, 4, 5, 6B, 7F, 9V, 14 and 23F are individually conjugated to PD.

103. The immunogenic composition of any one of paragraphs 79-96 or 102 wherein the glycoconjugate from *S. pneumoniae* serotype 18C is conjugated to TT.

104. The immunogenic composition of any one of paragraphs 79-96 or 102-103 wherein the glycoconjugate from *S. pneumoniae* serotype 19F is conjugated to DT.

105. The immunogenic composition of any one of paragraphs 79-96 or 102-103 wherein the glycoconjugates from *S. pneumoniae* serotypes 1, 4, 5, 6B, 7F, 9V, 14 and 23F are individually conjugated to PD, the glycoconjugate from *S. pneumoniae* serotype 18C is individually conjugated to TT and the glycoconjugate from *S. pneumoniae* serotype 19F is individually conjugated to DT.

106. The immunogenic composition of any one of paragraphs 53-105 which is a 2, 3, 4, 5, 6, 7, 8, 9, 10, 11, 12, 13, 14, 15, 16, 17, 18, 19, 20, 21, 22 or 23-valent pneumococcal conjugate composition.

107. The immunogenic composition of any one of paragraphs 53-106 further comprising at least one, two or three adjuvants.

108. The immunogenic composition of any one of paragraphs 53-106 further comprising any of the adjuvant of section 4 of the present document.

109. The immunogenic composition of any one of paragraphs 53-106 further comprising an adjuvant selected from the group consisting of alum, calcium phosphate, liposomes, an oil-in-water emulsions, a water-in-oil emulsion, and poly(D,L-lactide-co-glycolide) microparticles or nanoparticles.

110. The immunogenic composition of any one of paragraphs 53-106 further comprising aluminum phosphate, aluminum sulfate or aluminum hydroxide as adjuvant.

111. The immunogenic composition of any one of paragraphs 53-106 further comprising aluminum phosphate as adjuvant.

112. The immunogenic composition of any one of paragraphs 53-111 formulated in liquid form, preferably in aqueous liquid form.

113. The immunogenic composition of any one of paragraphs 53-111 formulated in a lyophilized form.

114. The immunogenic composition of any one of paragraphs 53-113 formulated with a physiologically acceptable vehicle.

115. The immunogenic composition of any one of paragraphs 53-113 formulated in a pharmaceutically acceptable excipient, carrier, or diluent.

116. The immunogenic composition of any one of paragraphs 53-113 comprising one or more of a buffer, a salt, a divalent cation, a non-ionic detergent, a cryoprotectant such as a sugar, and an anti-oxidant such as a free radical scavenger or chelating agent, or any multiple combinations thereof.

117. The glycoconjugate of any one of paragraphs 1-52 or the immunogenic composition of any one of paragraphs 53-116 for use as a medicament.

118. The glycoconjugate of any one of paragraphs 1-52 or the immunogenic composition of any one of paragraphs 53-116 for use as a vaccine.

119. The glycoconjugate of any one of paragraphs 1-52 or the immunogenic composition of any one of paragraphs 53-116 for use in a method of preventing, treating or ameliorating a *S. pneumoniae* infection, disease or condition in a subject.

120. A method of preventing, treating or ameliorating an infection, disease or condition associated with *S. pneumoniae* in a subject, comprising administering to the subject an immunologically effective amount of a glycoconjugate of any one of paragraphs 1-52 or an immunologically effective amount of an immunogenic composition of any one of paragraphs 53-116.

121. A method of inducing an immune response to *S. pneumoniae* in a subject comprising administering to the subject an immunologically effective amount of a glycoconjugate of any one of paragraphs 1-52 or an immunologically effective amount of an immunogenic composition of any one of paragraphs 53-116.

122. The glycoconjugate of any one of paragraphs 1-52 or the immunogenic composition of any one of paragraphs 53-116 for use in a method of preventing a *S. pneumoniae* infection in a subject.

123. A method of preventing an infection by *S. pneumoniae* in a subject comprising administering to the subject an immunologically effective amount of an immunologically effective amount of a glycoconjugate of any one of paragraphs 1-52 or an immunologically effective amount of an immunogenic composition of any one of paragraphs 53-116.

124. A serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B glycoconjugate prepared using reductive amination.

125. The glycoconjugate of any one of paragraphs 1-52 wherien said glycoconjugate is prepared using reductive amination 126. A process for the production of activated *S. pneumoniae* serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides comprising the step of (a) reacting a mixture of isolated serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides with an oxidizing agent.

127. The process of paragraph 126 further comprising (b) quenching the oxidation reaction by addition of a quenching agent resulting in activated saccharides.

128. A process for the production of activated *S. pneumoniae* serotypes 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B comprising the step of (a) individually reacting an isolated serotype 8/11A/12F/23A/23B, 8/11A/12F/23A, 8/11A/12F/23B, 8/11A/23A/23B, 8/12F/23A/23B, 11A/12F/23A/23B, 8/11A/12F, 8/11A/23A, 8/11A/23B, 8/12F/23A, 8/12F/23B, 8/23A/23B, 11A/12F/23A, 11A/12F/23B, 11A/23A/23B, 12F/23A/23B, 8/11A, 8/12F, 8/23A, 8/23B, 11A/12F, 11A/23A, 11A/23B, 12F/23A, 12F/23B or 23A/23B saccharides.

129. The process of paragraph 128 further comprising quenching the oxidation reaction by addition of a quenching agent.

130. The process of anyone of paragraphs 126-129 wherien said oxidizing agent is periodate.

131. The process of anyone of paragraphs 126-129 wherien said oxidizing agent is metaperiodate or orthoperiodate.

132. The process of anyone of paragraphs 126-129 wherien said oxidizing agent is sodium periodate or potassium periodate.

133. The process of anyone of paragraphs 126-132 wherein if present the quenching agent is any of the one disclosed herein.

134. The process of anyone of paragraphs 126-133 wherein the activated saccharides are purified.

135. The process of anyone of paragraphs 126-134 wherein the activated saccharides are purified according to any on the methods disclosed herein.

136. The process of anyone of paragraphs 126-135 wherein the degree of oxidation of the activated saccharides are between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25.

137. The process of anyone of paragraphs 126-135 wherein the degree of oxidation of the activated saccharides are between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25.

138. The process of anyone of paragraphs 126-135 wherein the degree of oxidation of the activated saccharides are between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20.

139. The process of anyone of paragraphs 126-138 wherein the activated saccharides have a molecular weight of between 10 kDa and 5,000 kDa; between 20 kDa and 4,000 kDa; between 50 kDa and 3,000 kDa; between 100 kDa and 2500 kDa; 100 kDa and 2,000 kDa; between 150 kDa and 2,000 kDa; between 150 kDa and 1,500 kDa; between 10 kDa and 2,000 kDa; between 20 kDa and 1,500 kDa; between 30 kDa and 1,250 kDa; between 50 kDa and 1,000 kDa; between 70 kDa and 900 kDa; between 100 kDa and 800 kDa; between 200 kDa to 600 kDa or between 400 kDa to 700 kDa.

140. The process of anyone of paragraphs 126-138 wherein the activated saccharides have a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa.

141. The process of anyone of paragraphs 126-138 wherein the mixture of saccharides have a molecular weight between 25 kDa and 1,000 kDa, between 100 kDa and 1,000 kDa, between 300 kDa and 800 kDa, between 300 kDa and 700 kDa, between 300 kDa and 600 kDa, between 400 kDa and 1,000 kDa, between 400 kDa and 800 kDa, between 400 kDa and 700 kDa or between 400 kDa and 600 kDa.

142. The process of anyone of paragraphs 126-138 wherein the mixture of saccharides have a molecular weight between 300 kDa and 800 kDa. or between 400 kDa and 600 kDa.

143. The process of anyone of paragraphs 126-142 wherein the activated saccharides are lyophilised.

144. The process of anyone of paragraphs 126-142 wherein the activated saccharides are lyophilised. in the presence of saccharide such as sucrose, trehalose, raffinose, stachyose, melezitose, dextran, mannitol, lactitol or palatinit 145. A conjugation process comprising activating saccharides according to any one of paragraphs 126-144.

146. A conjugation process comprising activating saccharides according to any one of paragraphs 126-144, (c) compounding said activated saccharides with a carrier protein and (d) reacting the compounded activated saccharides and carrier protein with a reducing agent to form a glycoconjugate.

147. The conjugation process of paragraph 146 wherein said compounding between the activated saccharides and the carrier protein is conducted using co-lyophilization.

148. The conjugation process of paragraph 146 wherein said compounding between the activated saccharides and the carrier protein is conducted using co-lyophilization in the presence of a saccharide such as sucrose, trehalose, raffinose, stachyose, melezitose, dextran, mannitol, lactitol and palatinit.

149. The conjugation process of any one of paragraphs 145-148 wherein the reduction reaction is carried out in aqueous solvent.

150. The conjugation process of any one of paragraphs 145-148 wherein the reduction reaction is carried out in aprotic solvent.

151. The conjugation process of any one of paragraphs 145-148 wherein the reduction reaction is carried out in DMSO (dimethylsulfoxide) or in DMF (dimethylformamide)) solvent.

152. The conjugation process of any one of paragraphs 145-148 wherein step (c) and step (d) are carried out in aprotic solvent.

153. The conjugation process of any one of paragraphs 145-148 wherein step (c) and step (d) are carried out in DMSO (dimethylsulfoxide) or in DMF (dimethylformamide)) solvent.

154. The conjugation process of any one of paragraphs 145-148 wherein step (c) and step (d) are carried out in DMSO (dimethylsulfoxide).

155. The conjugation process of any one of paragraphs 145-154 wherein the reducing agent is selected from the group consisting of sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^{i}$PrN—$BH_3$, benzylamine-$BH_3$ or 5-ethyl-2-methylpyridine borane (PEMB).

156. The conjugation process of any one of paragraphs 145-154 wherein the reducing agent is sodium cyanoborohydride.

157. The conjugation process of any one of paragraphs 145-156 wherein unreacted aldehyde groups are capped.

158. The conjugation process of any one of paragraphs 145-156 wherein unreacted aldehyde groups are capped using a capping agent.

159. The conjugation process of any one of paragraphs 145-156 wherein unreacted aldehyde groups are capped using a capping agent using sodium borohydride ($NaBH_4$).

160. The conjugation process of any one of paragraphs 145-156 wherein the glycoconjugate are purified.

161. A mixture of activated saccharides obtained or obtainable according to the process of any one of paragraphs 126-144.

162. A glycoconjugate obtained or obtainable according to the process of any one of paragraphs 145-160.

Particular embodiments of the invention are set forth in the following numbered paragraphs:

1. A glycoconjugate comprising at least two saccharides selected from the group consisting of a saccharide from *S. pneumoniae* serotype 10A, a saccharide from *S. pneumoniae* serotype 22F, a saccharide from *S. pneu-*

*moniae* serotype 33F and a saccharide from *S. pneumoniae* serotype 35B, conjugated to the same carrier protein.

2. The glycoconjugate of paragraph 1 comprising a saccharide from *S. pneumoniae* serotype 10A, a saccharide from *S. pneumoniae* serotype 22F, a saccharide from *S. pneumoniae* serotype 33F and a saccharide from *S. pneumoniae* serotype 35B, conjugated to the same carrier protein.
3. The glycoconjugate of paragraph 1 comprising a saccharide from *S. pneumoniae* serotype 10A, a saccharide from *S. pneumoniae* serotype 22F and a saccharide from *S. pneumoniae* serotype 33F conjugated to the same carrier protein.
4. The glycoconjugate of paragraph 1 comprising a saccharide from *S. pneumoniae* serotype 10A, a saccharide from *S. pneumoniae* serotype 22F and a saccharide from *S. pneumoniae* serotype 35B conjugated to the same carrier protein.
5. The glycoconjugate of paragraph 1 comprising a saccharide from *S. pneumoniae* serotype 10A, a saccharide from *S. pneumoniae* serotype 33F and a saccharide from *S. pneumoniae* serotype 35B conjugated to the same carrier protein.
6. The glycoconjugate of paragraph 1 comprising a saccharide from *S. pneumoniae* serotype 22F, a saccharide from *S. pneumoniae* serotype 33F and a saccharide from *S. pneumoniae* serotype 35B conjugated to the same carrier protein.
7. The glycoconjugate of paragraph 1 comprising a saccharide from *S. pneumoniae* serotype 10A and a saccharide from *S. pneumoniae* serotype 22F conjugated to the same carrier protein.
8. The glycoconjugate of paragraph 1 comprising a saccharide from *S. pneumoniae* serotype 10A and a saccharide from *S. pneumoniae* serotype 33F conjugated to the same carrier protein.
9. The glycoconjugate of paragraph 1 comprising a saccharide from *S. pneumoniae* serotype 10A and a saccharide from *S. pneumoniae* serotype 35B conjugated to the same carrier protein.
10. The glycoconjugate of paragraph 1 comprising a saccharide from *S. pneumoniae* serotype 22F and a saccharide from *S. pneumoniae* serotype 33F conjugated to the same carrier protein.
11. The glycoconjugate of paragraph 1 comprising a saccharide from *S. pneumoniae* serotype 22F and a saccharide from *S. pneumoniae* serotype 35B conjugated to the same carrier protein.
12. The glycoconjugate of paragraph 1 comprising a saccharide from *S. pneumoniae* serotype 33F and a saccharide from *S. pneumoniae* serotype 35B conjugated to the same carrier protein.
13. The glycoconjugate of any one of paragraphs 1 to 12 which is a 4-valent glycoconjugate.
14. The glycoconjugate of any one of paragraphs 3 to 12 which is a 3-valent glycoconjugate.
15. The glycoconjugate of any one of paragraphs 7 to 12 which is a 2-valent glycoconjugate.
16. The glycoconjugate of any one of paragraphs 1 to 15 wherein if present said serotype 10A saccharide have a molecular weight of between 10 kDa and 5,000 kDa.
17. The glycoconjugate of any one of paragraphs 1 to 15 wherein if present said serotype 10A saccharide have a molecular weight in any of the range disclosed herein.
18. The glycoconjugate of any one of paragraphs 1 to 17 wherein if present said serotype 22F saccharide have a molecular weight of between 10 kDa and 5,000 kDa.
19. The glycoconjugate of any one of paragraphs 1 to 17 wherein if present said serotype 22F saccharide have a molecular weight in any of the range disclosed herein.
20. The glycoconjugate of any one of paragraphs 1 to 19 wherein if present said serotype 33F saccharide have a molecular weight of between 10 kDa and 5,000 kDa.
21. The glycoconjugate of any one of paragraphs 1 to 19 wherein if present said serotype 33F saccharide have a molecular weight in any of the range disclosed herein.
22. The glycoconjugate of any one of paragraphs 1 to 21 wherein if present said serotype 35B saccharide have a molecular weight of between 10 kDa and 5,000 kDa.
23. The glycoconjugate of any one of paragraphs 1 to 21 wherein if present said serotype 35B saccharide have a molecular weight in any of the range disclosed herein.
24. The glycoconjugate of any one of paragraphs 1 to 23 wherein said glycoconjugate has a molecular weight of between 400 kDa and 15,000 kDa.
25. The glycoconjugate of any one of paragraphs 1 to 23 wherein said glycoconjugate has a molecular weight in any of the range disclosed herein.
26. The glycoconjugate of any one of paragraphs 1 to 25 wherein the degree of conjugation of said conjugate is between 2 and 15,
27. The glycoconjugate of any one of paragraphs 1 to 25 wherein the degree of conjugation of said conjugate is in any of the range disclosed herein.
28. The glycoconjugate of any one of paragraphs 1 to 25 wherein the degree of conjugation of said conjugate is about 2, about 3, about 4, about 5, about 6, about 7, about 8, about 9, about 10, about 11, about 12, about 13, about 14 or about 15.
29. The glycoconjugate of any one of paragraphs 1 to 28 wherein the ratio (weight/weight) of saccharide to carrier protein in the glycoconjugate is between 0.5 and 3.0.
30. The glycoconjugate of any one of paragraphs 1 to 28 wherein the ratio (weight/weight) of saccharide to carrier protein in the glycoconjugate is in any of the range disclosed herein.
31. The glycoconjugate of any one of paragraphs 1 to 28 wherein the ratio (weight/weight) of saccharide to carrier protein in the glycoconjugate is about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0.
32. The glycoconjugate of any one of paragraphs 1 to 31 wherein the ratio (weight/weight) of serotype 10A saccharide to serotype 22F saccharide in the glycoconjugate, if both present, is between 0.25 and 4.0.
33. The glycoconjugate of any one of paragraphs 1 to 31 wherein the ratio (weight/weight) of serotype 10A saccharide to serotype 22F saccharide in the glycoconjugate, if both present, is in any of the range disclosed herein.

34. The glycoconjugate of any one of paragraphs 1 to 31 wherein the ratio (weight/weight) of serotype 10A saccharide to serotype 22F saccharide in the glycoconjugate, if both present, is about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0.
35. The glycoconjugate of any one of paragraphs 1 to 34 wherein the ratio (weight/weight) of serotype 10A saccharide to serotype 33F saccharide in the glycoconjugate, if both present, is between 0.25 and 4.0.
36. The glycoconjugate of any one of paragraphs 1 to 34 wherein the ratio (weight/weight) of serotype 10A saccharide to serotype 33F saccharide in the glycoconjugate, if both present, is in any of the range disclosed herein.
37. The glycoconjugate of any one of paragraphs 1 to 34 wherein the ratio (weight/weight) of serotype 10A saccharide to serotype 33F saccharide in the glycoconjugate, if both present, is about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0.
38. The glycoconjugate of any one of paragraphs 1 to 38 wherein the ratio (weight/weight) of serotype 10A saccharide to serotype 35B saccharide in the glycoconjugate, if both present, is between 0.25 and 4.0.
39. The glycoconjugate of any one of paragraphs 1 to 38 wherein the ratio (weight/weight) of serotype 10A saccharide to serotype 35B saccharide in the glycoconjugate, if both present, is in any of the range disclosed herein.
40. The glycoconjugate of any one of paragraphs 1 to 38 wherein the ratio (weight/weight) of serotype 10A saccharide to serotype 35B saccharide in the glycoconjugate, if both present, is about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0.
41. The glycoconjugate of any one of paragraphs 1 to 40 wherein the ratio (weight/weight) of serotype 22F saccharide to serotype 33F saccharide in the glycoconjugate, if both present, is between 0.25 and 4.0.
42. The glycoconjugate of any one of paragraphs 1 to 40 wherein the ratio (weight/weight) of serotype 22F saccharide to serotype 33F saccharide in the glycoconjugate, if both present, is in any of the range disclosed herein.
43. The glycoconjugate of any one of paragraphs 1 to 40 wherein the ratio (weight/weight) of serotype 22F saccharide to serotype 33F saccharide in the glycoconjugate, if both present, is about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0.
44. The glycoconjugate of any one of paragraphs 1 to 43 wherein the ratio (weight/weight) of serotype 22F saccharide to serotype 35B saccharide in the glycoconjugate, if both present, is between 0.25 and 4.0.
45. The glycoconjugate of any one of paragraphs 1 to 43 wherein the ratio (weight/weight) of serotype 22F saccharide to serotype 35B saccharide in the glycoconjugate, if both present, is in any of the range disclosed herein.
46. The glycoconjugate of any one of paragraphs 1 to 43 wherein the ratio (weight/weight) of serotype 22F saccharide to serotype 35B saccharide in the glycoconjugate, if both present, is about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0.
47. The glycoconjugate of any one of paragraphs 1 to 44 wherein the ratio (weight/weight) of serotype 33F saccharide to serotype 35B saccharide in the glycoconjugate, if both present, is between 0.25 and 4.0.
48. The glycoconjugate of any one of paragraphs 1 to 44 wherein the ratio (weight/weight) of serotype 33F saccharide to serotype 35B saccharide in the glycoconjugate, if both present, is in any of the range disclosed herein.
49. The glycoconjugate of any one of paragraphs 1 to 44 wherein the ratio (weight/weight) of serotype 33F saccharide to serotype 35B saccharide in the glycoconjugate, if both present, is about 0.25, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or about 4.0.

50. The glycoconjugate of any one of paragraphs 1 to 49 wherein the relative proportion (weight/weight) of serotypes 10A saccharide, serotypes 22F saccharide and serotype 33F saccharide in the glycoconjugate, if present, is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | C | d | e | f | g | h | i | j | K | l | m | n | o | p | q | r | s |
| 10A | 1 | 1 | 1 | 2 | 2 | 2 | 4 | 4 | 4 | 1 | 1 | 1 | 2 | 4 | 1 | 1 | 1 | 2 | 4 |
| 22F | 1 | 1 | 1 | 1 | 1 | 1 | 1 | 1 | 1 | 2 | 2 | 2 | 2 | 2 | 4 | 4 | 4 | 4 | 4 |
| 33F | 4 | 2 | 1 | 4 | 2 | 1 | 4 | 2 | 1 | 4 | 2 | 1 | 1 | 1 | 4 | 2 | 1 | 1 | 1 |

51. The glycoconjugate of any one of paragraphs 1 to 50 wherein the relative proportion (weight/weight) of serotypes 10A saccharide, serotypes 22F saccharide and serotype 35B saccharide in the glycoconjugate, if present, is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | C | d | e | f | g | h | i | j | K | l | m | n | o | p | q | r | s |
| 10A | 1 | 1 | 1 | 2 | 2 | 2 | 4 | 4 | 4 | 1 | 1 | 1 | 2 | 4 | 1 | 1 | 1 | 2 | 4 |
| 22F | 1 | 1 | 1 | 1 | 1 | 1 | 1 | 1 | 1 | 2 | 2 | 2 | 2 | 2 | 4 | 4 | 4 | 4 | 4 |
| 35B | 4 | 2 | 1 | 4 | 2 | 1 | 4 | 2 | 1 | 4 | 2 | 1 | 1 | 1 | 4 | 2 | 1 | 1 | 1 |

52. The glycoconjugate of any one of paragraphs 1 to 51 wherein the relative proportion (weight/weight) of serotypes 10A saccharide, serotypes 33F saccharide and serotype 35B saccharide in the glycoconjugate, if present, is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 10A | 1 | 1 | 1 | 2 | 2 | 2 | 4 | 4 | 4 | 1 | 1 | 1 | 2 | 4 | 1 | 1 | 1 | 2 | 4 |
| 33F | 1 | 1 | 1 | 1 | 1 | 1 | 1 | 1 | 1 | 2 | 2 | 2 | 2 | 2 | 4 | 4 | 4 | 4 | 4 |
| 35B | 4 | 2 | 1 | 4 | 2 | 1 | 4 | 2 | 1 | 4 | 2 | 1 | 1 | 1 | 4 | 2 | 1 | 1 | 1 |

53. The glycoconjugate of any one of paragraphs 1 to 52 wherein the relative proportion (weight/weight) of serotypes 22F saccharide, serotypes 33F saccharide and serotype 35B saccharide in the glycoconjugate, if present, is according to any of the one of the below table:

| | Relative proportion in the glycoconjugate | | | | | | | | | | | | | | | | | | |
|---|---|---|---|---|---|---|---|---|---|---|---|---|---|---|---|---|---|---|---|
| | a | b | c | d | e | f | g | h | i | j | k | l | m | n | o | p | q | r | s |
| 22F | 1 | 1 | 1 | 2 | 2 | 2 | 4 | 4 | 4 | 1 | 1 | 1 | 2 | 4 | 1 | 1 | 1 | 2 | 4 |
| 33F | 1 | 1 | 1 | 1 | 1 | 1 | 1 | 1 | 1 | 2 | 2 | 2 | 2 | 2 | 4 | 4 | 4 | 4 | 4 |
| 35B | 4 | 2 | 1 | 4 | 2 | 1 | 4 | 2 | 1 | 4 | 2 | 1 | 1 | 1 | 4 | 2 | 1 | 1 | 1 |

54. The glycoconjugate of any one of paragraphs 1 to 53 wherein the relative proportion (weight/weight) of serotypes 10A saccharide, serotypes 22F saccharide, serotype 33F saccharide and serotype 35B saccharide in the glycoconjugate, is present, is according to any of the one of the below tables:

| | a | b | c | d | e | f | g | h | i | j | k | l | m | n | o | p | q | r | s | t | u | v | w | x | y | z | aa |
|---|---|---|---|---|---|---|---|---|---|---|---|---|---|---|---|---|---|---|---|---|---|---|---|---|---|---|---|
| 10A | 1 | 1 | 1 | 2 | 2 | 2 | 4 | 4 | 4 | 1 | 1 | 1 | 2 | 2 | 2 | 4 | 4 | 4 | 1 | 1 | 1 | 2 | 2 | 2 | 4 | 4 | 4 |
| 22F | 1 | 1 | 1 | 1 | 1 | 1 | 1 | 1 | 1 | 2 | 2 | 2 | 2 | 2 | 2 | 2 | 2 | 2 | 4 | 4 | 4 | 4 | 4 | 4 | 4 | 4 | 4 |
| 33F | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| 35B | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 | 1 | 2 | 4 |

| | ab | ac | ad | ae | af | ag | ah | ai | aj | ak | al | am | an | ao | ap | aq | ar | as | at |
|---|---|---|---|---|---|---|---|---|---|---|---|---|---|---|---|---|---|---|---|
| 10A | 1 | 1 | 1 | 2 | 2 | 2 | 4 | 4 | 4 | 1 | 1 | 1 | 2 | 4 | 1 | 1 | 1 | 2 | 4 |
| 22F | 1 | 1 | 1 | 1 | 1 | 1 | 1 | 1 | 1 | 2 | 2 | 2 | 2 | 2 | 4 | 4 | 4 | 4 | 4 |
| 33F | 2 | 2 | 2 | 2 | 2 | 2 | 2 | 2 | 2 | 2 | 2 | 2 | 2 | 2 | 2 | 2 | 2 | 2 | 2 |
| 35B | 1 | 2 | 4 | 1 | 2 | 4 | 1 | 2 | 4 | 1 | 2 | 4 | 1 | 1 | 1 | 2 | 4 | 1 | 1 |

| | au | av | aw | ax | ay | az | ba | bb | bc | bd | be | bf | bg | bh | bi | bj | bk | bl | bm |
|---|---|---|---|---|---|---|---|---|---|---|---|---|---|---|---|---|---|---|---|
| 10A | 1 | 1 | 1 | 2 | 2 | 2 | 4 | 4 | 4 | 1 | 1 | 1 | 2 | 4 | 1 | 1 | 1 | 2 | 4 |
| 22F | 1 | 1 | 1 | 1 | 1 | 1 | 1 | 1 | 1 | 2 | 2 | 2 | 2 | 2 | 4 | 4 | 4 | 4 | 4 |
| 33F | 4 | 4 | 4 | 4 | 4 | 4 | 4 | 4 | 4 | 4 | 4 | 4 | 4 | 4 | 4 | 4 | 4 | 4 | 4 |
| 35B | 1 | 2 | 4 | 1 | 2 | 4 | 1 | 2 | 4 | 1 | 2 | 4 | 1 | 1 | 1 | 2 | 4 | 1 | 1 |

55. The glycoconjugate of any one of paragraphs 1 to 54 wherein said glycoconjugate comprises at least 0.1, 0.2, 0.3, 0.4, 0.5, 0.6 or 0.7 or about 0.8 mM acetate per mM serotype 22F polysaccharide, if present.
56. The glycoconjugate of any one of paragraphs 1 to 55 wherein said glycoconjugate comprises at least 0.1, 0.2, 0.3, 0.4, 0.5, 0.6, 0.7 or 0.8 mM acetate per mM serotype 33F capsular polysaccharide, if present.
57. The glycoconjugate of any one of paragraphs 1 to 56 wherein said glycoconjugate comprises at least 0.1, 0.2, 0.3, 0.4, 0.5, 0.6, 0.7 or 0.8 mM acetate per mM serotype 35B capsular polysaccharide, if present.
58. The glycoconjugate of any one of paragraphs 1 to 57 wherein at least 30% of said glycoconjugate has a $K_d$ below or equal to 0.3 in a CL-4B column.
59. The glycoconjugate of any one of paragraphs 1 to 57 wherein at least 40%, 45%, 50%, 55%, 60%, 65%, 70%, 75%, 80%, or 85% of said glycoconjugate has a $K_d$ below or equal to 0.3 in a CL-4B column.
60. The glycoconjugate of any one of paragraphs 1 to 57 wherein between 50% and 80% of said glycoconjugate has a $K_d$ below or equal to 0.3 in a CL-4B column.
61. The glycoconjugate of any one of paragraphs 1 to 57 wherein between 65% and 80% of said glycoconjugate has a $K_d$ below or equal to 0.3 in a CL-4B column.
62. The glycoconjugate of any one of paragraphs 1 to 61 wherein said glycoconjugate comprises less than about 50%, 45%, 40%, 35%, 30%, 25%, 20% or 15% of free serotypes 10A and 22F saccharide compared to the total amount of serotypes 10A and 22F saccharide, if present.
63. The glycoconjugate of any one of paragraphs 1 to 62 wherein said glycoconjugate comprises less than about 50%, 45%, 40%, 35%, 30%, 25%, 20% or 15% of free serotypes 10A and 33F saccharide compared to the total amount of serotypes 10A and 33F saccharide, if present.
64. The glycoconjugate of any one of paragraphs 1 to 63 wherein said glycoconjugate comprises less than about 50%, 45%, 40%, 35%, 30%, 25%, 20% or 15% of free serotypes 10A and 35B saccharide compared to the total amount of serotypes 10A and 35B saccharide, if present.
65. The glycoconjugate of any one of paragraphs 1 to 64 wherein said glycoconjugate comprises less than about 50%, 45%, 40%, 35%, 30%, 25%, 20% or 15% of free serotypes 22F and 33F saccharide compared to the total amount of serotypes 22F and 33F saccharide, if present.
66. The glycoconjugate of any one of paragraphs 1 to 65 wherein said glycoconjugate comprises less than about 50%, 45%, 40%, 35%, 30%, 25%, 20% or 15% of free serotypes 22F and 35B saccharide compared to the total amount of serotypes 22F and 35B saccharide, if present.
67. The glycoconjugate of any one of paragraphs 1 to 66 wherein said glycoconjugate comprises less than about 50%, 45%, 40%, 35%, 30%, 25%, 20% or 15% of free serotypes 33F and 35B saccharide compared to the total amount of serotypes 33F and 35B saccharide, if present.
68. The glycoconjugate of any one of paragraphs 1 to 67 wherein said glycoconjugate comprises less than about 50%, 45%, 40%, 35%, 30%, 25%, 20% or 15% of free serotypes 10A, 22F and 33F saccharide compared to the total amount of serotypes 10A, 22F and 33F saccharide, if present.
69. The glycoconjugate of any one of paragraphs 1 to 68 wherein said glycoconjugate comprises less than about 50%, 45%, 40%, 35%, 30%, 25%, 20% or 15% of free serotypes 10A, 22F and 35B saccharide compared to the total amount of serotypes 10A, 22F and 35B saccharide, if present.
70. The glycoconjugate of any one of paragraphs 1 to 69 wherein said glycoconjugate comprises less than about 50%, 45%, 40%, 35%, 30%, 25%, 20% or 15% of free serotypes 10A, 33F and 35B saccharide compared to the total amount of serotypes 10A, 33F and 35B saccharide, if present.
71. The glycoconjugate of any one of paragraphs 1 to 70 wherein said glycoconjugate comprises less than about 50%, 45%, 40%, 35%, 30%, 25%, 20% or 15% of free serotypes 22F, 33F and 35B saccharide compared to the total amount of serotypes 22F, 33F and 35B saccharide, if present.
72. The glycoconjugate of any one of paragraphs 1 to 71 wherein said glycoconjugate comprises less than about 50%, 45%, 40%, 35%, 30%, 25%, 20% or 15% of free serotypes 10A, 22F, 33F and 35B saccharide compared to the total amount of serotypes 10A, 22F, 33F and 35B saccharide, if present.
73. The glycoconjugate of any one of paragraphs 1 to 72 wherein said carrier protein is selected in the group consisting of: DT (Diphtheria toxoid), TT (tetanus toxoid) or fragment C of TT, $CRM_{197}$, other DT mutants, CRM176, CRM228, CRM45, CRM9, CRM102, CRM103, CRM107, pneumococcal pneumolysin (ply), detoxified pneuolysin, PhtX, PhtA, PhtB, PhtD, PhtE, fusions of Pht proteins, PhtDE fusions, PhtBE fusions, Pht A-E, OMPC (meningococcal outer membrane protein), PorB (from *N. meningitidis*), PD (*Haemophilus influenzae* protein D), toxin A or B of *Clostridium difficile*, transferrin binding proteins, pneumococcal adhesion protein (PsaA), recombinant *Pseudomonas aeruginosa* exotoxin A, cholera toxoid, *Escherichia coli* LT, *E. coli* ST, and exotoxin A from *P. aeruginosa.*
74. The glycoconjugate of any one of paragraphs 1 to 72 wherein said carrier protein is selected in the group consisting of TT, DT, DT mutants (such as $CRM_{197}$), *H. influenzae* protein D, PhtX, PhtD, PhtDE fusions, detoxified pneumolysin, PorB, N19 protein, PspA, OMPC, toxin A or B of *C. difficile* and PsaA.
75. The glycoconjugate of any one of paragraphs 1 to 72 wherein said carrier protein is DT (Diphtheria toxoid).
76. The glycoconjugate of any one of paragraphs 1 to 72 wherein said carrier protein is TT (tetanus toxid).
77. The glycoconjugate of any one of paragraphs 1 to 72 wherein said carrier protein is PD (*H. influenzae* protein D).
78. The glycoconjugate of any one of paragraphs 1 to 72 wherein said carrier protein is detoxified pneumolysin or a mutant nontoxic form of pneumolysin.
79. The glycoconjugate of any one of paragraphs 1 to 72 wherein said carrier protein is $CRM_{197}$.
80. The glycoconjugate of any one of paragraphs 1 to 72 wherein said carrier protein is the A chain of $CRM_{197}$.
81. A process for the production of activated *S. pneumoniae* serotypes 10A, 22F, 33F and 35 B saccharides comprising the step of (a) reacting a mixture of isolated serotypes 10A, 22F, 33F and 35B saccharides with an oxidizing agent.
82. A process for the production of activated *S. pneumoniae* serotypes 10A, 22F and 33F saccharides comprising the step of (a) reacting a mixture of isolated serotypes 10A, 22F and 33F saccharides with an oxidizing agent.

83. A process for the production of activated *S. pneumoniae* serotypes 10A, 22F and 35B saccharides comprising the step of (a) reacting a mixture of isolated serotypes 10A, 22F and 35B saccharides with an oxidizing agent.

84. A process for the production of activated *S. pneumoniae* serotypes 10A, 33F and 35B saccharides comprising the step of (a) reacting a mixture of isolated serotypes 10A, 33F and 35B saccharides with an oxidizing agent.

85. A process for the production of activated *S. pneumoniae* serotypes 22F, 33F and 35B saccharides comprising the step of (a) reacting a mixture of isolated serotypes 22F, 33F and 35B saccharides with an oxidizing agent.

86. A process for the production of activated *S. pneumoniae* serotypes 10A and 22F saccharides comprising the step of (a) reacting a mixture of isolated serotypes 10A and 22F saccharides with an oxidizing agent.

87. A process for the production of activated *S. pneumoniae* serotypes 10A and 33F saccharides comprising the step of (a) reacting a mixture of isolated serotypes 10A and 33F saccharides with an oxidizing agent.

88. A process for the production of activated *S. pneumoniae* serotypes 10A and 35B saccharides comprising the step of (a) reacting a mixture of isolated serotypes 10A and 35B saccharides with an oxidizing agent.

89. A process for the production of activated *S. pneumoniae* serotypes 22F and 33F saccharides comprising the step of (a) reacting a mixture of isolated serotypes 22F and 33F saccharides with an oxidizing agent.

90. A process for the production of activated *S. pneumoniae* serotypes 22F and 35B saccharides comprising the step of (a) reacting a mixture of isolated serotypes 22F and 35B saccharides with an oxidizing agent.

91. A process for the production of activated *S. pneumoniae* serotypes 33F and 35B saccharides comprising the step of (a) reacting a mixture of isolated serotypes 33F and 35B saccharides with an oxidizing agent.

92. The process of anyone of paragraphs 81-92 further comprising (b) quenching the oxidation reaction by addition of a quenching agent resulting in activated saccharides.

93. A process for the production of activated *S. pneumoniae* serotypes 10A, 22F, 33F and 35 B comprising the step of (a) individually reacting an isolated serotype 10A, 22F, 33F and 35B saccharide with an oxidizing agent and (b) mixing the activated serotypes 10A, 22F, 33F and 35B saccharides.

94. A process for the production of activated *S. pneumoniae* serotypes 10A, 22F and 33F saccharides comprising the step of (a) individually reacting an isolated serotype 10A, 22F and 33F saccharides with an oxidizing agent and (b) mixing the activated serotypes 10A, 22F and 33F saccharides.

95. A process for the production of activated *S. pneumoniae* serotypes 10A, 22F and 35B saccharides comprising the step of (a) individually reacting an isolated serotype 10A, 22F and 35B saccharide with an oxidizing agent and (b) mixing the activated serotypes 10A, 22F and 35B saccharides.

96. A process for the production of activated *S. pneumoniae* serotypes 10A, 33F and 35B saccharides comprising the step of (a) individually reacting an isolated serotype 10A, 33F and 35B saccharide with an oxidizing agent and (b) mixing the activated serotypes 10A, 33F and 35B saccharides.

97. A process for the production of activated *S. pneumoniae* serotypes 22F, 33F and 35B comprising the step of (a) individually reacting an isolated serotype 22F, 33F and 35B saccharide with an oxidizing agent and (b) mixing the activated serotypes 22F, 33F and 35B saccharides.

98. A process for the production of activated *S. pneumoniae* serotypes 10A and 22F saccharides comprising the step of (a) individually reacting an isolated serotype 10A and 22F saccharide with an oxidizing agent and (b) mixing the activated serotypes 10A and 22F saccharides.

99. A process for the production of activated *S. pneumoniae* serotypes 10A and 33F saccharides comprising the step of (a) individually reacting an isolated serotype 10A and 33F saccharide with an oxidizing agent and (b) mixing the activated serotypes 10A and 33F saccharides.

100. A process for the production of activated *S. pneumoniae* serotypes 10A and 35B saccharides comprising the step of (a) individually reacting an isolated serotype 10A and 35B saccharide with an oxidizing agent and (b) mixing the activated serotypes 10A and 35B saccharides.

101. A process for the production of activated *S. pneumoniae* serotypes 22F and 33F saccharides comprising the step of (a) individually reacting an isolated serotype 22F and 33F saccharide with an oxidizing agent and (b) mixing the activated serotypes 22F and 33F saccharides.

102. A process for the production of activated *S. pneumoniae* serotypes 22F and 35B saccharides comprising the step of (a) individually reacting an isolated serotype 22F and 35B saccharide with an oxidizing agent and (b) mixing the activated serotypes 22F and 35B saccharides.

103. A process for the production of activated *S. pneumoniae* serotypes 33F and 35B saccharides comprising the step of (a) individually reacting an isolated serotype 33F and 35B saccharide with an oxidizing agent and (b) mixing the activated serotypes 33F and 35B saccharides.

104. The process of anyone of paragraphs 93-104 further comprising quenching the oxidation reaction by addition of a quenching agent.

105. The process of anyone of paragraphs 81-104 wherien said oxidizing agent is periodate.

106. The process of anyone of paragraphs 81-104 wherien said oxidizing agent is metaperiodate or orthoperiodate.

107. The process of anyone of paragraphs 81-104 wherien said oxidizing agent is sodium periodate or potassium periodate.

108. The process of anyone of paragraphs 81-107 wherein if present the quenching agent is any of the one disclosed herein.

109. The process of anyone of paragraphs 81-108 wherein the activated saccharides are purified.

110. The process of anyone of paragraphs 81-108 wherein the activated saccharides are purified according to any on the methods disclosed herein.

111. The process of anyone of paragraphs 81-110 wherein the degree of oxidation of the activated saccharides are between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25.

112. The process of anyone of paragraphs 81-110 wherein the degree of oxidation of the activated saccharides are between 2 and 30, between 2 and 25, between 2 and 20, between 2 and 15, between 2 and 10, between 2 and 5, between 5 and 30, between 5 and 25, between 5 and 20, between 5 and 15, between 5 and 10, between 10 and 30, between 10 and 25, between 10 and 20, between 10 and 15, between 15 and 30, between 15 and 25, between 15 and 20, between 20 to 30, or between 20 to 25.

113. The process of anyone of paragraphs 81-110 wherein the degree of oxidation of the activated saccharides are between 2 and 10, between 4 and 8, between 4 and 6, between 6 and 8, between 6 and 12, between 8 and 14, between 9 and 11, between 10 and 16, between 12 and 16, between 14 and 18, between 16 and 20, between 16 and 18, between 18 and 22, or between 18 and 20.

114. The process of anyone of paragraphs 81-113 wherein the activated saccharides have a molecular weight of between 10 kDa and 5,000 kDa; between 20 kDa and 4,000 kDa; between 50 kDa and 3,000 kDa; between 100 kDa and 2500 kDa; 100 kDa and 2,000 kDa; between 150 kDa and 2,000 kDa; between 150 kDa and 1,500 kDa; between 10 kDa and 2,000 kDa; between 20 kDa and 1,500 kDa; between 30 kDa and 1,250 kDa; between 50 kDa and 1,000 kDa; between 70 kDa and 900 kDa; between 100 kDa and 800 kDa; between 200 kDa to 600 kDa or between 400 kDa to 700 kDa.

115. The process of anyone of paragraphs 81-113 wherein the activated saccharides have a molecular weight of between 50 kDa and 2,000 kDa; between 50 kDa and 1,750 kDa; between 50 kDa and 1,500 kDa; between 50 kDa and 1,250 kDa; between 50 kDa and 1,000 kDa; between 50 kDa and 750 kDa; between 50 kDa and 500 kDa; between 50 kDa and 400 kDa; between 50 kDa and 300 kDa; between 50 kDa and 200 kDa; between 50 kDa and 100 kDa; between 100 kDa and 2,000 kDa; between 100 kDa and 1,750 kDa; between 100 kDa and 1,500 kDa; between 100 kDa and 1,250 kDa; between 100 kDa and 1,000 kDa; between 100 kDa and 750 kDa; between 100 kDa and 500 kDa; between 100 kDa and 400 kDa; between 100 kDa and 300 kDa; between 100 kDa and 200 kDa; between 200 kDa and 2,000 kDa; between 200 kDa and 1,750 kDa; between 200 kDa and 1,500 kDa; between 200 kDa and 1,250 kDa; between 200 kDa and 1,000 kDa; between 200 kDa and 750 kDa; between 200 kDa and 500 kDa between; 200 kDa and 400 kDa; between 200 kDa and 300 kDa; between 300 kDa and 2,000 kDa; between 300 kDa and 1,750 kDa; between 300 kDa and 1,500 kDa; between 300 kDa and 1,250 kDa; between 300 kDa and 1,000 kDa; between 300 kDa and 750 kDa; between 300 kDa and 500 kDa between; 300 kDa and 400 kDa; between 400 kDa and 2,000 kDa; between 400 kDa and 1,750 kDa; between 400 kDa and 1,500 kDa; between 400 kDa and 1,250 kDa; between 400 kDa and 1,000 kDa; between 400 kDa and 750 kDa; between 400 kDa and 500 kDa between; between 500 kDa and 2,000 kDa; between 500 kDa and 1,750 kDa; between 500 kDa and 1,500 kDa; between 500 kDa and 1,250 kDa; between 500 kDa and 1,000 kDa; between 500 kDa and 750 kDa; between 600 kDa and 2,000 kDa; between 600 kDa and 1,750 kDa; between 600 kDa and 1,500 kDa; between 600 kDa and 1,250 kDa; between 600 kDa and 1,000 kDa; between 600 kDa and 750 kDa; between 750 kDa and 2,000 kDa; between 750 kDa and 1,750 kDa; between 750 kDa and 1,500 kDa; between 750 kDa and 1,250 kDa; between 750 kDa and 1,000 kDa; between 1000 kDa and 2,000 kDa; between 1000 kDa and 1,750 kDa; between 1000 kDa and 1,500 kDa; between 1000 kDa and 1,250 kDa; between 1,250 kDa and 2,000 kDa; between 1,250 kDa and 1,750 kDa; between 1,250 kDa and 1,500 kDa; between 1,500 kDa and 2,000 kDa; between 1,500 kDa and 1,750 kDa or between 1,750 kDa and 2,000 kDa.

116. The process of anyone of paragraphs 81-115 wherein the activated saccharides are lyophilised.

117. The process of anyone of paragraphs 81-115 wherein the activated saccharides are lyophilised. in the presence of saccharide such as sucrose, trehalose, raffinose, stachyose, melezitose, dextran, mannitol, lactitol or palatinit 118. A conjugation process comprising activating saccharides according to any one of paragraphs 81-117.

119. A conjugation process comprising activating saccharides according to any one of paragraphs 81-117, (c) compounding said activated saccharides with a carrier protein and (d) reacting the compounded activated saccharides and carrier protein with a reducing agent to form a glycoconjugate.

120. The conjugation process of paragraph 119 wherein said compounding between the activated saccharides and the carrier protein is conducted using co-lyophilization.

121. The conjugation process of paragraph 119 wherein said compounding between the activated saccharides and the carrier protein is conducted using co-lyophilization in the presence of a saccharide such as sucrose, trehalose, raffinose, stachyose, melezitose, dextran, mannitol, lactitol and palatinit.

122. The conjugation process of any one of paragraphs 118-121 wherein the reduction reaction is carried out in aqueous solvent.

123. The conjugation process of any one of paragraphs 118-121 wherein the reduction reaction is carried out in aprotic solvent.

124. The conjugation process of any one of paragraphs 118-121 wherein the reduction reaction is carried out in DMSO (dimethylsulfoxide) or in DMF (dimethylformamide)) solvent.

125. The conjugation process of any one of paragraphs 118-121 wherein step (c) and step (d) are carried out in aprotic solvent.

126. The conjugation process of any one of paragraphs 118-121 wherein step (c) and step (d) are carried out in DMSO (dimethylsulfoxide) or in DMF (dimethylformamide)) solvent.

127. The conjugation process of any one of paragraphs 118-121 wherein step (c) and step (d) are carried out in DMSO (dimethylsulfoxide).

128. The conjugation process of any one of paragraphs 118-127 wherein the reducing agent is selected from the group consisting of sodium cyanoborohydride, sodium triacetoxyborohydride, sodium or zinc borohydride in the presence of Bronsted or Lewis acids, amine boranes such as pyridine borane, 2-Picoline Borane, 2,6-diborane-methanol, dimethylamine-borane, t-BuMe$^i$PrN—$BH_3$, benzylamine-$BH_3$ or 5-ethyl-2-methylpyridine borane (PEMB).

129. The conjugation process of any one of paragraphs 118-127 wherein the reducing agent is sodium cyanoborohydride.

130. The conjugation process of any one of paragraphs 118-129 wherein unreacted aldehyde groups are capped.

131. The conjugation process of any one of paragraphs 118-129 wherein unreacted aldehyde groups are capped using a capping agent.

132. The conjugation process of any one of paragraphs 118-129 wherein unreacted aldehyde groups are capped using a capping agent using sodium borohydride ($NaBH_4$).

133. The conjugation process of any one of paragraphs 118-133 wherein the glycoconjugate are purified.

134. A mixture of activated saccharides obtained or obtainable according to the process of any one of paragraphs 81-117.

135. A glycoconjugate obtained or obtainable according to the process of any one of paragraphs 118-133.

As used herein, the term "about" means within a statistically meaningful range of a value, such as a stated concentration range, time frame, molecular weight, temperature or pH. Such a range can be within an order of magnitude, typically within 20%, more typically within 10%, and even more typically within 5% or within 1% of a given value or range. Sometimes, such a range can be within the experimental error typical of standard methods used for the measurement and/or determination of a given value or range. The allowable variation encompassed by the term "about" will depend upon the particular system under study, and can be readily appreciated by one of ordinary skill in the art. Whenever a range is recited within this application, every whole number integer within the range is also contemplated as an embodiment of the disclosure.

The terms "comprising", "comprise" and "comprises" herein are intended by the inventors to be optionally substitutable with the terms "consisting essentially of", "consist essentially of", "consists essentially of", "consisting of", "consist of" and "consists of", respectively, in every instance.

All references or patent applications cited within this patent specification are incorporated by reference herein.

The invention is illustrated in the accompanying examples. The examples below are carried out using standard techniques, which are well known and routine to those of skill in the art, except where otherwise described in detail. The examples are illustrative, but do not limit the invention.

EXAMPLE

Example 1. Multi-Serotype ONE-POT Conjugation Process Using Individually Activated Polysaccharides The One-Pot conjugation phase consists of the following steps:

1. Mixing of the individually activated polysaccharides
2. Compounding of the activated polysaccharide with sucrose
3. Shell freezing and lyophilization.
4. Reconstitution of the lyophilized polysaccharide and $CRM_{197}$.
5. Conjugation of the activated polysaccharide to $CRM_{197}$.
6. Purification and dilution of the conjugate 1 Mixing of the Individually Activated Polysaccharides, Compounding with Sucrose, Shell Freezing and Lyophilization Individually activated (oxidized) polysaccharides of serotypes 10A, 22F, 33F and 35B of *S. pneumoniae* have been obtained using sodium periodate as oxidant.

The characteristics of said activated polysaccharides are summarized in Table 1.

TABLE 1

| Activated Polysaccharide Serotype 10A, 22F, 33F, 35B | | | | |
|---|---|---|---|---|
| Activated polysaccharide # | 1 | 2 | 3 | 4 |
| Serotype of Activated polysaccharide | 33F | 22F | 10A | 35B |
| Polysaccharide MW, kDa | 150 | 1086 | 745 | 943 |
| D.O. (Degreee of Oxidation) | 17.5 | 16.1 | 14.2 | 28.0 |
| Activated polysaccharide, MW, kDa | 167 | 985 | 257 | 44 |

The individually activated polysaccharides were mixed by equal amount (mg) and then compounded with sucrose (50% w/v in water for injection (WFI)) at a ratio of 25 grams of sucrose per gram of activated polysaccharide. The components were mixed for 5-15 minutes at 100±10 rpm. Temperature of the fill bottle containing the activated polysaccharide and sucrose was kept at 2-8° C. prior to shell freezing. The shell-frozen bottle of compounded mixture was stored at ≤−65° C. for NLT 6 hours and then lyophilized. Following lyophilization, bottles containing the activated polysaccharide were stored at −20±5° C. for 60 days from filling date or used immediately for conjugation. Calculated amount of $CRM_{197}$ protein was shell-frozen and lyophilized separately.

2 Reconstitution of Lyophilized Activated Polysaccharide and $CRM_{197}$ Protein Lyophilized activated polysaccharide and lyophilized $CRM_{197}$ were brought to ambient temperature (45-360 minutes). Lyophilized activated polysaccharide was reconstituted in dimethyl sulfoxide (DMSO). Upon the complete reconstitution of the activated polysaccharide, DMSO was added to lyophilized $CRM_{197}$. Typically, after reconstitution both the activated polysaccharide and $CRM_{197}$ in DMSO provide clear solutions (by visual appearance).

3 Conjugation of Activated Polysaccharide to $CRM_{197}$

The conjugation reaction vessel was charged first with the reconstituted activated polysaccharide followed by the addition of the reconstituted $CRM_{197}$. $CRM_{197}$ and polysaccharide were mixed for 60-180 minutes before initiating the conjugation. The final polysaccharide concentration in reaction solution is 1 g/L. Conjugation reaction was initiated by adding 1.5 MEq $NaCNBH_3$ to the reaction mixture and was incubated at 23±2° C. for 24±4 hours (see conjugation process parameter at Table 2).

TABLE 2

| Conjugation Process Parameters | |
|---|---|
| Conjugation Process Parameters | Target Setting |
| Saccharide/Protein Input Ratio | 0.9 ± 0.1 |
| $NaCNBH_3$ (MEq) | 1.5 ± 0.1 |
| Reaction Time (Hours) | 24 ± 4 |
| MEq $NaBH_4$ for Capping | 2.0 ± 0.1 |

After the conjugation reaction is completed, 2 MEq of $NaBH_4$ (sodium borohydride, 100 mg/mL solution) was added to terminate the reaction. The capping reaction was proceeded for a period of 3-4 hours at 23±2° C. with continuous mixing at 130±10 rpm.

4 Dilution and Purification of the Conjugate

The conjugate solution was diluted with 4× volumes of chilled 5 mM Succinate-0.9% NaCl (pH 6.0) in preparation for purification by tangential flow filtration using 100K MWCO regenerated cellulose membranes (Millipore Pellicon). The conjugate solution was then concentrated down to 1 g/L, diafiltration was performed using 5 mM Succinate-0.9% NaCl (pH 6.0) as the medium. After the diafiltration was completed, the purified conjugate was diluted with 5 mM Succinate-0.9% NaCl (pH 6.0) and then filtered through a 0.22 μm PVDF filter to a collection tank. The conjugate can be stored at 5±3° C. for 30 days.

Figure 1:
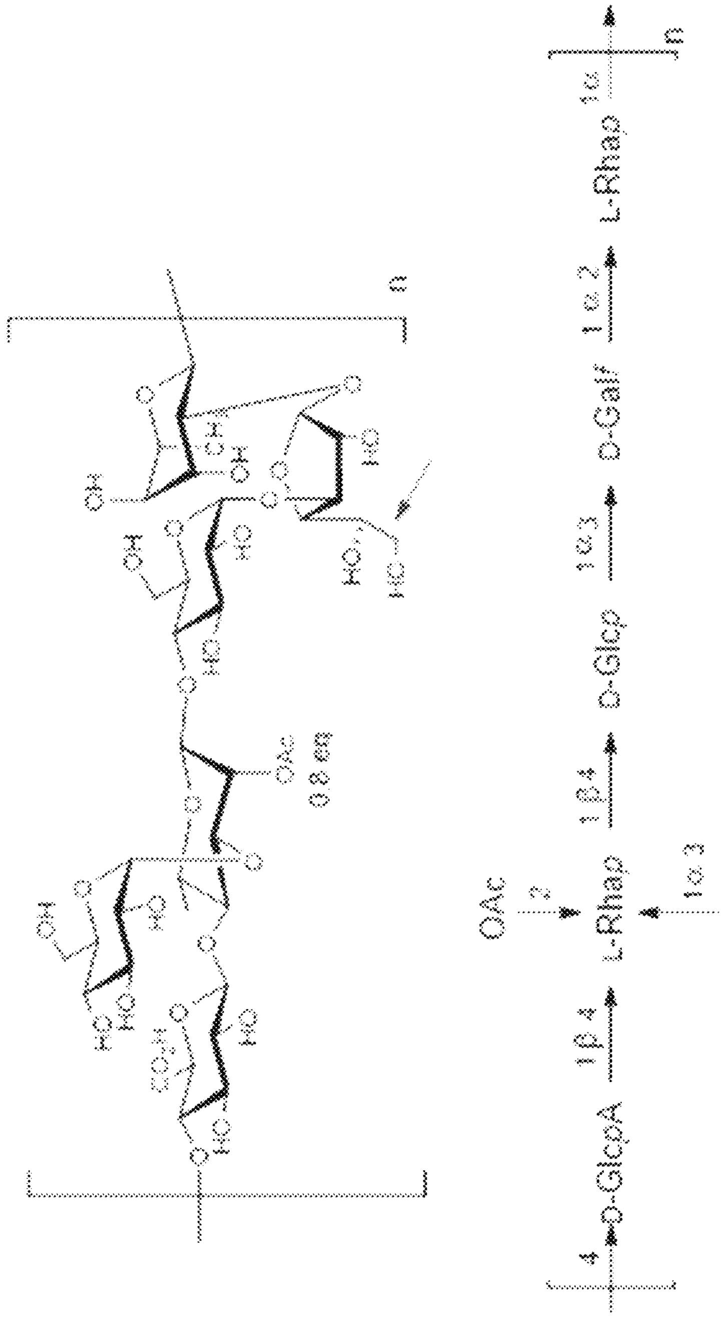
FIG. 1 shows the structure of serotype 22F pnemococcal polysaccharide having vicinal hydroxyls uniquely positioned to generate primary aldehydes (see arrow), which are significantly more reactive compared to secondary aldehydes positioned in a hindered structural position in the polysaccharide repeat unit.
Figure 2:
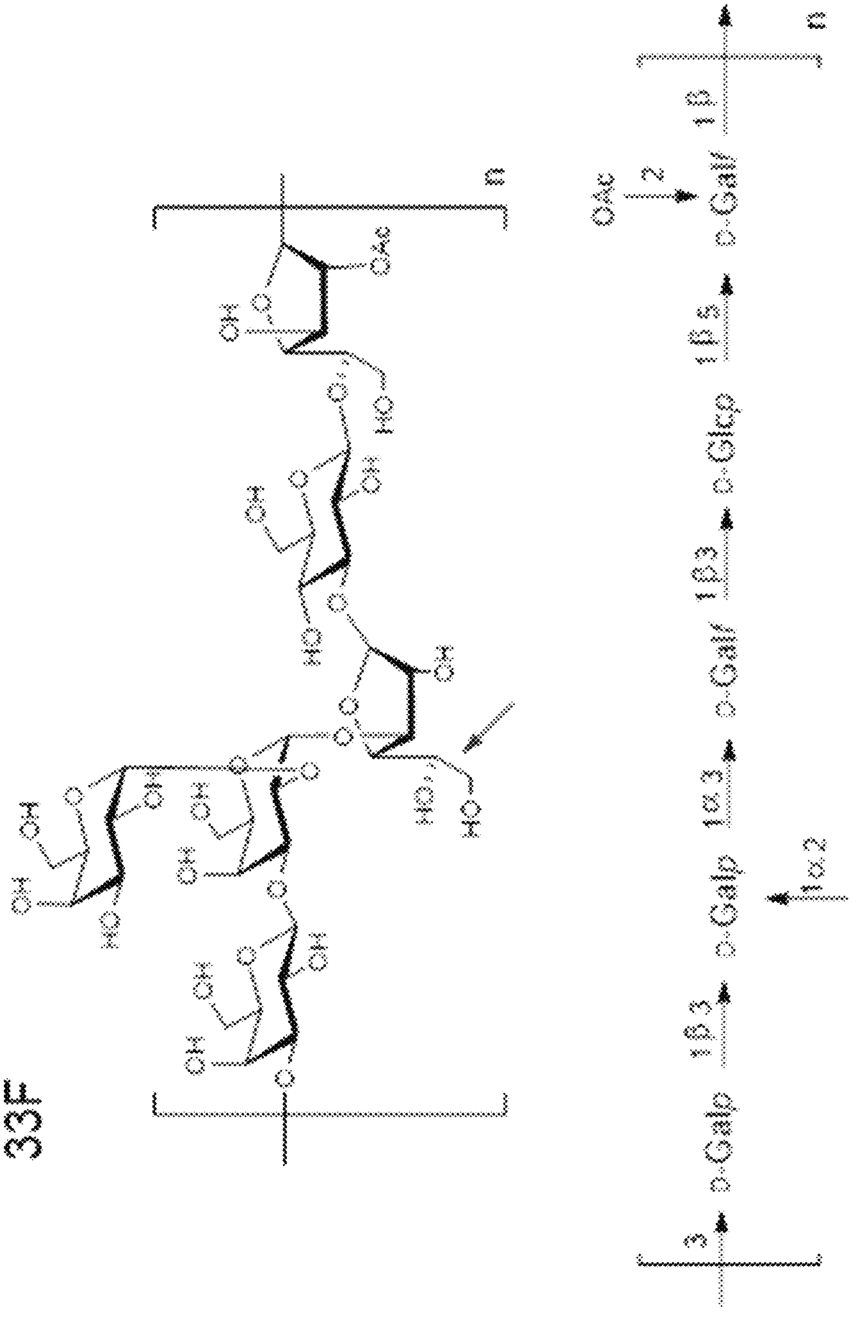
FIG. 2 shows the structure of serotype 33F pnemococcal polysaccharide having vicinal hydroxyls uniquely positioned to generate primary aldehydes (see arrow), which are significantly more reactive compared to secondary aldehydes positioned in a hindered structural position in the polysaccharide repeat unit.
Figure 3:
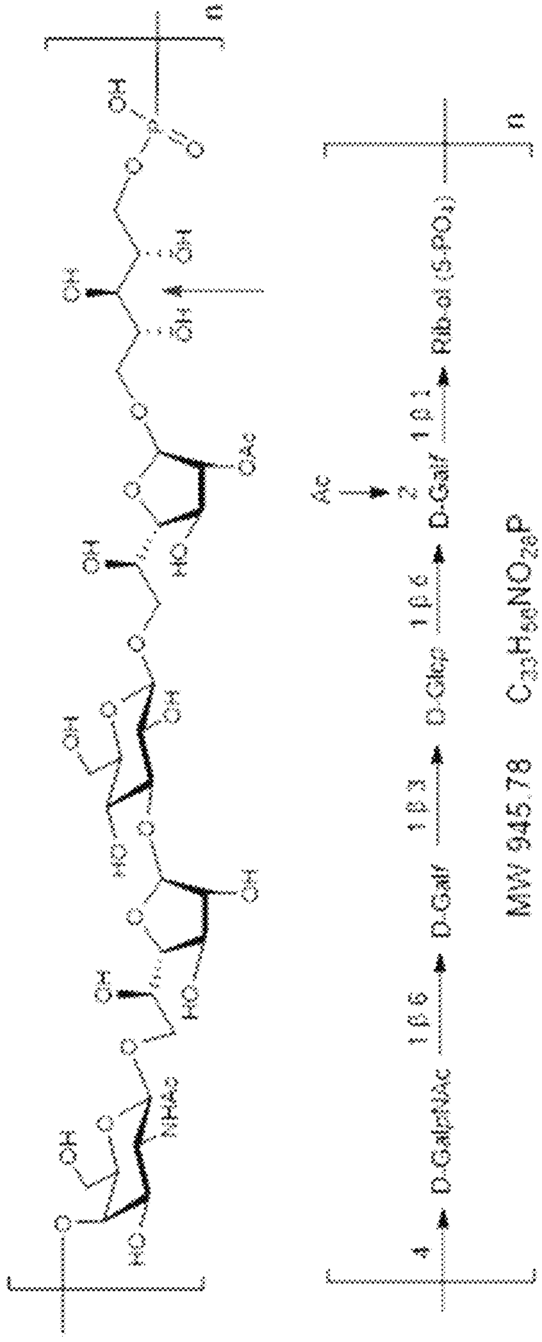
FIG. 3 shows the structure of serotype 35B pnemococcal polysaccharide having vicinal hydroxyls uniquely positioned to generate primary aldehydes (see arrow), which are significantly more reactive compared to secondary aldehydes positioned in a hindered structural position in the polysaccharide repeat unit.
Figure 4:
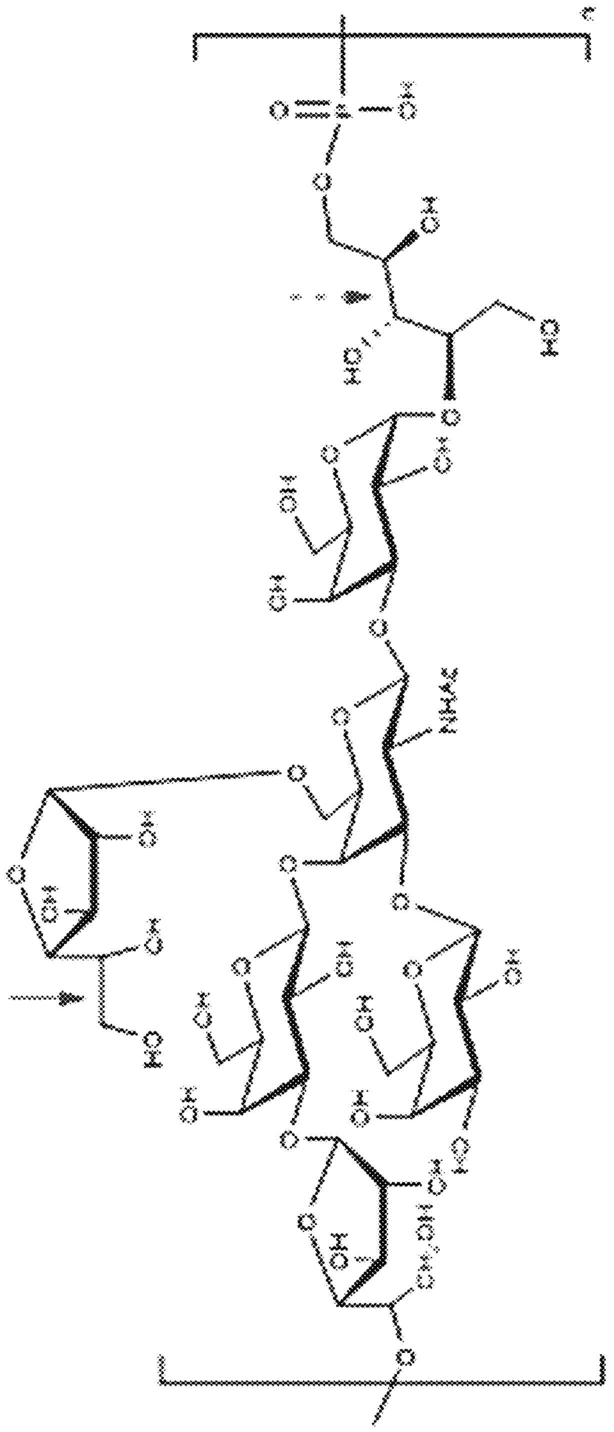
FIG. 4 shows the structure of serotype 10A pnemococcal polysaccharide having vicinal hydroxyls uniquely positioned to generate primary aldehydes (see arrow), which are significantly more reactive compared to secondary aldehydes positioned in a hindered structural position in the polysaccharide repeat unit.
Figure 5:
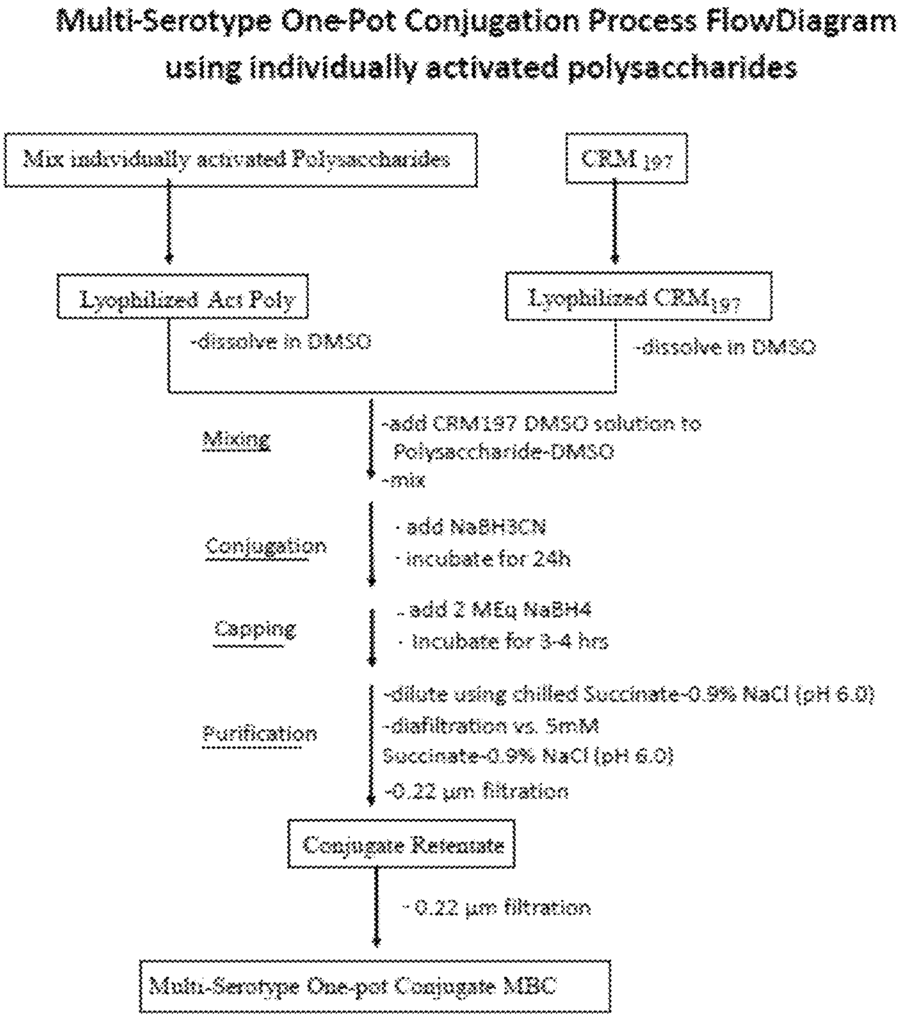
FIG. 5 shows a flow diagram of the multi-serotype one-pot conjugation process using individually activated polysaccharides as described at Example 1.

A flow Diagram of the above descried multi-serotype one-pot conjugation process using individually activated polysaccharides is provided at FIG. 5.

Example 2. Antigenicity by Nephelometry

In order to ensure that all the four serotypes were incorporated into the carrier protein, the conjugates were tested for antigenicity by Nephelometry. The antigenicity data indicated that the most reactive serotype 22F activated polysaccharide was incorporated relative at higher proportion compared to serotypes 10A and 33F (see FIG. 6). Serotype 35B was not been analyzed by nephelometry (due to the lack of a suitable antibody reagents).

Example 3. Multi-Serotype ONE-POT Conjugation Process Using Individually Activated Polysaccharides Several multiserotypes (2, 3 or 4 valents conjugates have been produced using the process of example 1.

The One-Pot conjugation phase consists of the same steps (see also FIG. 5).

The different multi-serotype conjugates obtained and their characteristics and are summarized in Table 3.

Example 4. Evaluation of Opsonophagocytic Immune Responses of *Streptococcus pneumoniae* Multi-Serotypes Host protection against *S. pneumoniae* is mediated primarily through anticapsular antibody dependent opsonophagocytosis. The pneumococcal opsonophagocytic assay (OPA), which measures killing of *S. pneumoniae* cells by phagocytic effector cells in the presence of functional antibody and complement, is considered to be an important surrogate for evaluating the effectiveness of pneumococcal vaccines.

The immunogenicity of the multi-serotype conjugate (see Example 3) was assessed in mice using serotype-specific OPAs.

Eight different groups of 25 Swiss Webster mice (6-8 weeks old) were immunized subcutaneously with different doses of conjugate or mixture of conjugates on week 0 (see study design at Table 4 for the 8 groups, group 1 was the control group and received no conjugate). The mice were boosted with the same dose of the same conjugate(s) on week 3 and then bled at week 4. Serotype-specific OPAs were performed on week 4 sera samples.

Opsonophagocytic activity (OPA) assays are used to measure functional antibodies in murine sera specific for the *S. pneumonia* serotypes 10A, 22F, 33F and 35B. Test serum is set up in assay reactions that measure the ability of capsular polysaccharide specific immunoglobulin to opsonize bacteria, trigger complement deposition, thereby facilitating phagocytosis and killing of bacteria by phagocytes. The OPA titer is defined as the reciprocal dilution that results in a 50% reduction in bacterial count over control wells without test serum. The OPA titer is interpolated from the two dilutions that encompass this 50% killing cut-off.

OPA procedures were based on methods described in Hu et al. (2005) Clin Diagn Lab Immunol12 (2):287-295 with the following modifications. Test serum was serially diluted 2.5-fold and added to microtiter assay plates. Live target

TABLE 3

| Multi-Serotype One-Pot Conjugate Groups | | | | | | | | | |
|---|---|---|---|---|---|---|---|---|---|
| Conjugate Lot# | | 1 | 2 | 3 | 4 | 5 | 6 | 7 | 8 |
| Conjugate variants | | 10A-22F | 22F-33F | 33F-35B | 10A-35B | 10A-22F-33F | 10A-22F-35B | 10A-33F-35B | 10A-22F-33F-35B |
| Act Poly | 10A | 10A | | | 10A | 10A | 10A | 10A | 10A |
| | 22F | 22F | 22F | | | 22F | 22F | | 22F |
| | 33F | | 33F | 33F | | 3F | | 33F | 33F |
| | 35B | | | 35B | 35B | | 35B | 35B | 35B |
| Coniugation | | | | | | | | | |
| Saccharide yield (by Anthrone), % | | 64 | 82 | 59 | 66 | 66 | 62 | 51 | 69 |
| Saccharide-Protein Ratio (Output Ratio) | | 0.87 | 1.05 | 0.86 | 0.86 | 0.90 | 0.89 | 0.82 | 1.0 |
| Free Saccharide, % | | <5 | <5 | <5 | <5 | <5 | <5 | <5 | <5 |
| Free Protein, % | | <1 | <1 | <1 | <1 | <1 | <1 | <1 | <1 |
| Conjugate MW, kDa | | 5667 | 4338 | 2656 | 3373 | 6029 | 3621 | 4455 | 4916 |
| Nephelometry | 10A | 206 | <LOQ | <LOQ | 264 | 138 | 155 | 116 | 139 |
| | 22F | 334 | 391 | <LOQ | <LOQ | 206 | 249 | <LOQ | 220 |
| | 33F | <LOQ | 236 | 264 | <LOQ | 112 | <LOQ | 95 | 111 |
| | 35B | n/a | n/a | n/a | n/a | n/a | n/a | n/a | n/a |

n/a: not applicable

<LOQ: below limit of quantitation bacterial strains were added to the wells and the plates were shaken at 25° C. or 37° C. for 30 minutes. Differentiated HL-60 cells (phagocytes) and baby rabbit serum (3- to 4-week old, PEL-FREEZ®, 12.5% final concentration) were added to the wells, and the plates were shaken at 37° C. for 45 or 60 minutes. To terminate the reaction, 80 μL of 0.9% NaCl was added to all wells, mixed, and a 10 μL aliquot were transferred to the wells of MULTISCREEN® HTS HV filter plates (MILLIPORE®) containing 200 μL of water. Liquid was filtered through the plates under vacuum, and 150 μL of HYSOY® medium was added to each well and filtered through. The filter plates were then incubated at 37° C., 5% $CO_2$ overnight and were then fixed with Destain Solution (Bio-Rad Laboratories, Inc., Hercules, CA). The plates were then stained with Coomassie Blue and destained once. Colonies were imaged and enumerated on a Cellular Technology Limited (CTL) (Shaker Heights, OH) IMMUNOSPOT® Analyzer. Raw colony counts were used to plot kill curves and calculate OPA titers.

TABLE 4

| Study design | | | | |
|---|---|---|---|---|
| Group Conjugate | | Conjugate Dose | $AlPO_4$ Dose | Vaccine Volume |
| 1 | Control | — | — | — |
| 2 | Control 20-valent^ | 0.1 μg/animal | 0.1 mg/animal | 0.1 mL |
| 3 | 22F | 0.1 μg/animal | 0.1 mg/animal | 0.1 mL |
| 4 | 22F | 0.01 μg/animal | 0.1 mg/animal | 0.1 mL |
| 5 | Multi-serotype 10A + 22F + 33F + 35B* | 0.1 μg/animal | 0.1 mg/animal | 0.1 mL |
| 6 | Multi-serotype 10A + 22F + 33F + 35B* | 0.01 μg/animal | 0.1 mg/animal | 0.1 mL |
| 7 | Multi control 10A, 22F, 33F, 35B ° | 0.1 μg/animal | 0.1 mg/animal | 0.1 mL |
| 8 | Multi control 10A, 22F, 33F, 35B° | 0.01 μg/animal | 0.1 mg/animal | 0.1 mL |

*Conjugate comprising saccharide from *S. pneumoniae* serotypes 10A, 22F, 33F and 35B conjugated to $CRM_{197}$ (conjugate Lot#8 of Table3)

°mixture of 4 conjugates independently conjugated to $CRM_{197}$

^mixture of 20 conjugates (from serotypes 1, 3,4, 5, 6A, 6B, 7F, 8, 9V, 10A, 11A, 12F,14, 15B,
18C, 19A, 19F, 22F, 23F and 33F) independently conjugated to $CRM_{197}$ (see WO2015110941)

Results—OPA Responses in 10A, 22F, 33F, and 35B

The response of mice sera immunized with the different conjugates was evaluated in the respective Opsonophagocytic Assays (OPAs).

As shown at Table 5, OPA titers showed no significant differences between the multi-serotypes conjugate comprising saccharide from *S. pneumoniae* serotypes 10A, 22F, 33F and 35B conjugated to $CRM_{197}$ and the corresponding control (mixture of 4 conjugates independently conjugated to $CRM_{197}$).

Table 5, OPA titers for the different serotypes. Sera from mice vaccinated with different pneumococcal conjugates (see study design at Table 4) were assessed in OPAs for the presence of functional antibodies against each serotype.

TABLE 5

OPA titers for the different serotypes. Sera from mice vaccinated with different pneumococcal conjugates (see study design at Table 4) were assessed in OPAs for the presence of functional antibodies against each serotype.

| | | Immunogen | | | | |
|---|---|---|---|---|---|---|
| Serotype | Dose (mcg/conjugate) | None (Control) (Group 1) | 20vPnC (Group 2) | 22F (Groups 3 and 4) | Multi (10A/22F/33F/35B) (Groups 5 and 6) | 10A + 22F + 33F + 35B (Groups 7 and 8) |
| 10A | 0.1 | 179 (45-707) | 3242 (1278-8227) | 191 (36-1010) | 1573 (512-4834) | 952 (302-3005) |
| | 0.01 | | | 109 (30-396) | 713 (154-3301) | 1633 (740-3602) |
| 22F | 0.1 | 5 (5-6) | 6660 (3297-13453) | 12562 (6369-24775) | 9524 (4109-22072) | 11478 (6016-21899) |
| | 0.01 | | | 2030 (709-5809) | 8057 (3898-16654) | 7786 (4311-14064) |
| 33F | 0.1 | 5 (5-5) | 27 (10-71) | 6 (5-7) | 12 (5-28) | 179 (42-771) |
| | 0.01 | | | 5 (5-5) | 9 (4-21) | 81 (27-239) |
| 35B | 0.1 | 5 (5-5) | 5 (5-6) | 7 (5-9) | 148 (71-308) | 317 (156-642) |
| | 0.01 | | | 5 (5-5) | 10 (6-16) | 68 (35-133) |

CONCLUSION

The multi-serotypes conjugate comprising saccharide from *S. pneumoniae* serotypes 10A, 22F, 33F and 35B conjugated to $CRM_{197}$ induced functional killing of serogroups 10A, 22F, 33F and 35B comparable to the mixture of 4 conjugates independently conjugated to $CRM_{197}$. Based on these data, a single multi-serotypes conjugate is likely to provide the same level of coverage for the 4 serotypes 10A/22F/33F/35B as a mixture of 4 conjugates independently conjugated to the carrier. This means a potential need for a lower dose of carrier in a multi-valent setting. This further mean for potentially simplifying the production of a multi-valent pneumococcal vaccine as less drug substance will be required and less steps. A multi-serotypes pneumococcal conjugate would also help to customize multi-valent vaccines more easily by providing protection against several serotypes with only a limited number of conjugates.

In view of the results of the four valent multi-serotypes conjugate (10A/22F/33F/35B), it is likely that a three valent (10A/22F/33F, 10A/22F/35B, 10A/33F/35B or 22F/33F/35B) or a two valent (10A/22F, 10A/33F, 10A/35B, 22F/33F, 22F/35B or 33F/35B) multi-serotypes conjugate will provide for similar benefits.

Example 5. Multi-Serotype One-Pot Conjugation Process Using Individually Activated Polysaccharides The One-Pot conjugation aqueous phase process consists of the following steps:

1. Shell freezing and co-lyophilization of activated polysaccharides and $CRM_{197}$ protein 2. Reconstitution of the activated polysaccharides and $CRM_{197}$ in aqueous buffer
3. Conjugation and capping
4. Purification of the conjugate 1 Individually Activated Polysaccharides, Mixing with $CRM_{197}$, Shell Freezing and Lyophilization Individually activated (oxidized) polysaccharides of serotypes 8, 15A, 15B, 23A and/or 23B of *S. pneumoniae* are obtained using sodium periodate as oxidant.

The individually activated polysaccharides are mixed with $CRM_{197}$ protein. The mixture is then shell-frozen and lyophilized 2 Reconstitution of Lyophilized Activated Polysaccharide and $CRM_{197}$ Protein Different serotype of lyophilized activated polysaccharide and $CRM_{197}$ mixture is selected based on their pH Compatibility and is combined. Phosphate buffer is added to reconstitute the mixture into a homogeneous solution 3 Conjugation of Activated Polysaccharide to $CRM_{197}$ Conjugation reaction is initiated by adding $NaCNBH_3$ (sodium cyanoborohydride) to the reaction mixture.

After the conjugation reaction is completed, $NaBH_4$ (sodium borohydride) is added to terminate the reaction.

4 Purification of the Conjugate

The conjugate solution is diluted with 5 mM Succinate-0.9% NaCl buffer and then purified by tangential flow filtration using 100K MWCO. The results are summarized in table below A flow Diagram of the above descried multi-serotype one-pot conjugation process using individually activated polysaccharides is provided at FIG. 12.

Example 6. Antigenicity by Nephelometry

In order to ensure that all the serotypes are incorporated into the carrier protein, the conjugates are tested for antigenicity by Nephelometry.

For example, a bivalent conjugate comprising serotypes 15A and 15B was tested for antigenicity by Nephelometry and total saccharide content measured by Anthrone assay (see FIG. 13). Serotype 15A has not been analyzed by nephelometry.

Example 7. Multi-Serotype One-Pot Conjugation Process Using Individually Activated Polysaccharides The One-Pot conjugation aqueous phase process consists of the following steps:

1. Shell freezing and co-lyophilization of activated polysaccharides and $CRM_{197}$ protein
2. Reconstitution of the activated polysaccharides and $CRM_{197}$ in aqueous buffer
3. Conjugation and capping
4. Purification of the conjugate 1 Individually Activated Polysaccharides, Mixing with $CRM_{197}$, Shell Freezing and Lyophilization Individually activated (oxidized) polysaccharides of serotypes 8, 11A, 12F, 23A and/or 23B of *S. pneumoniae* are obtained using sodium periodate as oxidant.

The individually activated polysaccharides are mixed with $CRM_{197}$ protein. The mixture is then shell-frozen and lyophilized 2 Reconstitution of Lyophilized Activated Polysaccharide and $CRM_{197}$ Protein Different serotype of lyophilized activated polysaccharide and $CRM_{197}$ mixture is selected based on their pH Compatibility and is combined. Phosphate buffer is added to reconstitute the mixture into a homogeneous solution 3 Conjugation of Activated Polysaccharide to $CRM_{197}$ Conjugation reaction is initiated by adding $NaCNBH_3$ (sodium cyanoborohydride) to the reaction mixture.

After the conjugation reaction is completed, $NaBH_4$ (sodium borohydride) is added to terminate the reaction.

4 Purification of the Conjugate

The conjugate solution is diluted with 5 mM Succinate-0.9% NaCl buffer and then purified by tangential flow filtration using 100K MWCO. The results are summarized in table 5 below.

TABLE 5

| Conjugation | 1 | 2 | 3 | 4 | 5 |
|---|---|---|---|---|---|
| Conjugation condition | S/P 0.8<br>pH 7.8<br>90h@23° C.<br>2meq SCY | S/P 0.8<br>pH 7.8<br>90h@23° C.<br>2meq SCY | S/P 0.8<br>pH 6.6<br>24h@23° C.<br>24h@30C<br>2meq SCY | S/P 0.8<br>pH 6.6<br>44h@23° C.<br>2meq SCY | S/P 0.8<br>pH 7.8<br>90h@23° C.<br>2.5meq SCY |
| Output S/P ratio | 0.73 | 1.05 | 0.83 | 1.0 | 1.2 |
| Free Saccharide(%) | <5% | 12% | 7.1% | 15% | 12.4% |
| Conjugate MW (kDa) | 3394 | 2035 | 3436 | 2300 | 1945 |

S/P: Sacharide Protein Ratio
SCY: sodium cyanoborohydride

Example 8. Antigenicity by Nephelometry

In order to ensure that all the serotypes are incorporated into the carrier protein, the conjugates are tested for antigenicity by Nephelometry (see FIGS. 16 and 17).

For example, two bivalent conjugates comprising serotypes 11A and 23B or serotypes 8 and 12F were tested for antigenicity by Nephelometry and total saccharide content measured by Anthrone assay (see FIGS. 16 and 17). Serotype 23B has not been analyzed by nephelometry.

The invention claimed is:

1. A glycoconjugate comprising at least two saccharides selected from the group consisting of a saccharide from *Streptococcus pneumoniae* (*S. pneumoniae*) serotype 10A, a saccharide from *S. pneumoniae* serotype 22F, a saccharide from *S. pneumoniae* serotype 33F and a saccharide from *S. pneumoniae* serotype 35B, each conjugated to the same carrier protein molecule, wherein each of said at least two saccharides conjugated to the same carrier protein molecule has a molecular weight of 20 kDa to 4000 kDa.

2. The glycoconjugate of claim 1 wherein the degree of conjugation of said conjugate is between 2 and 15, the ratio (weight/weight) of saccharide to carrier protein in the glycoconjugate is between 0.5 and 3.0, and/or the ratio (weight/weight) of the saccharides is between 0.5 and 1.5.

3. The glycoconjugate of claim 1 wherein said carrier protein is selected from the group consisting of TT, DT, DT mutants, $CRM_{197}$, *H. influenzae* protein D, PhtX, PhtD, PhtDE fusions, detoxified pneumolysin, PorB, N19 protein, PspA, OMPC, toxin A or B of *C. difficile* and PsaA.

4. The glycoconjugate of claim 1 wherein said carrier protein is $CRM_{197}$.

5. The glycoconjugate of claim 1 wherein said glycoconjugate is prepared using reductive amination.

6. The glycoconjugate of claim 1, wherein said glycoconjugate is a 2-valent glycoconjugate comprising saccharide from the group of *S. pneumoniae* serotypes consisting of: 10A and 22F; 10A and 33F; 10A and 35B; 22F and 33F; 22F and 35B; and 33F and 35B.

7. The glycoconjugate of claim 6 wherein said carrier protein is $CRM_{197}$.

8. The glycoconjugate of claim 1, wherein said glycoconjugate is a 3-valent glycoconjugate comprising saccharide from the group of *S. pneumoniae* serotypes consisting of: 10A, 22F and 33F; 10A, 22F and 35B; and 22F, 33F and 35B.

9. The glycoconjugate of claim 8 wherein said carrier protein is $CRM_{197}$.

10. The glycoconjugate of claim 1, wherein said glycoconjugate is a 4-valent glycoconjugate comprising saccharide from the group of *S. pneumoniae* serotypes consisting of 10A, 22F, 33F and 35B.

11. The glycoconjugate of claim 10 wherein said carrier protein is $CRM_{197}$.

12. A glycoconjugate comprising at least two saccharides selected from the group consisting of a saccharide from *Streptococcus pneumoniae* (*S. pneumoniae*) serotype 8, a saccharide from *S. pneumoniae* serotype 11A, a saccharide from *S. pneumoniae* serotype 12F, a saccharide from *S. pneumoniae* serotype 23A and a saccharide from *S. pneumoniae* serotype 23B, each conjugated to the same carrier protein molecule, wherein each of said at least two saccharides conjugated to the same carrier protein molecule has a molecular weight of 20 kDa to 4000 kDa.

13. The glycoconjugate of claim 12 which is a 2, 3 or a 4-valent glycoconjugate.

14. The glycoconjugate of claim 12 wherein the degree of conjugation of said conjugate is between 2 and 15, the ratio (weight/weight) of saccharide to carrier protein in the glycoconjugate is between 0.5 and 3.0, and/or the ratio (weight/weight) of the saccharides is between 0.5 and 1.5.

15. The glycoconjugate of claim 12 wherein said carrier protein is selected from the group consisting of TT, DT, DT mutants, $CRM_{197}$, *H. influenzae* protein D, PhtX, PhtD, PhtDE fusions, detoxified pneumolysin, PorB, N19 protein, PspA, OMPC, toxin A or B of *C. difficile* and PsaA.

16. The glycoconjugate of claim 12 wherein said carrier protein is $CRM_{197}$.

17. The glycoconjugate of claim 12 wherein said glycoconjugate is prepared using reductive amination.

18. A glycoconjugate comprising at least two saccharides selected from the group consisting of a saccharide from *Streptococcus pneumoniae* (*S. pneumoniae*) serotype 8, a saccharide from *S. pneumoniae* serotype 15A, a saccharide from *S. pneumoniae* serotype 15B, a saccharide from *S. pneumoniae* serotype 23A and a saccharide from *S. pneumoniae* serotype 23B, each conjugated to the same carrier protein molecule, wherein each of said at least two saccharides conjugated to the same carrier protein molecule has a molecular weight of 20 kDa to 4000 kDa.

19. The glycoconjugate of claim 18 which is a 2, 3 or a 4-valent glycoconjugate.

20. The glycoconjugate of claim 18 wherein the degree of conjugation of said conjugate is between 2 and 15, the ratio (weight/weight) of saccharide to carrier protein in the glycoconjugate is between 0.5 and 3.0, and/or the ratio (weight/weight) of the saccharides is between 0.5 and 1.5.

21. The glycoconjugate of claim 18 wherein said carrier protein is selected from the group consisting of TT, DT, DT mutants, $CRM_{197}$, *H. influenzae* protein D, PhtX, PhtD, PhtDE fusions, detoxified pneumolysin, PorB, N19 protein, PspA, OMPC, toxin A or B of *C. difficile* and PsaA.

22. The glycoconjugate of claim 18 wherein said carrier protein is $CRM_{197}$.

23. The glycoconjugate of claim 18 wherein said glycoconjugate is prepared using reductive amination.

24. An immunogenic composition comprising at least one glycoconjugate of claim 12, or 18.

25. The immunogenic composition of claim 24 further comprising at least one adjuvant.

* * * * *